(12) United States Patent
Beghyn et al.

(10) Patent No.: US 9,845,479 B2
(45) Date of Patent: *Dec. 19, 2017

(54) PLANTS RESISTANT TO INSECT PESTS

(75) Inventors: Myriam Beghyn, Zulte (BE); Thierry Andre Olivier Eddy Bogaert, Kortrijk (BE); Pascale Feldmann, Ghent-Mariakerke (BE); Romaan Raemaekers, De Pinte (BE)

(73) Assignee: Devgen NV (BE)

( * ) Notice: Subject to any disclaimer, the term of this patent is extended or adjusted under 35 U.S.C. 154(b) by 589 days.

This patent is subject to a terminal disclaimer.

(21) Appl. No.: 13/462,610

(22) Filed: May 2, 2012

(65) Prior Publication Data

US 2012/0297501 A1 Nov. 22, 2012

Related U.S. Application Data

(63) Continuation-in-part of application No. PCT/EP2012/057333, filed on Apr. 20, 2012.

(60) Provisional application No. 61/477,371, filed on Apr. 20, 2011, provisional application No. 61/508,826, filed on Jul. 18, 2011.

(51) Int. Cl.
*C12N 15/82* (2006.01)
*C12N 15/113* (2010.01)
*C07K 14/435* (2006.01)

(52) U.S. Cl.
CPC .... *C12N 15/8286* (2013.01); *C07K 14/43563* (2013.01); *C12N 15/8218* (2013.01)

(58) Field of Classification Search
None
See application file for complete search history.

(56) References Cited

U.S. PATENT DOCUMENTS

2006/0112447 A1* 5/2006 Bogdanova et al. ......... 800/279
2009/0300796 A1* 12/2009 Raemaekers et al. ........ 800/279

FOREIGN PATENT DOCUMENTS

WO  WO 2007/074405  7/2007
WO  WO 2009/091864  7/2009

OTHER PUBLICATIONS

Beall et al (1991) J. Cell Biol. 114: 941-951.*
GenBank Accession No. FJ810196, published 2009.*
Turner et al, Insect Mol. Biol. (2006) 15:383-391.*
Baum et al, Nature Biotech (2007) 25:1322-1326.*
Spencer et al, Plant Mol. Biol. (1992) 18:201-210.*
Genbank Submission; NCBI; Accession No. CB408878; Eigenheer et al.; Oct. 25, 2003.
Genbank Submission; NCBI; Accession No. DV392288; Loftus et al.; Oct. 21, 2005.
Mao et al., Nature Biotechnology, 25, 11, Nov. 2007, 1307-1313.
Gordon et al., Nature Biotechnology, 25, 11, Nov. 2007, 1231-1232.

* cited by examiner

*Primary Examiner* — Mykola V Kovalenko
(74) *Attorney, Agent, or Firm* — Yoshimi D. Barron

(57) ABSTRACT

The present invention relates to genetic control of infestation by insect pest species, particularly prevention and/or control of pest infestation of plants, using interfering ribonucleic acid (RNA) molecules. The invention provides transgenic plants that (i) express or are capable of expressing interfering RNAs of the invention and (ii) are resistant to infestation by insect pest species.

29 Claims, 32 Drawing Sheets

US 9,845,479 B2

PLANTS RESISTANT TO INSECT PESTS

RELATED APPLICATIONS

Figure 1:
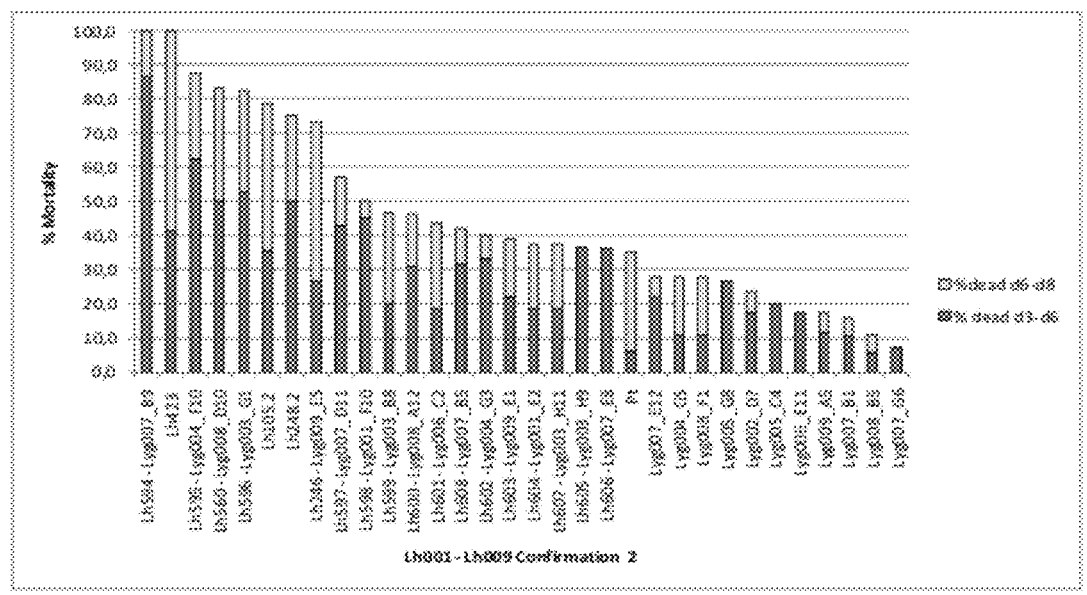

This application is a continuation-in-part of PCT/EP2012/057333, filed Apr. 20, 2012, which claims the benefit under 35 U.S.C. §119(e) of U.S. provisional application 61/477,371 filed Apr. 20, 2011, and U.S. provisional application 61/508,826 filed Jul. 18, 2011, each of which is incorporated by reference in its entirety herein.

SEQUENCE LISTING

The instant application contains a Sequence Listing which has been submitted in ASCII format via EFS-Web and is hereby incorporated by reference in its entirety.

FIELD OF THE INVENTION

The present invention relates generally to genetic control of infestation by insect pest species, particularly prevention and/or control of pest infestation of plants. More specifically, the invention relates to down-regulation of expression of target genes in insect pest species by interfering ribonucleic acid (RNA) molecules. Also provided are transgenic plants that (i) express or are capable of expressing interfering RNAs of the invention and (ii) are resistant to infestation by insect pest species.

BACKGROUND TO THE INVENTION

There exists an abundance of insect pest species that can infect or infest a wide variety of environments and host organisms. Insect pests include a variety of species from the insect Orders Hemiptera (true bugs), Coleoptera (beetles), Siphonaptera (fleas), Dichyoptera (cockroaches and mantids), Lepidoptera (moths and butterflies), Orthoptera (e.g. grasshoppers) and Diptera (true flies). Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as rice, cotton, soybean, potato and corn.

Traditionally, infestation with insect pests has been prevented or controlled through the use of chemical pesticides. However, these chemicals are not always suitable for use in the treatment of crops as they can be toxic to other species and can cause significant environmental damage. Over more recent decades, researchers have developed more environmentally-friendly methods of controlling pest infestation. For example, microorganisms such as *Bacillus thuringiensis* bacteria that naturally express proteins toxic to insect pests have been used. Scientists have also isolated the genes encoding these insecticidal proteins and used them to generate transgenic crops resistant to insect pests e.g. corn and cotton plants genetically engineered to produce proteins of the Cry family. Although bacterial toxins have been highly successful in controlling certain types of pest, they are not effective against all pest species. Researchers have therefore looked for other more targeted approaches to pest control and in particular to RNA interference or 'gene silencing' as a means to control pests at the genetic level.

RNA interference or 'RNAi' is a process whereby the expression of genes in the context of a cell or whole organism is down-regulated in a sequence-specific manner. RNAi is now a well-established technique in the art for inhibiting or down-regulating gene expression in a wide variety of organisms including pest organisms such as fungi, nematodes and insects. Furthermore, previous studies have shown that down-regulation of target genes in insect pest species can be used as a means to control pest infestation.

WO2007/074405 describes methods of inhibiting expression of target genes in invertebrate pests including Colorado potato beetle. Furthermore, WO2009/091864 describes compositions and methods for the suppression of target genes from insect pest species including pests from the *Lygus* genus.

Although the use of RNAi for down-regulating gene expression in pest species is known in the art, the success of this technique for use as a pest control measure depends on selection of the most appropriate target genes, namely those wherein loss of function results in significant disruption of an essential biological process and/or death of the organism. The present invention is thus directed towards the down-regulation of particular target genes in insect pests as a means to achieve more effective prevention and/or control of insect pest infestation, particularly of plants.

SUMMARY OF THE INVENTION

The current inventors sought to identify improved means for preventing and/or controlling insect pest infestation using genetic approaches. In particular, they investigated the use of RNAi to down-regulate genes in such a way as to impair the ability of the insect pest to survive, grow, progress through different stages of the insect's life cycle (for instance through metamorphosis from pupae to adult), colonize specific environments and/or infest host organisms and thus limit the damage caused by the pest.

Therefore, in accordance with one aspect of the invention, there is provided a transgenic plant, or reproductive or propagation material for a transgenic plant or a cultured transgenic plant cell, which expresses or is capable of expressing at least one an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene
(i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or having a nucleotide sequence that, when the two sequences are optimally aligned and compared, is at least 75%, preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or (ii) is selected from the group of genes having a nucleotide sequence consisting of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (v) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389.

In a particular aspect of the invention, interfering RNA molecules expressed by the plants of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

In one embodiment, the present invention relates to a transgenic plant, or reproductive or propagation material for a transgenic plant or a cultured transgenic plant cell which expresses or is capable of expressing an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene from the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to another aspect the present invention relates to a transgenic plant, or reproductive or propagation material for a transgenic plant or a cultured transgenic plant cell which expresses or is capable of expressing an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO. 80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO. 82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO. 85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO. 81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs. 86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO. 89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO. 357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO. 390.

In one embodiment, the target gene encodes the mitochondrial cytochrome c oxidase subunit II protein (e.g. an insect orthologue of the CG34069 Dm protein), said target gene being represented by SEQ ID NO 25 and 26. In a preferred embodiment, the insect orthologue has at least 85%, 90%, 92%, 94%, 96%, 98%, 99% or 100% amino acid sequence identity to SEQ ID NO. 91.

In one embodiment, the target gene encodes the ATP synthase-γ chain (e.g. an insect orthologue of the CG7610 Dm protein), said target gene being represented by SEQ ID NOs 129 and 138. In a preferred embodiment, the insect orthologue has at least 85%, 90%, 92%, 94%, 96%, 98%, 99% or 100% amino acid sequence identity to SEQ ID NO. 338.

In one embodiment, the target gene encodes the ubiquitin-5E (e.g. an insect orthologue of the CG32744 Dm protein) said target gene being represented by SEQ ID NOs. 186 and 187, 202 and 203. In a preferred embodiment, the insect orthologue has at least 85%, 90%, 92%, 94%, 96%, 98%, 99% or 100% amino acid sequence identity to one or both of SEQ ID NOs. 355 and 358.

In one embodiment, the target gene encodes the proteasome beta-type subunit (e.g. an insect orthologue of the CG17331 Dm protein) said target gene being represented by SEQ ID NO. 387. In a preferred embodiment, the insect orthologue has at least 85%, 90%, 92%, 94%, 96%, 98%, 99% or 100% amino acid sequence identity to SEQ ID NO. 391.

In one embodiment, the target gene encodes the protein which is an insect orthologue of the CG13704 Dm protein, said target gene being represented by SEQ ID NO. 388. In a preferred embodiment, the insect orthologue has at least 85%, 90%, 92%, 94%, 96%, 98%, 99% or 100% amino acid sequence identity to SEQ ID NO. 392.

In one embodiment, the target gene encodes the Rpn12 protein (e.g. an insect orthologue of the CG4157 Dm protein) said target gene being represented by SEQ ID NO. 389. In a preferred embodiment, the insect orthologue has at least 85%, 90%, 92%, 94%, 96%, 98%, 99% or 100% amino acid sequence identity to SEQ ID NO. 393.

In accordance with a further aspect of the invention, there is provided an isolated polynucleotide selected from the group consisting of:
(i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or
(ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 and
wherein said polynucleotide is no longer than 10000, 9000, 8000, 7000, 6000, 5000, 4000, 3000, 2000 or 1500 nucleotides.

The amino acid sequences encoded by the target genes of the invention are represented by SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

In a particular aspect of the invention, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. More particularly, the isolated polynucleotide is cloned in a DNA construct in a sense and antisense orientation so that the upon transcription of the sense and antisense polynucleotide a dsRNA molecule is formed, which functions upon uptake by a pest to inhibit or down-regulate the expression of a target gene within said pest.

In certain aspects the present invention relates to isolated polynucleotides that are cloned in a DNA construct in a sense and antisense orientation so that the upon transcription of the sense and antisense polynucleotide a dsRNA molecule is formed, which functions upon uptake by an insect to inhibit or down-regulate the expression of a target gene within the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to other embodiments, the present invention relates to an isolated polynucleotide that is cloned in a DNA construct in a sense and antisense orientation so that the upon transcription of the sense and antisense polynucleotide a dsRNA molecule is formed, which functions upon uptake by an insect to inhibit or down-regulate the expression of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO. 80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO. 82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO. 85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO. 81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs. 86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO. 89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO. 357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO. 390.

Preferably, the methods of the invention find practical application in the prevention and/or control of insect pest infestation, in particular, control of pest infestation of crop plants such as but not limited to cotton, potato, rice, strawberries, alfalfa, soy, tomato, canola, sunflower, sorghum, pearl millet, corn, eggplant, pepper and tobacco. In addition, the interfering RNA of the invention may be introduced into the plants to be protected by routine genetic engineering techniques.

Therefore, in accordance with another aspect of the invention, there is provided a method for generating a transgenic plant resistant to infestation by an insect pest species comprising:

(a) transforming a plant cell with a DNA construct comprising a polynucleotide sequence encoding an interfering ribonucleic acid (RNA) that functions upon uptake by an insect pest species to down-regulate expression of a target gene in said insect pest species, wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence that, when the two sequences are optimally aligned and compared, is at least 75%, preferably at least 80%, 85%, 90%, 95%, 98% or 99% identical any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (ii) is selected from the group of genes having a nucleotide sequence consisting of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or having a nucleotide sequence that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs. 1-26, 121-205, 386-389, 394, 400, or the complement thereof, or (v) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389;

(b) regenerating a plant from the transformed plant cell; and (c) growing the transformed plant under conditions suitable for the expression of the interfering RNA from the recombinant DNA construct, said plant thus being resistant to said pest as compared with an untransformed plant.

In a further aspect, provided herein is a method for preventing and/or controlling insect pest infestation in a field of crop plants, said method comprising expressing in said plants an effective amount of an interfering ribonucleic acid (RNA) that functions upon uptake by an insect pest species to down-regulate expression of a target gene in said insect pest species, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence so that, when the two sequences are optimally aligned and compared, is at least 75% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence of said fragment is at least 75% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% identical to any of the sequences represented by SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or (v) is selected from the group of genes having a nucleotide sequence encoding an amino acid sequence that, when the two amino acid sequences are optimally aligned and compared, is at least 85% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389.

In all aspects of the invention, in preferred embodiments, the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

In a preferred embodiment, the target gene encodes an insect protein chosen from the troponin/myofilament complex chosen from the group comprising the troponin I protein (e.g. an insect orthologue of the CG7178 Dm protein), the upheld protein (e.g. an insect orthologue of the CG7107 Dm protein), the tropomyosin 1 protein (e.g. an insect orthologue of the CG4898 Dm protein), the tropomyosin 2 protein (e.g. an insect orthologue of the CG4843 Dm protein), the myosin heavy chain (e.g. an insect orthologue of the CG17927 Dm protein), the myosin light chain cytoplasmic protein (e.g. an insect orthologue of the CG3201 Dm protein), the spaghetti squash protein (e.g. an insect orthologue of the CG3595 Dm protein), the zipper protein (e.g. an insect orthologue of the CG15792 Dm protein), and the troponin C protein (e.g. an insect orthologue of the CG2981, CG7930, CG9073, CG6514, CG12408, CG9073, CG7930, CG2981, CG12408 or CG6514 Dm protein).

In all aspects of the invention, in preferred embodiments, the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

In a preferred embodiment, the target gene encodes an insect ribosomal protein chosen from the group comprising the ribosomal protein S3A (e.g. an insect orthologue of the CG2168 Dm protein), the ribosomal protein LP1 (e.g. an insect orthologue of the CG4087 Dm protein), the ribosomal protein S3 (e.g. an insect orthologue of the CG6779 Dm protein), the ribosomal protein L10Ab (e.g. an insect orthologue of the CG7283 Dm protein), the ribosomal protein S18 (e.g. an insect orthologue of the CG8900 Dm protein), the ribosomal protein L4 (e.g. an insect orthologue of the CG5502 Dm protein), the ribosomal protein S27 (e.g. an insect orthologue of the CG10423 Dm protein), the ribosomal protein L6 (e.g. an insect orthologue of the CG11522 Dm protein), the ribosomal protein S13 (e.g. an insect orthologue of the CG13389 Dm protein), and the ribosomal protein L12 (e.g. an insect orthologue of the CG3195 Dm protein), the ribosomal protein L26 (e.g. an insect orthologue of the CG6846 Dm protein), the ribosomal protein L21 (e.g. an insect orthologue of the CG12775 Dm protein), the ribosomal protein S12 (e.g. an insect orthologue of the CG11271 Dm protein), the ribosomal protein S28b (e.g. an insect orthologue of the CG2998 Dm protein), the ribosomal protein L13 (e.g. an insect orthologue of the CG4651 Dm protein), the ribosomal protein L10 (e.g. an insect orthologue of the CG17521 Dm protein), the ribosomal protein L5 (e.g. an insect orthologue of the CG17489 Dm protein), the ribosomal protein S15Aa (e.g. an insect orthologue of the CG2033 Dm protein), the ribosomal protein L19 (e.g. an insect orthologue of the CG2746 Dm protein), and the ribosomal protein L27 (e.g. an insect orthologue of the CG4759 Dm protein)

In all aspects of the invention, in preferred embodiments, the target gene
(i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401.

In preferred embodiments, the target gene may encode an insect the troponin I protein (e.g. an insect orthologue of the CG7178 Dm protein). The insect troponin I protein may have an amino acid sequence which is at least 85%, 90%, 92%, 94%, 96%, 98%, 99% identical to the amino acid sequence as presented in any of SEQ ID NOs 79, 349, 405, 352 or 356 (when said encoded proteins are optimally aligned).

BRIEF DESCRIPTION OF THE TABLES AND FIGURES

Table 1 *Lygus hesperus* novel targets identified from first screen.

Table 1B *Lygus hesperus* novel targets in Lh594 pathway.

Table 1C *Lygus hesperus* novel targets identified from second round screen.

Table 2 Polynucleotide sequences of target genes identified in *Lygus hesperus*.

Table 3 Amino acid sequences of target genes identified in *Lygus hesperus*.

Table 4 dsRNAs (sense strand represented by equivalent DNA sequence) corresponding to *Lygus hesperus* target genes and primers for producing the dsRNAs.

Table 5 *Lygus hesperus* targets ranking according to dose response curves (DRCs) and compared to bench mark targets Lh423 & Lh105.

Table 6 *Lygus hesperus* targets from second round screen-ranking according to DRCs and compared to bench mark targets Lh423 & Lh594.

Table 7 Overview of the testing of transgenic potato carrying *Lygus hesperus* hairpins.

Table 8 Sequence of amplicons for target gene and the two house-keeping genes for qRT-PCR.

Table 9 Polynucleotide sequences of target genes identified in Colorado potato beetle (CPB).

Table 10 Amino acid sequences of target genes identified in CPB.

Table 11 dsRNAs (sense strand represented by equivalent DNA sequence) corresponding to CPB target genes and primers for producing the dsRNAs.

Table 12 Polynucleotide sequences of target genes identified in brown plant hopper (BPH).

Table 13 Amino acid sequences of target genes identified in BPH.

Table 14 dsRNAs (sense strand represented by equivalent DNA sequence) corresponding to BPH target genes and primers for producing the dsRNAs.

Table 15 Primers used for amplification of aphid cDNAs, based on pea aphid genomic sequence.

Table 16 Polynucleotide sequences of target genes identified in aphids.

Table 17 Amino acid sequences of target genes identified in aphids.

Table 18 dsRNAs (sense strand represented by equivalent DNA sequence) corresponding to aphid target genes and primers for producing the dsRNAs.

Table 19 Degenerate primers used for amplification of CPB Ld594 cDNA

Table 20 Degenerate primers used for amplification of BPH cDNAs

Table 21: *Leptinotarsa decemlineata* novel targets from the screen.

Table 22: *Nilaparvata lugens* novel identified target.

Table 23: *Acyrthosiphon pisum* novel identified targets.

FIG. 1: Plates Lh001_009 second confirmation assay. Dark bars: mortality at day 3 to 6, light bars: mortality at day 6 to 8. Candidate clones are named using the "Lygxxx" screening codes and the "Lhxxx" target nomenclature codes.

Figure 2:
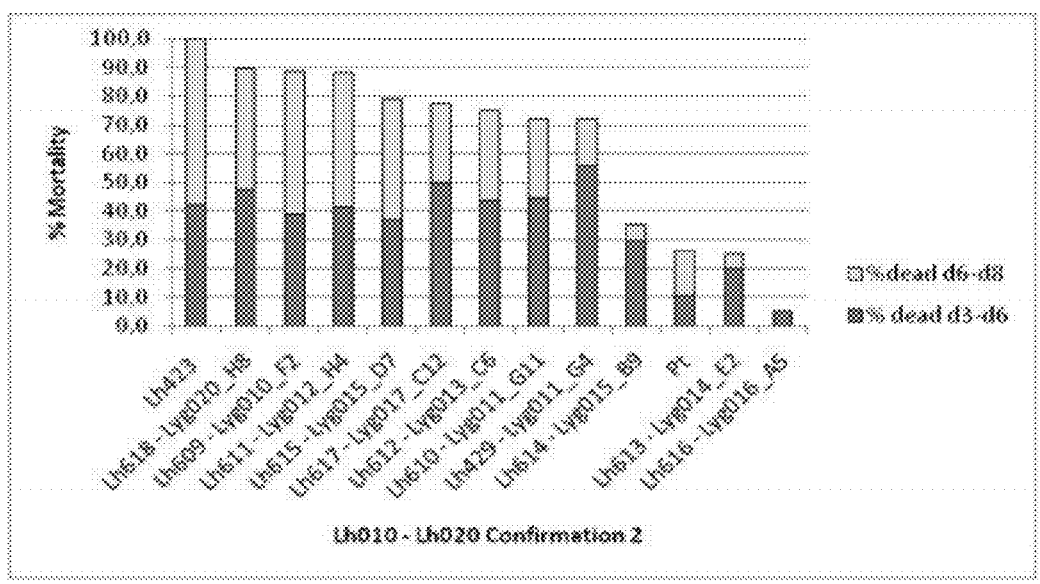

FIG. 2: Plates Lh010_020 second confirmation assay. Dark bars: mortality at day 3 to 6, light bars: mortality at day 6 to 8. Candidate clones are named using the "Lygxxx" screening codes and the "Lhxxx" target nomenclature codes.

Figure 3:
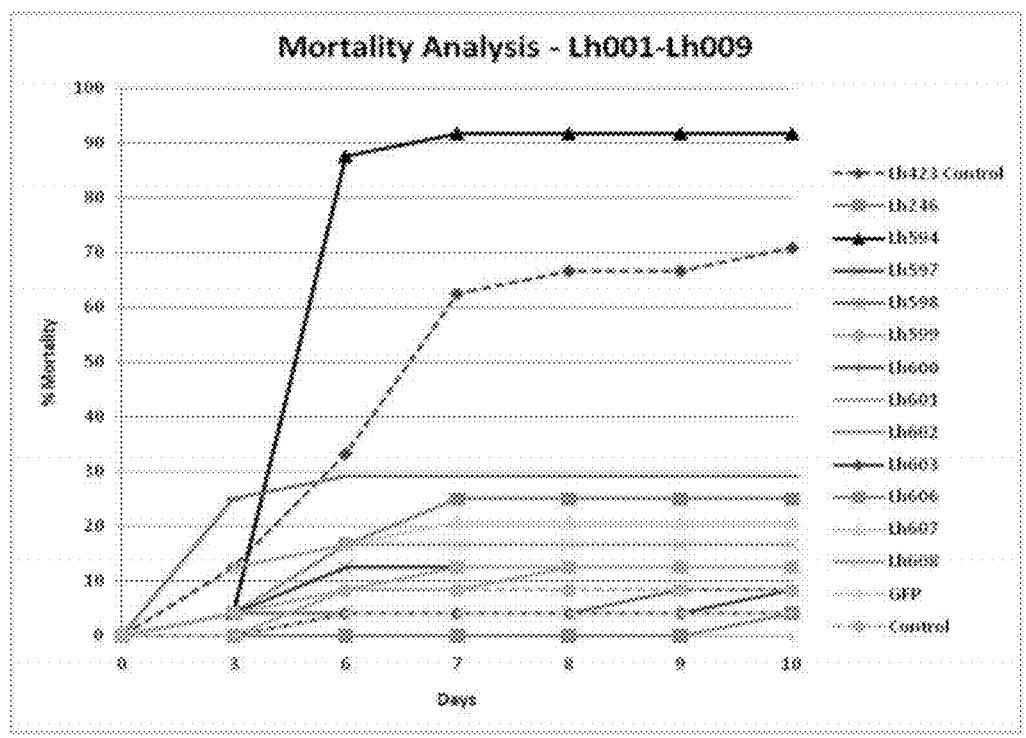

FIG. 3: Mortality analysis of *Lygus* novel targets from plates Lh001 to Lh009, expressed as % mortality over a 10 day period. Controls are indicated in dotted lines. Positive control: Lh423 dsRNA (RpL19). Negative controls: GFP dsRNA and diet only (Control).

Figure 4:
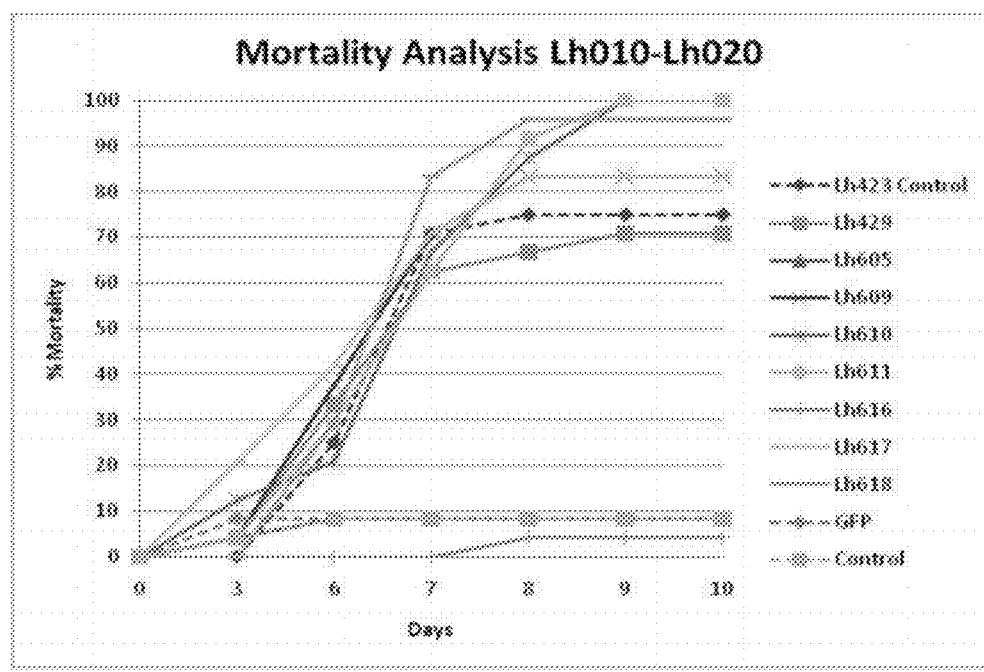

FIG. 4: Mortality analysis of *Lygus* novel targets from plates Lh010 to Lh020, expressed as % mortality over a 10 day period. Controls are indicated in dotted lines. Positive control: Lh423 (RpL19). Negative controls: GFP and diet only (Control).

Figure 5:
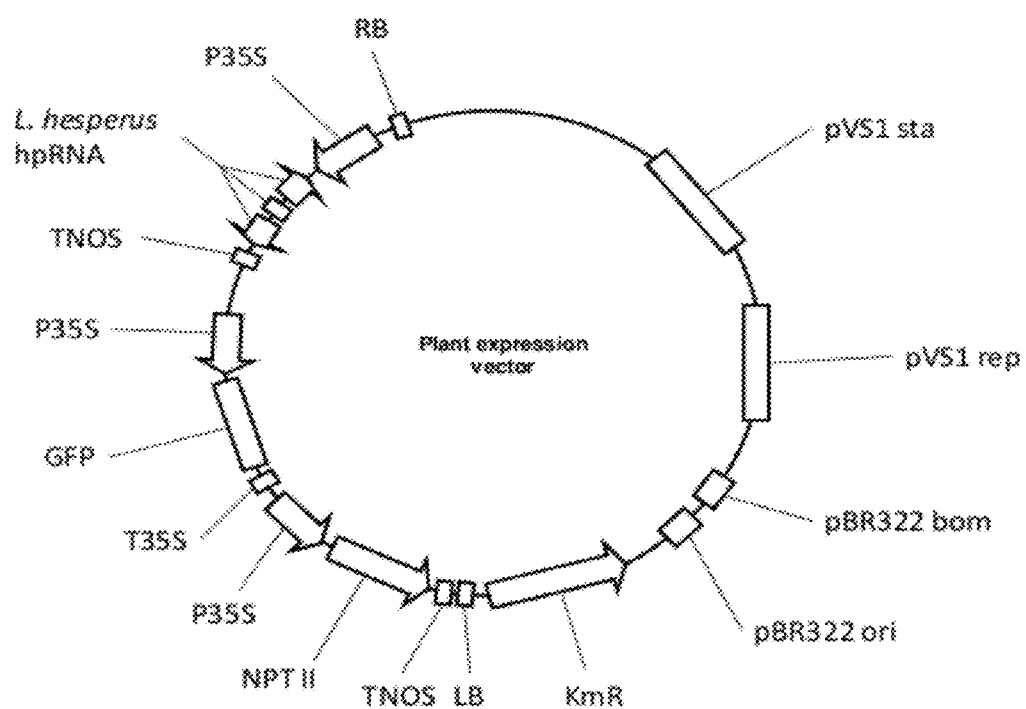

FIG. 5 Schematic representation of the plant expression vector harbouring the *Lygus hesperus* hpRNA cassette. RB: right border; LB: left border; P35S: Cauliflower Mosaic Virus 35S promoter; T35S: Cauliflower Mosaic Virus 35S terminator; TNOS: nopaline synthase terminator; GFP: green fluorescent reporter gene; NPT II: coding sequence of neomycin phosphotransferase II gene; KmR: Kanamycin resistance gene; pBR322 ori: pBR322 origin of replication; pBR322 bom: pBR322 mobilization; pVS1 rep: pVS1 replicon; pVS1 sta: pVS1 stability element.

Figure 6:
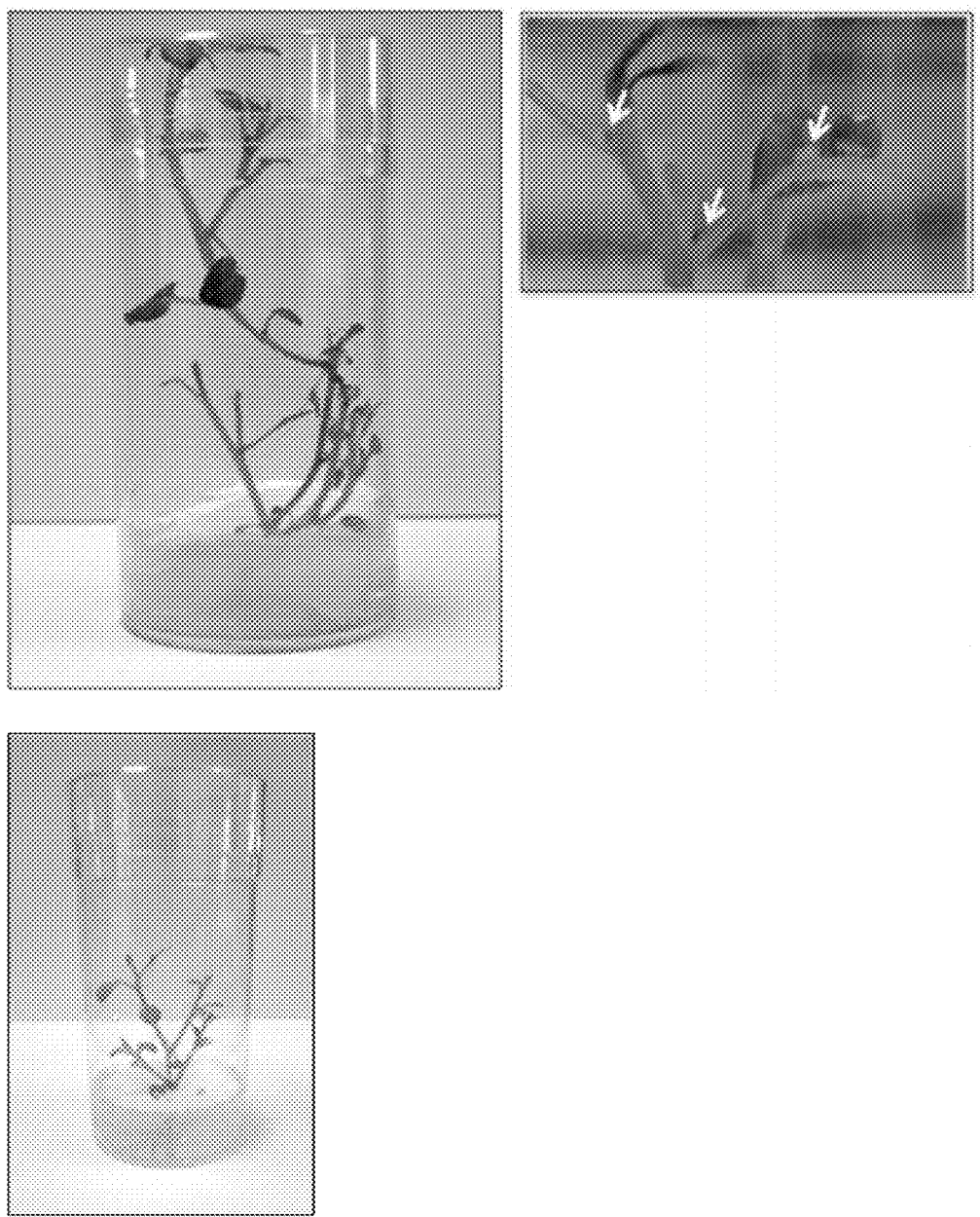
Figure 7:
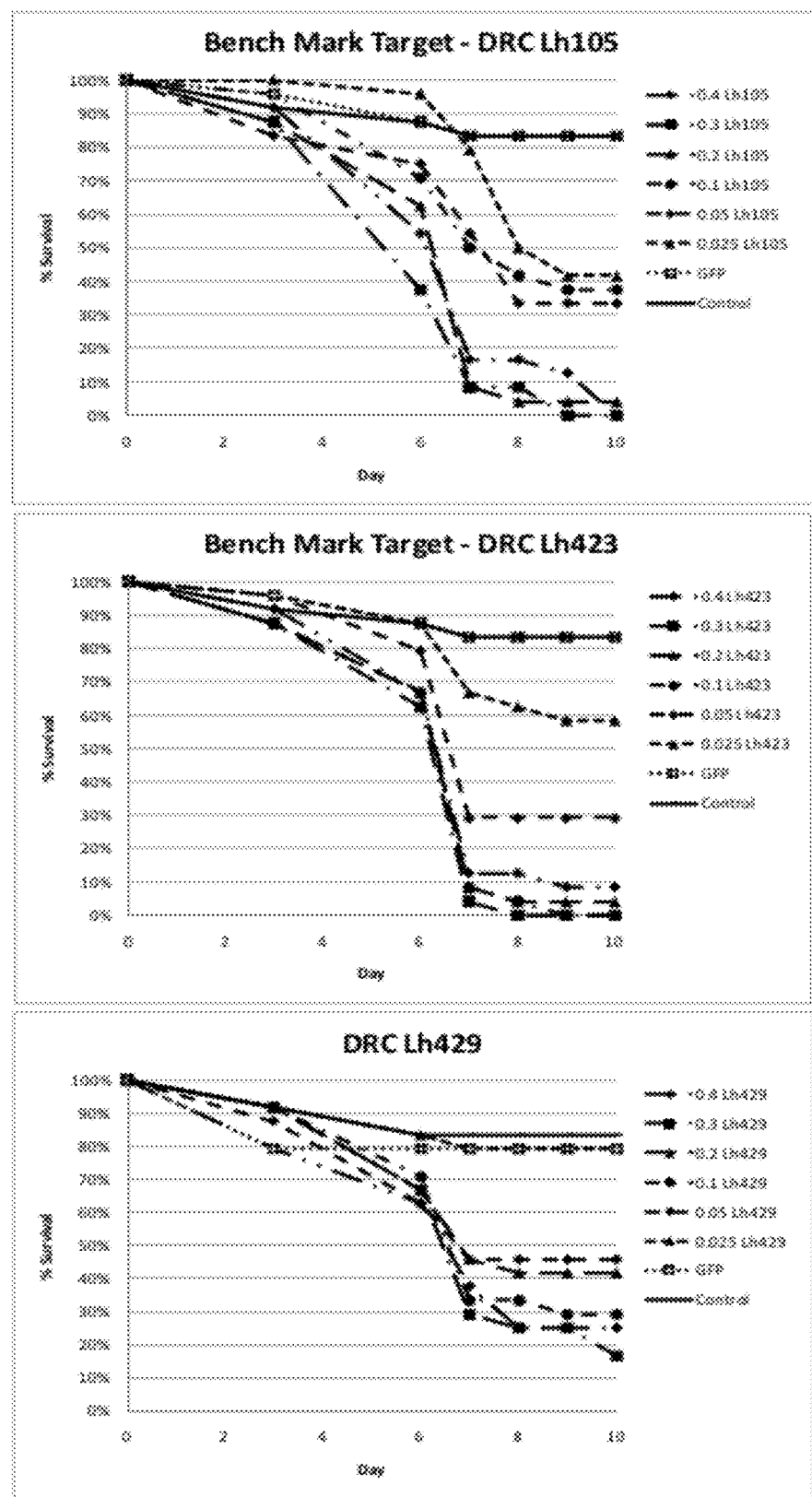
Figure 8:
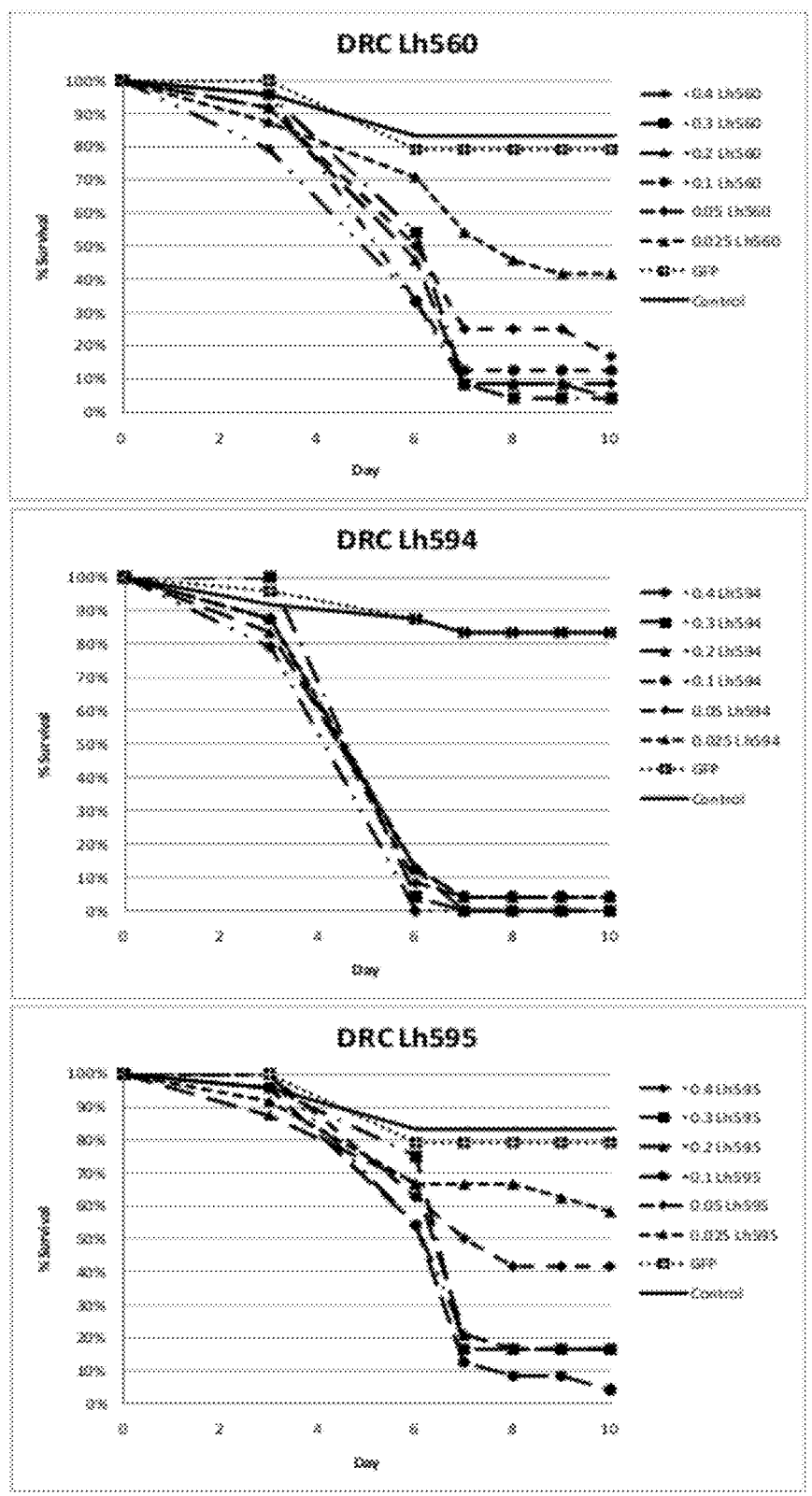
Figure 9:
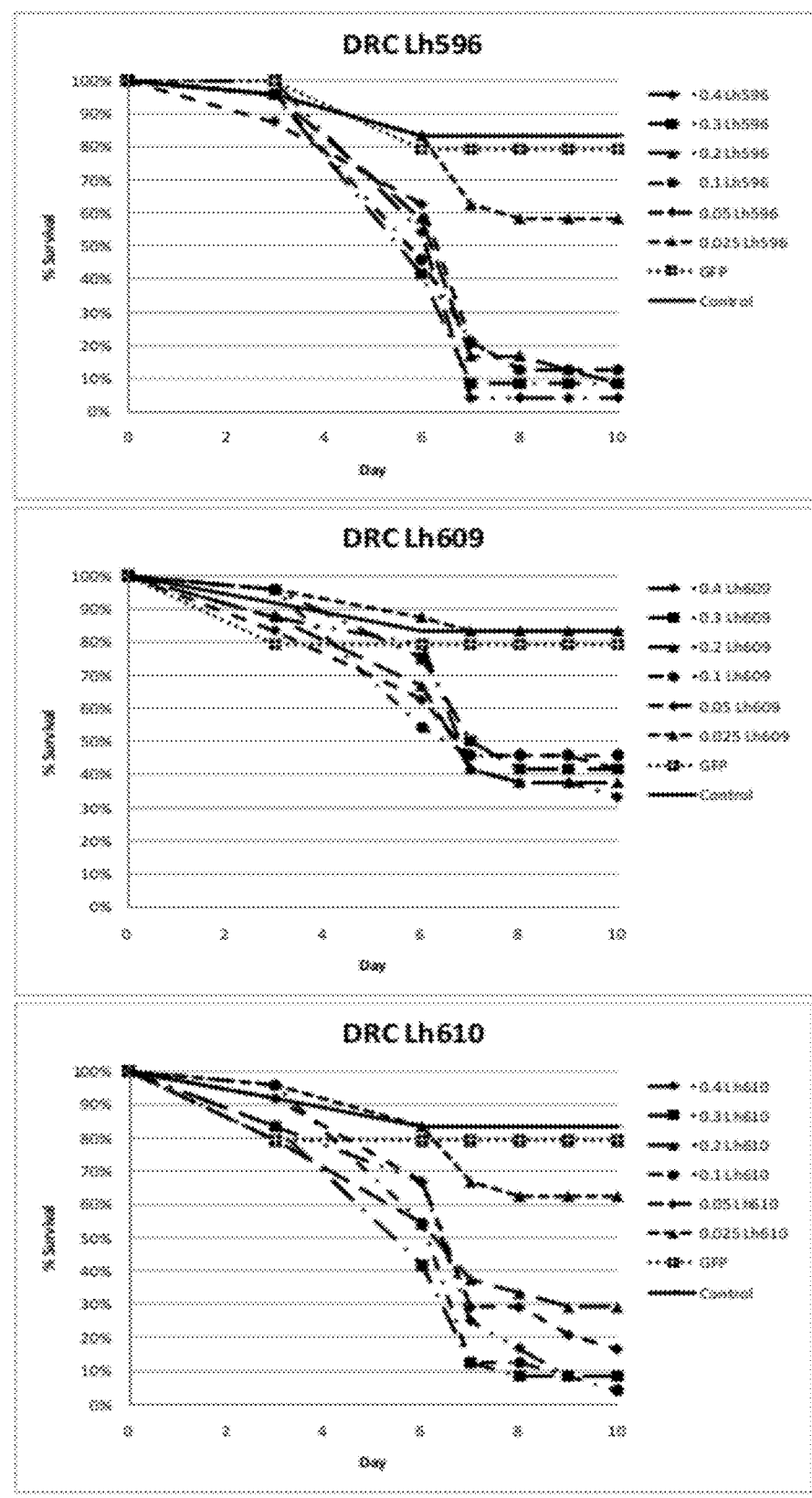
Figure 10:
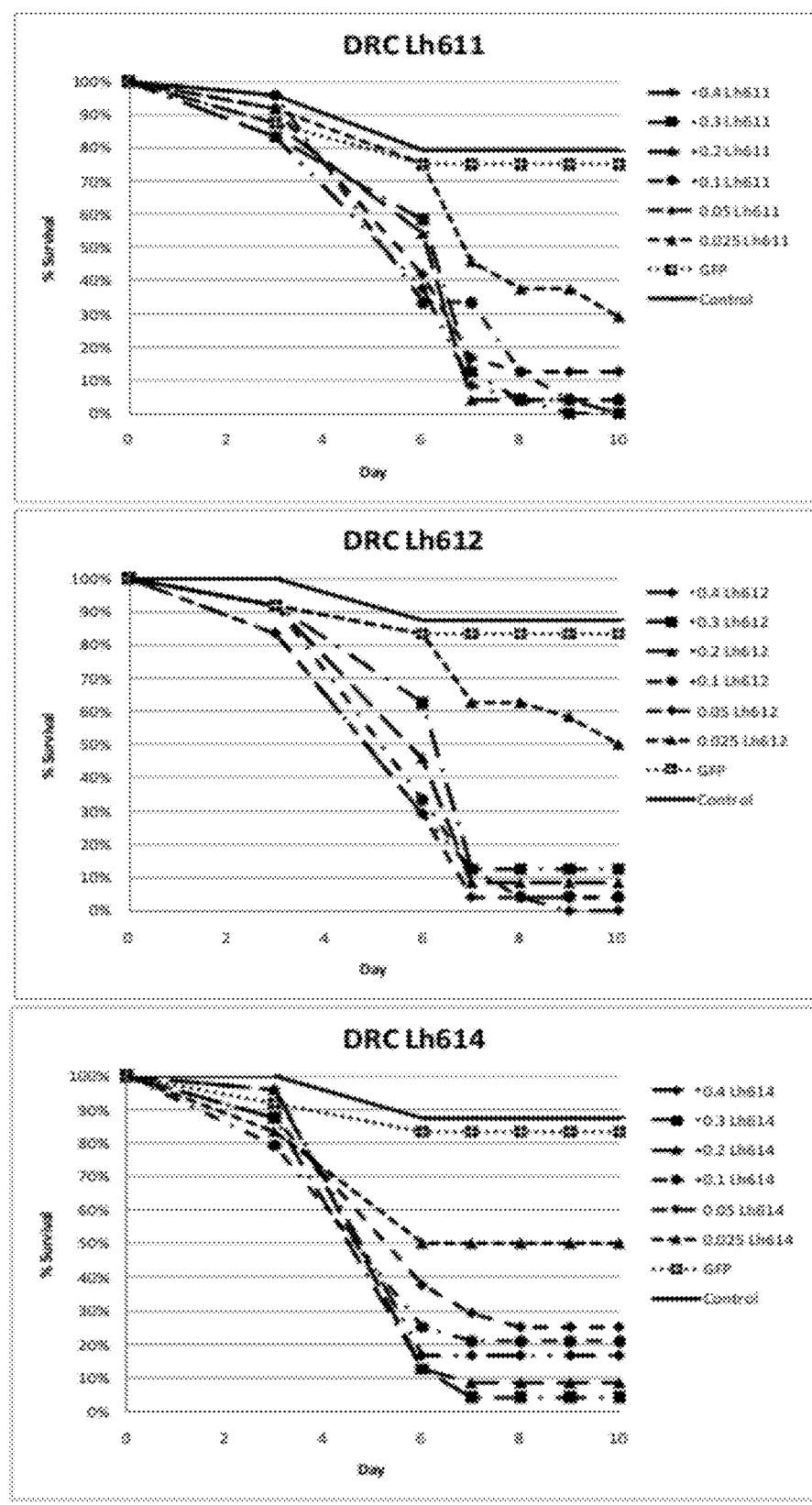
Figure 11:
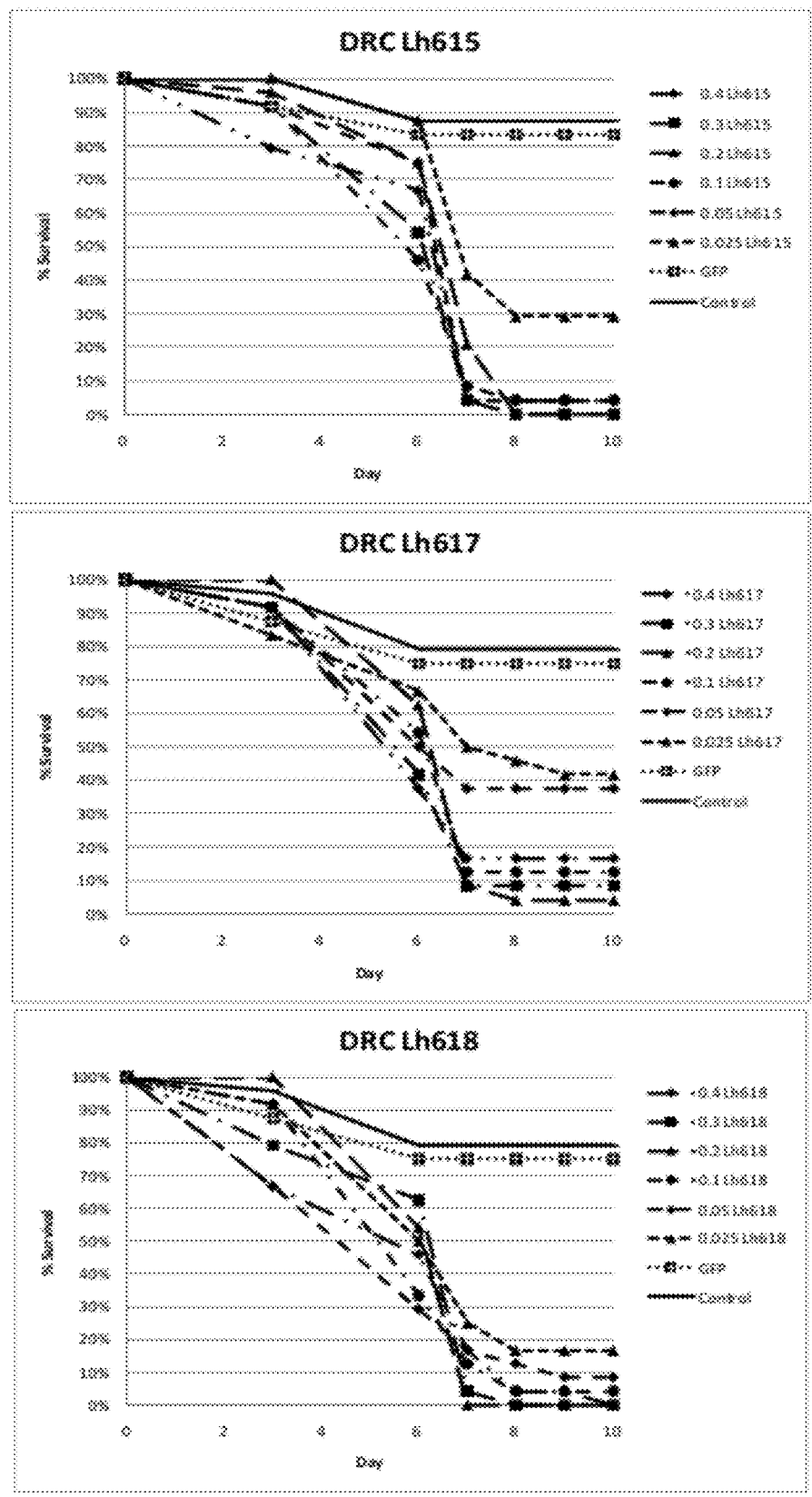

FIG. 6 Potato-*Lygus* in planta assay set up. White arrows indicate insect damage.

FIGS. 7 to 11 *Lygus hesperus* novel targets—dose response curves at concentrations of purified synthetic dsRNA ranging from 0.4 to 0.025 µg/µl (in the figure, the unit "µg/µl" is not displayed). GFP dsRNA and milliQ water were used negative controls. dsRNA of targets were produced using the primers as described in the example section 1.1.

Figure 12:
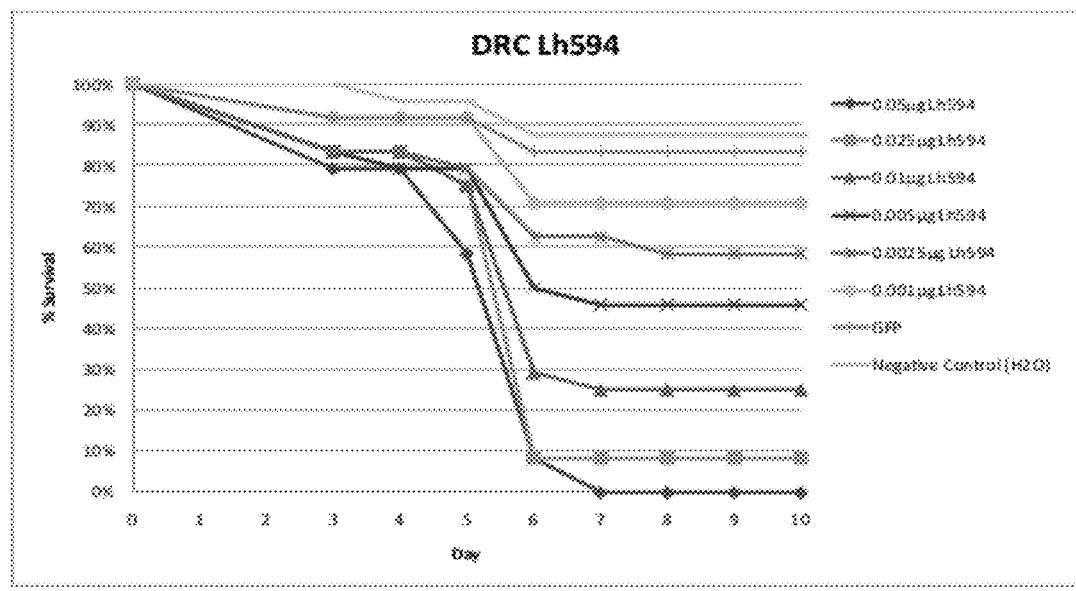

FIG. 12 Lh594 dose response curve, at dsRNA concentrations ranging from 0.05 to 0.001 µg/µl. GFP dsRNA and milliQ water were used negative controls.

Figure 13:
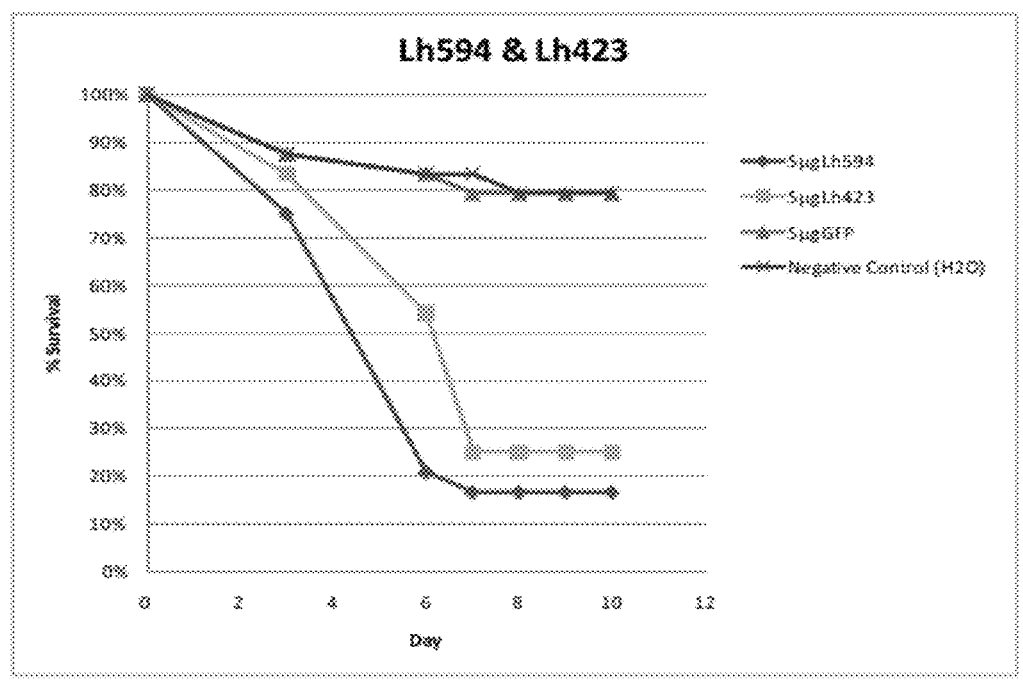
Figure 13:
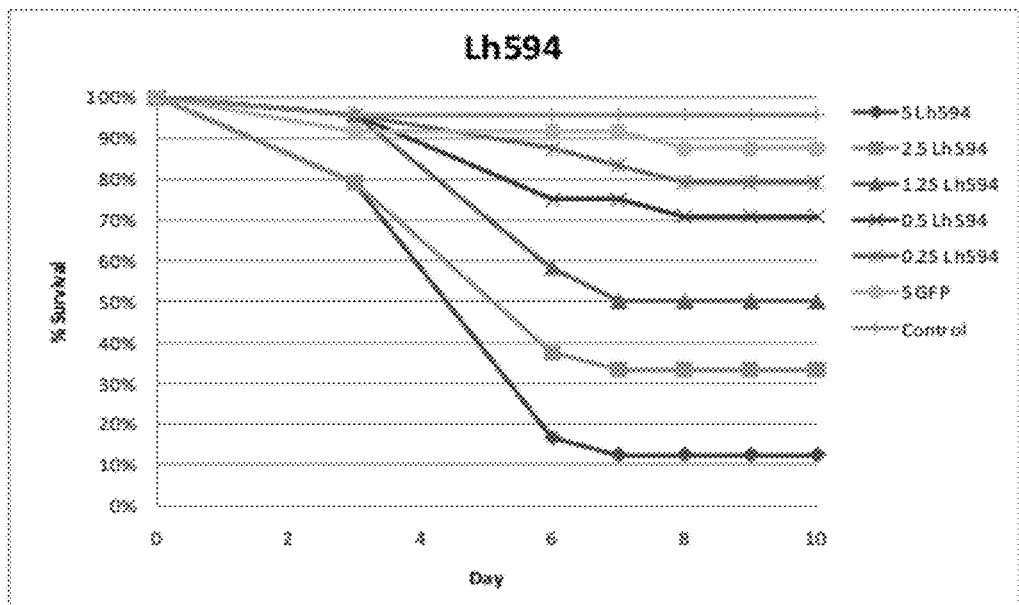

FIG. 13 A dsRNA activity in *Lygus hesperus* bioassay in absence of tRNA. Lh594 (5 µg/µl); positive control: Lh423 (5 µg/µl); negative controls: GFP dsRNA (5 µg/µl) and milliQ water; B Identification of Lh594 limit of activity using decreasing concentration of dsRNA (from 5 µg to 0.25 µg). Negative controls: GFP dsRNA (5 µg/µl) and milliQ water.

Figure 14:
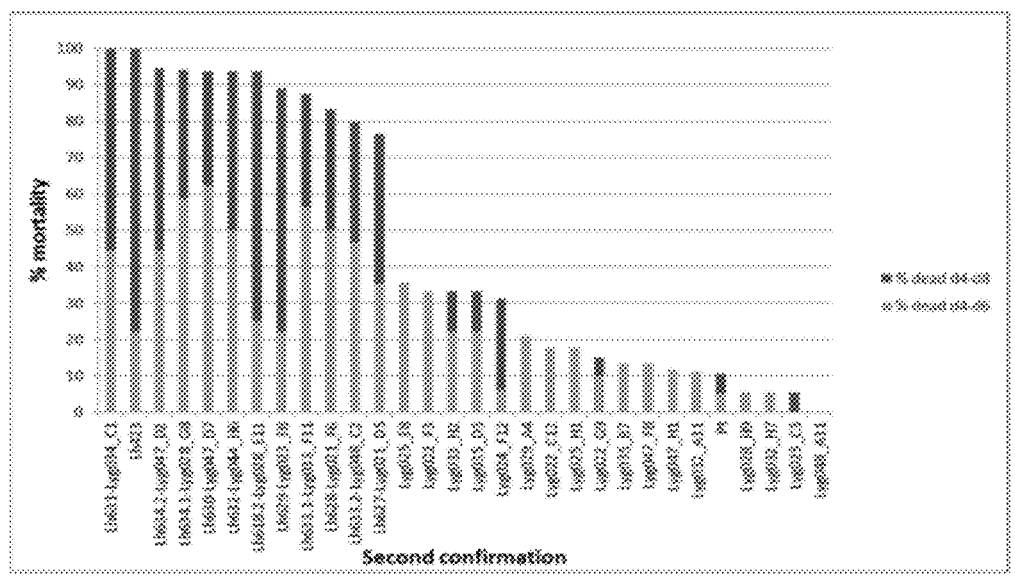

FIG. 14 Plates Lh010 to Lh020 second confirmation assay of second screen targets. Dark bars: mortality at day 4 to 8, light bars: mortality at day 4 to 6. Candidate clones are named using the "Lygxxx" screening codes and the "Lhxxx" target nomenclature codes.

Figure 15:
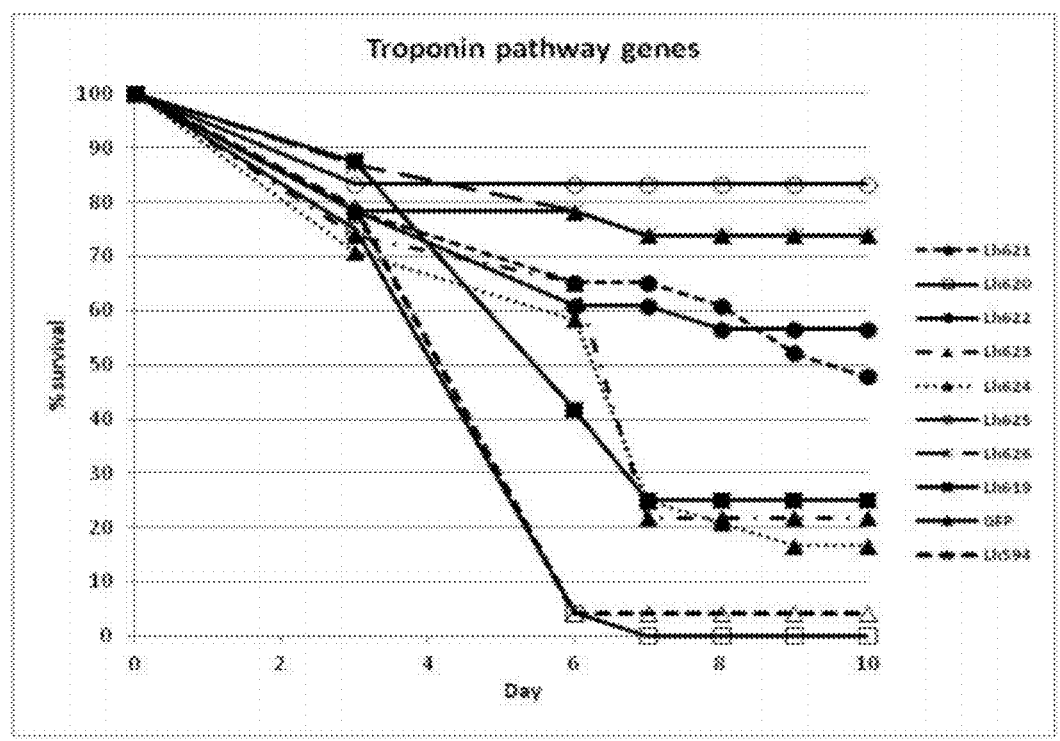

FIG. 15 Assay results for *Lygus* troponin pathway targets, tested at 0.5 µg/µl fixed.

Figure 16:
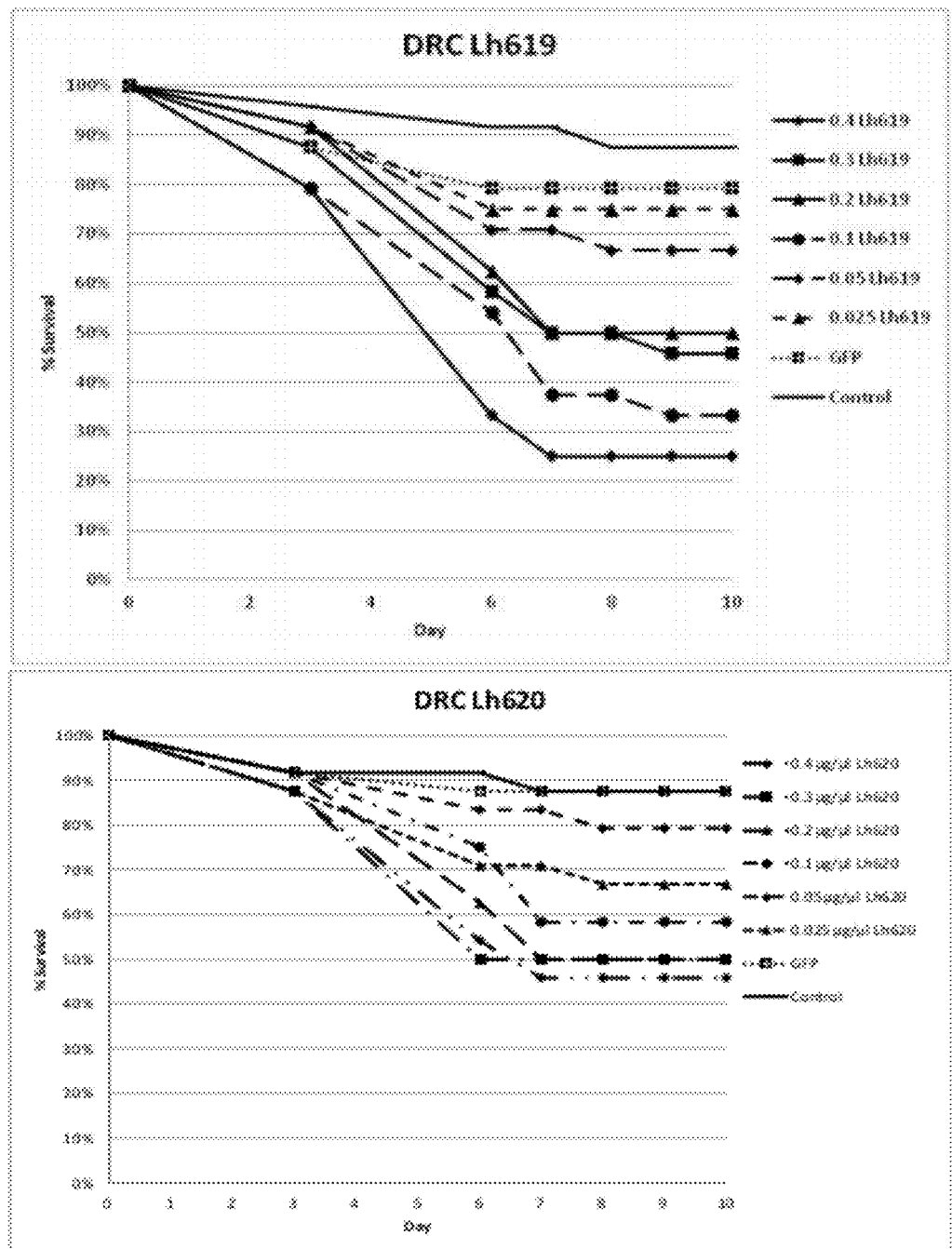
Figure 16:
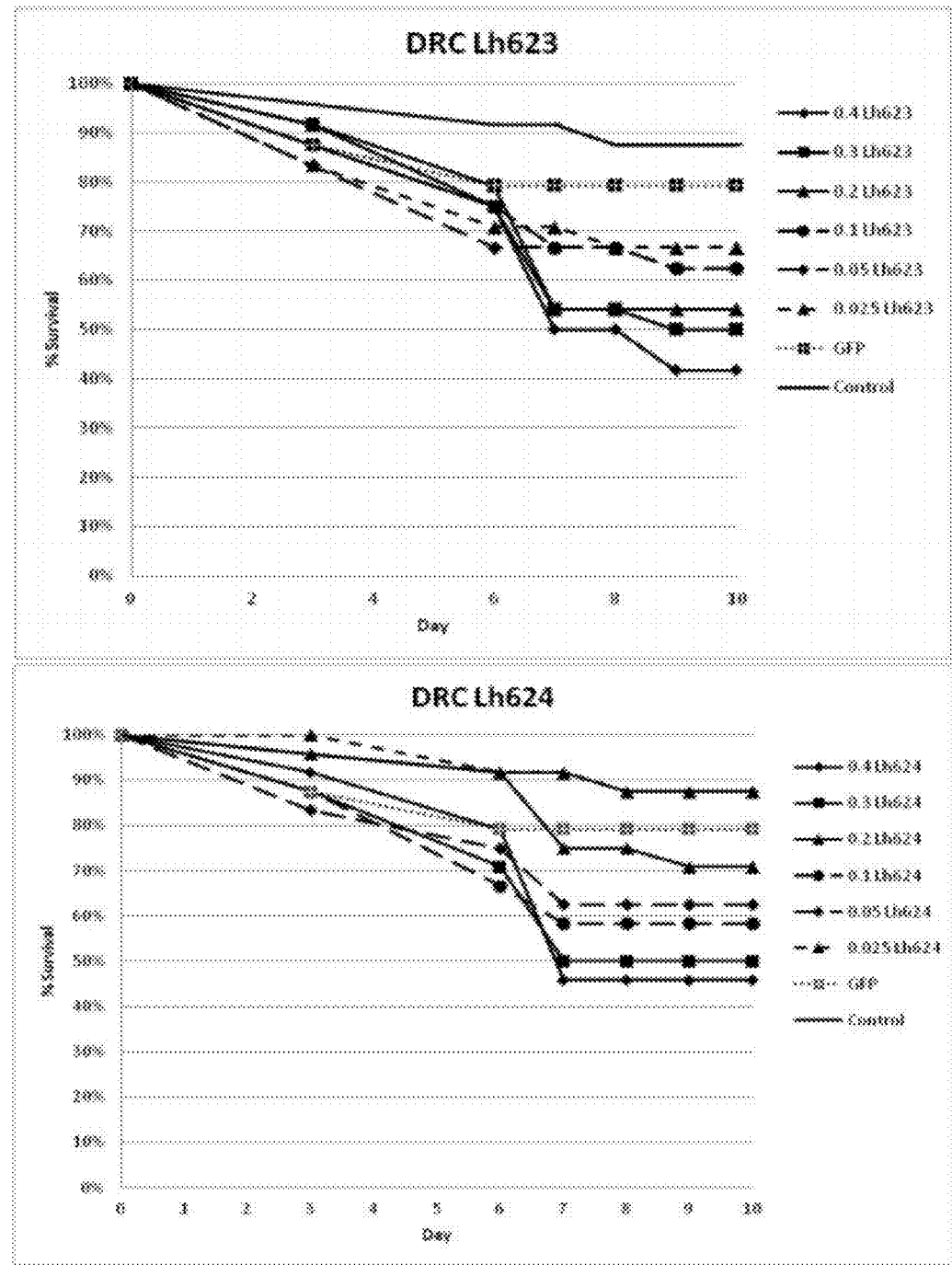

FIGS. 16 A-B *Lygus hesperus* novel targets from troponin pathway—dose response curves at concentrations of purified synthetic dsRNA ranging from 0.4 to 0.025 µg/µl (in the figure, the unit "µg/µl" is not always displayed). GFP dsRNA and milliQ water were used as negative controls.

Figure 17:
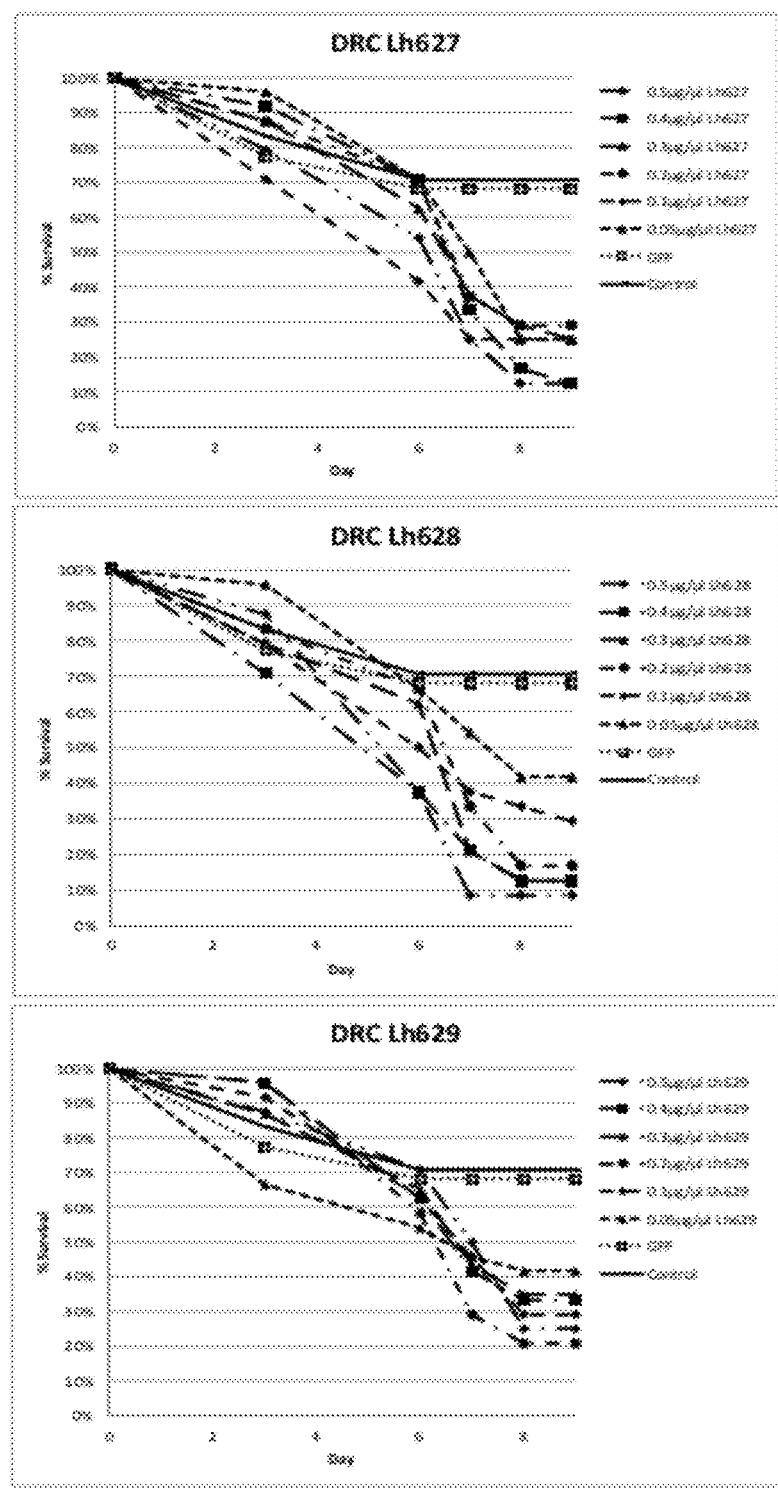
Figure 17:
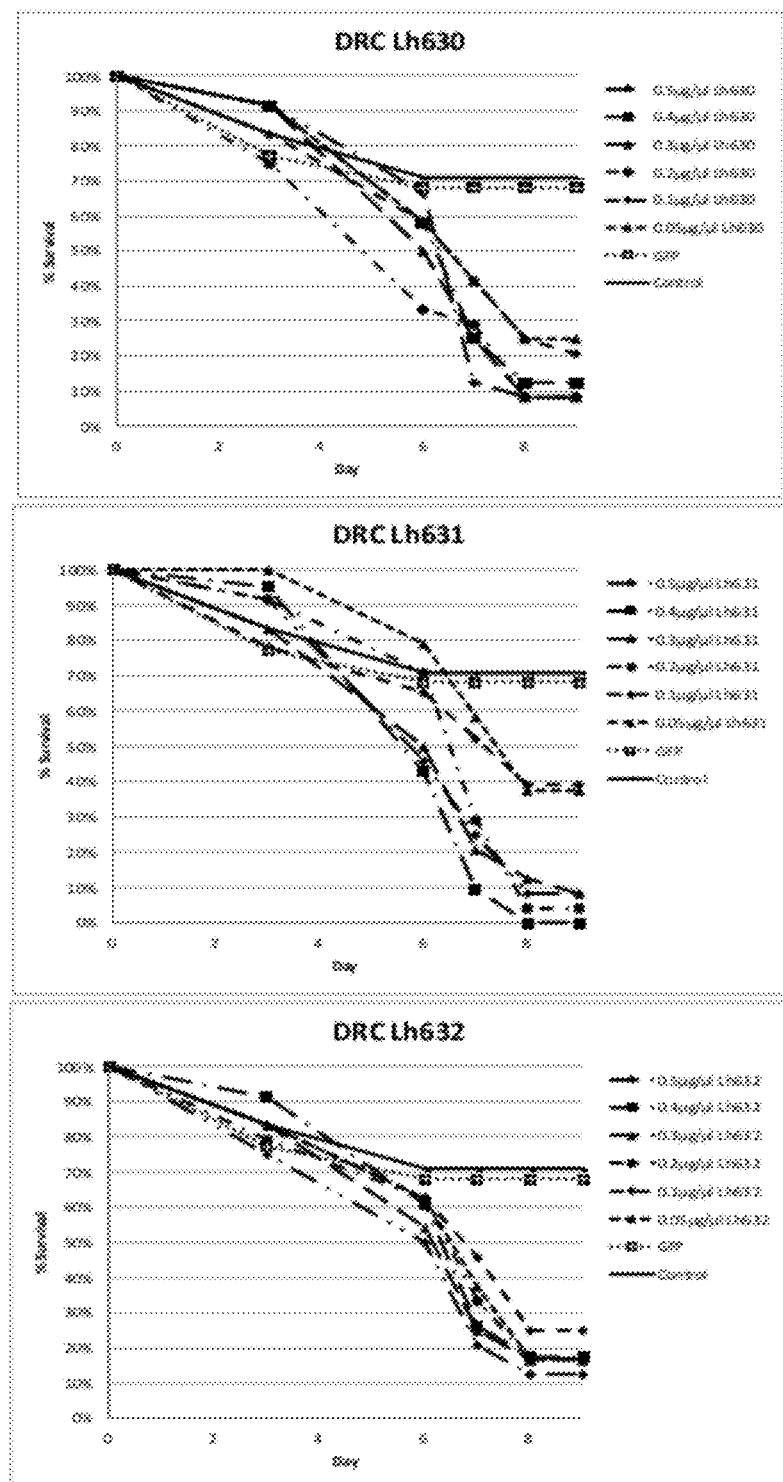
Figure 17:
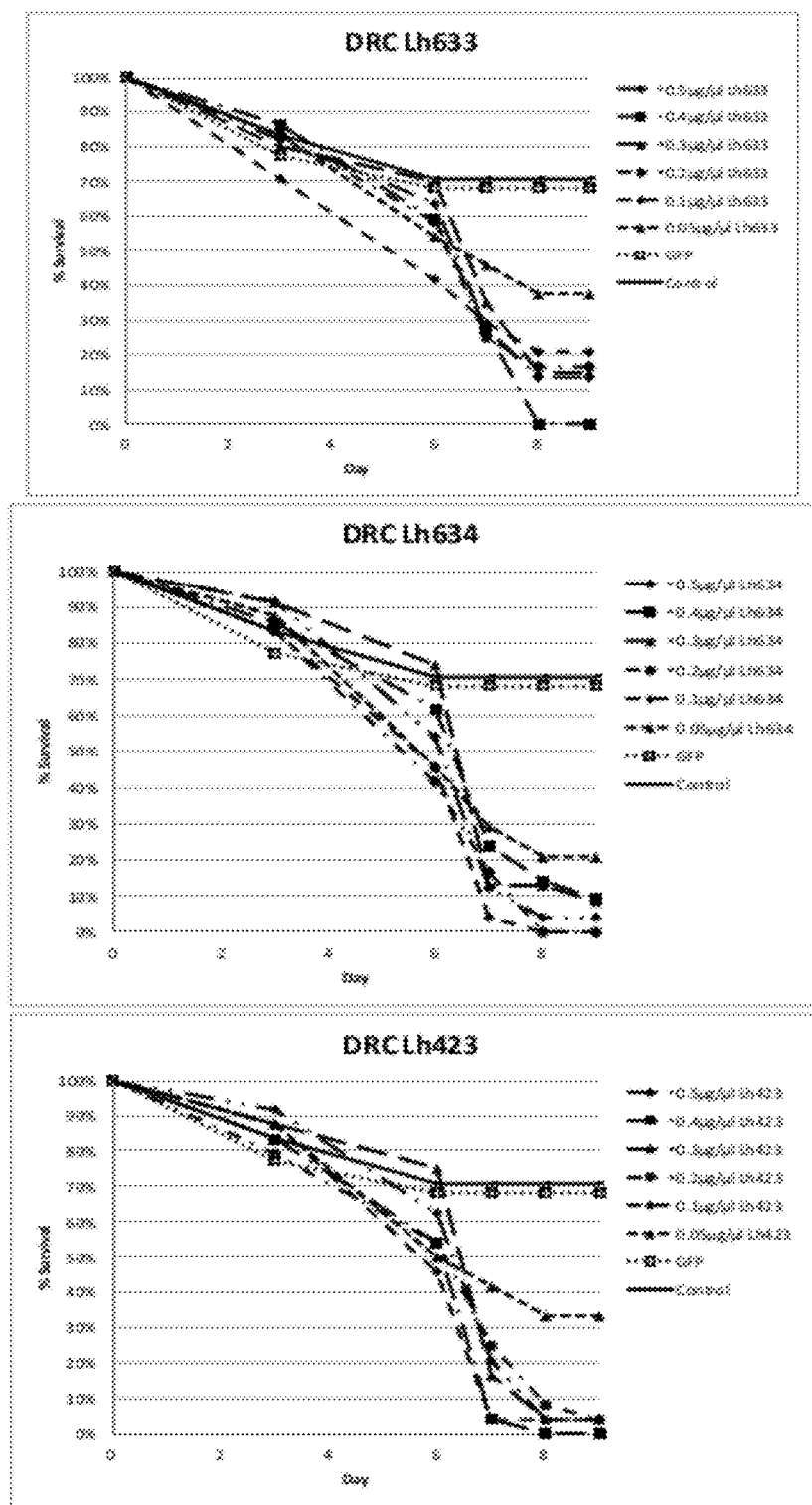
Figure 17:
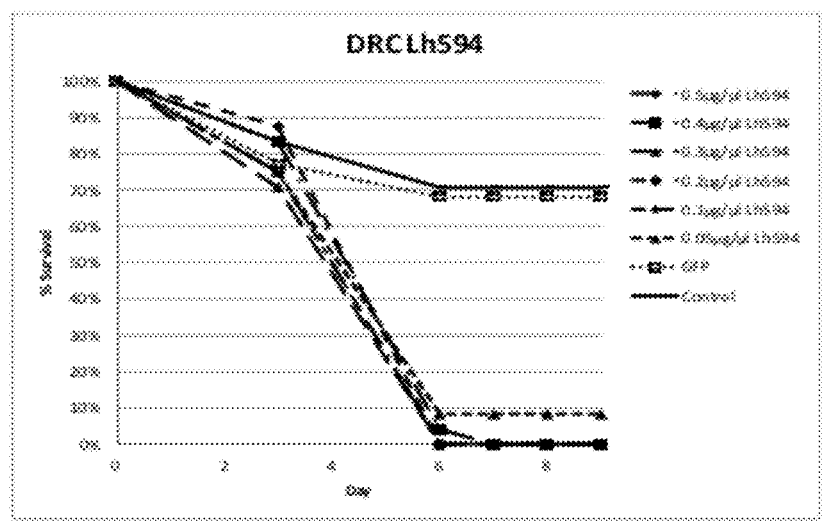

FIGS. 17 A-D *Lygus hesperus* novel targets of second screen targets—dose response curves at concentrations of purified synthetic dsRNA ranging from 0.5 to 0.05 µg/µl. GFP dsRNA and milliQ water were used as negative controls.

Figure 18:
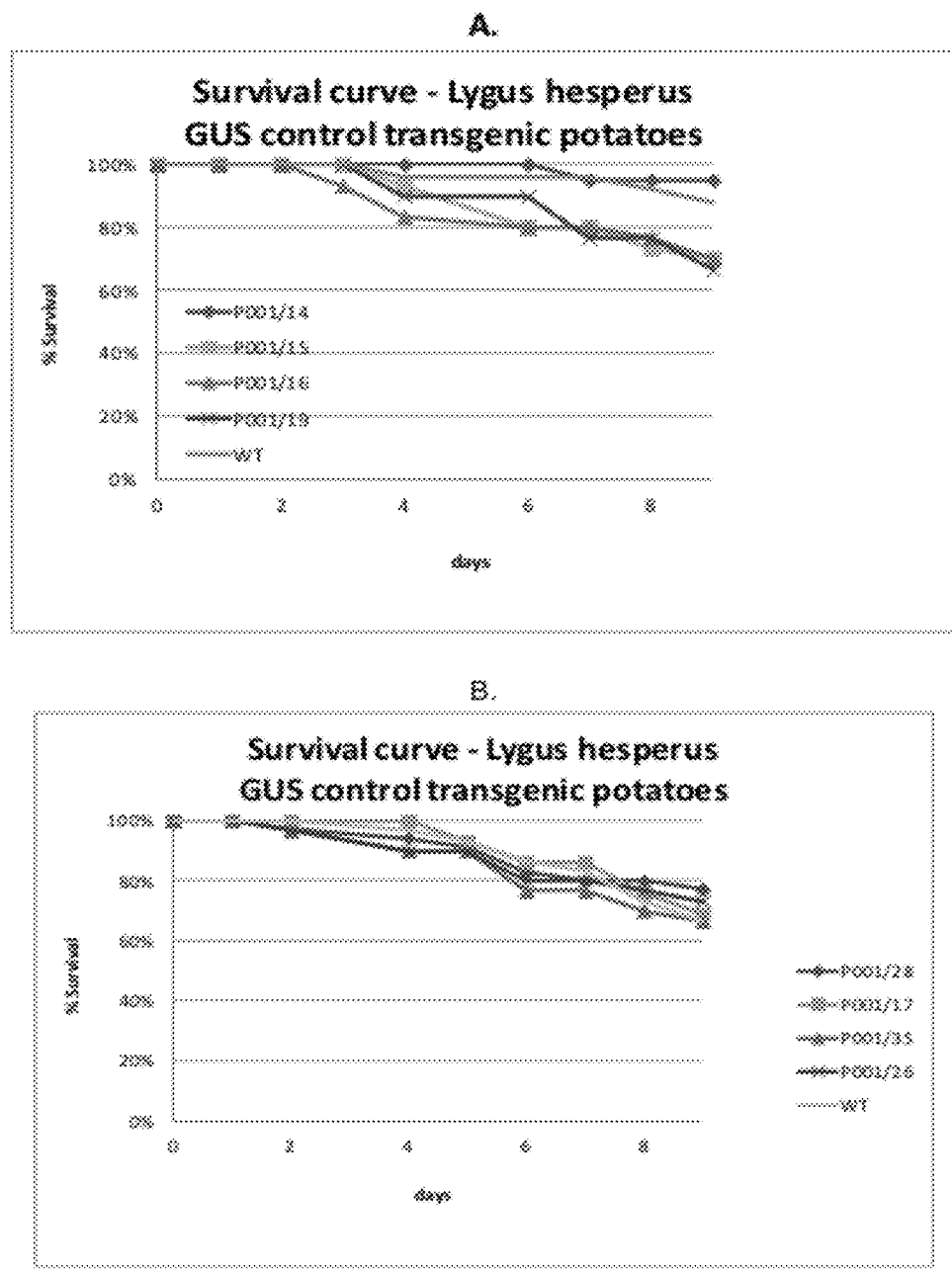

FIGS. 18 A-B Testing and selection of GUS transgenic events. Eight independent events of GUS hairpin transgenic line (P001) were tested in the *Lygus hesperus* single pot assay and compared to WT plantlets. All plantlets underwent the same treatment. One day old *Lygus hesperus* nymphs were added to each pot and the survival was checked over 9 days.

Figure 19:
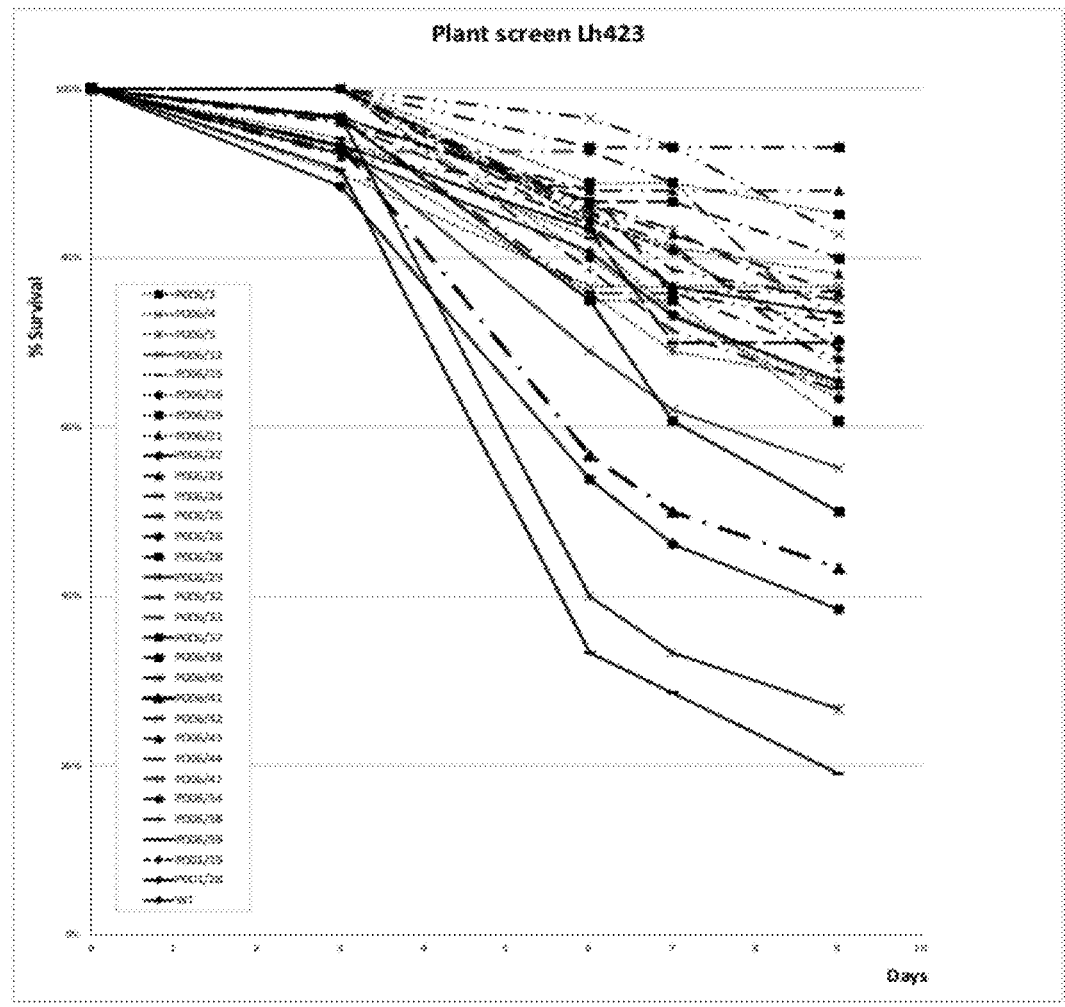

FIG. 19 Testing of Lh423 transgenic events: 28 independent transgenic events (P006 line) were tested in the *Lygus hesperus* single pot assay. Lh423 transgenic plantlets were compared to WT plantlets and to GUS transgenic events (P001 line). Single one day old *Lygus hesperus* nymphs were added to each pot and the survival was checked over 9 days.

Figure 20:
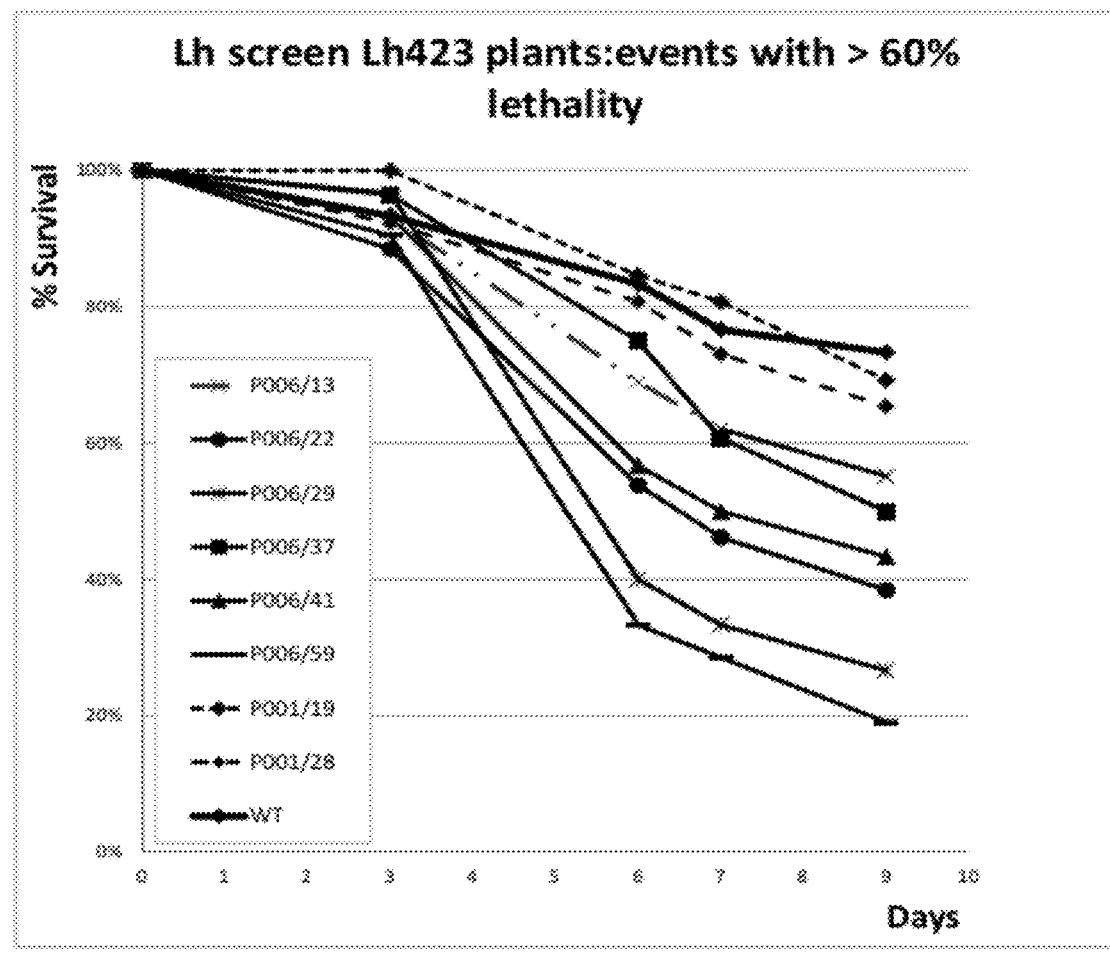

FIG. 20 Testing of Lh423 transgenic events: 6 independent transgenic events (P006) leading to >60% survival are shown. Lh423 transgenic plantlets were compared to WT plantlets and to GUS transgenic lines (P001). Single one day old *Lygus hesperus* nymphs were added to each pot and the survival was checked over 9 days.

Figure 21:
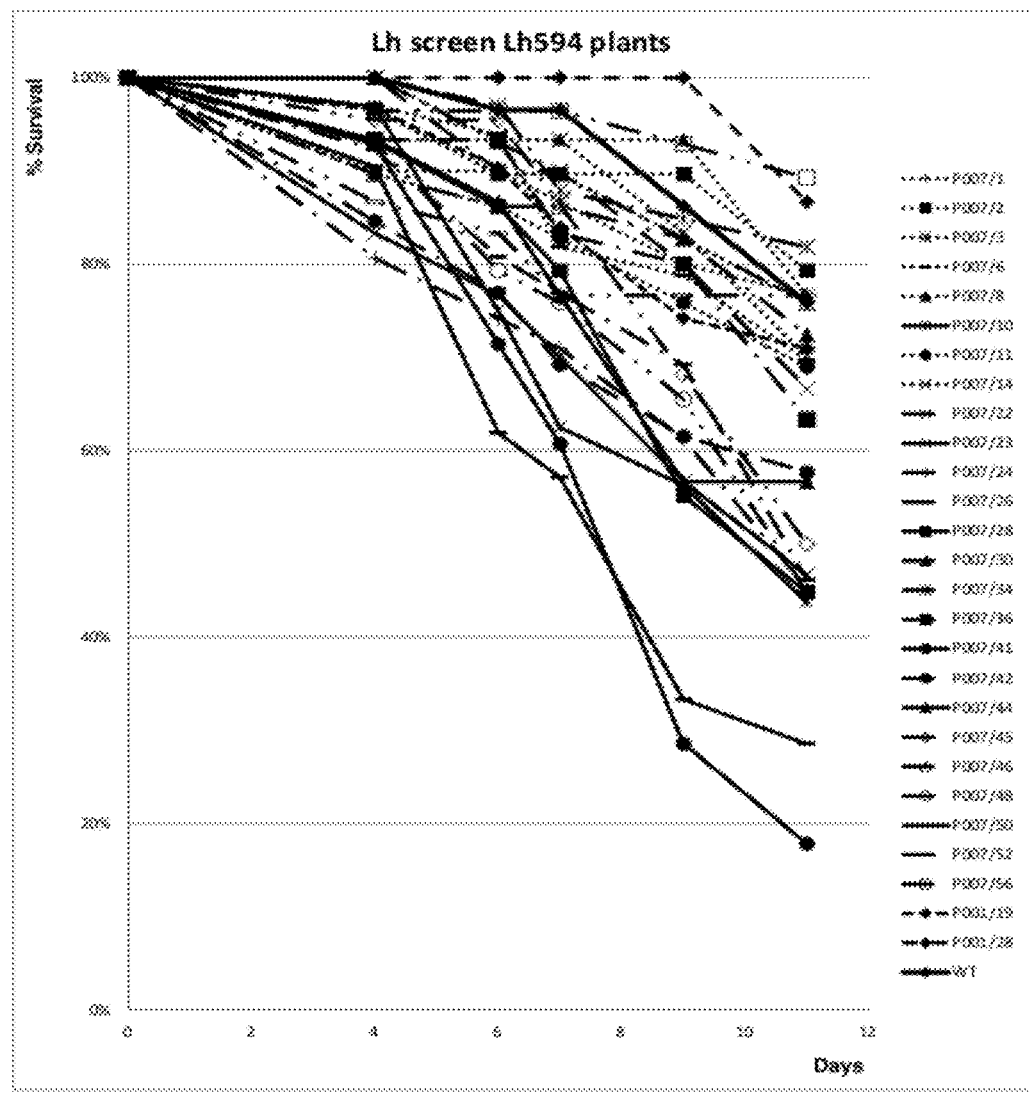

FIG. 21 Testing of Lh594 transgenic events: 25 independent transgenic events (P007) were tested in the *Lygus hesperus* single pot assay. Lh594 transgenic plantlets were compared to WT plantlets and to GUS transgenic events (P001). Single one day old *Lygus hesperus* nymphs were added to each pot and the survival was checked over 11 days.

Figure 22:
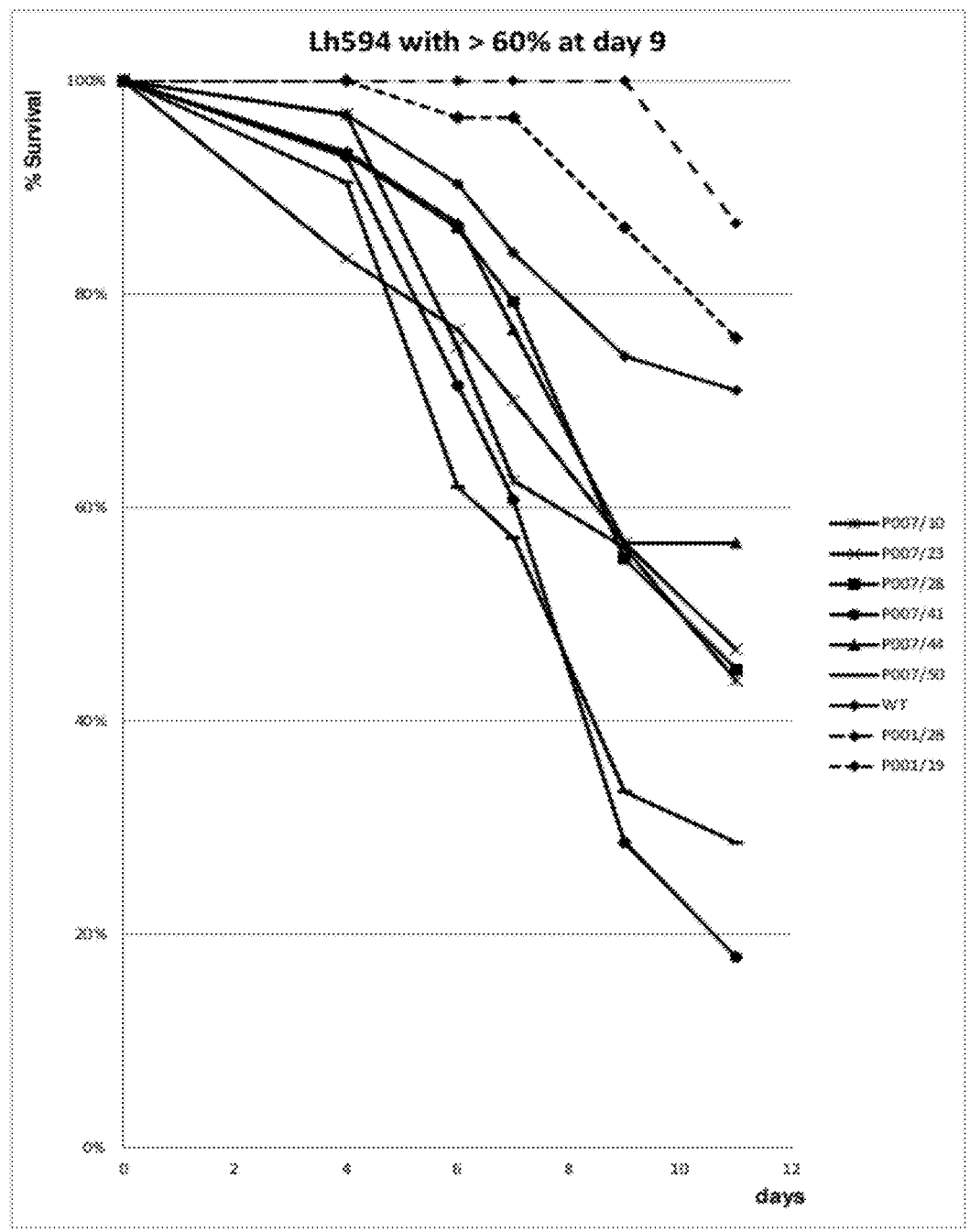

FIG. 22 Testing of Lh594 transgenic events: 6 independent transgenic events (P007) leading to 60% survival are shown. Lh594 transgenic plantlets were compared to WT plantlets and to GUS transgenic lines (P001). Single one day old *Lygus hesperus* nymphs were added to each pot and the survival was checked over 11 days.

Figure 23:
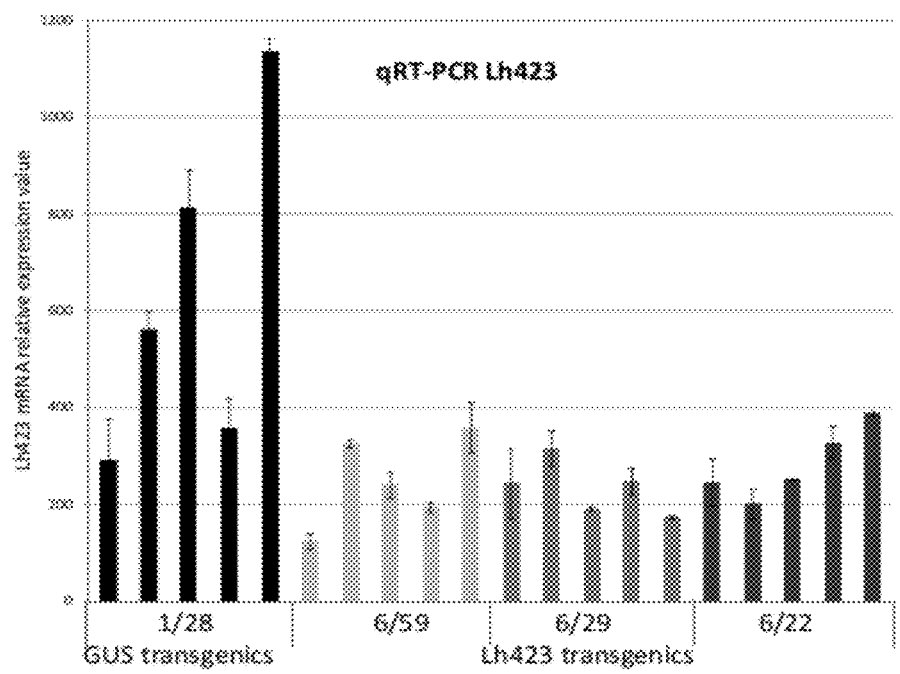

FIG. 23 Relative value of Lh423 mRNA levels in the insects after feeding for 5 days on transgenic plants containing a GUS hairpin or an Lh423 hairpin. Samples were analysed with primers amplifying Lh423. Data was normalized using GeNorm, with 2 house-keeping genes, Lh425 and Lh427.

Figure 24:
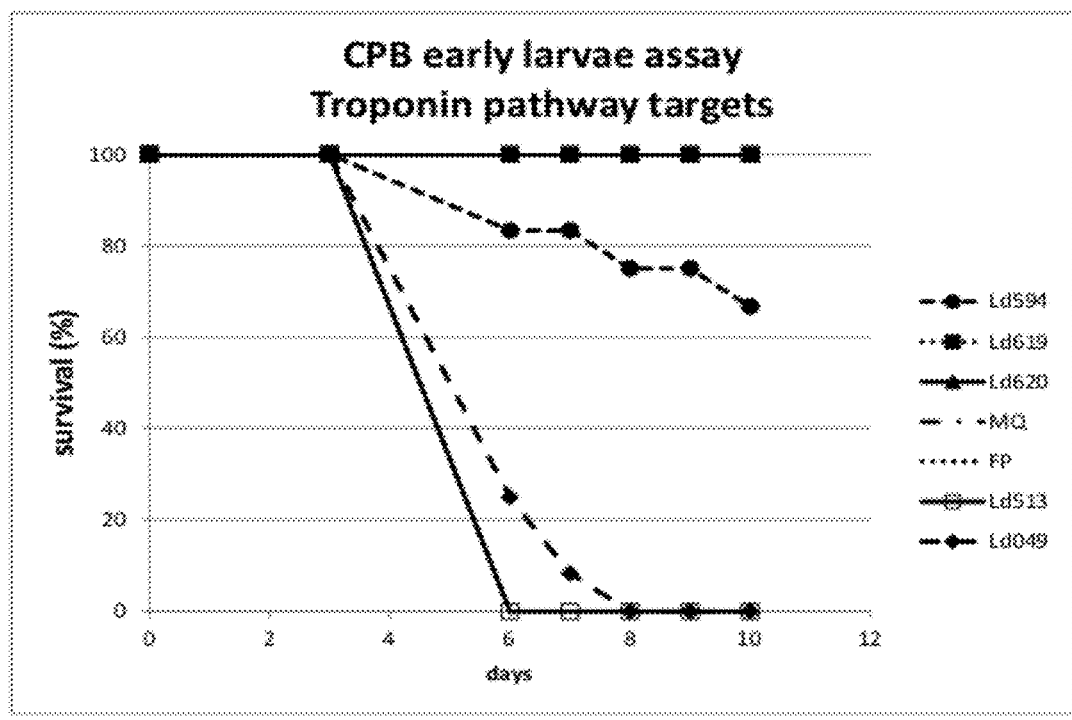

FIG. 24 Survival analysis of CPB larvae treated with 1 μg dsRNA Ld594, Ld619 and Ld620. Positive controls included 1 μg dsRNA of bench mark targets Ld513 and Ld049. Negative controls included milliQ water and FP.

Figure 25:
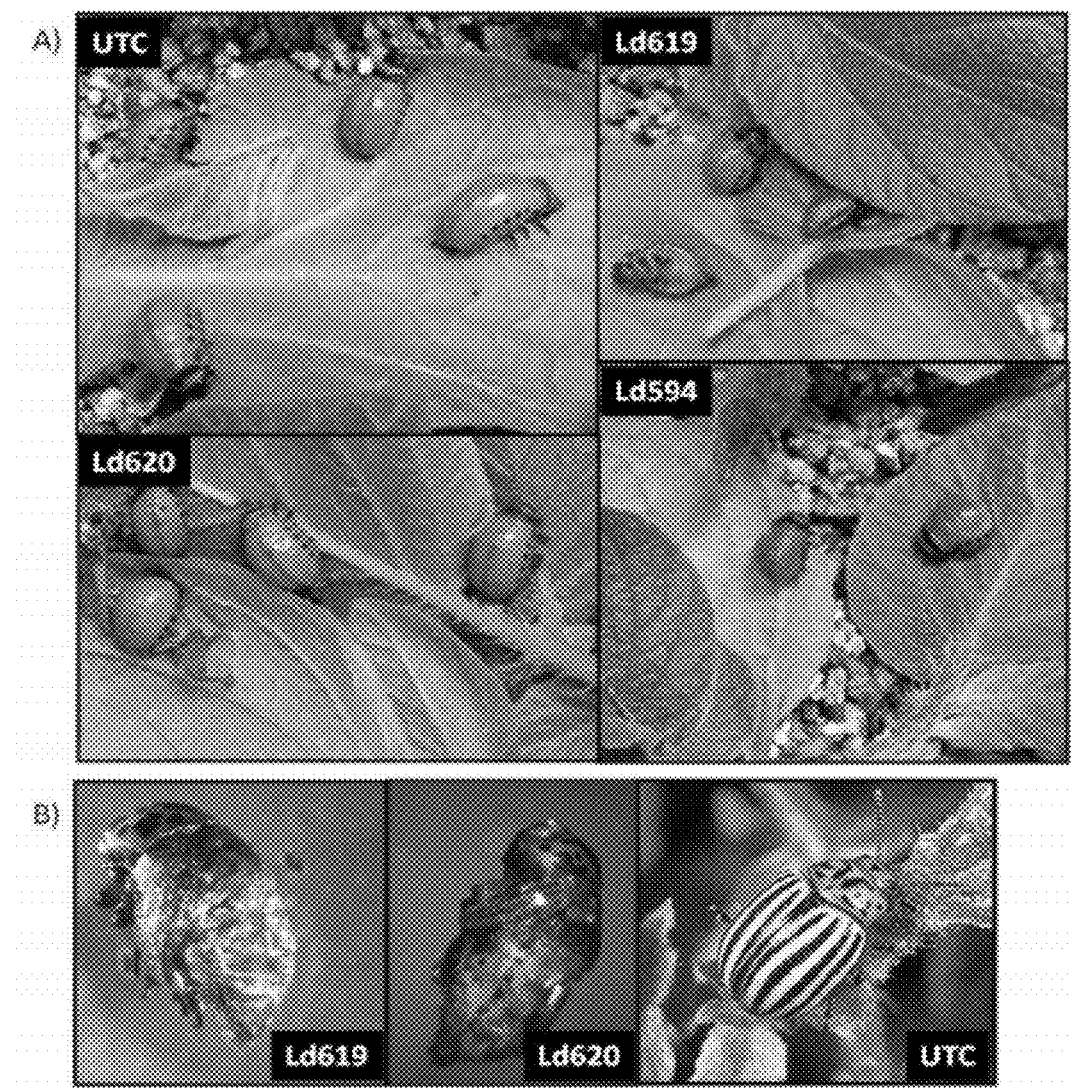

FIG. 25 Effects of Ld594, Ld619 and Ld620 dsRNAs on pupation of CPB 4$^{th}$ instar larvae, compared to untreated control (UTC). Bugs were fed 1 μg dsRNA dispensed in potato leaf disks, then were allowed to feed on untreated potato leaves (A) for 4 days before being placed on vermiculite. To assess the effect of the dsRNA, dead insects were excavated from the vermiculite (because of the strong effects induced by Ld594 dsRNA, no pupae could be recovered from the vermiculite and therefore, no image is available for this target dsRNA) (B).

Figure 26:
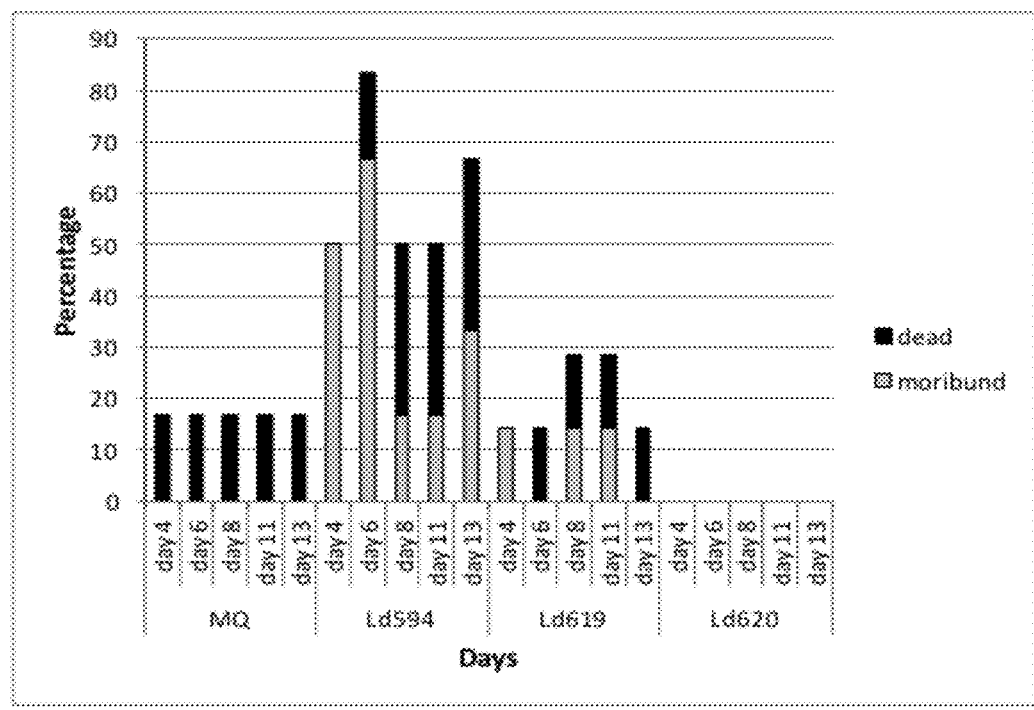

FIG. 26 Effect of CPB Ld594, 619 & 620 dsRNAs on survival and fitness of CPB adults. Assessments were performed on days 4, 6, 7, 8, 11 and 13. Control MQ: milliQ water.

Figure 27:
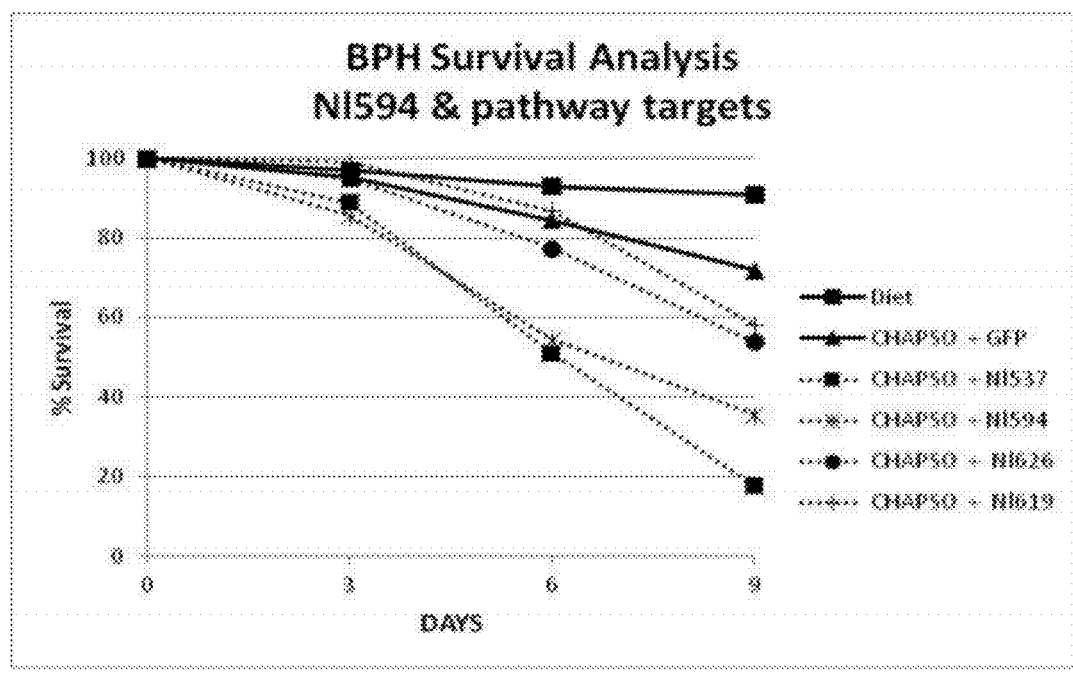

FIG. 27 Activity of dsRNA from Nl594 pathway in brown plant hopper. DsRNAs were tested at 0.5 μg/μl in presence of 0.1% CHAPSO. Positive control: Nl537 dsRNA (0.5 μg/μl), negative controls: GFP dsRNA (0.5 μg/μl) and diet alone.

Figure 28:
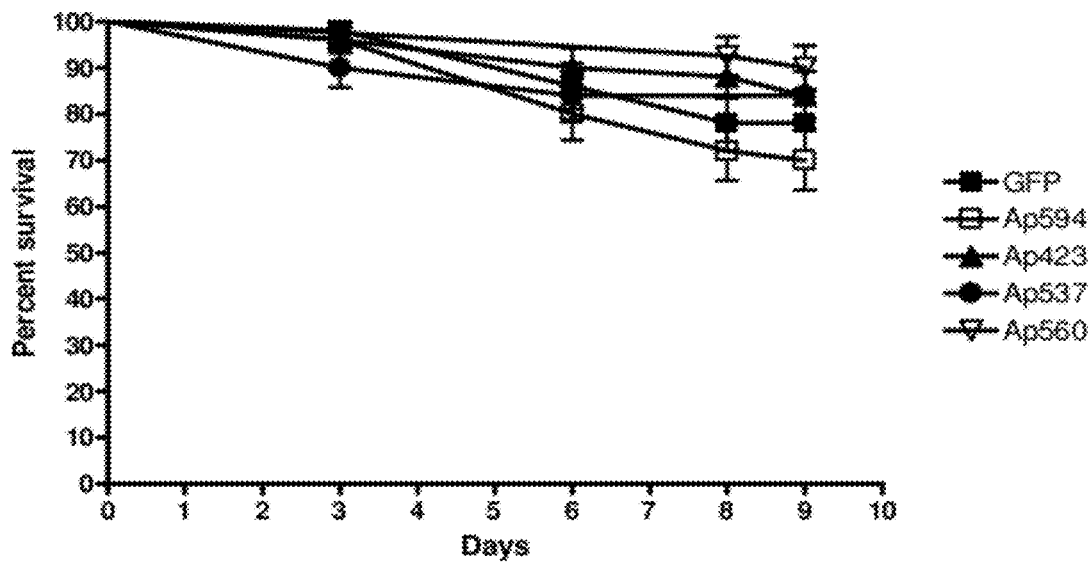

FIG. 28 Activity of dsRNA from Ap594, Ap423, Ap537 and Ap560 on *A. pisum*. DsRNAs were tested at 0.5 μg/μl in presence of 5 μg/μl tRNA. Negative control: GFP dsRNA (0.5 μg/μl).

Figure 29:
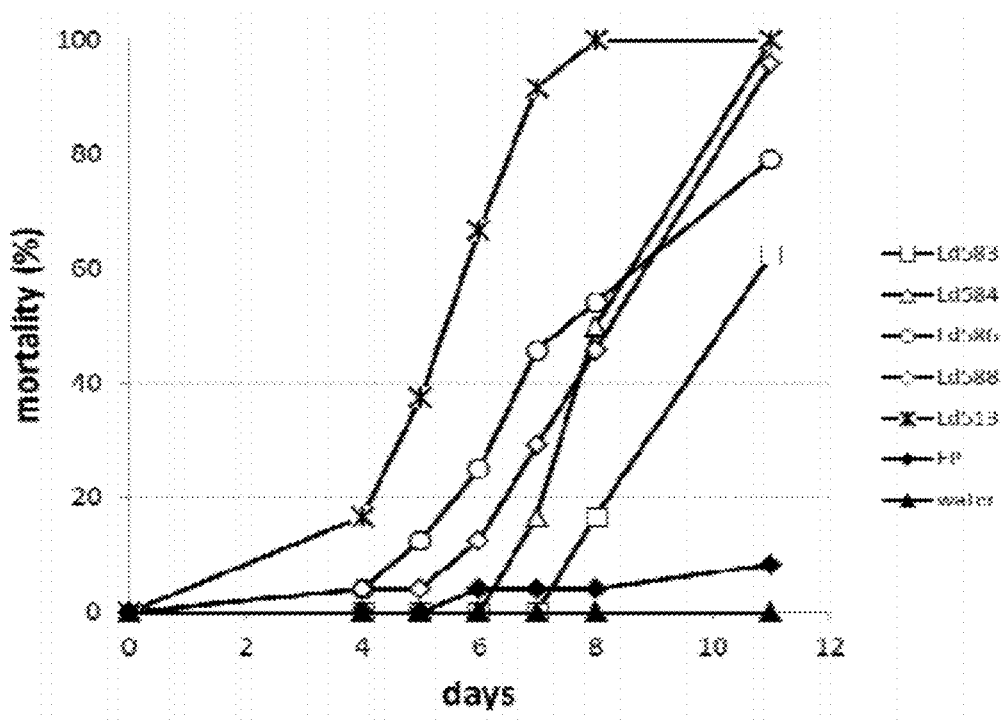

FIG. 29 Mortality percentages of *L. decemlineata* larvae on artificial diet treated with dsRNA. Ld583, Ld584, Ld586 & Ld588 represent target clones. Positive control: Ld513; negative control: FP.

DETAILED DESCRIPTION OF THE INVENTION

The present inventors have discovered that down-regulating the expression of particular target genes in insect pest species by RNAi can be used to effectively prevent and/or control infestation by said insect pest. The use of RNAi to down-regulate the expression of target genes in insect pest species is applied herein to the generation of plants resistant to infestation by insect pests.

Therefore, in a first aspect, the present invention provides transgenic plants resistant to infestation by insect pest species. In particular, provided herein are transgenic plants which express or are capable of expressing at least one interfering ribonucleic acid (RNA) that functions upon uptake by an insect pest species to down-regulate the expression of a target gene as described elsewhere herein within said pest. The interfering RNA may be any of those as disclosed herein below. Preferably, the interfering RNA comprises or consists of at least one silencing element and said silencing element is a region of double-stranded RNA comprising annealed complementary strands, one strand of which (the sense strand) comprises a sequence of nucleotides which is at least partially complementary to a target nucleotide sequence within a target gene. Down-regulation of a pest target gene can be used to disrupt an essential biological process or function in the pest, wherein 'essential' refers to the fact that the process or function is required for initiation or maintenance of pest infestation.

As used herein, the term 'plant' may include any reproductive or propagation material for a plant. Reference to a plant may also include plant cells, plant protoplasts, plant tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips and the like. Progeny, variants and mutants of any of the transgenic plants described herein are within the scope of the current invention. Also included is seed produced from any of said transgenic plants.

As used herein, the term "control" of pest infestation refers to any effect on a pest that serves to limit and/or reduce either the numbers of pest organisms and/or the damage caused by the pest.

Preferred target genes are therefore essential genes that control or regulate one or more essential biological functions within the insect pest, for example, cell division, reproduction, energy metabolism, digestion, neurological function and the like. Down-regulation of these essential genes by RNAi techniques can lead to death of the insect, or otherwise significantly retard growth and development or impair the ability of the pest to colonize an environment or infest host organisms.

The present inventors have now identified superior target genes of insect pest species belonging to the *Lygus, Leptinotarsa, Nilaparvata* and *Acyrthosiphum* genus, which targets are envisaged for use singly or in combination as an effective means for RNAi-mediated control of insect infestation of agronomically important crops. Orthologues of these newly identified target genes can be used in other insect species to control pest infestation of the corresponding relevant crops.

More specifically, the present inventors describe here that genes encoding for proteins of the troponin/myofilament complex form excellent target genes for suppression by the RNA inhibition machinery. One of these target genes encoded the insect troponin I protein (wings up A) which is an orthologue of the *Drosophila* CG7178 protein. This protein is involved in muscular contraction and belongs to a physiological pathway that was not yet fully explored for (insect) pest control through RNA inhibition. Moreover, since this protein complex is animal specific, no plant gene homologues or orthologues are known, reducing the risk of off-type plant phenotypes when expressing target dsRNA in plants. In addition, in *Drosophila*, troponin I is described as a haplo-insufficient gene, displaying a mutant phenotype in the heterozygote state. Such genes are particularly susceptible to reduced mRNA expression levels and as such can be considered as ideal RNAi targets.

Further interesting target genes in this troponin/myofilament complex are listed below and are being investigated further for RNAi control in *Lygus hesperus* and other insect pest species:

| Annotation ID | Cytology | Dm identifier |
| --- | --- | --- |
| up | upheld | CG7107 |
| Tm1 | tropomyosin 1 | CG4898 |
| Tm2 | tropomyosin 2 | CG4843 |
| Mhc | myosin heavy chain | CG17927 |
| Mlc-c | myosin light chain cytoplasmic | CG3201 |
| sqh | spaghetti squash | CG3595 |
| zip | zipper | CG15792 |

In one aspect, the invention provides a transgenic plant, reproductive or propagative material derived therefrom or a cultured plant cell which expresses or is capable of expressing an interfering ribonucleic acid (RNA) that functions upon uptake by an insect pest species to down-regulate expression of a target gene in said insect pest.

In one embodiment the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

In a preferred embodiment, the target gene encodes an insect protein chosen from the troponin/myofilament complex chosen from the group comprising the troponin I (e.g. an insect orthologue of the CG7178 Dm protein), the upheld protein (e.g. an insect orthologue of the CG7107 Dm protein), the tropomyosin 1 protein (e.g. an insect orthologue of the CG4898 Dm protein), the tropomyosin 2 protein (e.g. an insect orthologue of the CG4843 Dm protein), the myosin heavy chain (e.g. an insect orthologue of the CG17927 Dm protein), the myosin light chain cytoplasmic protein (e.g. an insect orthologue of the CG3201 Dm protein), the spaghetti squash protein (e.g. an insect orthologue of the CG3595 Dm protein), the zipper protein (e.g. an insect orthologue of the CG15792 Dm protein), the troponin C (e.g. an insect orthologue of the CG2981, CG7930, CG9073, CG6514, CG12408, CG9073, CG7930, CG2981, CG12408 or CG6514 Dm protein)

In other embodiments, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273 or the complement thereof, or having a nucleotide sequence so that, when the two sequences are optimally aligned and compared, is at least 75% preferably at least 80%, 85%, 90%, 95%, 98% or 99% identical to any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

In a preferred embodiment, the target gene encodes an insect ribosomal protein chosen from the group comprising the ribosomal protein S3A (e.g. an insect orthologue of the CG2168 Dm protein), the ribosomal protein LP1 (e.g. an insect orthologue of the CG4087 Dm protein), the ribosomal protein S3 (e.g. an insect orthologue of the CG6779 Dm protein), the ribosomal protein L10Ab (e.g. an insect orthologue of the CG7283 Dm protein), the ribosomal protein S18 (e.g. an insect orthologue of the CG8900 Dm protein), the ribosomal protein L4 (e.g. an insect orthologue of the CG5502 Dm protein), the ribosomal protein S27 (e.g. an insect orthologue of the CG10423 Dm protein), the ribosomal protein L6 (e.g. an insect orthologue of the CG11522 Dm protein), the ribosomal protein S13 (e.g. an insect orthologue of the CG13389 Dm protein), and the ribosomal protein L12 (e.g. an insect orthologue of the CG3195 Dm protein), the ribosomal protein L26 (e.g. an insect orthologue of the CG6846 Dm protein), the ribosomal protein L21 (e.g. an insect orthologue of the CG12775 Dm protein), the ribosomal protein S12 (e.g. an insect orthologue of the CG11271 Dm protein), the ribosomal protein S28b (e.g. an insect orthologue of the CG2998 Dm protein), the ribosomal protein L13 (e.g. an insect orthologue of the CG4651 Dm protein), the ribosomal protein L10 (e.g. an insect orthologue of the CG17521 Dm protein), the ribosomal protein L5 (e.g. an insect orthologue of the CG17489 Dm protein), the ribosomal protein S15Aa (e.g. an insect orthologue of the CG2033 Dm protein), the ribosomal protein L19 (e.g. an insect orthologue of the CG2746 Dm protein), the ribosomal protein L27 (e.g. an insect orthologue of the CG4759 Dm protein)

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401.

In preferred embodiments, the target gene may encode an insect the troponin I protein (e.g. an insect orthologue of the CG7178 Dm protein). The insect troponin I protein may have an amino acid sequence which is at least 85%, 90%, 92%, 94%, 96%, 98%, 99% identical to the amino acid sequence as presented in any of SEQ ID NOs 79, 349, 405, 352 or 356 (when said encoded proteins are optimally aligned).

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 141, 11, 12, or the complement thereof, or having a nucleotide sequence so that, when the two sequences are optimally aligned and compared, is at least 75% preferably at least 80%, 85%, 90%, 95%, 98% or 99% identical to any of SEQ ID NOs 141, 11, 12, or the complement thereof, or (ii) is selected from the group of genes having a nucleotide sequence comprising a fragment of at least 21 contiguous nucleotides of any of SEQ ID NOs 141, 11, 12, or the complement thereof, or having a nucleotide sequence so that, when said gene comprising said fragment is optimally aligned and compared with any of SEQ ID NOs 141, 11, 12, said nucleotide sequence is at least 75% preferably at least 80%, 85%, 90%, 95%, 98% or 99% identical to any of SEQ ID NOs 141, 11, 12, or the complement thereof, or (iii) is selected from the group of genes having a nucleotide sequence comprising a fragment of at least 21 contiguous nucleotides of any of SEQ ID NOs 141, 11, 12, or the complement thereof, and wherein when said fragment is optimally aligned and compared with the corresponding fragment in any of SEQ ID NOs 141, 11, 12, said nucleotide sequence of said fragment is at least 75% preferably at least 80%, 85%, 90%, 95%, 98% or 99% identical to said corresponding fragment of any of SEQ ID NOs 141, 11, 12, or the complement thereof, or (iv) is an insect pest orthologue of a gene having a nucleotide sequence comprising any of SEQ ID NOs 141, 11, 12, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 141, 11, 12, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 141, 11, 12.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 17, 18, or the complement thereof, or having a nucleotide sequence so that, when the two sequences are optimally aligned and compared, is at least 75% preferably at least 80%, 85%, 90%, 95%, 98% or 99% identical to any of SEQ ID NOs 17, 18, or the complement thereof, or (ii) is selected from the group of genes having a nucleotide sequence comprising a fragment of at least 21 contiguous nucleotides of any of SEQ ID NOs 17, 18, or the complement thereof, or having a nucleotide sequence so that, when said gene comprising said fragment is optimally aligned and compared with any of SEQ ID NOs 17, 18, said nucleotide sequence is at least 75% preferably at least 80%, 85%, 90%, 95%, 98% or 99% identical to any of SEQ ID NOs 17, 18, or the complement thereof, or (iii) is selected from the group of genes having a nucleotide sequence comprising a fragment of at least 21 contiguous nucleotides of any of SEQ ID NOs 17, 18, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 17, 18, or the complement thereof, or (iv) is an insect pest orthologue of a gene having a nucleotide sequence comprising any of SEQ ID NOs 17, 18, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 17, 18, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 17, 18.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 19, 20, or the complement thereof, or having a nucleotide sequence so that, when the two sequences are optimally aligned and compared, is at least 75% preferably at least 80%, 85%, 90%, 95%, 98% or 99% identical to any of SEQ ID NOs 19, 20, or the complement thereof, or (ii) is selected from the group of genes having a nucleotide sequence comprising a fragment of at least 21 contiguous nucleotides of any of SEQ ID NOs 19, 20, or the complement thereof, or having a nucleotide sequence so that, when said gene comprising said fragment is optimally aligned and compared with any of SEQ ID NOs 19, 20, said nucleotide sequence is at least 75% preferably at least 80%, 85%, 90%, 95%, 98% or 99% identical to any of SEQ ID NOs 19, 20, or the complement thereof, or (iii) is selected from the group of genes having a nucleotide sequence comprising a fragment of at least 21 contiguous nucleotides of any of SEQ ID NOs 19, 20, or the complement thereof, and wherein when said fragment is optimally aligned and compared with the corresponding fragment in any of SEQ ID NOs 19, 20, said nucleotide sequence of said fragment is at least 75% preferably at least 80%, 85%, 90%, 95%, 98% or 99% identical to said corresponding fragment of any of SEQ ID NOs 19, 20, or the complement thereof, or (iv) is an insect pest orthologue of a gene having a nucleotide sequence comprising any of SEQ ID NOs 19, 20, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 19, 20, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 19, 20.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene
(i) is selected from the group of genes having a nucleotide sequence comprising any of SEQ ID NOs 165, 166, 167, or the complement thereof, or having a nucleotide sequence so that, when the two sequences are optimally aligned and compared, is at least 75% preferably at least 80%, 85%, 90%, 95%, 98% or 99% identical to any of SEQ ID NOs 165, 166, 167, or the complement thereof, or
(ii) is selected from the group of genes having a nucleotide sequence comprising a fragment of at least 21 contiguous nucleotides of any of SEQ ID NOs 165, 166, 167, or the complement thereof, or having a nucleotide sequence so that, when said gene comprising said fragment is optimally aligned and compared with any of SEQ ID NOs 165, 166, 167, said nucleotide sequence is at least 75% preferably at least 80%, 85%, 90%, 95%, 98% or 99% identical to any of SEQ ID NOs 165, 166, 167, or the complement thereof, or
(iii) is selected from the group of genes having a nucleotide sequence comprising a fragment of at least 21 contiguous nucleotides of any of SEQ ID NOs 165, 166, 167, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 165, 166, 167, or the complement thereof, or
(iv) is an insect pest orthologue of a gene having a nucleotide sequence comprising any of SEQ ID NOs 165, 166, 167, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 165, 166, 167, or
(v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 165, 166, 167.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene
(i) is selected from the group of genes having a nucleotide sequence comprising any of SEQ ID NOs 143, 121, 142, 176, 182, 130, 177, 183, or the complement thereof, or having a nucleotide sequence so that, when the two sequences are optimally aligned and compared, is at least 75% preferably at least 80%, 85%, 90%, 95%, 98% or 99% identical to any of SEQ ID NOs 143, 121, 142, 176, 182, 130, 177, 183, or the complement thereof, or
(ii) is selected from the group of genes having a nucleotide sequence comprising a fragment of at least 21 contiguous nucleotides of any of SEQ ID NOs 143, 121, 142, 176, 182, 130, 177, 183, or the complement thereof, or having a nucleotide sequence so that, when said gene comprising said fragment is optimally aligned and compared with any of SEQ ID NOs 143, 121, 142, 176, 182, 130, 177, 183, said nucleotide sequence is at least 75% preferably at least 80%, 85%, 90%, 95%, 98% or 99% identical to any of SEQ ID NOs 143, 121, 142, 176, 182, 130, 177, 183, or the complement thereof, or
(iii) is selected from the group of genes having a nucleotide sequence comprising a fragment of at least 21 contiguous nucleotides of any of SEQ ID NOs 143, 121, 142, 176, 182, 130, 177, 183, or the complement thereof, and wherein when said fragment is optimally aligned and compared with the corresponding fragment in any of SEQ ID NOs 143, 121, 142, 176, 182, 130, 177, 183, said nucleotide sequence of said fragment is at least 75% preferably at least 80%, 85%, 90%, 95%, 98% or 99% identical to said corresponding fragment of any of SEQ ID NOs 143, 121, 142, 176, 182, 130, 177, 183, or the complement thereof, or
(iv) is an insect pest orthologue of a gene having a nucleotide sequence comprising any of SEQ ID NOs 143, 121, 142, 176, 182, 130, 177, 183, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 143, 121, 142, 176, 182, 130, 177, 183, or
(v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 143, 121, 142, 176, 182, 130, 177, 183.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene
(i) is selected from the group of genes having a nucleotide sequence comprising any of SEQ ID NOs 145, 122, 144, 178, 131, 179 or the complement thereof, or having a nucleotide sequence so that, when the two sequences are optimally aligned and compared, is at least 75% preferably at least 80%, 85%, 90%, 95%, 98% or 99% identical to any of SEQ ID NOs 145, 122, 144, 178, 131, 179, or the complement thereof, or (ii) is selected from the group of genes having a nucleotide sequence comprising a fragment of at least 21 contiguous nucleotides of any of SEQ ID NOs 145, 122, 144, 178, 131, 179, or the complement thereof, or having a nucleotide sequence so that, when said gene comprising said fragment is optimally aligned and compared with any of SEQ ID NOs 145, 122, 144, 178, 131, 179, said nucleotide sequence is at least 75% preferably at least 80%, 85%, 90%, 95%, 98% or 99% identical to any of SEQ ID NOs 145, 122, 144, 178, 131, 179, or the complement thereof, or (iii) is selected from the group of genes having a nucleotide sequence comprising a fragment of at least 21 contiguous nucleotides of any of SEQ ID NOs 145, 122, 144, 178, 131, 179, or the complement thereof, and wherein when said fragment is optimally aligned and compared with the corresponding fragment in any of SEQ ID NOs 145, 122, 144, 178, 131, 179, said nucleotide sequence of said fragment is at least 75% preferably at least 80%, 85%, 90%, 95%, 98% or 99% identical to said corresponding fragment of any of SEQ ID NOs 145, 122, 144, 178, 131, 179, or the complement thereof, or (iv) is an insect pest orthologue of a gene having a nucleotide sequence comprising any of SEQ ID NOs 145, 122, 144, 178, 131, 179, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 145, 122, 144, 178, 131, 179, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 145, 122, 144, 178, 131, 179.

In one embodiment, the present invention relates to a plant or reproductive or propagation material for a transgenic plant or a cultured transgenic plant cell which expresses or is capable of expressing an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 128, 149, 184, 137, or the complement thereof, or having a nucleotide sequence so that, when the two sequences are optimally aligned and compared, is at least 75% preferably at least 80%, 85%, 90%, 95%, 98% or 99% identical to any of SEQ ID NOs 128, 149, 184, 137, or the complement thereof, or (ii) is selected from the group of genes having a nucleotide sequence comprising a fragment of at least 21 contiguous nucleotides of any of SEQ ID NOs 128, 149, 184, 137, or the complement thereof, or having a nucleotide sequence so that, when said gene comprising said fragment is optimally aligned and compared with any of SEQ ID NOs 128, 149, 184, 137, said nucleotide sequence is at least 75% preferably at least 80%, 85%, 90%, 95%, 98% or 99% identical to any of SEQ ID NOs 128, 149, 184, 137, or the complement thereof, or (iii) is selected from the group of genes having a nucleotide sequence comprising a fragment of at least 21 contiguous nucleotides of any of SEQ ID NOs 128, 149, 184, 137, or the complement thereof, and wherein when said fragment is optimally aligned and compared with the corresponding fragment in any of SEQ ID NOs 128, 149, 184, 137, said nucleotide sequence of said fragment is at least 75% preferably at least 80%, 85%, 90%, 95%, 98% or 99% identical to said corresponding fragment of any of SEQ ID NOs 128, 149, 184, 137, or the complement thereof, or (iv) is an insect pest orthologue of a gene having a nucleotide sequence comprising any of SEQ ID NOs 128, 149, 184, 137, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 128, 149, 184, 137, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 128, 149, 184, 137.

As used herein, a "target gene" comprises any gene in the insect pest which one intends to down-regulate. In a preferred embodiment, the target gene is down-regulated so as to control pest infestation, for example by disrupting an essential biological process occurring in the pest, or by decreasing the pathogenicity of the pest. Preferred target genes therefore include but are not limited to those that play key roles in regulating feeding, survival, growth, development, reproduction, infestation and infectivity. According to one embodiment, the target gene is such that when its expression is down-regulated or inhibited, the insect pest is killed. According to another embodiment, the target gene is such that when its expression is down-regulated or inhibited, growth of the pest is prevented or retarded or stunted or delayed or impeded, pest reproduction is prevented, or transition through the life cycles of the pest is prevented. According to yet another embodiment of the invention, the target gene is such that when its expression is down-regulated or inhibited, the damage caused by the pest and/or the ability of the pest to infect or infest environments, surfaces and/or plant or crop species is reduced; or the pest stops feeding from its natural food resources such as plants and plant products. The terms "infest" and "infect" or "infestation" and "infection" are generally used interchangeably throughout.

The target genes may be expressed in all or some of the cells of the insect pest. Furthermore, the target genes may only be expressed by the insect pest at a particular stage of its life-cycle, for example, the mature adult phase, immature nymph or larval phase or egg phase. As used herein "pest" species are preferably insect species that cause infection or infestation, preferably of plants.

Preferred plant pathogenic insects according to the invention are plant pest are selected from the group consisting of *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or

*N. cincticeps* (green leafhopper), or *N. nigropictus* (rice leafhopper)); *Sogatella* spp. (e.g. *S. furcifera* (white-backed planthopper)); *Chilo* spp. (e.g. *C. suppressalis* (rice striped stem borer), *C. auricilius* (gold-fringed stem borer), or *C. polychrysus* (dark-headed stem borer)); *Sesamia* spp. (e.g. *S. inferens* (pink rice borer)); *Tryporyza* spp. (e.g. *T. innotata* (white rice borer), or *T. incertulas* (yellow rice borer)); *Anthonomus* spp. (e.g. *A. grandis* (boll weevil)); *Phaedon* spp. (e.g. *P. cochleariae* (mustard leaf beetle)); *Epilachna* spp. (e.g. *E. varivetis* (mexican bean beetle)); *Tribolium* spp. (e.g. *T. castaneum* (red floor beetle)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *Ostrinia* spp. (e.g. *O. nubilalis* (European corn borer)); *Anaphothrips* spp. (e.g. *A. obscrurus* (grass thrips)); *Pectinophora* spp. (e.g. *P. gossypiella* (pink bollworm)); *Heliothis* spp. (e.g. *H. virescens* (tobacco budworm)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (conspersa stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion thrips)); *Frankliniella* spp. (e.g. *F. fusca* (tobacco thrips), or *F. occidentalis* (western flower thrips)); *Acheta* spp. (e.g. *A. domesticus* (house cricket)); *Myzus* spp. (e.g. *M. persicae* (green peach aphid)); *Macrosiphum* spp. (e.g. *M. euphorbiae* (potato aphid)); *Blissus* spp. (e.g. *B. leucopterus leucopterus* (chinch bug)); *Acrosternum* spp. (e.g. *A. hilare* (green stink bug)); *Chilotraea* spp. (e.g. *C. polychrysa* (rice stalk borer)); *Lissorhoptrus* spp. (e.g. *L. oryzophilus* (rice water weevil)); *Rhopalosiphum* spp. (e.g. *R. maidis* (corn leaf aphid)); and *Anuraphis* spp. (e.g. *A. maidiradicis* (corn root aphid)).

According to more specific embodiments, the invention is applicable to species belonging to the family of Chrysomelidae or leaf beatles. Chrysomelid beetles such Colorado potato Beetles, Flea Beetles, Corn Rootworms and Curculionids such as Alfalfa Weevils are particularly important pests. Specific *Leptinotarsa* species to control according to the invention include Colorado Potato Beetle (*Leptinotarsa decemlineata* (Say) and False Potato Beetle (*Leptinotarsa juncta* (Say). CPB is a (serious) pest on our domestic potato, other cultivated and wild tuber bearing and non-tuber bearing potato species and other *Solanaceous* (nightshades) plant species including the crop species tomato, eggplant, peppers, tobacco (Nicotiana species including ornamentals), ground cherry, rice, corn or cotton; and the weed/herb species, horse nettle, common nightshade, thorn apple, henbane and buffalo burr. Corn rootworms include species found in the genus *Diabrotica* (e.g., *D. undecimpunctata undecimpunctata*, *D. undecimpunctata howardii*, *D. longicornis*, *D. virgifera* and *D. balteata*). Corn rootworms cause extensive damage to corn and curcubits.

According to a more specific embodiment, the invention is applicable to species belonging to the order of Hemipterans (family of Aphidoidea), such as *Myzus persicae* (green peach aphid, *Aphis fabae* (Black Bean Aphid), *Acyrthosiphum pisum* (Pea Aphid), *Brevicoryne brassicae* (Cabbage Aphid), *Sitobion avenae* (Grain Aphid), *Cavariella aegopodii* (Carrot Aphid), *Aphis craccivora* (Groundnut Aphid), *Aphis gossypii* (Cotton Aphid), *Toxoptera aurantii* (Black Citrus Aphid), *Cavariella* spp (Willow Aphid), *Chaitophorus* spp (Willow Leaf Aphids), *Cinara* spp. (Black Pine Aphids), *Drepanosiphum platanoides* (Sycamore Aphid) *Elatobium* spp (Spruce Aphids) which cause damage to plants such as *Prunus* trees, particularly peach, apricot and plum; trees that are mainly cultured for wood production such as willows and poplars, to row crops such as corn, cotton, soy, wheat and rice, to vegetable crops of the families Solanaceae, Chenopodiaceae, Compositae, Cruciferae, and Cucurbitaceae, including but not limited to, artichoke, asparagus, bean, beets, broccoli, Brussels sprouts, cabbage, carrot, cauliflower, cantaloupe, celery, corn, cucumber, fennel, kale, kohlrabi, turnip, eggplant, lettuce, mustard, okra, parsley, parsnip, pea, pepper, potato, radish, spinach, squash, tomato, turnip, watercress, and watermelon; or field crops such as, but not limited to, tobacco, sugar beet, and sunflower; a flower crop or other ornamental plant such as pine trees and conifers. Other Hemipterans belong to *Nilaparvata* ssp (e.g. *N. lugens*, *Sogatella furcifera*) and cause damage to rice plants. Other Hemipterans belong to *Lygus* ssp (e.g. *Lygus hesperus*, *Lygus rugulipennis*, *Lygus lineolaris*, *Lygus sully*) and other species of plant-feeding insects in the family of the Miridae, and cause damage to cotton, potato plants, strawberries, cotton, alfalfa, canola, peach, plums, grape, lettuce, eggplant, onion, green beans. As well as several Mediterranean trees and several ornamental trees such as elm tree (*Ulmus* spp.) pine nut (*Pinus Pinea*) London plane tree (*Platanus Acerifolia*), white redbud (*Malus alba*). Other Hemipterans belong to the family of the Pentatomoidea, they are commonly referred to as shield bugs, chust bugs, and stink bugs (eg; the brown marmorated stink bug (*Halyomorpha halys*), the Consperse stink bug (*Euschistus conspersus*), southern green stink bug (*Nezara viridula*), forest bug (*Pentatoma rufipes*), harlequin bug (*Murgantia histrionica*), rice stink bug (*Oebalus pugnax*)) and cause damage to fruits including apples, peaches, figs, mulberries, citrus fruits and persimmons, blackberry, and vegetables including sweetcorn, tomatoes, soy beans, lima beans and green peppers, cabbage, cauliflower, turnips, horseradish, collards, mustard, Brussels sprouts, potato, egg plant, okra, beans, asparagus, beets, weeds, fruit trees and field crops such as field corn and soy bean. Stink bugs are also a pest of grasses, sorghum and rice.

A plant to be used in the methods of the invention, or a transgenic plant according to the invention encompasses any plant, but is preferably a plant that is susceptible to infestation by a plant pathogenic insect.

Accordingly, the present invention extends to plants and to methods as described herein wherein the plant is chosen from the following group of plants (or crops): alfalfa, apple, apricot, artichoke, asparagus, avocado, banana, barley, beans, beet, blackberry, blueberry, broccoli, Brussels sprouts, cabbage, canola, carrot, cassava, cauliflower, a cereal, celery, cherry, citrus, clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini.

In specific embodiments, the present invention provides target genes which encode proteins involved in the function of a wings up A (troponin I), a mitochondrial cytochrome c oxidase subunit II protein, or one of the ribosomal proteins as specified in Table 1.

In preferred embodiments, the present invention provides target genes selected from the group of genes (i) having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence so that, when the two sequences are optimally aligned and compared, is at least 75%, preferably at least 80%, 85%, 90%, 95%, 98% or 99% identical any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (ii) having a nucleotide sequence consisting of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs. 1-26, 121-205, 386-389, 394, 400, or the complement thereof, or (v) having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or (vi) which gene is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389; and wherein the nucleotide sequence of said gene is no longer than 10000, 9000, 8000, 7000, 6000, 5000, 4000, 3000, 2000 or 1500 nucleotides.

The amino acid sequences encoded by the target genes of the present invention are represented by SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

As used herein, the term "having" has the same meaning as "comprising".

As used herein, the term "sequence identity" is used to describe the sequence relationship between two or more nucleotide or amino acid sequences. The percentage of "sequence identity" between two sequences is determined by comparing two optimally aligned sequences over a comparison window (a defined number of positions), wherein the portion of the sequence in the comparison window may comprise additions or deletions (i.e. gaps) as compared to the reference sequence in order to achieve optimal alignment. The percentage sequence identity is calculated by determining the number of positions at which the identical nucleotide base or amino acid residue occurs in both sequences to yield the number of 'matched' positions, dividing the number of matched positions by the total number of positions in the comparison window and multiplying the result by 100. Methods and software for determining sequence identity are available in the art and include the Blast software and GAP analysis. For nucleic acids, the percent identity is calculated preferably by the BlastN alignment tool whereby the percent identity is calculated over the entire length of the query nucleotide sequence.

A person skilled in the art will recognise that homologues or orthologues (homologues existing in different species) of the target genes represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 can be identified. These pest homologues and/or orthologues are also within the scope of the current invention. Preferred homologues and/or orthologues are genes similar in nucleotide sequence to such a degree that when the two genes are optimally aligned and compared, the homologue and/or orthologue has a sequence that is at least 75%, preferably at least 80% or 85%, more preferably at least 90% or 95%, and most preferably at least about 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof. Similarly, also preferred homologues and/or orthologues are proteins that are similar in amino acid sequence to such a degree that when the two amino acid sequences are optimally aligned and compared, the homologue and/or orthologue has a sequence that is at least 75%, preferably at least 80% or 85%, more preferably at least 90% or 95%, and most preferably at least about 99% identical to any of SEQ ID NOs 79 to 91, 326-359, 390-395.

Other homologues are genes which are alleles of a gene comprising a sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389. Further preferred homologues are genes comprising at least one single nucleotide polymorphism (SNP) compared to a gene comprising a sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389.

The 'interfering ribonucleic acid (RNA)' of the current invention encompasses any type of RNA molecule capable of down-regulating or 'silencing' expression of a target gene, including but not limited to sense RNA, antisense RNA, short interfering RNA (sRNA), microRNA (miRNA), double-stranded RNA (dsRNA), hairpin RNA (RNA) and the like. Methods to assay for functional interfering RNA molecules are well known in the art and are disclosed elsewhere herein.

The interfering RNA molecules of the current invention effect sequence-specific down-regulation of expression of a target gene by binding to a target nucleotide sequence within the target gene.

Binding occurs as a result of base pairing between complementary regions of the interfering RNA and the target nucleotide sequence. As used herein, the term 'silencing element' refers to the portion or region of the interfering RNA comprising or consisting of a sequence of nucleotides which is complementary, or at least partially complementary, to a target nucleotide sequence within the target gene, and which functions as the active portion of the interfering RNA to direct down-regulation of expression of said target gene. In one embodiment of the invention, the silencing element comprises or consists of a sequence of at least 17 contiguous nucleotides, preferably at least 18 or 19 contiguous nucleotides, more preferably at least 21 contiguous nucleotides, even more preferably at least 22, 23, 24 or 25 contiguous nucleotides complementary to a target nucleotide sequence within the target gene.

As used herein, "expression of a target gene" refers to the transcription and accumulation of the RNA transcript encoded by a target gene and/or translation of the mRNA into protein. The term 'down-regulate' is intended to refer to any of the methods known in the art by which interfering RNA molecules reduce the level of primary RNA transcripts, mRNA or protein produced from a target gene.

In certain embodiments, down-regulation refers to a situation whereby the level of RNA or protein produced from a gene is reduced by at least 10%, preferably by at least 33%, more preferably by at least 50%, yet more preferably by at least 80%. In particularly preferred embodiments, down-regulation refers to a reduction in the level of RNA or protein produced from a gene by at least 80%, preferably by at least 90%, more preferably by at least 95%, and most preferably by at least 99% within cells of the insect pest as compared with an appropriate control insect pest which has for example, not been exposed to an interfering RNA or has been exposed to a control interfering RNA molecule. Methods for detecting reductions in RNA or protein levels are well known in the art and include RNA solution hybridization, Northern hybridization, reverse transcription (e.g. quantitative RT-PCR analysis), microarray analysis, antibody binding, enzyme-linked immunosorbent assay (ELISA) and Western blotting. In another embodiment of the invention, down-regulation refers to a reduction in RNA or protein levels sufficient to result in a detectable change in a phenotype of the pest as compared with an appropriate pest control, for example, cell death, cessation of growth, or the like. Down-regulation can thus be measured by phenotypic analysis of the insect pest using techniques routine in the art.

In a preferred embodiment of the invention, the interfering RNA down-regulates gene expression by RNA interference or RNAi. RNAi is a process of sequence-specific gene regulation typically mediated by double-stranded RNA molecules such as short interfering RNAs (siRNAs). siRNAs comprise a sense RNA strand annealed by complementary basepairing to an antisense RNA strand. The sense strand or 'guide strand' of the siRNA molecule comprises a sequence of nucleotides complementary to a sequence of nucleotides located within the RNA transcript of the target gene. The sense strand of the siRNA is therefore able to anneal to the RNA transcript via Watson-Crick-type basepairing and target the RNA for degradation within a cellular complex known as the RNAi-induced silencing complex or RISC. Thus, in the context of preferred interfering RNA molecules of the current invention, the silencing element as referred to herein may be a double-stranded region comprising annealed complementary strands, at least one strand of which comprises or consists of a sequence of nucleotides which is complementary or at least partially complementary to a target nucleotide sequence within a target gene. In one embodiment the double-stranded region has a length of at least 21, 22, 23, 24, 25, 30, 35, 40, 50, 55, 60, 70, 80, 90, 100, 125, 150, 175, 200, 300, 400, 500, 600, 700, 800, 900, 1000, 1100, 1200, 1300, 1400, 1500, 2000 or 3000 base pairs.

Longer double-stranded RNA (dsRNA) molecules comprising one or more functional double-stranded silencing elements as described elsewhere herein, and capable of RNAi-mediated gene silencing are also contemplated within the scope of the current invention. Such longer dsRNA molecules comprise at least 80, 200, 300, 350, 400, 450, 500, 550, 600, 700, 800, 900, 1000, 1100, 1200, 1300, 1400, 1500, 2000 or 3000 base pairs. These dsRNA molecules may serve as precursors for the active siRNA molecules that direct the RNA transcript to the RISC complex for subsequent degradation. dsRNA molecules present in the environment surrounding an organism or the cells thereof may be taken up by the organism and processed by an enzyme called Dicer to yield siRNA molecules.

Alternatively, the dsRNA may be produced in vivo i.e. transcribed from a polynucleotide or polynucleotides encoding the same present within a cell, for instance a bacterial cell or a plant cell, and subsequently processed by Dicer either within the host cell or preferably within the insect pest cells following uptake of the longer precursor dsRNA. The dsRNA may be formed from two separate (sense and antisense) RNA strands that anneal by virtue of complementary basepairing.

Alternatively, the dsRNA may be a single strand that is capable of folding back on itself to form a hairpin RNA (RNA) or stem-loop structure. In the case of a RNA, the double-stranded region or 'stem' is formed from two regions or segments of the RNA that are essentially inverted repeats of one another and possess sufficient complementarity to allow the formation of a double-stranded region.

One or more functional double-stranded silencing elements may be present in this 'stem region' of the molecule. The inverted repeat regions are typically separated by a region or segment of the RNA known as the 'loop' region. This region can comprise any nucleotide sequence conferring enough flexibility to allow self-pairing to occur between the flanking complementary regions of the RNA. In general, the loop region is substantially single-stranded and acts as a spacer element between the inverted repeats.

All the interfering RNA molecules of the invention effect sequence-specific down-regulation of expression of a target gene by binding to a target nucleotide sequence within the target gene.

Binding occurs as a result of complementary base pairing between the silencing element of the interfering RNA and the target nucleotide sequence. The interfering RNA molecules of the invention comprise at least one or at least two silencing elements. In one embodiment of the current invention, the target nucleotide sequence comprises a sequence of nucleotides as represented by the RNA transcript of the target gene, or a fragment thereof wherein the fragment is preferably at least 17 nucleotides, more preferably at least 18, 19 or 20 nucleotides, or most preferably at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 nucleotides. In a preferred embodiment of the current invention, the target nucleotide sequence comprises a sequence of nucleotides equivalent to the RNA transcript encoded by any of the polynucleotides selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389. In a more preferred embodiment of the above, said polynucleotide is no longer than 10000, 9000, 8000, 7000, 6000, 5000, 4000, 3000, 2000 or 1500 nucleotides.

Preferably, the interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

The silencing element, or at least one strand thereof wherein the silencing element is double-stranded, may be fully complementary or partially complementary to the target nucleotide sequence of the target gene. As used herein, the term "fully complementary" means that all the bases of the nucleotide sequence of the silencing element are complementary to or 'match' the bases of the target nucleotide sequence. The term "at least partially complementary" means that there is less than a 100% match between the bases of the silencing element and the bases of the target nucleotide sequence. The skilled person will understand that the silencing element need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the silencing element and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the silencing element may comprise 1, 2 or 3 mismatches as compared with the target nucleotide sequence over every length of 24 partially complementary nucleotides.

It will be appreciated by the person skilled in the art that the degree of complementarity shared between the silencing element and the target nucleotide sequence may vary depending on the target gene to be down-regulated or depending on the insect pest species in which gene expression is to be controlled.

In another embodiment of the current invention, the silencing element comprises a sequence of nucleotides that is the RNA equivalent of any of the polynucleotides selected from the group consisting of a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or (ii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs. 1-26, 121-205, 386-389, 394, 400, said nucleotide sequence is at least 75% preferably at least 80%, 85%, 90%, 95%, 98% or 99% identical to said corresponding fragment of any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, wherein said polynucleotide is no longer than 10000, 9000, 8000, 7000, 6000, 5000, 4000, 3000, 2000 or 1500 nucleotides. It will be appreciated that in such embodiments the silencing element may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene.

The skilled person will be aware of methods of identifying the most suitable target nucleotide sequences within the context of the full-length target gene. For example, multiple silencing elements targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

The interfering RNAs of the current invention may comprise one silencing element or multiple silencing elements, wherein each silencing element comprises or consists of a sequence of nucleotides which is at least partially complementary to a target nucleotide sequence within a target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single silencing element i.e. repeats of a silencing element that binds to a particular target nucleotide sequence within a specific target gene. In another embodiment, the silencing elements within the interfering RNA comprise or consist of different sequences of nucleotides complementary to different target nucleotide sequences. It should be clear that combinations of multiple copies of the same silencing element combined with silencing elements binding to different target nucleotide sequences are within the scope of the current invention.

The different target nucleotide sequences may originate from a single target gene in an insect pest species in order to achieve improved down-regulation of a specific target gene in an insect pest species. In this case, the silencing elements may be combined in the interfering RNA in the original order in which the target nucleotide sequences occur in the target gene, or the silencing elements may be scrambled and combined randomly in any rank order in the context of the interfering RNA as compared with the order of the target nucleotide sequences in the target gene.

Alternatively, the different target nucleotide sequences are representing a single target gene but originating from different insect pest species.

Alternatively, the different target nucleotide sequences may originate from different target genes. If the interfering RNA is for use in preventing and/or controlling pest infestation, it is preferred that the different target genes are chosen from the group of genes regulating essential biological functions of insect pest species, including but not limited to survival, growth, development, reproduction and pathogenicity. The target genes may regulate the same or different biological pathways or processes.

In one embodiment, at least one of the silencing elements comprises or consists of a sequence of nucleotides which is at least partially complementary to a target nucleotide sequence within a target gene wherein the target gene is selected from the group of genes as described earlier.

In a further embodiment of the invention, the different genes targeted by the different silencing elements originate from the same insect pest species. This approach is designed to achieve enhanced attack against a single insect pest species. In particular, the different target genes may be expressed differentially in the different stages of the insect's life cycle, for example, the mature adult, immature larval and egg stages. The interfering RNA of the invention may thus be used to prevent and/or control insect pest infestation at more than one stage of the insect's life cycle.

In an alternative embodiment of the invention, the different genes targeted by the different silencing elements originate from different insect pest species. The interfering RNA of the invention can thus be used to prevent and/or control infestation by more than one insect pest species simultaneously.

The silencing elements may be arranged as one contiguous region of the interfering RNA or may be separated by the presence of linker sequences. The linker sequence may comprise a short random nucleotide sequence that is not complementary to any target nucleotide sequences or target genes.

In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the silencing element(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The length of the interfering RNA of the invention needs to be sufficient for uptake by the cells of an insect pest species and down-regulation of target genes within the pest as described elsewhere herein. However, the upper limit on length may be dependent on (i) the requirement for the interfering RNA to be taken up by cells of the pest and (ii) the requirement for the interfering RNA to be processed in the cells of the pest to mediate gene silencing via the RNAi pathway. The length may also be dictated by the method of production and the formulation for delivery of the interfering RNA to cells. Preferably, the interfering RNA of the current invention will be between 21 and 10000 nucleotides in length, preferably between 50 and 5000 nucleotides or between 100 and 2500 nucleotides, more preferably between 80 and 2000 nucleotides in length.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions.

Alternatively, the interfering RNA may be transcribed from a polynucleotide encoding the same.

Thus, provided herein is an isolated polynucleotide encoding any of the interfering RNAs of the current invention.

Also provided herein is an isolated polynucleotide selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs. 1-26, 121-205, 386-389, 394, 400, said nucleotide sequence is at least 75% preferably at least 80%, 85%, 90%, 95%, 98% or 99% identical to said corresponding fragment of any of SEQ ID NOs. 1-26, 121-205, 386-389, 394, 400 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs. 1-26, 121-205, 386-389, 394, 400, said nucleotide sequence is at least 75% preferably at least 80%, 85%, 90%, 95%, 98% or 99% identical to said corresponding fragment of any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, and wherein said polynucleotide is no longer than 10000, 9000, 8000, 7000, 6000, 5000, 4000, 3000, 2000 or 1500 nucleotides.

In preferred embodiments, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. The sense strand of the dsRNA is therefore able to anneal to the RNA transcript and target the RNA for degradation within the RNAi-induced silencing complex or RISC.

The polynucleotides of the invention may be inserted via routine molecular cloning techniques into DNA constructs or vectors known in the art. Therefore, according to one embodiment, a DNA construct comprising any of the polynucleotides of the current invention is provided. Preferably, provided herein is a DNA construct comprising a polynucleotide encoding at least one of the interfering RNAs of the current invention. The DNA construct may be a recombinant DNA vector, for example a bacterial or yeast vector or plant vector. In a preferred embodiment of the invention, the DNA construct is an expression construct and the polynucleotide is operably linked to at least one regulatory sequence capable of driving expression of the polynucleotide sequence. The term 'regulatory sequence' is to be taken in a broad context and is intended to refer to any nucleotide sequence capable of effecting expression of polynucleotides to which it is operably linked including but not limited to promoters, enhancers and other naturally-occurring or synthetic transcriptional activator elements. The regulatory sequence may be located at the 5' or 3' end of the polynucleotide sequence. The term 'operably linked' refers to a functional linkage between the regulatory sequence and the polynucleotide sequence such that the regulatory sequence drives expression of the polynucleotide. Operably linked elements may be contiguous or non-contiguous.

Preferably, the regulatory sequence is a promoter selected from the group comprising but not limited to constitutive promoters, inducible promoters, tissue-specific promoters and growth/developmental stage-specific promoters. In one embodiment, the polynucleotide is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus 34S promoter. In another embodiment, the regulatory sequence is a plant promoter for use in regulating expression of the polynucleotide in plants. Plant promoters, in particular, tissue-specific plant promoters encompassed within the scope of the current invention are described in more detail elsewhere herein.

Optionally, one or more transcription termination sequences may be incorporated in the expression construct of the invention. The term 'transcription termination sequence' encompasses a control sequence at the end of a transcriptional unit, which signals termination of transcription, 3' processing and poly-adenylation of a primary transcript. Additional regulatory sequences including but not limited to transcriptional or translational enhancers may be incorporated in the expression construct, for instance as with the double enhanced CaMV35S promoter.

The present invention also encompasses a method for generating any of the interfering RNAs of the invention comprising the steps of (i) contacting a polynucleotide encoding said interfering RNA or a DNA construct comprising the same with cell-free components; or (ii) introducing (e.g. by transformation, transfection or injection) a polynucleotide encoding said interfering RNA or a DNA construct comprising the same into a cell.

The invention thus also relates to any double stranded ribonucleotide produced from the expression of a polynucleotide described herein.

Accordingly, also provided herein is a host cell transformed with any of the polynucleotides described herein. Further encompassed by the present host cells comprising any of the interfering RNA's of the current invention, any of the polynucleotides of the current invention or a DNA construct comprising the same. The host cell may be a prokaryotic cell including but not limited to gram-positive and gram-negative bacterial cells, or an eukaryotic cell including but not limited to yeast cells or plant cells.

Preferably, said host cell is a bacterial cell or a plant cell. The bacterial cell can be chosen from the group comprising, but not limited to, Gram positive and Gram negative cells comprising *Escherichia* spp. (e.g. *E. coli*), *Bacillus* spp. (e.g. *B. thuringiensis*), *Rhizobium* spp., *Lactobacillus* spp., *Lactococcus* spp., *Pseudomonas* spp. and *Agrobacterium* spp. The polynucleotide or DNA construct of the invention may exist or be maintained in the host cell as an extra-chromosomal element or may be stably incorporated into the genome of the host cell. Characteristics of particular interest in selecting a host cell for the purposes of the current invention include the ease with which the polynucleotide or DNA construct encoding the interfering RNA can be introduced into the host, the availability of compatible expression systems, the efficiency of expression, and the stability of the interfering RNA in the host.

Preferably, the interfering RNAs of the invention are expressed in a plant host cells. Preferred plants of interest include but are not limited to cotton, potato, rice, tomato, canola, soy, sunflower, sorghum, pearl millet, corn, alfalfa, strawberries, eggplant, pepper and tobacco.

In situations wherein the interfering RNA is expressed within a host cell and/or is used to prevent and/or control pest infestation of a host organism, it is preferred that the interfering RNA does not exhibit significant 'off-target' effects i.e. the interfering RNA does not affect expression of genes within the host. Preferably, the silencing element does not exhibit significant complementarity with nucleotide sequences other than the intended target nucleotide sequence of the target gene. In one embodiment of the invention, the silencing element shows less than 30%, more preferably less than 20%, more preferably less than 10% and even more preferably less than 5% sequence identity with any gene of the host cell or organism. If genomic sequence data is available for the host organism, one can cross-check identity with the silencing element using standard bioinformatics tools. In one embodiment, there is no sequence identity between the silencing element and a gene from the host cell or host organism over a region of 17, more preferably over a region of 18 or 19 and most preferably over a region of 20 or 21 contiguous nucleotides.

In the practical application of the invention, the interfering RNAs of the invention may be used for the prevention and/or control of any insect pest belonging to the Orders Coleoptera, Lepidoptera, Diptera, Dichyoptera, Orthoptera, Hemiptera and Siphonaptera.

Also provided herein is a method for preventing and/or controlling pest infestation, comprising contacting an insect pest species with an effective amount of at least one interfering RNA wherein the RNA functions upon uptake by said pest to down-regulate expression of an essential pest target gene. The essential target gene may be any pest gene involved in the regulation of an essential biological process required by the pest to initiate or maintain infestation including but not limited to survival, growth, development, reproduction and pathogenicity. In particular, the target gene may be any of the pest genes as described elsewhere herein.

Furthermore, there is provided herein a method for preventing and/or controlling insect pest infestation in a field of crop plants, said method comprising expressing in said plants an effective amount of an interfering RNA as described herein.

Wherein the method is for the control of pest infestation, the phrase 'effective amount' extends to the quantity or concentration of interfering RNA required to produce a phenotypic effect on the pest such that the numbers of pest organisms infesting a host organism are reduced and/or the amount of damage caused by the pest is reduced. In one embodiment, the phenotypic effect is death of the pest and the interfering RNA is used to achieve at least 20%, 30%, 40%, preferably at least 50%, 60%, 70%, more preferably at least 80% or 90% pest mortality as compared to control insect pests. In a further embodiment, the phenotypic effects include but are not limited to stunting of pest growth, cessation of feeding and reduced egg-laying. The total numbers of pest organisms infesting a host organism may thus be reduced by at least 20%, 30%, 40%, preferably at least 50%, 60%, 70%, more preferably at least 80% or 90% as compared with control pests. Alternatively, the damage caused by the insect pest may be reduced by at least 20%, 30%, 40%, preferably at least 50%, 60%, 70%, more preferably at least 80% or 90% as compared with control insect pests. Hence, the method of the invention can be used to achieve at least 20%, 30%, 40%, preferably at least 50%, 60%, 70%, more preferably at least 80% or 90% pest control.

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides of any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical the amino acid sequence as presented in any of SEQ ID NOs 79, 349, 405, 352 or 356 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 328 or 84 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 87 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 88 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L.

*juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 347 or 348 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 330, 350 or 353 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 331 or 351 (when said encoded proteins are optimally aligned).

In the methods described herein to down-regulate expression of a target gene in an insect pest species, double stranded RNA molecules comprising or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 337 or 354 (when said encoded proteins are optimally aligned).

In one embodiment, the plant to be treated is engineered to express the interfering RNA intracellularly via transcription from a polynucleotide incorporated therein. As the pest feeds on tissues of the plant, the cells containing the interfering RNA will be broken down inside the insect's digestive tract and the interfering RNA will thus be distributed within the insect's body resulting in down-regulation of target genes.

Thus, in accordance with another aspect of the present invention is provided a method for generating a transgenic plant resistant to infestation by an insect pest species comprising the steps of (a) transforming a plant cell with a DNA construct comprising a polynucleotide sequence encoding an interfering ribonucleic acid (RNA) that functions upon uptake by an insect pest species to down-regulate expression of a target gene in said insect pest species, (b) regenerating a plant from the transformed plant cell; and (c) growing the transformed plant under conditions suitable for the expression of the interfering RNA from the recombinant DNA construct, said plant thus being resistant to said pest as compared with an untransformed plant.

The interfering RNA expressed by the plant or part thereof may be any of those as disclosed elsewhere herein. Preferably, the interfering RNA comprises or consists of at least one silencing element and said silencing element is a region of double-stranded RNA comprises annealed complementary strands, one strand of which (the sense strand) comprises a sequence of nucleotides which is at least partially complementary to a target nucleotide sequence within a target gene.

Wherein part of the interfering RNA is double-stranded, the two strands of the molecule may be expressed from at least two separate polynucleotides or may be encoded by a single polynucleotide encoding an interfering RNA with for example, a stem-loop structure or a so-called hairpin structure as described elsewhere herein.

The interfering RNA expressed by the plant or part thereof may target any of the pest genes as described elsewhere herein. In particular, the target gene may be selected from the group of genes having a nucleotide sequence comprising any of SEQ ID NOs. 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or having a nucleotide sequence that, when the two sequences are optimally aligned and compared, is at least 75%, preferably at least 80%, 85%, 90%, 95%, 98% or 99% identical any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or is selected from the group of genes having a nucleotide sequence consisting of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs. 1-26, 121-205, 386-389, 394, 400, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, or is selected from the group of genes having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof. The target gene may also be an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 402, 186, 202, 187, 203, 306 to 309, 318 to 321, 386, 387, 388, 389.

In one embodiment, the target gene
(i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

In one embodiment, the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273 or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

In one embodiment, the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313 or 401, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313 or 401, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, or 401, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or 401, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or 401, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, or 401, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, or 401, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, or 401, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 401, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 401.

Preferably the nucleotide sequence of said target gene is no longer than 10000, 9000, 8000, 7000, 6000, 5000, 4000, 3000, 2000 or 1500 nucleotides. Furthermore, it is important that the interfering RNA does not disrupt expression of any genes of the plant host.

As used herein, the term 'transgenic plant' or 'transgenic plant cell' refers to any plant or plant cell that has been genetically engineered or is descended from a plant that has been genetically engineered so as to carry an exogenous polynucleotide sequence. 'Exogenous' refers to the fact that the polynucleotide originates from outside the plant cell. Typically, the exogenous polynucleotide is non-native to the transgenic plant i.e. it is not found naturally within the genome of the plant.

As used herein, the term 'transformation' refers to the introduction of exogenous polynucleotide molecules into a plant or a cell thereof. Techniques for introducing polynucleotides into plants are known in the art. In one embodiment of the current invention, the plants are 'stably transformed' with a polynucleotide or DNA construct comprising the same, i.e. the polynucleotide or DNA construct introduced into the plant cell integrates into the genome of the plant and is capable of being inherited by the progeny thereof. Transformation protocols for introducing polynucleotides or DNA constructs into the cells of plants may vary depending on the type of plant concerned. Suitable transformation methods include but are not limited to microinjection, electroporation, *Agrobacterium*-mediated transformation, and ballistic particle acceleration. Methods are also known in the art for the targeted insertion of a polynucleotide or DNA construct at a specific location in the plant genome using site-specific recombination systems.

The DNA construct comprising the polynucleotide encoding the active interfering RNA molecule may be any vector suitable for transformation of plant cells. Suitable vectors include but are not limited to bacterial plasmids, for example the Ti plasmid of *Agrobacterium tumefaciens*, and viral vector systems. The DNA construct introduced into the cells of a plant must not be harmful or toxic to the plant and/or must not be harmful or toxic to any organisms higher up the food chain that feed on said plants.

In one embodiment, the DNA construct is an expression construct comprising a polynucleotide encoding an interfering RNA operably linked to a regulatory sequence capable of driving expression of the polynucleotide sequence in plants such as any selected from the group comprising the CaMV35S promoter, doubled CaMV35S promoter, ubiquitin promoter, actin promoter, rubisco promoter, GOS2 promoter, Figwort mosaic virus 34S promoter and the double enhanced CaMV35S promoter. Preferably, the regulatory sequence is a plant promoter selected from those known in the art. In some embodiments, it may be preferred that the plant produces interfering RNA molecules only in the parts of the plant which will come into contact with and/or are damaged by the insect pest species, for example, the aerial parts of the plant, the roots etc. This effect can be achieved through the use of tissue-specific plant promoters including but not limited to leaf-specific promoters, root-specific promoters, stem-specific promoters, flower-specific promoters and fruit-specific promoters known in the art. Suitable examples of a root specific promoter are PsMTA and the Class III Chitinase promoter. Examples of leaf- and stem-specific or photosynthetic tissue-specific promoters that are also photoactivated are promoters of two chlorophyll binding proteins (cab1 and cab2) from sugar beet, ribulose-bisphosphate carboxylase (Rubisco), encoded by rbcS, A (gapA) and B (gapB) subunits of chloroplast glyceraldehyde-3-phosphate dehydrogenase, promoter of the *Solanum tuberosum* gene encoding the leaf and stem specific (ST-LS1) protein, stem-regulated, defense-inducible genes, such as JAS promoters, flower-specific promoters such as chalcone synthase promoter and fruit-specific promoters such as that of RJ39 from strawberry.

In other embodiments, it may be preferred that the plant produces interfering RNA molecules only at a particular stage of its growth. This effect can be achieved through the use of development-specific plant promoters that drive expression only during certain periods of plant development. In particular, it is important to protect plants from pest infestation during the early stages of plant growth or during flowering (for instance in case of rice) or during fructification or fruit maturation or seed-filling, as this is the time when the plant can be most severely damaged.

The DNA construct for use in transformation of a plant according to the present method may comprise more than one polynucleotide encoding an interfering RNA molecule of the current invention. In one embodiment, the different polynucleotides may encode interfering RNA molecules targeting different nucleotide sequences within the same target gene. In a further embodiment, the different polynucleotides may encode interfering RNA molecules targeting different nucleotide sequences within different target genes, wherein the different target genes originate from the same or different insect pest species. Wherein the DNA construct encodes more than one interfering RNA, these RNAs may be expressed differentially within different tissues of the plant by virtue of being under the control of different tissue-specific promoter sequences as described elsewhere herein. In one embodiment, the plant is engineered to express an interfering RNA in the leaves which down-regulates expression of a target gene in an insect that feeds on the leaves, and to additionally express an interfering RNA in the roots which down-regulates expression of a target gene in an insect that colonizes the soil and feeds on the plant roots.

The DNA construct may also comprise at least one other polynucleotide of interest, for example a polynucleotide encoding an additional regulatory RNA molecule, a polynucleotide encoding a protein toxic to insect pest species and/or a polynucleotide encoding a protein conferring herbicide resistance or tolerance.

In accordance with the present method, a plant is regenerated from a transformed plant cell using techniques known in the art. One such technique comprises enzymatic digestion of the plant cell wall to produce a plant protoplast, which can subsequently undergo multiple rounds of cell division and differentiation to produce an adult plant. Adult plants generated in such a way can be subsequently tested for resistance to pest infestation. 'Resistant' as used herein should be interpreted broadly and relates to the ability of the plant to defend against attack from a pest that is typically capable of inflicting damage or loss to the plant. Resistant may either be taken to mean that the plant is no longer susceptible to pest infestation or that any disease symptoms resulting from pest infestation are reduced by at least about 20%, preferably at least 30%, 40% or 50%, more preferably at least 60%, 70% or 80% and most preferably by at least 90%. Techniques to measure the resistance of a plant to insect pest species are commonly known in the art and include but are not limited to measuring over time the average lesion diameter, the pest biomass or weight, the pest survival and/or mortality, and/or the overall percentage of decayed plant tissues.

In one embodiment, the present method of producing a transgenic plant also includes the step of generating offspring or progeny from the transgenic plant and testing the progeny for resistance to the insect pest. Two or more generations may be produced to ensure that expression of the resistance trait is stably maintained and inherited. Seeds may also be harvested from the parent transgenic plant and/or its progeny to test for resistance to an insect pest.

Also encompassed within the present invention is a method for generating transgenic plants resistant to infestation by an insect pest species comprising the steps of crossing a first transgenic plant carrying a DNA construct encoding an interfering RNA that functions to down-regulate expression of a pest target gene, with a second plant lacking said DNA construct, and selecting progeny resistant to said pest. Crossing may be carried out by any methods routinely used in the context of plant breeding. The progeny selected for pest resistance may additionally be self-pollinated or 'selfed' to produce a subsequent generation of pest resistant progeny. In one embodiment, multiple rounds of self pollination or selfing may be carried out to generate 2, 3, 4, 5 or more generations of progeny.

The resultant progeny may be tested for pest resistance to ensure that expression of the resistance trait is stably maintained and inherited.

In a further embodiment, any pest resistant progeny plants derived from a cross between a first transgenic parent plant carrying a DNA construct of interest and a second parent plant lacking said DNA construct may be back-crossed to the second parent plant and subsequent progeny tested for resistance to pest infestation. Plants or their progeny may be tested for resistance to pest infestation either by phenotypic analysis as described elsewhere herein or by standard molecular techniques.

For example, the pest resistant plants may be identified by the detection of the presence of a polynucleotide sequence encoding an interfering RNA that functions upon uptake by an insect pest species to down-regulate expression of a target gene. Techniques for detecting the presence of specific polynucleotide sequences within cells are known in the art and include PCR, enzymatic digestion and SNP analysis.

The methods of the invention can be used to generate 'stacked transgenic' plants that are resistant to insect pest species and that optionally possess at least one other desirable trait. As used herein, a 'stacked' transgenic plant refers to a plant carrying more than one exogenous polynucleotide sequence. The phrase 'more than one' refers to the possibility of a plant carrying at least 2, at least 3, at least 4 exogenous polynucleotides. In one embodiment, the plant cell transformed with the DNA construct encoding the interfering RNA targeting a pest gene may have previously been engineered to carry a separate exogenous polynucleotide. Alternatively, the method for generating a transgenic plant from a plant cell as described herein may comprise a co-transformation protocol wherein the DNA construct encoding an interfering RNA of the invention is delivered to a plant cell simultaneously or sequentially with a separate exogenous polynucleotide.

Stacked transgenic plants demonstrating pest resistance may also be generated by standard plant breeding techniques. In one embodiment, a first pest-resistant transgenic plant is crossed with a second plant engineered to express an exogenous polynucleotide or heterologous gene conferring a desirable plant trait. Any progeny produced can be tested for pest resistance and acquisition of the additional desirable trait. Alternatively or in addition, any pest-resistant progeny produced from the cross may be back-crossed to the second parent in order to generate further progeny that can be selected for inheritance of the heterologous gene carried by the second parent and thus the additional desirable plant trait. The exogenous polynucleotides carried by a stacked transgenic plant of the invention may be expressed in the same parts of the plant or may be expressed differentially by virtue of the fact that expression of each is controlled by a different tissue-specific promoter.

In one embodiment, the exogenous polynucleotide or heterologous gene conferring a further desirable trait encodes another interfering RNA targeting the same or different insect pest species. In a further embodiment, the heterologous gene encodes a protein harmful or toxic to a plant insect pest species, for example an insecticidal protein selected from the group including but not limited to Bacillus thuringiensis insecticidal proteins, Xenorhabdus insecticidal proteins, Photorhabdus insecticidal proteins, Bacillus laterosporous insecticidal proteins, Bacillus sphaericus insecticidal proteins, and VIP insecticidal proteins, such as a protein selected from the group including but not limited to Cry1Ab, Cry1C, Cry2Aa, Cry3, CryET70, Cry22, CryET33, CryET34, CryET80, CryET76, TIC100, TIC101, TIC851, TIC900, TIC901, TIC1201, TIC407, TIC417 and PS149B1 insecticidal proteins. In a yet further embodiment, the heterologous gene encodes a protein conferring herbicide resistance or tolerance. Examples of genes conferring herbicide resistance or tolerance include Bar, EPSPS which confers glyphosate resistance, ALS which confers imidazolinone and sulphonylurea resistance and bxn which confers bromoxynil resistance.

Also provided herein is a method for producing hybrid seed from any of the transgenic plants generated by the methods of the current invention, said method comprising the steps of (i) planting the seed obtained from a first inbred plant and the seed obtained from a second inbred plant, wherein at least one of the inbred plants is a transgenic plant resistant to pest infestation (ii) cultivating the seeds into plants that bear flowers, (iii) preventing self-pollination of at least one of the first or second adult plants, (iv) allowing cross-pollination to occur between the first and second plants; and (v) harvesting the seeds resulting from the cross-pollination. Hybrid seed produced by this method and hybrid plants produced by cultivating said seed are within the scope of the current invention. Hybrid plants produced by this method will typically be genetically uniform and are likely to exhibit heterosis or hybrid vigour. Thus, crops with the potential for increased yield may be generated by such a method.

Included within the group of transgenic plants of the current invention are transgenic plants produced by any of the methods described herein. Thus in one embodiment of the invention the transgenic plants comprise stacked transgenic traits carrying a first exogenous polynucleotide conferring pest resistance and at least one other exogenous polynucleotide or heterologous gene conferring an additional desirable plant trait. The additional heterologous genes may comprise genes encoding additional pesticidal agents, genes encoding proteins toxic or harmful to insect pest species and/or genes encoding proteins conferring herbicide resistance as described elsewhere herein.

Preferred transgenic plants according to the invention include but are not limited to cotton, potato, rice, tomato, canola, soy, sunflower, sorghum, pearl millet, corn, alfalfa, strawberries, eggplant, pepper and tobacco.

Also provided herein is the use of the interfering ribonucleic acid (RNA) as described herein or the DNA construct as described herein for preventing and/or controlling insect pest infestation, preferably insect pest infestation of plants.

The invention will be further understood with reference to the following non-limiting examples.

EXAMPLES

Example 1 Identification of Target Genes in Insect Pest Species 1.1. *Lygus Hesperus* Normalized cDNA Library and Preparation of dsRNAs in Multiwell Plates for the Screening Assays Nucleic acids were isolated from *Lygus hesperus* nymphs of different life stages, including freshly hatched nymphs 2, 4, 6 and 9 days old nymphs and adults. A cDNA library was prepared using the SMARTer™ PCR cDNA Synthesis Kit, following the manufacturer's instructions (Clontech Cat. No 634925). The cDNA library was normalized using the Trimmer kit (Evrogen Cat No NK001) and cloned in the PCR4-TOPO vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of *Escherichia coli* strain TOP10 (Invitrogen). The transformed cells were subsequently diluted and plated so as to obtain single colonies or clones. The clones were checked to ensure that clone redundancy for the library did not exceed 5%. Single clones were picked in liquid LB (Luria-broth) media, in 96-deep-well plates, and grown overnight at 37° C. The plates also included positive (Lh423) and negative (FP) control clones.

To generate the dsRNA, sense and antisense DNA fragments, containing T7 promoter sequence, were generated by PCR. In brief, per clone, 1 µl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAG-GAAGCAGTGGTATCAACGCAG) based on the M2 and the T7-M2 sequences respectively. The PCR reaction was followed by in vitro transcription, where per clone, 6 µl PCR product were added to 9 µl RiboMAX™ Large Scale RNA Production System—T7 (Promega Cat No P1300) and incubated overnight at 37° C. The final dsRNA solution was diluted 2 times in *L. hesperus* sucrose diet, containing 15% sucrose and 5 µg/µl yeast tRNA (Invitrogen Cat No 15401-029) and used for screening. The dsRNA corresponding to the positive Lh423 control clone is SEQ ID NO 101 and to the negative FP control clone is SEQ ID NO 104 (see Table 4).

1.2. Screen for Novel and Potent *Lygus hesperus* Target Genes Using a dsRNA Expression cDNA Library A new screening assay for potent *Lygus hesperus* targets has been developed. The assay set-up was as follows: each well of a 96-well plate houses a one-day-old *L. hesperus* nymph exposed to a parafilm sachet containing sucrose diet which includes either test dsRNA or control dsRNA in the presence of tRNA. Each plate contained dsRNA from 90 different clones, 3×Lh423 (positive control) and 3×FP (fluorescent protein; negative control). Each clone (test dsRNA) was replicated over three plates. After three days exposure, the nymphal survival number was recorded and the diet replaced with fresh rearing (complex) diet in absence of dsRNA. The mortality was assessed at days 4, 6 and 8. An identical set up was used for the first and second round confirmation assays, with 8 and 20 insects respectively, with one nymph per well.

The assay system was validated using dsRNA corresponding to Lh423 target as the positive control and a fluorescent protein dsRNA as the negative control: over 90% were true positives and under 5% were false positives, respectively.

Twenty 96 well-plates, named Lh001 to Lh020 (see bottom line in FIGS. 1 & 2), containing 1800 individual clones have been tested. 205 candidates were identified and tested in a first confirmation assay. Setting the threshold at showing ≥50% mortality, 41 independent clones were identified and progressed to a second round of confirmation. In the assay, the clones were compared to the positive controls Lh423 (RpL19) and Lh105.2 (Sec23) and the negative control Pt (encoding a coral fluorescent protein). The dsRNA corresponding to the positive (Lh423) control clone is SEQ ID NO 101, to the positive Lh105.2 control clone is SEQ ID NO 102 and to the negative (Pt) control clone is SEQ ID NO 104 (see Table 4).

Second round confirmation assays, testing 20 insects/test dsRNA, were initiated for all the test dsRNAs displaying ≥50% mortality in the first confirmation (FIGS. 1 and 2). Candidate targets corresponding to the confirmed test dsRNAs were named with an "Lhxxx number" (see Table 1). Using the same cut-off at ≥50% mortality, 15 targets were confirmed in the first screen.

A second screen for identifying more *Lygus hesperus* targets was performed. The results of the second round confirmation assays are represented in FIG. 14. Using the same cut-off at ≥50% mortality, several targets were confirmed in the second screen (see Table 1 C).

1.3. Identification of *Lygus* Targets

In parallel to the confirmation insect assays, the inserts corresponding to the positive clones were sequenced and BlastX searches against both *Drosophila* and *Tribolium* protein databases were used to confirm the identity of the targets. Table 1 provides a summary of the bio-informatics analysis and current annotation of the novel identified *L. hesperus* target sequences.

Fifteen novel *L. hesperus* targets were identified in the first screen and 11 novel *L. Hesperus* targets were identified in the second screen. All targets exhibit high potency against *L. hesperus* nymphs indicating that the cDNAs encoding double-stranded RNAs contained therein are essential for pest survival and thus represent target genes of interest for the purposes of pest control. The DNA sequences and deduced amino acid sequences of these target genes were therefore determined and are provided in Tables 2 and 3 respectively.

Lh594, the *Lygus hesperus* orthologue of *Drosophila* troponin I, involved in muscle contraction—and therefore absent in plants—, represents a novel class of target belonging to an animal specific physiological pathway not yet explored for GM-RNAi. In the fruit fly, troponin I is described as a haplo-insufficient gene, displaying a mutant phenotype in the heterozygote state. Such genes may be particularly susceptible to reduced mRNA expression levels and as such can be considered as ideal RNAi targets.

In this Lh594 pathway, eight targets were selected (see table 1B). For each target, up to 4 pairs of degenerated PCR primers were designed based on the alignments of the sequences of various insects, including bee, *Tribolium* and aphid. The primers are being used to amplify fragments from *Lygus hesperus* targets. The DNA sequences and deduced amino acid sequences of these target genes were determined and are provided in Tables 2 and 3 respectively.

TABLE 1

*Lygus hesperus* novel targets ranked in % mortality according to the second confirmation assay results (first screen).

| Target ID | rank 2nd confirmation | Best *Drosophila* hit | NAME | SYMBOL |
|---|---|---|---|---|
| Lh594 | 1 | CG7178 | wings up A (troponin I) | wupA |
| Lh618 | 2 | CG2168 | ribosomal protein S3A | RpS3A |
| Lh609 | 3 | CG4087 | ribosomal protein LP1 | RpLP1 |
| Lh595 | 4 | — | no *Drosophila* hit found, *Lygus* specific target/sequence | |
| Lh611 | 5 | CG6779 | ribosomal protein S3 | RpS3 |
| Lh560 | 6 | CG10423 | ribosomal protein S27 | RpS27 |
| Lh596 | 7 | — | no *Drosophila* hit found, *Lygus* specific target/sequence | RpL34b |
| Lh615 | 8 | CG11522 | ribosomal protein L6 | RpL6 |

TABLE 1-continued

Lygus hesperus novel targets ranked in % mortality according to the second confirmation assay results (first screen).

| Target ID | Best rank 2nd confirmation | Drosophila hit | NAME | SYMBOL |
|---|---|---|---|---|
| Lh617 | 9 | CG7283 | ribosomal protein L10Ab | RpL10Ab |
| Lh612 | 10 | CG13389 | ribosomal protein S13 | RpS13 |
| Lh246 | 11 | CG3195 | ribosomal protein L12 | RpL12 |
| Lh429 | 12 | CG8900 | ribosomal protein S18 | RpS18 |
| Lh610 | 13 | CG5502 | ribosomal protein L4 | RpL4 |
| Lh597 | 14 | no hit found | | |
| Lh598 | 15 | CG34069 | mitochondrial cytochrome c oxidase subunit II | mt:CoII |
| Lh614 | — | CG7610 | ATP synthase-γ chain | ATPsyn-γ |

TABLE 1B

Lygus hesperus novel targets in Lh594 pathway

| Target ID | Best Drosophila hit(s) | NAME | SYMBOL |
|---|---|---|---|
| Lh619 | CG7107 | troponin T (upheld) | up |
| Lh620 | CG17927 | myosin heavy chain | Mhc |
| Lh621 | CG4843 | tropomyosin2 (Tm2) | Tm2 |
| Lh622 | CG3201 | myosin light chain cytoplasmic | Mlc-c |
| Lh623 | CG3595 | spaghetti squash | sqh |
| Lh624 | CG15792 | zipper | zip |
| Lh625 | *CG2981, CG7930, CG9073, CG6514, CG12408 | troponin C | |
| Lh626 | *CG9073, CG7930, CG2981, CG12408, CG6514 | troponin C | |

*unclear: multiple hits in family—ranked according e-value

TABLE 1C

Lygus hesperus novel targets ranked in % mortality according to the second confirmation assay results (second screen).

| Target ID | Best rank 2nd confirmation | Drosophila hit | NAME | SYMBOL |
|---|---|---|---|---|
| Lh631 | 1 | CG6846 | Ribosomal protein L26 | RpL26 |
| Lh634.2 | 2 | CG12775 | Ribosomal protein L21 | RpL21 |
| Lh634.1 | 3 | CG12775 | Ribosomal protein L21 | RpL21 |
| Lh630 | 4 | CG11271 | Ribosomal protein S12 | RpS12 |
| Lh632 | 5 | CG2998 | Ribosomal protein S28b | RpS28b |
| Lh618.2 | 6 | CG2168 | Ribosomal protein S3A | RpS3A |
| Lh629 | 7 | CG4651 | Ribosomal protein L13 | RpL13 |
| Lh633.2 | 8 | CG17521 | Ribosomal protein L10 | RpL10 |
| Lh628 | 9 | CG17489 | Ribosomal protein L5 | RpL5 |
| Lh633 | 10 | CG17521 | Ribosomal protein L10 | RpL10 |
| Lh627 | 11 | CG2033 | Ribosomal protein S15Aa | RpS15A |

1.4. Full Length cDNA Cloning by Race (Rapid Amplification of cDNA Ends)

In order to clone full length cDNA, starting from a known clone of internal fragment from the most potent targets, the 573' RACE kit was used (Roche, Cat. No. 1 734 792; based on Sambrook, J. & Russell, D. M). The standard protocol, described in the Instruction Manual, was followed. Briefly, for a 5' RACE, a target sequence specific antisense primer was designed on the known sequence and used for a first strand cDNA synthesis, using Lygus RNA as template. A tail was added to the first strand cDNA and used as an anchor for the second strand synthesis and amplification of an unknown end portion of the transcript. For a 3' RACE, an oligo dT anchor primer was used for the first strand cDNA synthesis. For the 5' and 3' RACEs, nested primers, specific to the target sequence were used in a second PCR reaction. The PCR fragments were analysed on agarose gel, purified, cloned and sequenced for confirmation.

Full length cDNA sequences corresponding to the targets were assembled in Vector NTi, a fully integrated sequence analysis software package for DNA sequence analysis (Invitrogen).

Example 2 In Vitro Production of Double-Stranded RNAs for Gene Silencing 2.2. Production of dsRNAs Corresponding to the Partial Sequences of the Lygus hesperus Target Genes Double-stranded RNA was synthesized in milligram quantities. First, two separate 5' T7 RNA polymerase promoter templates (a sense template and an antisense template) were generated by PCR. PCRs were designed and carried out so as to produce sense and antisense template polynucleotides, each having the T7 promoter in a different orientation relative to the target sequence to be transcribed.

For each of the target genes, the sense template was generated using a target-specific T7 forward primer and a target-specific reverse primer. The antisense templates were generated using target-specific forward primers and target-specific T7 reverse primers. The sequences of the respective primers for amplifying the sense and antisense templates via PCR for each of the target genes are provided in Table 4. The PCR products were analysed by agarose gel electrophoresis and purified. The resultant T7 sense and antisense templates were mixed and transcribed by the addition of T7 RNA polymerase. The single-stranded RNAs produced by transcription from the templates were allowed to anneal, were treated with DNase and RNase, and were purified by precipitation. The sense strand of the resulting dsRNA produced from each of the target genes is provided in Table 4.

2.2. Survival Analysis Assays for Novel Lygus hesperus Targets

To enable ranking according to potency, in vitro dsRNAs corresponding to the novel targets were synthesized and applied to L. hesperus in 10 days survival analysis bioassays. Briefly, one day old L. hesperus nymphs were placed in 96 well-plates with sucrose seals containing 0.5 µg/µl target dsRNA, supplemented with 5 µg/µl yeast tRNA. The plates were incubated for 3 days under standard Lygus rearing conditions. At day 3, 6 and 8, the diet seals were refreshed with seals containing Lygus diet only. Lh423 (RpL19) was used as positive control and GFP dsRNA and sucrose diet were used as negative controls.

The results from the survival analyses confirmed the data from the first and second confirmation assays. Lh594 was established as a highly potent target, with activity and speed-to-kill stronger than the strong control Lh423.

So far, the Lygus screen for novel targets identified new targets with activities higher or in the range of the positive control Lh423, these include Lh429, Lh594, Lh609, Lh610, Lh611, Lh617 and Lh618. The mortality induced by these targets is show in the FIGS. 3 and 4.

To allow a more precise ranking of the targets according to their activity, dose response concentration analyses were made. The novel targets were tested in in vitro assays, with concentrations ranging from 0.4 to 0.025 µg/µl. Per condition, 24 one day old nymphs were tested in the 96 well-plate set-up, in sucrose diet supplemented with dsRNA and tRNA carrier. The results are presented as % survival over a 10 day experiment (FIGS. 7 to 11) and are summarized in Table 5.

Based on the concentration curve analyses, the targets were ranked by comparison to the bench mark controls Lh423 and Lh105 (Table 5).

TABLE 5

*Lygus* novel targets ranking according to DRCs and compared to bench mark targets Lh423 & Lh105.

| Target ID | Potency expressed as µg/µl dsRNA needed to reach 90% kill at day 7 |
|---|---|
| Lh594 | 0.025 (at day 6) |
| Lh618 | 0.05-0.1 |
| Lh612 | 0.05 |
| Lh615 | 0.05 |
| Lh423 | 0.1 |
| Lh595 | 0.1 |
| Lh560 | 0.1 |
| Lh610 | 0.1 |
| Lh617 | 0.1 |
| Lh105 | 0.2 |
| Lh614 | 0.2 (at day 6) |
| Lh611 | 0.2 |
| Lh596 | 0.3 |
| Lh609 | ND |
| Lh429 | ND |

The potency of Lh594 was further confirmed. This target effect is clearly observed at least one day before the other targets and the bench mark positive control Lh105 and Lh423. Because Lh594 was highly potent, the LD50 was not reached in the standard DRC experiment, with concentration ranging from 0.4 to 0.025 µg/µl dsRNA (FIG. 8), the Lh594 experiment was therefore repeated, including lower concentrations ranging from 0.05 to 0.001 µg/µl dsRNA (FIG. 12). In conclusion, Lh594 activity was observed at concentration as low as 0.0025 µg/µl and about 90% kill (corresponding to about 10% survival) was obtained at day 6 with 0.025 µg dsRNA.

To further explore the potency of Lh594 and the role of tRNA carrier in the RNAi response in *Lygus hesperus*, additional in vitro feeding assays were set up in the absence of carrier tRNA. Lh594, Lh423 (bench mark control) and GFP (negative control) dsRNAs were produced in vitro, using the standard method. The dsRNAs were purified and tested at 5 µg/µl in the absence of tRNA (FIG. 13 A).

In absence of tRNA, targets Lh594 and Lh423, induced high lethality in *Lygus* nymphs. The results from this experiment have been since reproduced. Target dsRNA was able to induce RNAi-by-feeding effects in *Lygus* nymphs in the absence of tRNA.

To investigate the activity of dsRNA at lower concentrations in the absence of carrier tRNA, additional experiments were set up, using decreasing amounts of dsRNA (FIG. 13 B).

A similar approach was followed for the *lygus* targets that were identified in the second screen. To allow a ranking of the targets according to their activity, dose response concentration analyses were made. The novel targets were tested in in vitro assays, with concentrations ranging from 0.5 to 0.05 µg/µl. Per condition, 24 one day old nymphs were tested in the 96 well-plate set-up, in sucrose diet supplemented with dsRNA and tRNA carrier. The results are presented as % survival over a 9 day experiment (FIGS. 17 A-D). Lh594 and Lh423 have been included in the assay as a reference targets. The results are summarized in Table 6.

Based on the concentration curve analyses, the targets were ranked by comparison to the bench mark control Lh423.

TABLE 6

*Lygus* novel targets from second screen-ranking according to DRCs and compared to bench mark targets Lh423 & Lh594.

| Target ID | Potency expressed as µg/µl dsRNA needed to reach 90% kill at day 7 |
|---|---|
| Lh594 | 0.025 (at day 6) |
| Lh634 | 0.1 |
| Lh423 | 0.1 |
| Lh631 | 0.4 |
| Lh633 | 0.4 |
| Lh627 | 0.5 |
| Lh628 | 0.5 |
| Lh630 | 0.5 |
| Lh632 | 0.5 |
| Lh629 | ND |

Example 3 Troponin Pathway Screen

To enable testing of the Troponin pathway targets, in vitro produced dsRNAs corresponding to Lh619, Lh620, Lh621, Lh622, Lh623, Lh624, Lh625 and Lh626 were synthesized and applied to *L. hesperus* in 10 days survival analysis bioassays. Briefly, one day old *L. hesperus* nymphs were placed in 96 well-plates with sucrose seals containing 0.5 µg/µl target dsRNA, supplemented with 5 µg/µl yeast tRNA. The plates were incubated for 3 days under standard *Lygus* rearing conditions. At day 3, 6 and 8, the diet seals were refreshed with seals containing *Lygus* diet only. Lh594 (Troponin I) was used as positive control and GFP dsRNA and sucrose diet were used as negative controls (FIG. 15). Four targets were then included in dose response curve analyses in an in vitro assay, with concentrations ranging from 0.4 to 0.025 µg/µl. Per condition, 24 one day old nymphs were tested in the 96 well-plate set-up, in sucrose diet supplemented with dsRNA and tRNA carrier. The results are presented as % survival over a 10 day experiment (FIGS. 16 A-B).

Example 4 Generation of Plants Resistant to Insect Pest Species 4.1. Assembly of Plant Expression Vectors Comprising a *Lygus hesperus* Hairpin Sequence for Transformation of Potato or Cotton Since the mechanism of RNA interference operates through dsRNA fragments, the target polynucleotide sequences were cloned in anti-sense and sense orientation, separated by a spacer (SEQ ID NO 98: CTCGAGCCTGAGAGAAAAGCATGAAGTATACCCATAACTAACCCATTAGTTATGCATTTATGTTAT ATCTATTCATGCTTCTACTTTAGATAATCAATCACCAAACAATGAGAATCTCAACGGTCGCAATAA TGTTCATGAAAATGTAGTGTGTACACTTACCTTCTAGA, or SEQ ID NO 385: TCTAGAAGGTAAGTGTACACACTACATTTTCATGAACATTATTGCGACCGTTGAGATTCTCATTGT TTGGTGATTGATTATCTAAAGTAGAAGCATGAATAGATATAACATAAACTAGTAACTAATGGGTTA GTTATGGGTATACTTCATGCTTTTCTCTCAGGCTCGAG), to form a dsRNA hairpin construct. The dsRNA hairpin constructs encoding the *L. hesperus* dsRNA molecules derived from the target genes as mentioned herein were subcloned into a plant expression vector. Similarly a GUS dsRNA hairpin control construct, wherein the sense polynucleotide sequence encoding GUS (SEQ ID NO 97: CCAGCGTATCGTGCTGCGTTTCGATGCGGTCACT-CATTACGGCAAAGTGTGATGGAGCATCAGG GCG-GCTATACGCCATTTGAAGCCGATGTCACGCCGTAT-GTTATTGCCGGGAAAAGTGTACGTAT CTGAAATCAAAAAACTCGACGGCCTGTGGGCAT-TCAGTCTGGATCGCGAAAACTGTGGAATTGAT CCAGCGCCGTCGTCGGTGAACAGGTATG-GAATTTCGCCGATTTTGCGACCTCGCAAGGCATATT CGGGTGAAGGTTATCTCTATGAACTGTGCGTCACA-GCCAAAAGCCAGACAGAGT) was cloned in anti-sense and sense orientation, separated by the same intron (SEQ ID NO 98 or SEQ ID NO 385), was subcloned into a plant expression vector.

The plant expression vector comprises as well elements necessary for the maintenance of the plasmid in a bacterial cell. The dsRNA hairpin construct is located between the left border (LB) and right border (RB), 3' downstream from the Cauliflower Mosaic Virus 35S promoter (P35S) and 5' upstream from the TNOS terminator. A GFP reporter expression cassette comprising the GFP sequence flanked by the P35S promoter and terminator was subcloned into the plant transformation vector harbouring the *L. hesperus* hairpin cassette. The NPT II expression cassette comprising the NPT II sequence flanked by the P35S promoter and terminator is used for selecting plants that have been effectively transformed. Correct assembly of the genetic fragments in the plant expression vector was confirmed by sequencing (FIG. 5).

The plant expression vectors comprising the individual *L. hesperus* target hairpins were subsequently transformed into *Agrobacterium tumefaciens*. For all *L. hesperus* target genes mentioned herein, fragments can be selected and cloned as hairpins in a similar manner.

4.2. Transformation of Potato with a Plant Expression Vector Comprising a *Lygus hesperus* Hairpin Sequence and Testing of the Transformed Potato Plants for Resistance Towards *L. hesperus*

The example provided below is an exemplification of the finding that transgenic potato plants expressing target gene-specific hairpin RNAs adversely affect survival and/or development of insect pest species.

*Lygus hesperus* RNAi-by-Feeding In Planta

Following the positive results obtained in the dsRNA feeding experiments in *L. hesperus*, proof-of-principle in planta experiments were performed.

The in planta assay was developed with in vitro potato plantlets which can sustain insect survival at least 8 days, keeping background mortality low. *L. hesperus* nymphs survive and feed on wild type potato plantlets. This is supported by the visual damage caused by insects which can be observed on the leaves and buds (FIG. 6).

In the assay, *L. hesperus* is fed with transgenic potato, expressing hairpin dsRNA targeting the *L. hesperus* targets identified herein. Plasmids carrying hairpin constructs and a GUS control were generated.

The plantlets were analysed by PCR to confirm the integration of the T-DNA and the presence of the hairpin, before being propagated. Excess explants were produced with the aim of obtaining at least 30 independent events for each construct.

Potato Transformation

Stably transformed potato plants were obtained using an adapted protocol received through Julie Gilbert at the NSF Potato Genome Project (www.potatogenome.org). Stem internode explants of potato 'Line V' (originally obtained from the Laboratory of Plant Breeding at PRI Wageningen, the Netherlands) which is derived from the susceptible diploid *Solanum tuberosum* 6487-9 were used as starting material for transformation. In vitro-derived explants were inoculated with *Agrobacterium tumefaciens* $C58C_1Rif^R$ containing the hairpin constructs. After three days co-cultivation, the explants were put onto a selective medium containing 100 mg/L Kanamycin and 300 mg/L Timentin. After 6 weeks post-transformation, the first putative shoots were removed and rooted on selective medium. Shoots originating from different explants were treated as independent events, shoots originating from the same callus were termed 'siblings' until their clonal status can be verified by Southern blotting, and nodal cuttings of a shoot were referred to as 'clones'.

The transgenic status of the rooting shoots was checked either by GFP fluorescence or by plus/minus PCR for the inserted target sequence. Positive shoots were then clonally propagated in tissue culture to ensure enough replicates were available for the *Lygus hesperus* assays. These shoots were either kept in tissue culture medium or transferred to soil allowing for greater flexibility to test for resistance towards *L. hesperus* nymphs/adults. The first plants were available to test fourteen weeks post transformation.

Bioassay

Young transgenic potato plants were either kept in tissue culture medium or were grown in soil in a plant growth room chamber with the following conditions: 25±1° C., 50±5% relative humidity, 16:8 hour light:dark photoperiod. Per construct, a number of events (for example, twenty) were generated with a suitable number of clones (for example, ten) per event. A number of young *Lygus* nymphs/adults were placed on the individually caged young (for example, at the 4-5 unfolded leaf stage) potato plants and left for at least seven days before assessing resistance towards *Lygus hesperus* in terms of reduced nymph/larva/adult survival, delayed development and stunted growth, and/or decreased plant feeding damage.

The feasibility of in planta RNAi for crop protection against *Lygus* was tested in an assay using transgenic potatoes expressing hairpins corresponding to *Lygus* target genes. Table 7 summarizes the numbers of transgenic potatoes generated and tested. Transgenic events were generated with hairpins corresponding to *Lygus* targets Lh423 (the hairpin sequence for Lh423 is represented in SEQ ID NO 402; the sense sequence of target Lh423 is represented in SEQ ID NO 101) and Lh594 (the hairpin sequence for Lh594 is represented in SEQ ID NO 401; the sense sequence of target Lh594 is represented in SEQ ID NO 2), and GUS as control (the hairpin sequence for GUS is represented in SEQ ID NO 403; the sense sequence of GUS is represented in SEQ ID NO 97). In this assay SEQ ID NO 385 was used as intron.

TABLE 7

| Gene | Construct | Nr of events | Nr of plantlets | Transformation line |
|---|---|---|---|---|
| GUS | pGCC121 | 46 | 20 × 2 | P001 |
| Lh423 | pGCC133 | 28 | 20 × 30 | P006 |
| Lh594 | pGCC135 | 25 | 20 × 30 | P007 |
| Wild type | — | | 20 | |

The plantlets were propagated first in boxes then in individual pots, containing MS rooting medium (4.4 g/L MS salts & vitamins, 30 g/L sucrose, 10 g/L Gelrite, pH 5.7), in preparation for the *Lygus* feeding assays. Two independent GUS events were selected from 8 independent events tested in 2 independent experiments (FIG. 18 A-B). In the assay, 20-30 transgenic plants of the same event, each planted in a separate pot, were tested and compared to WT plantlets. For the transgenic lines carrying the Lh423 and Lh594 hairpins, 28 and 25 independent events were tested respectively and for each independent transgenic event 20 to 30 plantlets, each planted in a separate pot were tested (FIG. 6).

As expected in primary transformants, a range of activity was observed for the 28 independent Lh423 transgenic events (FIG. 19); 6 independent P006 events induced above 60% lethality at day 9 and in one event, lethality reached 80% at day 9 (FIG. 20).

As expected in primary transformants and as seen for the Lh423 primary transformants, a range of activity was also observed for the 25 independent Lh594 transgenic events (FIG. 21); 6 independent P007 events induced above 60% lethality at day 9 and in one event, lethality reached 80% at day 9 (FIG. 22). In addition, growth delays and stunting were clearly observed in the survivor insects.

Results from pRT-PCR on Plants Fed Lygus

To prove that the observed decrease in survival of Lygus feeding on transgenic potato plantlets expressing hairpins directed against endogenous genes was a true RNAi response, the level of down-regulation of the target mRNA (Lh423) was measured by quantitative real time PCR (qRT-PCR).

Insects were allowed to feed on 3 events carrying the Lh423 hairpin (P006/59, /22 and /29) and on one event carrying GUS hairpin control (P001/28) as control. The insects were collected after 5 days and were immediately frozen in liquid nitrogen. Total RNA was extracted from 5 pools of 5 insects using TRI reagent and according to the manufacturer's instructions (SIGMA). After treatment with DNaseI (Promega) to remove the genomic DNA followed by phenol-chloroform extraction and ethanol precipitation, precipitated RNAs were dissolved in water. For each sample, 1 µg RNA was reverse transcribed with a mix of random hexamers and anchored oligo dT primers. qRT-PCR PCR was performed on the BioRad I-Cycler, using iQ SYBR Green Supermix (Biorad) and using the manufacture's recommended conditions. The qRT-PCR primers (Table 8) were designed using Beacon Design; to avoid PCR artifacts foreseeable in presence of the plant expressed dsRNA ingested by the insects, the primer sequences were located 3' of the dsRNA sequence. The GeNorm algorithm was used to normalize the level of target mRNA using 2 house-keeping genes, Lh425 (SDHAand) and Lh427 (rpl 11).

In the control, GUS transgenics, no down-regulation of the insect Lh423 endogenous target mRNA was observed. But the results clearly showed a down-regulation of the endogenous Lygus Lh423 mRNA corresponding to the dsRNA ingested by the animals fed on 3 different events of Lh423 transgenics plants (FIG. 23).

4.3. Transformation of Cotton with a Plant Expression Vector Comprising a Lygus hesperus Hairpin Sequence and Testing of the Transformed Cotton Callus Material or Plants for Resistance Towards L. hesperus The example provided below is an exemplification of the finding that transgenic cotton plants or callus expressing target gene-specific hairpin RNAs adversely affect survival and/or development of insect pest species.

Cotton Transformation

Coker 312 seed is surface sterilized using first, a 5 minute wash in 70% ethanol and then shaking in a 20% bleach (Clorox Co. USA, 1% available chlorine) solution plus 10 drops of the non-ionic detergent, Tween® 20, per liter. The seed is then rinsed 3 times in sterile distilled water before blotting dry on sterile filter papers. The sterile seed is germinated on Germination (SG) medium for 4-6 days, and at this point the hypocotyls are harvested and cut into 0.5 cm lengths ready for Agrobacterium inoculation. The cut sections are placed on sterile filter papers overlaying a Murashige and Skoog based medium containing no phytohormones. The explants are incubated on a 16:8 hours day:night cycle at 28° C.+/−2° C. for 3 days prior to inoculation.

For the inoculation, an Agrobacterium tumefaciens liquid LB culture (10 ml), strain GV3101 (pMP90) Gent$^R$ or strain LBA4404 containing the RNA hairpin target of choice and a hygromycin resistance encoding plant selection cassette, is grown up overnight and 5 ml used to inoculate a 100 ml culture the evening prior to the inoculation. The culture is spun down, resuspended and diluted to an OD600 of 0.15 in the bacterial dilution medium.

The hypocotyl segments are inoculated with the Agrobacterium suspension for 5 minutes. After this the explants are blotted onto sterile filter paper to remove the excess bacterial suspension. The explants are incubated in the dark on Cotton Co-cultivation Medium (CCM) for 48 hours. The explants are then placed on Selective Callus Induction Medium (SCIM) containing 10 mg/l Hygromycin and 500 mg/l Cefotaxime and including the phytohormones 2,4-dichlorophenoxyacetic acid (0.1 µg/ml) and kinetin (0.1 µg/ml). After 4-6 weeks the first resistant calli are observed, and these can be removed to fresh SCIM and further amplified for molecular assessment and insect bioassays. Plates are refreshed every 4-6 weeks to maintain nutrients and antibiotic selection.

Calli that are shown to give a positive result in the insect feeding bioassay are chosen for regeneration and callus is transferred to non-selective medium for the maturation of the somatic embryos, the recipe is based on the publication of Trolinder and Goodin, 1986. Once the embryos have reached 4 mm in length and have differentiated cotyledons and radicles (2-3 months after transfer to maturation medium), they can be transferred Elongation Rooting Medium. This consists of sterilized vermiculite in large test tubes soaked with a Stewart & Hsu (1977) based liquid medium supplemented with kinetin, giberellic acid both added at the final concentration of 0.1 mg/l. The embryos are incubated at 28° C. in a 16:8 day/night cycle, and once they reach the 2-3 leaf stage the plantlets can be hardened off in pots of vermiculite enclosed in a propagator to maintain humidity. Once the plants are fully hardened (4-6 true leaf stage) they can be potted into a 50:50 peat:loam mix and grown in a 14:10 light cycle at 30/20° C. day/night.

Bioassay

L. hesperus nymphs are placed in a Petri dish containing undifferentiated cotton callus tissue expressing target hairpin RNA. Per construct, a number of transformed cotton calli are generated and tested in a feeding bioassay for reduced nymph/adult survival and/or delayed development and stunted growth. Transgenic calli not expressing L. hesperus target hairpin RNA gene fragment serve as a negative control. Furthermore, young regenerated cotton plants from transgenic calli are grown in soil in a plant growth room chamber with the following conditions: 30/20° C. day/night, 50±5% relative humidity, 14:10 hour light:dark photoperiod. Per construct, a number of events (for example, twenty) are generated. A number of young L. hesperus nymphs/adults are placed on the individually caged young (for example, at the 4-5 unfolded leaf stage) plants and left for at least seven days before assessing resistance towards L. hesperus in terms of reduced nymph/adult survival, delayed development and stunted growth, and/or decreased plant feeding damage. Cotton plants not transformed with the *L. hesperus* target hairpin RNA gene fragment serve as a negative control.

Example 5 Identification of Target Genes in *Leptinotarsa decemlineata*

5.1. *Leptinotarsa decemlineata* Normalized cDNA Library and Preparation of dsRNAs in Multiwell Plates for the Screening Assays Nucleic acids were isolated from *Leptinotarsa decemlineata* larvae of different stages. A cDNA library was prepared using the SMARTer™ PCR cDNA Synthesis Kit, following the manufacturer's instructions (Clontech Cat. No 634925). The cDNA library was normalized using the Trimmer kit (Evrogen Cat No NK001) and cloned in the PCR®-BLUNTII-TOPO® vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of *Escherichia coli* strain TOP10 (Invitrogen). The transformed cells were subsequently diluted and plated so as to obtain single colonies or clones. The clones were checked to ensure that clone redundancy for the library did not exceed 5%. Single clones were inoculated into liquid LB (Luria-broth) media, in 96-well plates, and grown overnight at 37° C. The plates also included positive (Ld513) and negative (FP) control clones.

To generate the dsRNA, sense and antisense DNA fragments, containing T7 promoter sequence, were generated by PCR. In brief, per clone, 1 μl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAGGAAGCAGTGGTATCAACGCAG) based on the M2 and the T7-M2 sequences, respectively. The PCR reaction was followed by in vitro transcription, where, per clone, 6 PCR product was used in a 20 μl reaction volume containing the transcription reagents provided by the RiboMAX™ Large Scale RNA Production System—T7 kit (Promega Cat No P1300) and incubated overnight at 37° C. The final dsRNA solution was diluted in sterile Milli-Q water and used for screening. The dsRNA corresponding to the positive Ld513 control clone is SEQ ID NO 400 (see Table 11) and to the negative FP control clone is SEQ ID NO 104 (see Table 4).

5.2. Screen for Novel and Potent *Leptinotarsa decemlineata* Target Genes Using a dsRNA Expression cDNA Library Each well of a 48-well plate contained 0.5 mL artificial diet pretreated with a topical overlay of 25 μl (or 1 μg) of the test or control dsRNA. One L2 larva was placed in each well and 3 larvae were tested per clone. CPB survival numbers were assessed at days 4, 7 and 10.

In a second bioassay, CPB larvae were fed on diet treated with topically applied test dsRNA generated from clones derived from a normalized cDNA library. One larva was placed in a well of a 48-well multiplate containing 0.5 mL diet pretreated with a topical overlay of 25 μL of a 40 ng/μL dsRNA solution. A total of twenty-four larvae were tested per treatment (clone). The number of surviving insects were assessed at days 4, 5, 6, 7, 8 & 11. The larval mortality percentage was calculated relative to day 0 (start of assay) (see FIG. 29).

5.3. Identification of *L. decemlineata* Beetle Targets

The new target sequences from the screen in 5.2. and the target sequences corresponding to the troponin pathway targets, orthologuous to the *Lygus* Lh594, Lh619 and Lh620 sequences, have been identified in *L. decemlineata*. The primers which provided relevant cDNA fragment for Ld594 are listed in Table 19. The cDNA sequences and deduced amino acid sequences of these target genes were determined and are provided in Tables 9 and 10 respectively.

5.4. Production of ds RNAs Corresponding to the Partial Sequences of the *L. Decemlineata* Target Genes dsRNA was synthesized using the primers as provided in Table 11. The sense strand of the resulting dsRNA produced from the target genes is provided in Table 11.

5.5. Survival Analysis Assays for Novel *L. decemlineata* Targets

Early Larval Assay

Synthetic dsRNAs were produced for the 3 targets, Ld594, Ld619 and Ld620, and were tested in a feeding assay on CPB larvae (see FIG. 24). A 10 day assay was performed in 48 well plates, on artificial diet (based on Gelman et al, J Ins Sc, 1:7, 1-10: Artificial diets for rearing the Colorado Potato Beetle), supplemented with 1 μg dsRNA/well, with 12 larvae per condition.

A clear effect on the development of the larvae could be observed. A second assay was set up to investigate the effect of these dsRNAs during the course of pupation and metamorphosis (see pupation assay underneath).

Pupation Assay

A CPB pupation assay was set up to investigate the effect of RNAi knock-down of Ld594, Ld619 and Ld620 during pupation and metamorphosis. Fourth instar larvae were fed 1 μg in vitro synthesized dsRNA dispensed on a potato leaf disk and were then transferred to a box containing untreated fresh potato leaves. Four days later the surviving insects were placed on vermiculite to allow pupation.

Lh594 treated insects were slow, smaller and mostly were unable to go through pupation. The hatching of the pupa was assessed at the end of the experiment. For the untreated control 24 larvae pupated and all hatched into healthy adults. For Ld620, a decrease in numbers of larvae progressing into pupation was observed. For the three targets tested, no larvae progressed into healthy pupae and none emerged into adult. Dead insects recovered from the vermiculite showed various degrees of malformations (FIG. 25).

Ld594, Ld619 and Ld620, first appeared as not lethal targets in the CPB larval assay, although a reduction of vitality was clearly observed in the dsRNA treated insects. On the other hand, in the pupation assay, all 3 targets induced strong effects and inhibited the entry in pupation and/or metamorphosis.

Adult Assay

To assess activity of Ld594, Ld619 and Ld620 in CPB adults, a leaf disc assay was set up. A potato leaf disc (1.7 cm diameter) was painted with dsRNA or controls and was placed in a 3.5 cm Petri dish with one adult beetle. The next day a fresh treated leaf disc was provided to the insects. On the third day, the adults were transferred to a box containing enough fresh, untreated potato leaves to sustain the survival of the untreated controls. Per treatment, 6 adults were tested and the numbers of survivors and moribund insects were counted at regular intervals from day 6 to day 13. The insects were considered moribund if they were unable to right themselves after being placed on their back. Despite the relatively high level of background in the negative control in this particular assay, clear effects were observed for the insects that had been exposed to Ld594 or Ld619 dsRNAs (FIG. 26).

Example 6 Identification of Target Genes in *Nilaparvata lugens*

6.1. Identification of *Nilaparvata lugens* Targets

New target sequences, corresponding to Troponin pathway targets and named Nl594 (Troponin I), Nl619 (Troponin T) and Nl626 (Troponin C) have been identified in brown plant hopper, *Nilaparvata lugens*. Orthologous sequences of the *Lygus* genes, named Nl594 (Troponin I), Nl619 (Troponin T) and Nl625/626 (Troponin C), were cloned through degenerated primer PCR, using BPH cDNA as template. In addition, full length cDNA was identified for Nl594, using RACE (see above for method). AmpliTaq Gold PCR system (Applied Biosystems) was used following the manufactures' instructions and with standard conditions for the degenerate primer PCR reactions, typically as follows: 1 cycle with 10 minutes at 95° C., followed by 40 cycles with 30 seconds at 95° C., 1 minute at 50° C. and 1 minute at 72° C., followed by 10 minutes at 72° C. To increase the rate of success, up to 10 different degenerated primers, forward and reverse, were designed, based on alignments of orthologous sequences in other species, and used in various combinations. PCR fragments obtained were purified from the gel by gel extraction kit (Qiagen Cat. No 28706) and cloned into a TOPO TA vector (Invitrogen). The clones were sequenced and the consensus sequences were used in Blast searches against various available insect sequence databases to confirm the relevance of the insert. The degenerated primers that resulted in successful amplification are listed in Table 20. The DNA sequences and deduced amino acid sequences of these target genes and one other target gene (Nl537) were determined and are provided in Tables 12 and 13 respectively.

6.2. Production of dsRNAs Corresponding to the Partial Sequences of the *Nilaparvata lugens* Target Genes dsRNA was synthesized using the primers as provided in Table 14. The sense strand of the resulting dsRNA produced from each of the target genes is provided in Table 14.

6.3. Survival Analysis Assays for Novel *Nilaparvata lugens* Targets dsRNAs were synthesized and tested in the previously optimized BPH RNAi-by-feeding assays, in the presence of the zwitterionic detergent, CHAPSO, at 0.1% final concentration. The dsRNAs were tested at 0.5 µg/µl final concentration. Nl537, a potent target in the BPH assays was used as bench mark target in the assay. The insect survival was assessed over the course of 9 days. The results of the bioassay showed that in BPH Nl594, Nl619 and Nl626 were also potent RNAi targets in BPH (FIG. 27).

Example 7 Identification of Target Genes in *Acyrthosiphon pisum*

7.1 Identification of *Acyrthosiphon pisum* Targets

New target sequences have been identified in aphids and were named Ap423, Ap537, Ap560 and Ap594, following the same nomenclature: "Apxxx", where "Ap" corresponds to *Acyrthosiphon pisum* and "xxx" to the ID of the target. Primers were designed based on public domain gene prediction in AphidBase (ref: www.aphidbase.com (Table 15).

The DNA sequences and deduced amino acid sequences of these target genes were determined and are provided in Tables 16 and 17 respectively.

7.2 Production of dsRNAs Corresponding to the Partial Sequences of the Aphid Target Genes dsRNA was synthesized using the primers as provided in Table 18. The sense strand of the resulting dsRNA produced from each of the target genes is provided in Table 18.

7.3 Survival Analysis Assays for Novel Aphid Targets

RNAi-by-feeding was tested in *Acyrthosiphon pisum* (pea aphid) with 4 targets Ap594, Ap423, Ap560, Ap537. The sequences were amplified by PCR using primers, designed on public domain sequence information (www.aphidbase.com), and cDNA prepared from aphids. The synthetic dsRNAs were prepared and tested at a final concentration of 0.5 µg/µl in presence of 5 µg/µl yeast tRNA in a sucrose diet. Ten neonate pea aphid nymphs were placed in a small Petri dish (32 mm). Fifty µl diet (with tRNA and dsRNA) was pipetted on top of the first layer of parafilm. A second layer of parafilm covered the diet and created a feeding sachet where the aphids could feed. Per target five replicates of 10 neonate nymphs were set-up. GFP dsRNA was used as a negative control. The diet was refreshed on day 4 and 7 of the assays and survival was assessed (FIG. 28).

TABLE 2

| Target ID | cDNA Sequence (sense strand) 5' → 3' |
|---|---|
| Lh594 | SEQ ID NO 1 |
| Lh609 | SEQ ID NO 3 |
| Lh610 | SEQ ID NO 5 |
| Lh610 (b) | SEQ ID NO 139 |
| Lh611 | SEQ ID NO 7 |
| Lh611 (b) | SEQ ID NO 140 |
| Lh617 | SEQ ID NO 9 |
| Lh618 | SEQ ID NO 11 |
| Lh618 (b) | SEQ ID NO 141 |
| Lh429 | SEQ ID NO 13 |
| Lh423 | SEQ ID NO 95 |
| Lh105.2 | SEQ ID NO 96 |
| Lh560 | SEQ ID NO 15 |
| Lh615 | SEQ ID NO 17 |
| Lh612 | SEQ ID NO 19 |
| Lh246 | SEQ ID NO 21 |
| Lh597 | SEQ ID NO 23 |
| Lh598 | SEQ ID NO 25 |
| Lh619 | SEQ ID NO 121 |
| Lh619 (b) | SEQ ID NO 142 |
| Lh619 (c) | SEQ ID NO 143 |
| Lh620 | SEQ ID NO 122 |
| Lh620 (b) | SEQ ID NO 144 |
| Lh620 (c) | SEQ ID NO 145 |
| Lh621 | SEQ ID NO 123 |
| Lh622 | SEQ ID NO 124 |
| Lh623 | SEQ ID NO 125 |
| Lh623 (b) | SEQ ID NO 146 |
| Lh624 | SEQ ID NO 126 |
| Lh624 (b) | SEQ ID NO 147 |
| Lh625 | SEQ ID NO 127 |
| Lh625 (b) | SEQ ID NO 148 |
| Lh626 | SEQ ID NO 128 |
| Lh626 (b) | SEQ ID NO 149 |
| Lh614 | SEQ ID NO 129 |
| Lh627 | SEQ ID NO 150 |
| Lh628 | SEQ ID NO 152 |
| Lh629 | SEQ ID NO 154 |
| Lh630 | SEQ ID NO 156 |
| Lh631 | SEQ ID NO 158 |
| Lh632 | SEQ ID NO 160 |
| Lh633.1 | SEQ ID NO 162 |
| Lh633.2 | SEQ ID NO 163 |
| Lh634.1 | SEQ ID NO 165 |
| Lh634.2 | SEQ ID NO 167 |
| Lh595.1 | SEQ ID NO 168 |
| Lh595.2 | SEQ ID NO 170 |
| Lh596 | SEQ ID NO 172 |

TABLE 3

| Target ID | Corresponding amino acid sequence of cDNA clone as represented in Table 2 |
|---|---|
| Lh594 | SEQ ID NO 79 |
| Lh609 | SEQ ID NO 80 |
| Lh610 | SEQ ID NO 81 |
| Lh610 (b) | SEQ ID NO 326 |
| Lh611 | SEQ ID NO 82 |
| Lh611 (b) | SEQ ID NO 327 |
| Lh617 | SEQ ID NO 83 |
| Lh618 | SEQ ID NO 84 |
| Lh618 (b) | SEQ ID NO 328 |
| Lh429 | SEQ ID NO 85 |
| Lh429 (b) | SEQ ID NO 329 |
| Lh423 | SEQ ID NO 99 |
| Lh105.2 | SEQ ID NO 100 |
| Lh560 | SEQ ID NO 86 |
| Lh615 | SEQ ID NO 87 |
| Lh612 | SEQ ID NO 88 |
| Lh246 | SEQ ID NO 89 |
| Lh597 | SEQ ID NO 90 |
| Lh598 | SEQ ID NO 91 |
| Lh619 | SEQ ID NO 330 |
| Lh620 | SEQ ID NO 331 |
| Lh621 | SEQ ID NO 332 |
| Lh622 | SEQ ID NO 333 |
| Lh623 | SEQ ID NO 334 |
| Lh624 | SEQ ID NO 335 |
| Lh625 | SEQ ID NO 336 |
| Lh626 | SEQ ID NO 337 |
| Lh614 | SEQ ID NO 338 |
| Lh627 | SEQ ID NO 339 |
| Lh628 | SEQ ID NO 340 |
| Lh629 | SEQ ID NO 341 |
| Lh630 | SEQ ID NO 342 |
| Lh631 | SEQ ID NO 343 |
| Lh632 | SEQ ID NO 344 |
| Lh633.1 | SEQ ID NO 345 |
| Lh633.2 | SEQ ID NO 346 |
| Lh634.1 | SEQ ID NO 347 |
| Lh634.2 | SEQ ID NO 348 |

TABLE 4

| Target ID | Primers Forward 5' → 3' | Primers Reverse 5' → 3' | dsRNA: sense strand represented by equivalent DNA Sequence 5' → 3' |
|---|---|---|---|
| Lh594 | SEQ ID NO 27<br>SEQ ID NO 29 | SEQ ID NO 28<br>SEQ ID NO 30 | SEQ ID NO 2 |
| Lh609 | SEQ ID NO 31<br>SEQ ID NO 33 | SEQ ID NO 32<br>SEQ ID NO 34 | SEQ ID NO 4 |
| Lh610 | SEQ ID NO 35<br>SEQ ID NO 37 | SEQ ID NO 36<br>SEQ ID NO 38 | SEQ ID NO 6 |
| Lh611 | SEQ ID NO 39<br>SEQ ID NO 41 | SEQ ID NO 40<br>SEQ ID NO 42 | SEQ ID NO 8 |
| Lh617 | SEQ ID NO 43<br>SEQ ID NO 45 | SEQ ID NO 44<br>SEQ ID NO 46 | SEQ ID NO 10 |
| Lh618 | SEQ ID NO 47<br>SEQ ID NO 49 | SEQ ID NO 48<br>SEQ ID NO 50 | SEQ ID NO 12 |
| Lh429 | SEQ ID NO 51<br>SEQ ID NO 53 | SEQ ID NO 52<br>SEQ ID NO 54 | SEQ ID NO 14 |
| Lh423 | SEQ ID NO 105<br>SEQ ID NO 107 | SEQ ID NO 106<br>SEQ ID NO 108 | SEQ ID NO 101 |
| Lh105.2 | SEQ ID NO 109<br>SEQ ID NO 111 | SEQ ID NO 110<br>SEQ ID NO 112 | SEQ ID NO 102 |
| GFP | SEQ ID NO 113<br>SEQ ID NO 115 | SEQ ID NO 114<br>SEQ ID NO 116 | SEQ ID NO 103 |
| Pt | SEQ ID NO 117<br>SEQ ID NO 119 | SEQ ID NO 118<br>SEQ ID NO 120 | SEQ ID NO 104 |
| Lh560 | SEQ ID NO 55<br>SEQ ID NO 57 | SEQ ID NO 56<br>SEQ ID NO 58 | SEQ ID NO 16 |
| Lh615 | SEQ ID NO 59<br>SEQ ID NO 61 | SEQ ID NO 60<br>SEQ ID NO 62 | SEQ ID NO 18 |
| Lh612 | SEQ ID NO 63<br>SEQ ID NO 65 | SEQ ID NO 64<br>SEQ ID NO 66 | SEQ ID NO 20 |
| Lh246 | SEQ ID NO 67<br>SEQ ID NO 69 | SEQ ID NO 68<br>SEQ ID NO 70 | SEQ ID NO 22 |
| Lh597 | SEQ ID NO 71<br>SEQ ID NO 73 | SEQ ID NO 72<br>SEQ ID NO 74 | SEQ ID NO 24 |
| Lh598 | SEQ ID NO 75<br>SEQ ID NO 77 | SEQ ID NO 76<br>SEQ ID NO 78 | SEQ ID NO 26 |
| Lh619 | SEQ ID NO 206<br>SEQ ID NO 208 | SEQ ID NO 207<br>SEQ ID NO 209 | SEQ ID NO 130 |
| Lh620 | SEQ ID NO 210<br>SEQ ID NO 212 | SEQ ID NO 211<br>SEQ ID NO 213 | SEQ ID NO 131 |
| Lh621 | SEQ ID NO 214<br>SEQ ID NO 216 | SEQ ID NO 215<br>SEQ ID NO 217 | SEQ ID NO 132 |
| Lh622 | SEQ ID NO 218<br>SEQ ID NO 220 | SEQ ID NO 219<br>SEQ ID NO 221 | SEQ ID NO 133 |
| Lh623 | SEQ ID NO 222<br>SEQ ID NO 224 | SEQ ID NO 223<br>SEQ ID NO 225 | SEQ ID NO 134 |
| Lh624 | SEQ ID NO 226<br>SEQ ID NO 228 | SEQ ID NO 227<br>SEQ ID NO 229 | SEQ ID NO 135 |
| Lh625 | SEQ ID NO 230<br>SEQ ID NO 232 | SEQ ID NO 231<br>SEQ ID NO 233 | SEQ ID NO 136 |
| Lh626 | SEQ ID NO 234<br>SEQ ID NO 236 | SEQ ID NO 235<br>SEQ ID NO 237 | SEQ ID NO 137 |
| Lh614 | SEQ ID NO 238<br>SEQ ID NO 240 | SEQ ID NO 239<br>SEQ ID NO 241 | SEQ ID NO 138 |
| Lh627 | SEQ ID NO 242<br>SEQ ID NO 244 | SEQ ID NO 243<br>SEQ ID NO 245 | SEQ ID NO 151 |
| Lh628 | SEQ ID NO 246<br>SEQ ID NO 248 | SEQ ID NO 247<br>SEQ ID NO 249 | SEQ ID NO 153 |
| Lh629 | SEQ ID NO 250<br>SEQ ID NO 25 | SEQ ID NO 251<br>SEQ ID NO 253 | SEQ ID NO 155 |
| Lh630 | SEQ ID NO 254<br>SEQ ID NO 256 | SEQ ID NO 255<br>SEQ ID NO 257 | SEQ ID NO 157 |
| Lh631 | SEQ ID NO 258<br>SEQ ID NO 260 | SEQ ID NO 259<br>SEQ ID NO 261 | SEQ ID NO 159 |
| Lh632 | SEQ ID NO 262<br>SEQ ID NO 264 | SEQ ID NO 263<br>SEQ ID NO 265 | SEQ ID NO 161 |
| Lh633.2 | SEQ ID NO 266<br>SEQ ID NO 268 | SEQ ID NO 267<br>SEQ ID NO 269 | SEQ ID NO 164 |
| Lh634.1 | SEQ ID NO 270<br>SEQ ID NO 272 | SEQ ID NO 271<br>SEQ ID NO 273 | SEQ ID NO 166 |
| Lh595 | SEQ ID NO 274<br>SEQ ID NO 276 | SEQ ID NO 275<br>SEQ ID NO 277 | SEQ ID NO 169 |
| Lh596 | SEQ ID NO 278<br>SEQ ID NO 280 | SEQ ID NO 279<br>SEQ ID NO 281 | SEQ ID NO 173 |

TABLE 8

| Target ID | Primers Forward 5' → 3' | Primers Reverse 5' → 3' | qRT-PCR Amplicon 5' → 3' |
|---|---|---|---|
| Lh423 | SEQ ID NO 360 | SEQ ID NO 361 | SEQ ID 362 |
| Lh425 | SEQ ID 363 | SEQ ID 364 | SEQ ID 365 |
| Lh427 | SEQ ID 366 | SEQ ID 367 | SEQ ID 368 |

TABLE 9

| Target ID | cDNA sequence (sense strand) 5' → 3' |
|---|---|
| Ld594 | SEQ ID NO 174 |
| Ld594(b) | SEQ ID NO 404 |
| Ld619 | SEQ ID NO 176 |
| Ld620 | SEQ ID NO 178 |
| Ld583 | SEQ ID NO 386 |
| Ld584 | SEQ ID NO 387 |
| Ld586 | SEQ ID NO 388 |
| Ld588 | SEQ ID NO 389 |
| Ld513 | SEQ ID NO 394 |

TABLE 10

| Target ID | Corresponding amino acid sequence of cDNA clone as represented in Table 9 |
|---|---|
| Ld594 | SEQ ID NO 349 |
| Ld619 | SEQ ID NO 350 |
| Ld594(b) | SEQ ID NO 405 |
| Ld620 | SEQ ID NO 351 |
| Ld583 | SEQ ID NO 390 |
| Ld584 | SEQ ID NO 391 |
| Ld586 | SEQ ID NO 392 |
| Ld588 | SEQ ID NO 393 |
| Ld513 | SEQ ID NO 395 |

TABLE 11

| Target ID | Primers Forward 5' → 3' | Primers Reverse 5' → 3' | dsRNA: sense strand represented by equivalent DNA Sequence 5' → 3' |
|---|---|---|---|
| Ld594 | SEQ ID NO 282 | SEQ ID NO 283 | SEQ ID NO 175 |
|  | SEQ ID NO 284 | SEQ ID NO 285 |  |
| Ld619 | SEQ ID NO 286 | SEQ ID NO 287 | SEQ ID NO 177 |
|  | SEQ ID NO 288 | SEQ ID NO 289 |  |
| Ld620 | SEQ ID NO 290 | SEQ ID NO 291 | SEQ ID NO 179 |
|  | SEQ ID NO 292 | SEQ ID NO 293 |  |
| Ld513 | SEQ ID NO 396 | SEQ ID NO 397 | SEQ ID NO 400 |
|  | SEQ ID NO 398 | SEQ ID NO 399 |  |

TABLE 12

| Target ID | cDNA Sequence (sense strand) 5' → 3' |
|---|---|
| Nl594 | SEQ ID NO 180 |
| Nl619 | SEQ ID NO 182 |
| Nl626 | SEQ ID NO 184 |
| Nl537 | SEQ ID NO 186 |

TABLE 13

| Target ID | Corresponding amino acid sequence of cDNA clone as represented in Table 12 |
|---|---|
| Nl594 | SEQ ID NO 352 |
| Nl619 | SEQ ID NO 353 |
| Nl626 | SEQ ID NO 354 |
| Nl537 | SEQ ID NO 355 |

TABLE 14

| Target ID | Primers Forward 5' → 3' | Primers Reverse 5' → 3' | dsRNA: sense strand represented by equivalent DNA Sequence 5' → 3' |
|---|---|---|---|
| Nl594 | SEQ ID NO 294 | SEQ ID NO 295 | SEQ ID NO 181 |
|  | SEQ ID NO 296 | SEQ ID NO 297 |  |
| Nl619 | SEQ ID NO 298 | SEQ ID NO 299 | SEQ ID NO 183 |
|  | SEQ ID NO 300 | SEQ ID NO 301 |  |
| Nl626 | SEQ ID NO 302 | SEQ ID NO 303 | SEQ ID NO 185 |
|  | SEQ ID NO 304 | SEQ ID NO 305 |  |
| Nl537 | SEQ ID NO 306 | SEQ ID NO 307 | SEQ ID NO 187 |
|  | SEQ ID NO 308 | SEQ ID NO 309 |  |

TABLE 15

| Target | Fw primer sequence | Reverse primer sequence |
|---|---|---|
| Ap594 | SEQ ID NO 369 | SEQ ID NO 370 |
| Ap423 | SEQ ID NO 371 | SEQ ID NO 372 |
| Ap537 | SEQ ID NO 373 | SEQ ID NO 374 |
| Ap560 | SEQ ID NO 375 | SEQ ID NO 376 |

TABLE 16

| Target ID | cDNA Sequence (sense strand) 5' → 3' |
|---|---|
| Ap594 | SEQ ID NO 188 |
| Ap423 | SEQ ID NO 200 |
| Ap537 | SEQ ID NO 202 |
| Ap560 | SEQ ID NO 204 |

TABLE 17

| Target ID | Corresponding amino acid sequence of cDNA clone as represented in Table 16 |
|---|---|
| Ap594 | SEQ ID NO 356 |
| Ap423 | SEQ ID NO 357 |
| Ap537 | SEQ ID NO 358 |
| Ap560 | SEQ ID NO 359 |

TABLE 18

| Target ID | Primers Forward 5' → 3' | Primers Reverse 5' → 3' | dsRNA: sense strand represented by equivalent DNA sequence 5' → 3' |
|---|---|---|---|
| Ap594 | SEQ ID NO 310 | SEQ ID NO 311 | SEQ ID NO 189 |
|  | SEQ ID NO 312 | SEQ ID NO 313 |  |
| Ap423 | SEQ ID NO 314 | SEQ ID NO 315 | SEQ ID NO 201 |
|  | SEQ ID NO 316 | SEQ ID NO 317 |  |
| Ap537 | SEQ ID NO 318 | SEQ ID NO 319 | SEQ ID NO 203 |
|  | SEQ ID NO 320 | SEQ ID NO 321 |  |
| Ap560 | SEQ ID NO 322 | SEQ ID NO 323 | SEQ ID NO 205 |
|  | SEQ ID NO 324 | SEQ ID NO 325 |  |

TABLE 19

| Target | Forward primer | Reverse primer |
|---|---|---|
| Ld594 | SEQ ID NO 377 | SEQ ID NO 378 |

TABLE 20

| Target | Forward primer | Reverse primer |
|---|---|---|
| Nl594 | seq id no 379 | seq id no 380 |
| Nl619 | seq id no 381 | seq id no 382 |
| Nl626 | seq id no 383 | seq id no 384 |

TABLE 21

| Target ID | Best Drosophila hit | NAME | SYMBOL |
|---|---|---|---|
| Ld583 | CG4759 | Ribosomal protein L27 | RpL27 |
| Ld584 | CG 17331 | Proteasome, beta-type subunit |  |

TABLE 21-continued

| Target ID | Best *Drosophila* hit | NAME | SYMBOL |
|---|---|---|---|
| Ld586 | CG13704 | unknown | |
| Ld588 | CG4157 | Rpn12 | |

TABLE 22

| Target ID | Best *Drosophila* hit | NAME | SYMBOL |
|---|---|---|---|
| NI594 | CG7178 | wings up A (troponin I) | wupA |
| NI619 | CG7107 | troponin T (upheld) | up |
| NI626 | *CG9073, CG7930, CG2981, CG12408, CG6514, CG2981, CG7930, CG9073, CG6514, CG12408 | troponin C | |
| NI537 | CG32744 | Ubiquitin-5E; protein modification process | |

*unclear: multiple hits in family

TABLE 23

| Target ID | Best *Drosophila* hit | NAME | SYMBOL |
|---|---|---|---|
| Ap594 | CG7178 | wings up A (troponin I) | wupA |
| Ap423 | CG2746 | ribosomal protein L19 | RpL19 |
| Ap537 | CG32744 | Ubiquitin-5E; protein modification process | |
| Ap560 | CG10423 | ribosomal protein S27 | RpS27 |

It will be appreciated by persons skilled in the art that numerous variations and/or modifications may be made to the above mentioned assays without departing from the spirit or scope of this assay as generically described. Those skilled in the art will recognize, or be able to ascertain using no more than routine experimentation, many equivalents to the specific examples, and such equivalents are intended to be encompassed by the present invention. The present example, therefore, is to be considered in all respects as illustrative and not restrictive.

What is claimed is:

1. A transgenic plant, reproductive or propagation material from a transgenic plant, or a cultured plant cell, which comprises a nucleic acid molecule that produces an interfering ribonucleic acid (RNA), wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91 complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

2. The transgenic plant, reproductive or propagation material from a transgenic plant, or cultured transgenic plant cell of claim 1, wherein the interfering RNA comprises at least two silencing elements, wherein each silencing element comprises or consists of a sequence of nucleotides which is at least partially complementary to said troponin I target nucleotide sequence within the target gene.

3. The transgenic plant, reproductive or propagation material from a transgenic plant, or cultured transgenic plant cell of claim 2, wherein each of the silencing elements comprises or consists of a different sequence of nucleotides which is complementary to a different target nucleotide sequence within said troponin I target gene.

4. The transgenic plant, reproductive or propagation material from a transgenic plant, or cultured transgenic plant cell of claim 1, wherein the transgenic plant, material therefrom or plant cell additionally comprises a heterologous gene.

5. The transgenic plant, reproductive or propagation material from a transgenic plant, or cultured transgenic plant cell of claim 4, wherein the heterologous gene encodes a protein toxic to a plant pest species.

6. The transgenic plant, reproductive or propagation material from a transgenic plant, or cultured transgenic plant cell of claim 5, wherein the protein is selected from the group consisting of a patatin, a *Bacillus thuringiensis* insecticidal protein, a Xenorhabdus insecticidal protein, a *Photorhabdus* insecticidal protein, a *Bacillus laterosporus* insecticidal protein, and a *Bacillus sphaericus* insecticidal protein.

7. The transgenic plant, reproductive or propagation material from a transgenic plant, or cultured transgenic plant of claim 6, wherein said *Bacillus thuringiensis* insecticidal protein is selected from the group consisting of a Cry1, a Cry3, and a Cry 22.

8. The transgenic plant, reproductive or propagation material from a transgenic plant, or cultured transgenic plant cell of claim 4, wherein the heterologous gene encodes a protein conferring herbicide tolerance.

9. The transgenic plant, reproductive or propagation material from a transgenic plant, or cultured transgenic plant cell of claim 8, wherein the protein is selected from a glyphosate-insensitive 5-enolpyruvylshikimate-3-phosphate synthase (EPSPS), a dicamba monooxygenase or a phosphinothricin acetyl transferase.

10. Seed produced from the transgenic plant of claim 1, wherein the seed is transgenic and comprises the nucleic acid molecule that produces an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

11. A method for generating a transgenic plant resistant to infestation by *Lygus hesperus* comprising transforming a plant cell with a DNA construct comprising a polynucleotide sequence encoding an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest, and regenerating a transformed plant from said plant cell.

12. A method for generating a transgenic plant of claim 1, comprising transforming a plant cell with a DNA construct comprising a polynucleotide sequence encoding an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

13. The method of claim 11, wherein the method further comprises the steps of generating progeny from the transformed plant and testing the progeny for resistance to a *Lygus hesperus* insect.

14. A method for generating a transgenic plant resistant to infestation by *Lygus hesperus* comprising:
(i) crossing a transgenic plant obtained by the method of claim 11 with a second plant, wherein the second plant is not resistant to infestation by *Lygus hesperus*,
(ii) selecting progeny resistant to said pest.

15. The method of claim 14 further comprising the step of backcrossing the progeny plant that is resistant to infestation by *Lygus hesperus* with the second plant, wherein the second plant is not resistant to infestation by *Lygus hesperus*, and further selecting for progeny resistant to said pest.

16. A method of generating a transgenic plant resistant to infestation by *Lygus hesperus* comprising:
(i) sexually crossing a transgenic plant obtained by the method of claim 11 with a second plant that lacks the resistance to *Lygus hesperus* thereby producing a plurality of progeny plants;
(ii) selecting a first progeny plant that is resistant to *Lygus hesperus*;
(iii) selfing said first progeny plant, thereby producing a plurality of second progeny plants;
(iv) repeated selfing of said progeny for 1, 2, 3, 4, or 5 more generations; and
(v) selecting from any of the progeny plants a plant that is resistant to infestation by *Lygus hesperus*.

17. The method of claim 14, further comprising identifying the insect-resistant progeny by detecting the presence of a polynucleotide encoding an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

18. The method of claim 14, wherein the second plant comprises a heterologous gene.

19. The method of claim 18, wherein the heterologous gene encodes a protein toxic to a plant pest species.

20. The method of claim 19, wherein the protein is selected from the group consisting of a patatin, a *Bacillus thuringiensis* insecticidal protein, a Xenorhabdus insecticidal protein, a *Photorhabdus* insecticidal protein, a *Bacillus laterosporus* insecticidal protein, and a *Bacillus sphaericus* insecticidal protein.

21. The method of claim 20, wherein the *Bacillus thuringiensis* insecticidal protein is selected from the group consisting of a Cry1, a Cry3, and a Cry 22.

22. The method of claim 18, wherein the heterologous gene encodes a protein conferring herbicide tolerance.

23. The method according to claim 11 or claim 20, wherein the plant resistant to infestation by *Lygus hesperus* is selected from the group consisting of cotton, potato, rice, canola, sunflower, sorghum, pearl millet, corn, strawberry, soy, alfalfa, tomato, eggplant, pepper and tobacco.

24. A transgenic plant produced by the method of claim 11.

25. Seed produced by the plant of claim 24, wherein the seed is transgenic and comprises a DNA construct comprising a polynucleotide sequence encoding an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

26. A method for preventing and/or controlling infestation by *Lygus hesperus* in a field of crop plants, said method comprising expressing in said plants an effective amount of an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

27. A host cell comprising a polynucleotide encoding an interfering RNA, wherein the interfering RNA comprises at least one silencing element, wherein the silencing element is a region of double-stranded RNA comprising annealed complementary strands, one strand of which comprises or consists of a sequence of at least 70 contiguous nucleotides that is at least 91% complementary to a fragment of SEQ ID NO: 1 or SEQ ID NO: 2, or a sequence of at least 27 contiguous nucleotides that is complementary to SEQ ID NO: 1 or SEQ ID NO: 2, wherein the interfering RNA down regulates the troponin I gene in a *Lygus hesperus* pest.

28. The host cell of claim 27 wherein the host cell is a prokaryotic or a eukaryotic cell.

29. The host cell of claim 28 wherein the host cell is a bacterial cell or a plant cell.

* * * * *

SEQUENCE LISTING

```
<160> NUMBER OF SEQ ID NOS: 405

<210> SEQ ID NO 1
<211> LENGTH: 1096
<212> TYPE: DNA
<213> ORGANISM: Lygus hesperus

<400> SEQUENCE: 1
gcgatctaag gcaggtggca gacagctcga tgacggcagt gggccaagca ataatggata      60
gtcattcata gcaccccagc tttactaagc tctgccgtag tgttggattg ggagcggata     120
caattcacca cagaacagct atgacatgat acgcagtccg aataccctca taaaggacta     180
gtctgcaggt ttaacgatcg cgtagcagtg tatcacgcag agtacatggg gagtgactgt     240
gtgaacctgc tgggtacatc atcacccctc tccttcttca gttatataag acacagtccc     300
taaaggacac cagcaaaaat ggcggatgat gaggcgaaga aggccaaaca ggccgaaatc     360
gagaggaagc gcgctgaagt gcgcaagagg atggaggaag cctctaaggc gaagaaagcc     420
aagaagggtt tcatgacccc ggaaaggaag aagaaactcc gactcctgct gaggaaaaaa     480
gccgctgagg aactgaagaa ggagcaggaa cgcaaagcag ctgagaggag gcgaacgatt     540
gaggagcgct gcgggcaaat tgccgacgtc gacaacgcca atgaagcaac cttgaagaaa     600
ctctgcacag actaccataa gcgaattgac gctctggaga ggagtaaaat tgacatcgaa     660
ttcgaagtgg agagacgtga ccttgagatc gccgacctca acagccaggt caacgacctc     720
cgtggtaaat tcgtcaaacc taccttgaaa aaggtttcca agtacgaaaa caaattcgcc     780
aagctccaga agaaggctgc cgagttcaac ttcagaaacc aactcaaggt cgtcaaaaag     840
aaagaattca ccctggaaga agaagacaaa gagccgaaga aatcggaaaa ggcggagtgg     900
cagaagaaat gaagggaaaa caagcacacc atctcacaaa ataaaataaa cgaaaatctt     960
tcacacgttt accaatttta taacacggtc ctcacaaatt atgttcctta aataatttgt    1020
ataatccatc ctcgcactac aatcaatatt aatatttaaa tacaaaacca aaaaaaaaaa    1080
aaaaaaaaaa aaaaaa                                                   1096
```

<210> SEQ ID NO 2
<211> LENGTH: 491
<212> TYPE: DNA
<213> ORGANISM: Lygus hesperus

<400> SEQUENCE: 2

```
caaacaggcc gaaatcgaga ggaagcgcgc tgaagtgcgc aagaggatgg aggaagcctc      60
taaggcgaag aaagccaaga agggtttcat gaccccggaa aggaagaaga aactccgact     120
cctgctgagg aaaaaagccg ctgaggaact gaagaaggag caggaacgca agcagctga     180
gaggaggcga acgattgagg agcgctgcgg gcaaattgcc gacgtcgaca cgccaatga     240
agcaaccttg aagaaactct gcacagacta ccataagcga attgacgctc tggagaggag     300
taaaattgac atcgaattcg aagtggagag acgtgacctt gagatcgccg acctcaacag     360
ccaggtcaac gacctccgtg gtaaattcgt caaacctacc ttgaaaaagg tttccaagta     420
cgaaaacaaa ttcgccaagc tccagaagaa ggctgccgag ttcaacttca gaaaccaact     480
caaggtcgtc a                                                           491
```

<210> SEQ ID NO 3
<211> LENGTH: 431
<212> TYPE: DNA
<213> ORGANISM: Lygus hesperus

<400> SEQUENCE: 3

```
atgggcatca tgtcgaaagc tgaactcgct tgtgtttact ccgctctcat cctcatcgac      60
gacgatgtcg ccgtgacggg tgagaagatt caaaccatcc tgaaggctgc cagtgtcgac     120
atcgagccgt actggcccgg tctgttcgcc aaggccctcg agggtatcaa ccccaaagac     180
ctcatctcct ccattggaag cggagttggt gctggagcgc cggctgtcgg tggagctgca     240
cctgccgccg ctgctgcccc tgccgctgag gctaagaagg aagagaagaa gaaggtcgaa     300
agcgatccag aatccgatga tgacatgggc ttcggtcttt tcgactaaga gcattccaca     360
gcgggtctct atttgttttt aagattttct tttaaaaaat aaaacttcca aaaaaaaaa     420
aaaaaaaaaa g                                                           431
```

<210> SEQ ID NO 4
<211> LENGTH: 332
<212> TYPE: DNA
<213> ORGANISM: Lygus hesperus

<400> SEQUENCE: 4

```
gggcatcatg tcgaaagctg aactcgcttg tgtttactcc gctctcatcc tcatcgacga      60
cgatgtcgcc gtgacgggtg agaagattca aaccatcctg aaggctgcca gtgtcgacat     120
cgagccgtac tggcccggtc tgttcgccaa ggccctcgag ggtatcaacc ccaaagacct     180
catctcctcc attggaagcg gagttggtgc tggagcgccg gctgtcggtg gagctgcacc     240
tgccgccgct gctgcccctg ccgctgaggc taagaaggaa gagaagaaga aggtcgaaag     300
cgatccagaa tccgatgatg acatgggctt cg                                    332
```

<210> SEQ ID NO 5
<211> LENGTH: 468
<212> TYPE: DNA
<213> ORGANISM: Lygus hesperus

<400> SEQUENCE: 5

```
atgggggcag gtcttctcca taaccataga ttatcttcgt gtatcgtgtc gggctttcgg      60
ctgaggtcct aattagtaaa taatgattcc gcctacgtcg cggcctcagg tcactgtcta     120
cagtgacaaa aatgaggcca ccgggactct cctcaacctc ccggctgtct caacgcccc     180
cattcgcccc gatgttgtga acttcgttca ccaaaatgtc gctaaaaacc acaggcagcc     240
ctactgtgtc tccgctcaag ctggtcatca gacttcagct gagtcctggg gtaccggtcg     300
tgctgtggct cgtatccccc gtgttcgcgg aggtggtact caccgctcag gtcagggtgc     360
ttttggcaac atgtgtcgcg gcggtaggat gttcgctccc actcgcccat ggcgtcgttg     420
gcaccgcaaa atcaacgtta accaaaaaaa aaaaaaaaaa aaaaaaaa                  468
```

<210> SEQ ID NO 6
<211> LENGTH: 429
<212> TYPE: DNA
<213> ORGANISM: Lygus hesperus

<400> SEQUENCE: 6

```
gggcaggtct tctccataac catagattat cttcgtgtat cgtgtcgggc tttcggctga      60
ggtcctaatt agtaaataat gattccgcct acgtcgcggc tcaggtcac tgtctacagt     120
gacaaaaatg aggccaccgg gactctcctc aacctcccgg ctgtcttcaa cgcccccatt     180
cgccccgatg ttgtgaactt cgttcaccaa aatgtcgcta aaaccacag gcagccctac     240
tgtgtctccg ctcaagctgg tcatcagact tcagctgagt cctggggtac cggtcgtgct     300
gtggctcgta tccccgtgt tcgcggaggt ggtactcacc gctcaggtca gggtgctttt     360
ggcaacatgt gtcgcggcgg taggatgttc gctcccactc gcccatggcg tcgttggcac     420
cgcaaaatc                                                             429
```

<210> SEQ ID NO 7
<211> LENGTH: 523
<212> TYPE: DNA
<213> ORGANISM: Lygus hesperus

<400> SEQUENCE: 7

```
atgggatctc tatgctgaaa aggtcgccac cagaggtttg tgtgctattg cacaagctga      60
atccctccgt tacaaactca ttggcggtct tgctgtccga ggggcttgct atggtgtcct     120
tcgcttcatc atggaaaatg gtgccaaggg ttgcgaagtc gtagtatctg aaaactgcg     180
tggtcagaga gccaagtcaa tgaagttcgt ggatggtttg atgatccaca gtggggatcc     240
ctgtaacgaa tatgttgata ctgctacccg acatgtgctc cttagacaag gtgtcctggg     300
aataaaggtg aagattatgt tgccgtggga cgttaccggc aaaaatgggc gaagaaccc     360
tcttcccgac cacgtcagcg ttctcttacc taaggaggag ctaccaaatt tggccgttag     420
tgtgcctgga tccgacatca aaccaaagcc tgaagtacca gcaccgctt tgtgaatata     480
aacttctttt ttgtaaaaaa aaaaaaaaaa aaaaaaaaaa aaa                       523
```

<210> SEQ ID NO 8
<211> LENGTH: 431
<212> TYPE: DNA
<213> ORGANISM: Lygus hesperus

<400> SEQUENCE: 8

```
attgcacaag ctgaatccct ccgttacaaa ctcattggcg gtcttgctgt ccgaggggct      60
tgctatggtg tccttcgctt catcatggaa aatggtgcca agggttgcga agtcgtagta     120
tctggaaaac tgcgtggtca gagagccaag tcaatgaagt tcgtggatgg tttgatgatc     180
```

```
cacagtgggg atccctgtaa cgaatatgtt gatactgcta cccgacatgt gctccttaga    240
caaggtgtcc tgggaataaa ggtgaagatt atgttgccgt gggacgttac cggcaaaaat    300
gggccgaaga accctcttcc cgaccacgtc agcgttctct tacctaagga ggagctacca    360
aatttggccg ttagtgtgcc tggatccgac atcaaaccaa agcctgaagt accagcaccc    420
gctttgtgaa t                                                         431

<210> SEQ ID NO 9
<211> LENGTH: 823
<212> TYPE: DNA
<213> ORGANISM: Lygus hesperus

<400> SEQUENCE: 9
catggggaca ctctcttttt cttcatcgcg tggctcgctg ccgtgtggtt agggagtttc     60
ctactttaat tttttagtgt aattcatctt caaaatgacg tcgaaggttt ctcgtgagac    120
cctctacgag tgcatcaatg gagtcatcca gtcctcccag gagaagaaga ggaacttcgt    180
ggagactgtg gagatccaga tcggtctgaa gaactacgat ccccagaagg acaagcgttt    240
ctcgggaact gtcaagctga agcacattcc aaggcctaaa atgcaggttt gcatcctcgg    300
agatcaacag cattgcgacg aggccaaagc caacaacgtg ccctacatgg acgtcgaggc    360
tctgaagaag ctcaacaaaa acaagaagct cgtcaagaaa ttggccaaga atacgacgc     420 tttcctcgcc tcagaagccc tcatcaagca gatccccagg ctcctcggac ccggtctcaa    480
caaggcgggc aagttccctg gtctcctctc tcaccaggag tccatgatga tgaagatcga    540
cgaagtcaag gccaccatca agttccaaat gaagaaggtg ttgtgcctct cagtggctgt    600
cggtcacgtc ggcatgactg ctgatgagct cgtccagaac gtgcacttgt cggtcaactt    660
cctcgtttcg ctcctcaaga agcactggca gaacgtcagg tctctccacg tcaaatccac    720 gatgggaccct ccccagaggc tttactaaac atcttgtttt ttacttttga cgaataaaat    780 tcgtttttatt ctcgaaaaaa aaaaaaaaaa aaaaaaaaaa aaa                      823

<210> SEQ ID NO 10
<211> LENGTH: 607
<212> TYPE: DNA
<213> ORGANISM: Lygus hesperus

<400> SEQUENCE: 10
ccctctacga gtgcatcaat ggagtcatcc agtcctccca ggagaagaag aggaacttcg     60
tggagactgt ggagatccag atcggtctga agaactacga tccccagaag gacaagcgtt    120
tctcgggaac tgtcaagctg aagcacattc caaggcctaa aatgcaggtt tgcatcctcg    180
gagatcaaca gcattgcgac gaggccaaag ccaacaacgt gccctacatg gacgtcgagg    240
ctctgaagaa gctcaacaaa aacaagaagc tcgtcaagaa attggccaag aaatacgacg    300
ctttcctcgc ctcagaagcc ctcatcaagc agatccccag gctcctcgga cccggtctca    360
acaaggcggg caagttccct ggtctcctct ctcaccagga gtccatgatg atgaagatcg    420
acgaagtcaa ggccaccatc aagttccaaa tgaagaaggt gttgtgcctc tcagtggctg    480
tcggtcacgt cggcatgact gctgatgagc tcgtccagaa cgtgcacttg tcggtcaact    540
tcctcgtttc gctcctcaag aagcactggc agaacgtcag gtctctccac gtcaaatcca    600
cgatggg                                                              607

<210> SEQ ID NO 11
```

```
<211> LENGTH: 435
<212> TYPE: DNA
<213> ORGANISM: Lygus hesperus

<400> SEQUENCE: 11
atgggaccaa taaagatcaa ctttcccaga gaaagacttg ctatgcccag cataatcagg      60
tccgagaaat ccgcaaaaag atggttaaaa acatcagtga cagcatttcc agctgtgatt     120
tgaggagtgt tgtgaacaag ctgatcccag actccatcgc taaagatata gaaaagaatt     180
gccaaggaat ctacccactc cacgatgtgt acattcggaa ggtgaaggtg ttgaagaagc     240
cgaggttcga gctcagcaag ctccttgagc ttcacgtcga tggcaaaggg atcgacgaac     300
ccggcgcgaa agtgacgagg actgacgctt acgagcctcc agttcaagag tctgtctaag     360
taaacatttt atataaagtt aacaaaaaat aaaggtgtct cgcctgacta aaaaaaaaa      420
aaaaaaaaaa aaaaa                                                      435

<210> SEQ ID NO 12
<211> LENGTH: 353
<212> TYPE: DNA
<213> ORGANISM: Lygus hesperus

<400> SEQUENCE: 12
ccaataaaga tcaactttcc cagagaaaga cttgctatgc ccagcataat caggtccgag      60
aaatccgcaa aaagatggtt aaaaacatca gtgacagcat tccagctgt gatttgagga     120
gtgttgtgaa caagctgatc ccagactcca tcgctaaaga tatagaaaag aattgccaag     180
gaatctaccc actccacgat gtgtacattc ggaaggtgaa ggtgttgaag aagccgaggt     240
tcgagctcag caagctcctt gagcttcacg tcgatggcaa agggatcgac gaacccggcg     300
cgaaagtgac gaggactgac gcttacgagc ctccagttca agagtctgtc taa           353

<210> SEQ ID NO 13
<211> LENGTH: 474
<212> TYPE: DNA
<213> ORGANISM: Lygus hesperus

<400> SEQUENCE: 13
catgggtacg aatatcgacg gtaaaagaaa ggtgatgttc gccatgaccg ccatcaaagg      60
tgtcggcaga cggtacgcca acattgtcct caagaaggcc gatgtcaact tggacaagag     120
ggccggcgaa tgctccgaag aagaagttga aaagatcgtt accatcatgc aaaaccctag     180
gcaatacaaa attcccaact ggttcctcaa cagacaaaaa gacaccgtcg agggcaaata     240
ctctcagttg acttcctccc tgctggattc caagctccgt gacgaccttg agcgactcaa     300
gaagatcagg gccacagag gcatgaggca ctactgggt tgagggtgc gtggtcaaca        360
cacgaagacc accggaagga gaggacgaac tgttggtgtg tccaagaaga agtaattta      420
atttcctaat aaattggttt tttcaaaaaa aaaaaaaaa aaaaaaaaa aaaa              474

<210> SEQ ID NO 14
<211> LENGTH: 332
<212> TYPE: DNA
<213> ORGANISM: Lygus hesperus

<400> SEQUENCE: 14
gaaaggtgat gttcgccatg accgccatca aggtgtcgg cagacggtac gccaacattg       60
tcctcaagaa ggccgatgtc aacttggaca gagggccgg cgaatgctcc gaagaagaag     120
ttgaaaagat cgttaccatc atgcaaaacc ctaggcaata caaaattccc aactggttcc     180
```

```
tcaacagaca aaaagacacc gtcgagggca aatactctca gttgacttcc tccctgctgg      240
attccaagct ccgtgacgac cttgagcgac tcaagaagat cagggcccac agaggcatga      300
ggcactactg gggtttgagg gtgcgtggtc aa                                    332

<210> SEQ ID NO 15
<211> LENGTH: 440
<212> TYPE: DNA
<213> ORGANISM: Lygus hesperus

<400> SEQUENCE: 15
gtgagttctt ctgttgatta gttttttcctt ccctgaaatt atttcgttga agttaatttg     60
gattaccctg aaagaatccg ctgcttttc tctcgctaaa aatctttac acccgtcacc       120 acggccccct gtgggcaggc acaagctgaa gcacctgccc gtgcaccca actcgcactt       180 catggacgtc aactgccctg ggtgttataa atcccaacg gtgttctccc cgcccagaa        240 cgacttcggc tgctggacct gttccaccat cctctgcctg ccacaggggg gccgtgccga      300
cctcaccaaa agatgctcgt ttaggagaaa tcaacattat tattcttggt gggaacactt      360
attttttttg taattaaatt tcaaactaca aataacttt tccgaaaaac actacaaaaa       420
aaattaaaaa caaaaaaaaa                                                  440

<210> SEQ ID NO 16
<211> LENGTH: 324
<212> TYPE: DNA
<213> ORGANISM: Lygus hesperus

<400> SEQUENCE: 16
cttccctgaa attatttcgt tgaagttaat ttggattacc ctgaaagaat ccgctgcttt      60
ttctctcgct aaaaatcttt tacacccgtc accacggccc cctgtgggca ggcacaagct     120
gaagcacctg cccgtgcacc ctaactcgca cttcatggac gtcaactgcc ctgggtgtta     180
taaaatccca acggtgttct cccccgccca gaacgacttc ggctgctgga cctgttccac     240
catcctctgc ctgcccacag ggggccgtgc cgacctcacc aaaagatgct cgtttaggag     300
aaatcaacat tattattctt ggtg                                            324

<210> SEQ ID NO 17
<211> LENGTH: 357
<212> TYPE: DNA
<213> ORGANISM: Lygus hesperus

<400> SEQUENCE: 17
atgggttcaa gagagttaaa gccaagaggg ccaagaagga cgacggtgag atatttgccg     60
ctaaaaagga agtctacaag ccctctgagc agaggaaagc agaccagaaa acattgaca     120 aacagaccct gaaagccatc aagcgactca agggagacgc ttgcctcatg aggaaatacc     180
tttgcaccat gttcggattc aggagcagtc aatatcccca ccgtatgaag ttttaatatg     240
ttttcagcca ataaataagt gaaagtttct cttttttatt actacagact caaattttta     300
ttttctgaaa attattaaaa attcttaatg gcaaaaaaaa aaaaaaaaa aaaaaaa         357

<210> SEQ ID NO 18
<211> LENGTH: 223
<212> TYPE: DNA
<213> ORGANISM: Lygus hesperus

<400> SEQUENCE: 18
```

```
gttcaagaga gttaaagcca agagggccaa gaaggacgac ggtgagatat tgccgctaa      60 aaaggaagtc tacaagccct ctgagcgaga gaaagcagac cagaaaaaca ttgacaaaca    120
gaccctgaaa gccatcaagc gactcaaggg agacgcttgc ctcatgagga aataccttg     180 caccatgttc ggattcagga gcagtcaata tccccaccgt atg                      223

<210> SEQ ID NO 19
<211> LENGTH: 632
<212> TYPE: DNA
<213> ORGANISM: Lygus hesperus

<400> SEQUENCE: 19
atgggacctt ttttccgtgt gtctggctta ggcctcgcgt gttcttgtat ttttacggga     60
aatttagtga aaaagtgtaa atttaacgcg taaaaatggg tcgtatgcac gcacctggta    120
agggtatttc ccagtcagct ctccctatc gtcgtagcgc cccaacatgg ctgaagctca    180
ctcctgacga cgtcaaggat cagattttca aactccaccaa gaaaggactg actccatctc    240
agatcggtgt catcctcagg gattctcacg gtgtggctca agtcagattc gtcaccgggt    300
cgaagatcct caggatcatg aaagccatcg gcctcgctcc tgacctccca gaggacctct    360
acttcctcat caaaaaagcc gttgctatca ggaaacatct tgaaagaaat aggaaagaca    420
aagactctaa attcggactt atcccgtcg agtccaggat ccacaggttg gcaagatact    480
acaaaaccaa gggcaccctt ccacccacct ggaaatacga gtccagcacc gcctctgctc    540
tggtggcttg aatattcaac tttttatttg tctactgttt aattaatata atgtgattta    600 gcaaaaaaa aaaaaaaaaa aaaaaaaaaa aa                                   632

<210> SEQ ID NO 20
<211> LENGTH: 457
<212> TYPE: DNA
<213> ORGANISM: Lygus hesperus

<400> SEQUENCE: 20
gggtcgtatg cacgcacctg gtaagggtat ttcccagtca gctctcccct atcgtcgtag     60
cgtcccaaca tggctgaagc tcactcctga cgacgtcaag gatcagattt tcaaactcac    120
caagaaagga ctgactccat ctcagatcgg tgtcatcctc agggattctc acggtgtggc    180
tcaagtcaga ttcgtcaccg ggtcgaagat cctcaggatc atgaaagcca tcggcctcgc    240
tcctgacctc ccagaggacc tctacttcct catcaaaaaa gccgttgcta tcaggaaaca    300
tcttgaaaga aataggaaag acaaagactc taaattcgga cttatccccg tcgagtccag    360
gatccacagg ttggcaagat actacaaaac caagggcacc cttccaccca cctggaaata    420
cgagtccagc accgcctctg ctctggtggc ttgaata                             457

<210> SEQ ID NO 21
<211> LENGTH: 407
<212> TYPE: DNA
<213> ORGANISM: Lygus hesperus

<400> SEQUENCE: 21
atgggaccgt ttgcctcaca atccagaaca gacaggctgc catatccgtc gtcccctctg     60
cagcctccct cgtaatcaag gccctcaaag agccccgag ggacaggaag aagaacaaga    120
acatcaaaca cgacggtaac ctgagtatgg atgacattct cggaattgcc aaaaccatga    180
ggccgaggtc gatgtccagg aaactggaag gaaccgtcaa ggaaatcctt gggacagctc    240
agtctgtcgg atgcacgatc gaaggccgag ctccccacga cgtcatcgac tccatcaaca    300
```

```
acggcgaaat ggaaatccct gacgaataaa ctgttcatga gtttatggat tttatataaa        360
aaataaaaag ttgaaaaatc caaaaaaaaa aaaaaaaaag aaaaaaa                     407

<210> SEQ ID NO 22
<211> LENGTH: 302
<212> TYPE: DNA
<213> ORGANISM: Lygus hesperus

<400> SEQUENCE: 22
accgtttgcc tcacaatcca gaacagacag gctgccatat ccgtcgtccc ctctgcagcc        60
tccctcgtaa tcaaggccct caaagagccc ccgagggaca ggaagaagaa caagaacatc       120
aaacacgacg gtaacctgag tatggatgac attctcggaa ttgccaaaac catgaggccg       180
aggtcgatgt ccaggaaact ggaaggaacc gtcaaggaaa tccttgggac agctcagtct       240
gtcggatgca cgatcgaagg ccgagctccc cacgacgtca tcgactccat caacaacggc       300
ga                                                                     302

<210> SEQ ID NO 23
<211> LENGTH: 794
<212> TYPE: DNA
<213> ORGANISM: Lygus hesperus

<400> SEQUENCE: 23
catggggagt caatttggat ctatcgccag atgaagatgt ctcctgccgt gttcgctgtt        60
ctgctggtac tttcagcttc ccaggtcttg ggagatgatg catccaagtt ccaacacgag       120
gaaatcatgg aagtcctcag ctcggtcaac aaaaccgtca caaaattgta cgacttgatg       180
tccacgcaga aggaaagaga tattgacttt atcgagaaga aatggatgac gacgtaccag       240
caactcagga acaagaggga ggcgccggct gagaaccctg aagccattga caagatccaa       300
aacgcgttca aaagctttca agacggcgtc aaggacttcg tcaagtccgc ttcttcctcg       360
gacctctaca agaaggttca ggaaatcggc gaggacctgt agaacaaagg caaagagctc       420
ggagagaagc tgcaagaaac catcaataac gccagaacga aaaactcaga cgagaagaag       480
gactaaactg aggattttga ctctgcacaa acgcccgttg gtgtttaaac gtatttctta       540
cgtttattat catcggggtt catgaaatca aaaatacacc atcgcatacc acctcgaaaa       600
gaacataata tatgtgaaaa gacaagaaaa ggtgttcaat tgtgtcttta actggtggtt       660
atcacgattc acatgaaata ctactaagaa aacccaaaaa ccgtcatgaa acccgaagta       720
tgcttctgta ttacctaatt gtgctgataa ttcttaataa aatattatac tgagaaaaaa       780
aaaaaaaaaa aaaa                                                         794

<210> SEQ ID NO 24
<211> LENGTH: 278
<212> TYPE: DNA
<213> ORGANISM: Lygus hesperus

<400> SEQUENCE: 24
ttctgctggt actttcagct tcccaggtct tgggagatga tgcatccaag ttccaacacg        60
aggaaatcat ggaagtcctc agctcggtca acaaaaccgt caacaaattg tacgacttga       120
tgtccacgca gaaggaaaga gatattgact ttatcgagaa gaaatggatg agacgtacc        180 agcaactcag gaacaagagg gaggcgccgg ctgagaaccc tgaagccatt gacaagatcc       240
aaaacgcgtt caaaagcttt caagacggcg tcaaggac                              278
```

<210> SEQ ID NO 25
<211> LENGTH: 437
<212> TYPE: DNA
<213> ORGANISM: Lygus hesperus

<400> SEQUENCE: 25

| | | | | | |
|---|---|---|---|---|---|
| atgggatcca | ataataacca | ttaaggcaat | tggacatcaa | tgatactgaa | catatgaata | 60 |
| ttcagatatc | aaaaatatcg | aaatagaatc | atatataaaa | ccaactaacg | cattagaaaa | 120 |
| taacgaattc | cgattacttg | aagtagacaa | tcgaatcgta | ttacctataa | aatcaactat | 180 |
| ccgaattcta | gttacatcat | ctgatgtaat | tcattcatga | accatcccaa | gtttgggaat | 240 |
| caaaattgat | ggcacaccag | gacgattaaa | tcaagggaga | ataaacataa | accgaccagg | 300 |
| actaatatat | gggcaatgtt | ctgaaatttg | tggagcaaac | cacagattta | taccaatcgt | 360 |
| aattgaaaga | gtttcaatta | atcaatttat | aaactgatta | aattcaaaat | aaaaaaaaaa | 420 |
| aaaaaaaaaa | aaaaaaa | | | | | 437 |

<210> SEQ ID NO 26
<211> LENGTH: 327
<212> TYPE: DNA
<213> ORGANISM: Lygus hesperus

<400> SEQUENCE: 26

| | | | | | |
|---|---|---|---|---|---|
| aacgcagagt | acatgggatc | caataataac | cattaaggca | attggacatc | aatgatactg | 60 |
| aacatatgaa | tattcagata | tcaaaaatat | cgaaatagaa | tcatatataa | aaccaactaa | 120 |
| cgcattagaa | aataacgaat | tccgattact | tgaagtagac | aatcgaatcg | tattacctat | 180 |
| aaaatcaact | atccgaattc | tagttacatc | atctgatgta | attcattcat | gaaccatccc | 240 |
| aagtttggga | atcaaaattg | atggcacacc | aggacgatta | aatcaaggga | gaataaacat | 300 |
| aaaccgacca | ggactaatat | atgggca | | | | 327 |

<210> SEQ ID NO 27
<211> LENGTH: 42
<212> TYPE: DNA
<213> ORGANISM: Artificial
<220> FEATURE:
<223> OTHER INFORMATION: Primer

<400> SEQUENCE: 27
gcgtaatacg actcactata ggcaaacagg ccgaaatcga ga      42

<210> SEQ ID NO 28
<211> LENGTH: 23
<212> TYPE: DNA
<213> ORGANISM: Artificial
<220> FEATURE:
<223> OTHER INFORMATION: Primer

<400> SEQUENCE: 28
tgacgacctt gagttggttt ctg      23

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
caaacaggcc gaaatcgaga      20

<210> SEQ ID NO 30
<211> LENGTH: 45
<212> TYPE: DNA
<213> ORGANISM: Artificial
<220> FEATURE:
<223> OTHER INFORMATION: Primer

<400> SEQUENCE: 30
gcgtaatacg actcactata ggtgacgacc ttgagttggt ttctg        45

<210> SEQ ID NO 31
<211> LENGTH: 42
<212> TYPE: DNA
<213> ORGANISM: Artificial
<220> FEATURE:
<223> OTHER INFORMATION: Primer

<400> SEQUENCE: 31
gcgtaatacg actcactata gggggcatca tgtcgaaagc tg           42

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cgaagcccat gtcatcatcg                                    20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
gggcatcatg tcgaaagctg                                    20

<210> SEQ ID NO 34
<211> LENGTH: 42
<212> TYPE: DNA
<213> ORGANISM: Artificial
<220> FEATURE:
<223> OTHER INFORMATION: Primer

<400> SEQUENCE: 34
gcgtaatacg actcactata ggcgaagccc atgtcatcat cg           42

<210> SEQ ID NO 35
<211> LENGTH: 44
<212> TYPE: DNA
<213> ORGANISM: Artificial
<220> FEATURE:
<223> OTHER INFORMATION: Primer

<400> SEQUENCE: 35
gcgtaatacg actcactata gggggcaggt cttctccata acca         44

<210> SEQ ID NO 36
<211> LENGTH: 20
<212> TYPE: DNA
<213> ORGANISM: Artificial
<220> FEATURE:

<223> OTHER INFORMATION: Primer

<400> SEQUENCE: 36
gattttgcgg tgccaacgac                                                           20

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
gggcaggtct tctccataac ca                                                        22

<210> SEQ ID NO 38
<211> LENGTH: 42
<212> TYPE: DNA
<213> ORGANISM: Artificial
<220> FEATURE:
<223> OTHER INFORMATION: Primer

<400> SEQUENCE: 38
gcgtaatacg actcactata gggattttgc ggtgccaacg ac                                  42

<210> SEQ ID NO 39
<211> LENGTH: 44
<212> TYPE: DNA
<213> ORGANISM: Artificial
<220> FEATURE:
<223> OTHER INFORMATION: Primer

<400> SEQUENCE: 39
gcgtaatacg actcactata ggattgcaca agctgaatcc ctcc                                44

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
attcacaaag cgggtgctgg                                                           20

<210> SEQ ID NO 41
<211> LENGTH: 22
<212> TYPE: DNA
<213> ORGANISM: Artificial
<220> FEATURE:
<223> OTHER INFORMATION: Primer

<400> SEQUENCE: 41
attgcacaag ctgaatccct cc                                                        22

<210> SEQ ID NO 42
<211> LENGTH: 42
<212> TYPE: DNA
<213> ORGANISM: Artificial
<220> FEATURE:
<223> OTHER INFORMATION: Primer

<400> SEQUENCE: 42
gcgtaatacg actcactata ggattcacaa agcgggtgct gg                                  42

```
<210> SEQ ID NO 43
<211> LENGTH: 44
<212> TYPE: DNA
<213> ORGANISM: Artificial
<220> FEATURE:
<223> OTHER INFORMATION: Primer

<400> SEQUENCE: 43
gcgtaatacg actcactata ggccctctac gagtgcatca atgg          44

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
cccatcgtgg atttgacgtg                                     20

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
ccctctacga gtgcatcaat gg                                  22

<210> SEQ ID NO 46
<211> LENGTH: 42
<212> TYPE: DNA
<213> ORGANISM: Artificial
<220> FEATURE:
<223> OTHER INFORMATION: Primer

<400> SEQUENCE: 46
gcgtaatacg actcactata ggcccatcgt ggatttgacg tg            42

<210> SEQ ID NO 47
<211> LENGTH: 47
<212> TYPE: DNA
<213> ORGANISM: Artificial
<220> FEATURE:
<223> OTHER INFORMATION: Primer

<400> SEQUENCE: 47
gcgtaatacg actcactata ggccaataaa gatcaacttt cccagag       47

<210> SEQ ID NO 48
<211> LENGTH: 25
<212> TYPE: DNA
<213> ORGANISM: Artificial
<220> FEATURE:
<223> OTHER INFORMATION: Primer

<400> SEQUENCE: 48
ttagacagac tcttgaactg gaggc                               25

<210> SEQ ID NO 49
<211> LENGTH: 25
<212> TYPE: DNA
<213> ORGANISM: Artificial
<220> FEATURE:
<223> OTHER INFORMATION: Primer
```

<400> SEQUENCE: 49
ccaataaaga tcaactttcc cagag    25

<210> SEQ ID NO 50
<211> LENGTH: 47
<212> TYPE: DNA
<213> ORGANISM: Artificial
<220> FEATURE:
<223> OTHER INFORMATION: Primer

<400> SEQUENCE: 50
gcgtaatacg actcactata ggttagacag actcttgaac tggaggc    47

<210> SEQ ID NO 51
<211> LENGTH: 44
<212> TYPE: DNA
<213> ORGANISM: Artificial
<220> FEATURE:
<223> OTHER INFORMATION: Primer

<400> SEQUENCE: 51
gcgtaatacg actcactata gggaaaggtg atgttcgcca tgac    44

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
ttgaccacgc accctcaaac    20

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
gaaaggtgat gttcgccatg ac    22

<210> SEQ ID NO 54
<211> LENGTH: 42
<212> TYPE: DNA
<213> ORGANISM: Artificial
<220> FEATURE:
<223> OTHER INFORMATION: Primer

<400> SEQUENCE: 54
gcgtaatacg actcactata ggttgaccac gcaccctcaa ac    42

<210> SEQ ID NO 55
<211> LENGTH: 47
<212> TYPE: DNA
<213> ORGANISM: Artificial
<220> FEATURE:
<223> OTHER INFORMATION: Primer

<400> SEQUENCE: 55
gcgtaatacg actcactata ggcttccctg aaattatttc gttgaag    47

<210> SEQ ID NO 56
<211> LENGTH: 28

```
<212> TYPE: DNA
<213> ORGANISM: Artificial
<220> FEATURE:
<223> OTHER INFORMATION: Primer

<400> SEQUENCE: 56
caccaagaat aataatgttg atttctcc                                    28

<210> SEQ ID NO 57
<211> LENGTH: 25
<212> TYPE: DNA
<213> ORGANISM: Artificial
<220> FEATURE:
<223> OTHER INFORMATION: Primer

<400> SEQUENCE: 57
cttccctgaa attatttcgt tgaag                                       25

<210> SEQ ID NO 58
<211> LENGTH: 50
<212> TYPE: DNA
<213> ORGANISM: Artificial
<220> FEATURE:
<223> OTHER INFORMATION: Primer

<400> SEQUENCE: 58
gcgtaatacg actcactata ggcaccaaga ataataatgt tgatttctcc            50

<210> SEQ ID NO 59
<211> LENGTH: 47
<212> TYPE: DNA
<213> ORGANISM: Artificial
<220> FEATURE:
<223> OTHER INFORMATION: Primer

<400> SEQUENCE: 59
gcgtaatacg actcactata gggttcaaga gagttaaagc caagagg               47

<210> SEQ ID NO 60
<211> LENGTH: 22
<212> TYPE: DNA
<213> ORGANISM: Artificial
<220> FEATURE:
<223> OTHER INFORMATION: Primer

<400> SEQUENCE: 60
catacggtgg ggatattgac tg                                          22

<210> SEQ ID NO 61
<211> LENGTH: 25
<212> TYPE: DNA
<213> ORGANISM: Artificial
<220> FEATURE:
<223> OTHER INFORMATION: Primer

<400> SEQUENCE: 61
gttcaagaga gttaaagcca agagg                                       25

<210> SEQ ID NO 62
<211> LENGTH: 44
<212> TYPE: DNA
<213> ORGANISM: Artificial
<220> FEATURE:
<223> OTHER INFORMATION: Primer

<400> SEQUENCE: 62
```

-continued

```
gcgtaatacg actcactata ggcatacggt ggggatattg actg                44
```

<210> SEQ ID NO 63
<211> LENGTH: 42
<212> TYPE: DNA
<213> ORGANISM: Artificial
<220> FEATURE:
<223> OTHER INFORMATION: Primer

<400> SEQUENCE: 63

```
gcgtaatacg actcactata gggggtcgta tgcacgcacc tg                  42
```

<210> SEQ ID NO 64
<211> LENGTH: 23
<212> TYPE: DNA
<213> ORGANISM: Artificial
<220> FEATURE:
<223> OTHER INFORMATION: Primer

<400> SEQUENCE: 64

```
tattcaagcc accagagcag agg                                       23
```

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65

```
gggtcgtatg cacgcacctg                                           20
```

<210> SEQ ID NO 66
<211> LENGTH: 45
<212> TYPE: DNA
<213> ORGANISM: Artificial
<220> FEATURE:
<223> OTHER INFORMATION: Primer

<400> SEQUENCE: 66

```
gcgtaatacg actcactata ggtattcaag ccaccagagc agagg               45
```

<210> SEQ ID NO 67
<211> LENGTH: 42
<212> TYPE: DNA
<213> ORGANISM: Artificial
<220> FEATURE:
<223> OTHER INFORMATION: Primer

<400> SEQUENCE: 67

```
gcgtaatacg actcactata ggaccgtttg cctcacaatc ca                  42
```

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68

```
tcgccgttgt tgatggagtc                                           20
```

<210> SEQ ID NO 69
<211> LENGTH: 20
<212> TYPE: DNA
<213> ORGANISM: Artificial

```
<220> FEATURE:
<223> OTHER INFORMATION: Primer

<400> SEQUENCE: 69
accgtttgcc tcacaatcca                                                    20

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
gcgtaatacg actcactata ggtcgccgtt gttgatggag tc                           42

<210> SEQ ID NO 71
<211> LENGTH: 45
<212> TYPE: DNA
<213> ORGANISM: Artificial
<220> FEATURE:
<223> OTHER INFORMATION: Primer

<400> SEQUENCE: 71
gcgtaatacg actcactata ggggtatcaa cgcagagtac atggg                        45

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
gtccttgacg ccgtcttgaa                                                    20

<210> SEQ ID NO 73
<211> LENGTH: 23
<212> TYPE: DNA
<213> ORGANISM: Artificial
<220> FEATURE:
<223> OTHER INFORMATION: Primer

<400> SEQUENCE: 73
ggtatcaacg cagagtacat ggg                                                23

<210> SEQ ID NO 74
<211> LENGTH: 42
<212> TYPE: DNA
<213> ORGANISM: Artificial
<220> FEATURE:
<223> OTHER INFORMATION: Primer

<400> SEQUENCE: 74
gcgtaatacg actcactata gggtccttga cgccgtcttg aa                           42

<210> SEQ ID NO 75
<211> LENGTH: 44
<212> TYPE: DNA
<213> ORGANISM: Artificial
<220> FEATURE:
<223> OTHER INFORMATION: Primer

<400> SEQUENCE: 75
gcgtaatacg actcactata ggtgcccata tattagtcct ggtc                         44
```

<210> SEQ ID NO 76
<211> LENGTH: 20
<212> TYPE: DNA
<213> ORGANISM: Artificial
<220> FEATURE:
<223> OTHER INFORMATION: Primer

<400> SEQUENCE: 76
aacgcagagt acatgggatc					20

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
tgcccatata ttagtcctgg tc				22

<210> SEQ ID NO 78
<211> LENGTH: 42
<212> TYPE: DNA
<213> ORGANISM: Artificial
<220> FEATURE:
<223> OTHER INFORMATION: Primer

<400> SEQUENCE: 78
gcgtaatacg actcactata ggaacgcaga gtacatggga tc		42

<210> SEQ ID NO 79
<211> LENGTH: 197
<212> TYPE: PRT
<213> ORGANISM: Lygus hesperus

<400> SEQUENCE: 79

Met Ala Asp Asp Glu Ala Lys Lys Ala Lys Gln Ala Glu Ile Glu Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Glu Glu Leu Lys Lys Glu Gln Glu
    50                  55                  60

Arg Lys Ala Ala Glu Arg Arg Arg Thr Ile Glu Glu Arg Cys Gly Gln
65                  70                  75                  80

Ile Ala Asp Val Asp Asn Ala Asn Glu Ala Thr Leu Lys Lys Leu Cys
                85                  90                  95

Thr Asp Tyr His Lys Arg Ile Asp Ala Leu Glu Arg Ser Lys Ile Asp
            100                 105                 110

Ile Glu Phe Glu Val Glu Arg Arg Asp Leu Glu Ile Ala Asp Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Glu
                165                 170                 175

Phe Thr Leu Glu Glu Glu Asp Lys Glu Pro Lys Lys Ser Glu Lys Ala
            180                 185                 190

-continued

```
Glu Trp Gln Lys Lys
        195

<210> SEQ ID NO 80
<211> LENGTH: 115
<212> TYPE: PRT
<213> ORGANISM: Lygus hesperus

<400> SEQUENCE: 80

Met Gly Ile Met Ser Lys Ala Glu Leu Ala Cys Val Tyr Ser Ala Leu
1               5                   10                  15

Ile Leu Ile Asp Asp Val Ala Val Thr Gly Glu Lys Ile Gln Thr
            20                  25                  30

Ile Leu Lys Ala Ala Ser Val Asp Ile Glu Pro Tyr Trp Pro Gly Leu
        35                  40                  45

Phe Ala Lys Ala Leu Glu Gly Ile Asn Pro Lys Asp Leu Ile Ser Ser
    50                  55                  60

Ile Gly Ser Gly Val Gly Ala Gly Ala Pro Ala Val Gly Gly Ala Ala
65                  70                  75                  80

Pro Ala Ala Ala Ala Pro Ala Ala Glu Ala Lys Lys Glu Glu Lys
                85                  90                  95

Lys Lys Val Glu Ser Asp Pro Glu Ser Asp Asp Met Gly Phe Gly
                100                 105                 110

Leu Phe Asp
        115

<210> SEQ ID NO 81
<211> LENGTH: 121
<212> TYPE: PRT
<213> ORGANISM: Lygus hesperus

<400> SEQUENCE: 81

Met Ile Pro Pro Thr Ser Arg Pro Gln Val Thr Val Tyr Ser Asp Lys
1               5                   10                  15

Asn Glu Ala Thr Gly Thr Leu Leu Asn Leu Pro Ala Val Phe Asn Ala
            20                  25                  30

Pro Ile Arg Pro Asp Val Val Asn Phe Val His Gln Asn Val Ala Lys
        35                  40                  45

Asn His Arg Gln Pro Tyr Cys Val Ser Ala Gln Ala Gly His Gln Thr
    50                  55                  60

Ser Ala Glu Ser Trp Gly Thr Gly Arg Ala Val Ala Arg Ile Pro Arg
65                  70                  75                  80

Val Arg Gly Gly Gly Thr His Arg Ser Gly Gln Gly Ala Phe Gly Asn
                85                  90                  95

Met Cys Arg Gly Gly Arg Met Phe Ala Pro Thr Arg Pro Trp Arg Arg
                100                 105                 110

Trp His Arg Lys Ile Asn Val Asn Gln
        115                 120

<210> SEQ ID NO 82
<211> LENGTH: 133
<212> TYPE: PRT
<213> ORGANISM: Lygus hesperus

<400> SEQUENCE: 82

Trp Asp Leu Tyr Ala Glu Lys Val Ala Thr Arg Gly Leu Cys Ala Ile
1               5                   10                  15
```

```
Ala Gln Ala Glu Ser Leu Arg Tyr Lys Leu Ile Gly Gly Leu Ala Val
             20                  25                  30

Arg Gly Ala Cys Tyr Gly Val Leu Arg Phe Ile Met Glu Asn Gly Ala
         35                  40                  45

Lys Gly Cys Glu Val Val Ser Gly Lys Leu Arg Gly Gln Arg Ala
     50                  55                  60

Lys Ser Met Lys Phe Val Asp Gly Leu Met Ile His Ser Gly Asp Pro
65                  70                  75                  80

Cys Asn Glu Tyr Val Asp Thr Ala Thr Arg His Val Leu Leu Arg Gln
                 85                  90                  95

Gly Val Leu Gly Ile Lys Val Lys Ile Met Leu Pro Trp Asp Val Thr
            100                 105                 110

Gly Lys Asn Gly Pro Lys Asn Pro Leu Pro Asp His Val Ser Val Leu
        115                 120                 125

Leu Pro Lys Glu Glu
    130
```

<210> SEQ ID NO 83
<211> LENGTH: 217
<212> TYPE: PRT
<213> ORGANISM: Lygus hesperus

<400> SEQUENCE: 83

```
Met Thr Ser Lys Val Ser Arg Glu Thr Leu Tyr Glu Cys Ile Asn Gly
1               5                   10                  15

Val Ile Gln Ser Ser Gln Glu Lys Lys Arg Asn Phe Val Glu Thr Val
             20                  25                  30

Glu Ile Gln Ile Gly Leu Lys Asn Tyr Asp Pro Gln Lys Asp Lys Arg
         35                  40                  45

Phe Ser Gly Thr Val Lys Leu Lys His Ile Pro Arg Pro Lys Met Gln
     50                  55                  60

Val Cys Ile Leu Gly Asp Gln Gln His Cys Asp Glu Ala Lys Ala Asn
65                  70                  75                  80

Asn Val Pro Tyr Met Asp Val Glu Ala Leu Lys Lys Leu Asn Lys Asn
                 85                  90                  95

Lys Lys Leu Val Lys Lys Leu Ala Lys Lys Tyr Asp Ala Phe Leu Ala
            100                 105                 110

Ser Glu Ala Leu Ile Lys Gln Ile Pro Arg Leu Leu Gly Pro Gly Leu
        115                 120                 125

Asn Lys Ala Gly Lys Phe Pro Gly Leu Leu Ser His Gln Glu Ser Met
    130                 135                 140

Met Met Lys Ile Asp Glu Val Lys Ala Thr Ile Lys Phe Gln Met Lys
145                 150                 155                 160

Lys Val Leu Cys Leu Ser Val Ala Val Gly His Val Gly Met Thr Ala
                165                 170                 175

Asp Glu Leu Val Gln Asn Val His Leu Ser Val Asn Phe Leu Val Ser
            180                 185                 190

Leu Leu Lys Lys His Trp Gln Asn Val Arg Ser Leu His Val Lys Ser
        195                 200                 205

Thr Met Gly Pro Pro Gln Arg Leu Tyr
    210                 215
```

<210> SEQ ID NO 84
<211> LENGTH: 118
<212> TYPE: PRT
<213> ORGANISM: Lygus hesperus

```
<400> SEQUENCE: 84

Gly Thr Asn Lys Asp Gln Leu Ser Gln Arg Lys Thr Cys Tyr Ala Gln
1               5                   10                  15

His Asn Gln Val Arg Glu Ile Arg Lys Lys Met Val Lys Asn Ile Ser
            20                  25                  30

Asp Ser Ile Ser Ser Cys Asp Leu Arg Ser Val Val Asn Lys Leu Ile
        35                  40                  45

Pro Asp Ser Ile Ala Lys Asp Ile Glu Lys Asn Cys Gln Gly Ile Tyr
    50                  55                  60

Pro Leu His Asp Val Tyr Ile Arg Lys Val Lys Val Leu Lys Lys Pro
65                  70                  75                  80

Arg Phe Glu Leu Ser Lys Leu Leu Glu Leu His Val Asp Gly Lys Gly
                85                  90                  95

Ile Asp Glu Pro Gly Ala Lys Val Thr Arg Thr Asp Ala Tyr Glu Pro
            100                 105                 110

Pro Val Gln Glu Ser Val
            115

<210> SEQ ID NO 85
<211> LENGTH: 128
<212> TYPE: PRT
<213> ORGANISM: Lygus hesperus

<400> SEQUENCE: 85

Lys Val Met Phe Ala Met Thr Ala Ile Lys Gly Val Gly Arg Arg Tyr
1               5                   10                  15

Ala Asn Ile Val Leu Lys Lys Ala Asp Val Asn Leu Asp Lys Arg Ala
            20                  25                  30

Gly Glu Cys Ser Glu Glu Val Glu Lys Ile Val Thr Ile Met Gln
        35                  40                  45

Asn Pro Arg Gln Tyr Lys Ile Pro Asn Trp Phe Leu Asn Arg Gln Lys
    50                  55                  60

Asp Thr Val Glu Gly Lys Tyr Ser Gln Leu Thr Ser Ser Leu Leu Asp
65                  70                  75                  80

Ser Lys Leu Arg Asp Asp Leu Glu Arg Leu Lys Lys Ile Arg Ala His
                85                  90                  95

Arg Gly Met Arg His Tyr Trp Gly Leu Arg Val Arg Gly Gln His Thr
            100                 105                 110

Lys Thr Thr Gly Arg Arg Gly Arg Thr Val Gly Val Ser Lys Lys Lys
        115                 120                 125

<210> SEQ ID NO 86
<211> LENGTH: 122
<212> TYPE: PRT
<213> ORGANISM: Lygus hesperus

<400> SEQUENCE: 86

Val Leu Leu Leu Ile Ser Phe Ser Phe Pro Glu Ile Ile Ser Leu Lys
1               5                   10                  15

Leu Ile Trp Ile Thr Leu Lys Glu Ser Ala Ala Phe Ser Leu Ala Lys
            20                  25                  30

Asn Leu Leu His Pro Ser Pro Arg Pro Val Gly Arg His Lys Leu
        35                  40                  45

Lys His Leu Pro Val His Pro Asn Ser His Phe Met Asp Val Asn Cys
    50                  55                  60
```

-continued

```
Pro Gly Cys Tyr Lys Ile Pro Thr Val Phe Ser Pro Ala Gln Asn Asp
 65                  70                  75                  80

Phe Gly Cys Trp Thr Cys Ser Thr Ile Leu Cys Leu Pro Thr Gly Gly
                 85                  90                  95

Arg Ala Asp Leu Thr Lys Arg Cys Ser Phe Arg Arg Asn Gln His Tyr
            100                 105                 110

Tyr Ser Trp Trp Glu His Leu Phe Phe Leu
            115                 120

<210> SEQ ID NO 87
<211> LENGTH: 77
<212> TYPE: PRT
<213> ORGANISM: Lygus hesperus

<400> SEQUENCE: 87

Gly Phe Lys Arg Val Lys Ala Lys Arg Ala Lys Lys Asp Asp Gly Glu
  1               5                  10                  15

Ile Phe Ala Ala Lys Lys Glu Val Tyr Lys Pro Ser Glu Gln Arg Lys
                 20                  25                  30

Ala Asp Gln Lys Asn Ile Asp Lys Gln Thr Leu Lys Ala Ile Lys Arg
            35                  40                  45

Leu Lys Gly Asp Ala Cys Leu Met Arg Lys Tyr Leu Cys Thr Met Phe
 50                  55                  60

Gly Phe Arg Ser Ser Gln Tyr Pro His Arg Met Lys Phe
 65                  70                  75

<210> SEQ ID NO 88
<211> LENGTH: 151
<212> TYPE: PRT
<213> ORGANISM: Lygus hesperus

<400> SEQUENCE: 88

Met Gly Arg Met His Ala Pro Gly Lys Gly Ile Ser Gln Ser Ala Leu
  1               5                  10                  15

Pro Tyr Arg Arg Ser Val Pro Thr Trp Leu Lys Leu Thr Pro Asp Asp
                 20                  25                  30

Val Lys Asp Gln Ile Phe Lys Leu Thr Lys Lys Gly Leu Thr Pro Ser
            35                  40                  45

Gln Ile Gly Val Ile Leu Arg Asp Ser His Gly Val Ala Gln Val Arg
 50                  55                  60

Phe Val Thr Gly Ser Lys Ile Leu Arg Ile Met Lys Ala Ile Gly Leu
 65                  70                  75                  80

Ala Pro Asp Leu Pro Glu Asp Leu Tyr Phe Leu Ile Lys Lys Ala Val
                 85                  90                  95

Ala Ile Arg Lys His Leu Glu Arg Asn Arg Lys Asp Lys Asp Ser Lys
            100                 105                 110

Phe Gly Leu Ile Pro Val Glu Ser Arg Ile His Arg Leu Ala Arg Tyr
            115                 120                 125

Tyr Lys Thr Lys Gly Thr Leu Pro Pro Thr Trp Lys Tyr Glu Ser Ser
            130                 135                 140

Thr Ala Ser Ala Leu Val Ala
145                 150

<210> SEQ ID NO 89
<211> LENGTH: 108
<212> TYPE: PRT
<213> ORGANISM: Lygus hesperus
```

-continued

<400> SEQUENCE: 89

Gly Thr Val Cys Leu Thr Ile Gln Asn Arg Gln Ala Ala Ile Ser Val
1               5                   10                  15

Val Pro Ser Ala Ala Ser Leu Val Ile Lys Ala Leu Lys Glu Pro Pro
            20                  25                  30

Arg Asp Arg Lys Lys Asn Lys Asn Ile Lys His Asp Gly Asn Leu Ser
        35                  40                  45

Met Asp Asp Ile Leu Gly Ile Ala Lys Thr Met Arg Pro Arg Ser Met
    50                  55                  60

Ser Arg Lys Leu Glu Gly Thr Val Lys Glu Ile Leu Gly Thr Ala Gln
65                  70                  75                  80

Ser Val Gly Cys Thr Ile Glu Gly Arg Ala Pro His Asp Val Ile Asp
                85                  90                  95

Ser Ile Asn Asn Gly Glu Met Glu Ile Pro Asp Glu
            100                 105

<210> SEQ ID NO 90
<211> LENGTH: 133
<212> TYPE: PRT
<213> ORGANISM: Lygus hesperus

<400> SEQUENCE: 90

His Gly Glu Ser Ile Trp Ile Tyr Arg Gln Met Lys Met Ser Pro Ala
1               5                   10                  15

Val Phe Ala Val Leu Leu Val Leu Ser Ala Ser Gln Val Leu Gly Asp
            20                  25                  30

Asp Ala Ser Lys Phe Gln His Glu Glu Ile Met Glu Val Leu Ser Ser
        35                  40                  45

Val Asn Lys Thr Val Asn Lys Leu Tyr Asp Leu Met Ser Thr Gln Lys
    50                  55                  60

Glu Arg Asp Ile Asp Phe Ile Glu Lys Lys Met Asp Glu Thr Tyr Gln
65                  70                  75                  80

Gln Leu Arg Asn Lys Arg Glu Ala Pro Ala Glu Asn Pro Glu Ala Ile
                85                  90                  95

Asp Lys Ile Gln Asn Ala Phe Lys Ser Phe Gln Asp Gly Val Lys Asp
            100                 105                 110

Phe Val Lys Ser Ala Ser Ser Ser Asp Leu Tyr Lys Lys Val Gln Glu
        115                 120                 125

Ile Gly Glu Asp Leu
    130

<210> SEQ ID NO 91
<211> LENGTH: 118
<212> TYPE: PRT
<213> ORGANISM: Lygus hesperus

<400> SEQUENCE: 91

Thr Tyr Glu Tyr Ser Asp Ile Lys Asn Ile Gly Ile Glu Ser Tyr Ile
1               5                   10                  15

Lys Pro Thr Asn Ala Leu Glu Asn Asn Glu Phe Arg Leu Leu Glu Val
            20                  25                  30

Asp Asn Arg Ile Val Leu Pro Ile Lys Ser Thr Ile Arg Ile Leu Val
        35                  40                  45

Thr Ser Ser Asp Val Ile His Ser Thr Ile Pro Ser Leu Gly Ile Lys
    50                  55                  60

Ile Asp Gly Thr Pro Gly Arg Leu Asn Gln Gly Arg Ile Asn Ile Asn

```
                65                  70                  75                  80
Arg Pro Gly Leu Ile Tyr Gly Gln Cys Ser Glu Ile Cys Gly Ala Asn
                    85                  90                  95
His Arg Phe Ile Pro Ile Val Ile Glu Arg Val Ser Ile Asn Gln Phe
                100                 105                 110
Ile Asn Leu Asn Ser Lys
        115

<210> SEQ ID NO 92
<211> LENGTH: 20
<212> TYPE: DNA
<213> ORGANISM: Artificial
<220> FEATURE:
<223> OTHER INFORMATION: Adaptor

<400> SEQUENCE: 92
aagcagtggt atcaacgcag                                                     20

<210> SEQ ID NO 93
<211> LENGTH: 20
<212> TYPE: DNA
<213> ORGANISM: Artificial
<220> FEATURE:
<223> OTHER INFORMATION: Primer

<400> SEQUENCE: 93
aagcagtggt atcaacgcag                                                     20

<210> SEQ ID NO 94
<211> LENGTH: 42
<212> TYPE: DNA
<213> ORGANISM: Artificial
<220> FEATURE:
<223> OTHER INFORMATION: Primer

<400> SEQUENCE: 94
gcgtaatacg actcactata ggaagcagtg gtatcaacgc ag                            42

<210> SEQ ID NO 95
<211> LENGTH: 717
<212> TYPE: DNA
<213> ORGANISM: Lygus hesperus

<400> SEQUENCE: 95
aaagtgtggt tctcttcgtc cgaccatgag ttcgctcaaa ctgcagaaga ggctcgccgc         60
ctcggtgatg agatgcggca agaagaaagt gtggttggac cctaatgaaa tcaacgaaat        120
cgccaacacc aactctaggc aaaacatccg taagctgatc aaggatggtt tgatcatcaa        180
aaagcctgtg gctgtccact ccagagcccg cgtccgtaaa acacagaaag ccagacggaa        240
gggtcgtcat tgtggcttcg gtaagaggaa gggtaccgcc aacgccagaa tgcctgtgaa        300
ggtcctgtgg gtcaacagaa tgagagtcct gcgacggctc cttaaaaaat acagagaagc        360
caagaagatc gataggcaaa tgtaccacga cctttacatg aaagccaaag gtaacgtctt        420
caaaaacaag agggtactga tggacttcat tcacaagaag aaggctgaaa aggcgagatc        480
aaagatgttg aaggaccagg cagaggcgag acgtttcaag gtcaaggagg cgaagaagag        540
gcgcgaggag aggatcgcca ccaagaagca agagatcatg caggcgtacg cccgagaaga        600
cgaggctgcc gtcaaaaagt gatctcgccc cctccgtttt taaattttaa acaaaaaacg        660
tattttgtac aaaaatttac aaaaaaaaaa aaaaaaaaa aaaaaaaaa aaaaaa              717
```

<210> SEQ ID NO 96
<211> LENGTH: 2304
<212> TYPE: DNA
<213> ORGANISM: Lygus hesperus

<400> SEQUENCE: 96

| | | | | | | |
|---|---|---|---|---|---|---|
| atgacgacct | acgaggagtt | cattcaacag | agcgaggagc | gcgacggtat | caggttcact | 60 |
| tggaacgtct | ggccatcaag | tcgcatcgaa | gccaccaggt | tggtcgtacc | cgtaggatgt | 120 |
| ctctatcaac | cactaaaaga | acgcacggat | cttccagcta | ttcaatacga | tcccgttcta | 180 |
| tgcactagga | atacctgtag | agccatactc | aacccgatgt | gccaagtaaa | ctatagggca | 240 |
| aagttgtggg | tgtgtaactt | ctgtttccag | aggaatccgt | tcccaccaca | atacgccgca | 300 |
| atttccgagc | agcatcagcc | tgctgagttg | attccatcat | tctcaactat | agagtatact | 360 |
| atatctagag | ctcaattttt | gcctcctata | ttcctattgg | tggtggatac | gtgtttggat | 420 |
| gatgacgagc | taggagctct | gaaagattcg | ttacaaacgt | ctctatcttt | gctaccaacc | 480 |
| aactccctag | ttggtctgat | cacgtttggt | aaaatggtcc | aagttcacga | acttgggtgt | 540 |
| gaaggttgtt | cccggagcta | cgtgttcaga | ggcaccaagg | atttgacgtc | caagcaagta | 600 |
| caggacatgc | ttgggatcgg | aaaggtttcc | gcttctcctc | agcaacagca | gcaaagggca | 660 |
| atgggcggtc | agcagccatt | ccccaccaat | cggttcattc | agccgattca | aagttgtgac | 720 |
| atgagcctca | ccgacttgtt | gggcgaaatg | cagcgtgatc | catggccagt | gggtcagggt | 780 |
| aagcgacctc | ttagatcaac | gggtgctgct | ctagctattg | ccattgggtt | gttggagtgc | 840 |
| tcctacccca | acacgggagc | aaaagtcatg | ttgttccttg | gtggcccttg | ttcccaaggg | 900 |
| cctggtcaag | ttgtcaatga | tgacctgagg | gaacctatcc | gctctcatca | tgacatccag | 960 |
| aaagataatg | cccgctacat | gaaaaaagcc | attaaacatt | acgattcttt | ggcattgaga | 1020 |
| gcagccacta | atgggcattc | agtagacatt | tattcctgtg | ctttagatca | gacaggtttg | 1080 |
| gcggaaatga | agcaatgttg | caattctact | ggggtcata | tggtgatggg | tgacaccttc | 1140 |
| aactccactt | tgttcaaaca | gacgttccag | agggtgctct | cccgtgatca | aaaaggcgaa | 1200 |
| ttcaaaatgg | ctttcaatgg | cgtagttgaa | gtcaaaacct | cccgagagct | aaaagttatg | 1260 |
| ggagccattg | ggccttgcgt | ttcattgaat | acgaaaggtc | cgtgtgttag | tgaaactgac | 1320 |
| atagggcttg | gaggaacttg | ccagtggaag | ttctgcacat | taaccaaaa | taccactgct | 1380 |
| gccatgttct | ttgaggtagt | aaaccaacac | gctgctccta | tccctcaagg | tggaagagga | 1440 |
| tgtatacagt | tcataactca | ataccagcat | gcgtcgggcc | aaaggcgcat | ccgagtaacc | 1500 |
| actgtagcca | ggaattgggc | tgatgcgact | accaacatgc | accatgttag | tgcaggattt | 1560 |
| gatcaggaag | ctggagcggt | actcatggcc | aggatggtcg | ttcacagagc | tgaaactgat | 1620 |
| gatggacctg | atgtcatgag | atgggctgat | cgcatgttga | ttcgtctttg | ccagaaattc | 1680 |
| ggcgagtaca | acaaggatga | tccaaatagt | ttccgcctcc | cagaaaactt | ctcgctttac | 1740 |
| ccacagttca | tgtatcactt | gagaaggtcc | caattcttgc | aggtattcaa | caacagccca | 1800 |
| gacgaaacgt | cgtactatcg | tcacatcttg | atgcgggaag | atttgtcgca | gagcttgatc | 1860 |
| atgattcagc | cgatcctgta | cagttacagt | ttcaacggtc | cagaaccagt | ccttttggac | 1920 |
| acttccagca | ttcaacctga | tcggatcctg | ctgatggaca | ccttcttcca | aatcctcatc | 1980 |
| ttccacggcg | agaccatcgc | ccagtggcgt | gcccaaaggt | accaggacct | acctgaatat | 2040 |
| gagaacttca | agcagctcct | acaggctcct | gtagacgatg | ctaaggaaat | cctgcacact | 2100 |
| cggttcccca | tgccgaggta | cattgacacc | gaacagggcg | gatcacaagc | tagattcctt | 2160 |

```
ctctccaaag tcaacccatc ccaaactcac aacaacatgt acggctatgg agggaattt        2220 ggagccctg tgctcactga tgatgtttcc ctccaagtct tcatggaaca ccttaaaaag        2280
ctagccgttt catttactgc ctag                                              2304
```

<210> SEQ ID NO 97
<211> LENGTH: 311
<212> TYPE: DNA
<213> ORGANISM: Artificial
<220> FEATURE:
<223> OTHER INFORMATION: GUS

<400> SEQUENCE: 97

```
ccagcgtatc gtgctgcgtt tcgatgcggt cactcattac ggcaaagtgt gatggagcat         60
cagggcggct atacgccatt tgaagccgat gtcacgccgt atgttattgc cgggaaaagt        120
gtacgtatct gaaatcaaaa aactcgacgg cctgtgggca ttcagtctgg atcgcgaaaa       180
ctgtggaatt gatccagcgc cgtcgtcggt gaacaggtat ggaatttcgc cgattttgcg       240
acctcgcaag gcatattcgg gtgaaggtta tctctatgaa ctgtgcgtca cagccaaaag       300
ccagacagag t                                                            311
```

<210> SEQ ID NO 98
<211> LENGTH: 170
<212> TYPE: DNA
<213> ORGANISM: Artificial
<220> FEATURE:
<223> OTHER INFORMATION: Intron

<400> SEQUENCE: 98

```
ctcgagcctg agagaaaagc atgaagtata cccataacta acccattagt tatgcattta         60
tgttatatct attcatgctt ctactttaga taatcaatca ccaaacaatg agaatctcaa       120
cggtcgcaat aatgttcatg aaaatgtagt gtgtacactt accttctaga                 170
```

<210> SEQ ID NO 99
<211> LENGTH: 198
<212> TYPE: PRT
<213> ORGANISM: Lygus hesperus

<400> SEQUENCE: 99

```
Met Ser Ser Leu Lys Leu Gln Lys Arg Leu Ala Ala Ser Val Met Arg
1               5                   10                  15

Cys Gly Lys Lys Lys Val Trp Leu Asp Pro Asn Glu Ile Asn Glu Ile
            20                  25                  30

Ala Asn Thr Asn Ser Arg Gln Asn Ile Arg Lys Leu Ile Lys Asp Gly
        35                  40                  45

Leu Ile Ile Lys Lys Pro Val Ala Val His Ser Arg Ala Arg Val Arg
    50                  55                  60

Lys Asn Thr Glu Ala Arg Arg Lys Gly Arg His Cys Gly Phe Gly Lys
65                  70                  75                  80

Arg Lys Gly Thr Ala Asn Ala Arg Met Pro Val Lys Val Leu Trp Val
                85                  90                  95

Asn Arg Met Arg Val Leu Arg Arg Leu Leu Lys Lys Tyr Arg Glu Ala
            100                 105                 110

Lys Lys Ile Asp Arg Gln Met Tyr His Asp Leu Tyr Met Lys Ala Lys
        115                 120                 125

Gly Asn Val Phe Lys Asn Lys Arg Val Leu Met Asp Phe Ile His Lys
    130                 135                 140
```

```
Lys Lys Ala Glu Lys Ala Arg Ser Lys Met Leu Lys Asp Gln Ala Glu
145                 150                 155                 160

Ala Arg Arg Phe Lys Val Lys Glu Ala Lys Lys Arg Arg Glu Glu Arg
            165                 170                 175

Ile Ala Thr Lys Lys Gln Glu Ile Met Gln Ala Tyr Ala Arg Glu Asp
        180                 185                 190

Glu Ala Ala Val Lys Lys
        195
```

<210> SEQ ID NO 100
<211> LENGTH: 767
<212> TYPE: PRT
<213> ORGANISM: Lygus hesperus

<400> SEQUENCE: 100

```
Met Thr Thr Tyr Glu Glu Phe Ile Gln Gln Ser Glu Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Val Gly Cys Leu Tyr Gln Pro Leu Lys Glu Arg
        35                  40                  45

Thr Asp Leu Pro Ala Ile Gln Tyr Asp Pro Val Leu Cys Thr Arg Asn
    50                  55                  60

Thr Cys Arg Ala Ile Leu Asn Pro Met Cys Gln Val Asn Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Ile Pro
            100                 105                 110

Ser Phe Ser Thr Ile Glu Tyr Thr Ile Ser Arg Ala Gln Phe Leu Pro
        115                 120                 125

Pro Ile Phe Leu Leu Val Val Asp Thr Cys Leu Asp Asp Asp Glu Leu
    130                 135                 140

Gly Ala Leu Lys Asp Ser Leu Gln Thr Ser Leu Ser Leu Leu Pro Thr
145                 150                 155                 160

Asn Ser Leu Val Gly Leu Ile Thr Phe Gly Lys Met Val Gln Val His
                165                 170                 175

Glu Leu Gly Cys Glu Gly Cys Ser Arg Ser Tyr Val Phe Arg Gly Thr
            180                 185                 190

Lys Asp Leu Thr Ser Lys Gln Val Gln Asp Met Leu Gly Ile Gly Lys
        195                 200                 205

Val Ser Ala Ser Pro Gln Gln Gln Gln Arg Ala Met Gly Gly Gln
    210                 215                 220

Gln Pro Phe Pro Thr Asn Arg Phe Ile Gln Pro Ile Gln Ser Cys Asp
225                 230                 235                 240

Met Ser Leu Thr Asp Leu Leu Gly Glu Met Gln Arg Asp Pro Trp Pro
                245                 250                 255

Val Gly Gln Gly Lys Arg Pro Leu Arg Ser Thr Gly Ala Ala Leu Ala
            260                 265                 270

Ile Ala Ile Gly Leu Leu Glu Cys Ser Tyr Pro Asn Thr Gly Ala Lys
        275                 280                 285

Val Met Leu Phe Leu Gly Gly Pro Cys Ser Gln Gly Pro Gly Gln Val
    290                 295                 300

Val Asn Asp Asp Leu Arg Glu Pro Ile Arg Ser His His Asp Ile Gln
```

```
            305                 310                 315                 320
Lys Asp Asn Ala Arg Tyr Met Lys Lys Ala Ile Lys His Tyr Asp Ser
                325                 330                 335

Leu Ala Leu Arg Ala Ala Thr Asn Gly His Ser Val Asp Ile Tyr Ser
                340                 345                 350

Cys Ala Leu Asp Gln Thr Gly Leu Ala Glu Met Lys Gln Cys Cys Asn
                355                 360                 365

Ser Thr Gly Gly His Met Val Met Gly Asp Thr Phe Asn Ser Thr Leu
370                 375                 380

Phe Lys Gln Thr Phe Gln Arg Val Leu Ser Arg Asp Gln Lys Gly Glu
385                 390                 395                 400

Phe Lys Met Ala Phe Asn Gly Val Val Glu Val Lys Thr Ser Arg Glu
                405                 410                 415

Leu Lys Val Met Gly Ala Ile Gly Pro Cys Val Ser Leu Asn Thr Lys
                420                 425                 430

Gly Pro Cys Val Ser Glu Thr Asp Ile Gly Leu Gly Thr Cys Gln
                435                 440                 445

Trp Lys Phe Cys Thr Phe Asn Gln Asn Thr Thr Ala Ala Met Phe Phe
450                 455                 460

Glu Val Val Asn Gln His Ala Ala Pro Ile Pro Gln Gly Gly Arg Gly
465                 470                 475                 480

Cys Ile Gln Phe Ile Thr Gln Tyr Gln His Ala Ser Gly Gln Arg Arg
                485                 490                 495

Ile Arg Val Thr Thr Val Ala Arg Asn Trp Ala Asp Ala Thr Thr Asn
                500                 505                 510

Met His His Val Ser Ala Gly Phe Asp Gln Glu Ala Gly Ala Val Leu
                515                 520                 525

Met Ala Arg Met Val Val His Arg Ala Glu Thr Asp Asp Gly Pro Asp
                530                 535                 540

Val Met Arg Trp Ala Asp Arg Met Leu Ile Arg Leu Cys Gln Lys Phe
545                 550                 555                 560

Gly Glu Tyr Asn Lys Asp Asp Pro Asn Ser Phe Arg Leu Pro Glu Asn
                565                 570                 575

Phe Ser Leu Tyr Pro Gln Phe Met Tyr His Leu Arg Arg Ser Gln Phe
                580                 585                 590

Leu Gln Val Phe Asn Asn Ser Pro Asp Glu Thr Ser Tyr Tyr Arg His
                595                 600                 605

Ile Leu Met Arg Glu Asp Leu Ser Gln Ser Leu Ile Met Ile Gln Pro
610                 615                 620

Ile Leu Tyr Ser Tyr Ser Phe Asn Gly Pro Glu Pro Val Leu Leu Asp
625                 630                 635                 640

Thr Ser Ser Ile Gln Pro Asp Arg Ile Leu Leu Met Asp Thr Phe Phe
                645                 650                 655

Gln Ile Leu Ile Phe His Gly Glu Thr Ile Ala Gln Trp Arg Ala Gln
                660                 665                 670

Arg Tyr Gln Asp Leu Pro Glu Tyr Glu Asn Phe Lys Gln Leu Leu Gln
                675                 680                 685

Ala Pro Val Asp Asp Ala Lys Glu Ile Leu His Thr Arg Phe Pro Met
                690                 695                 700

Pro Arg Tyr Ile Asp Thr Glu Gln Gly Gly Ser Gln Ala Arg Phe Leu
705                 710                 715                 720

Leu Ser Lys Val Asn Pro Ser Gln Thr His Asn Asn Met Tyr Gly Tyr
                725                 730                 735
```

Gly Gly Glu Phe Gly Ala Pro Val Leu Thr Asp Asp Val Ser Leu Gln
            740                 745                 750

Val Phe Met Glu His Leu Lys Lys Leu Ala Val Ser Phe Thr Ala
            755                 760                 765

<210> SEQ ID NO 101
<211> LENGTH: 511
<212> TYPE: DNA
<213> ORGANISM: Lygus hesperus

<400> SEQUENCE: 101

| | | | | | |
|---|---|---|---|---|---|
| ggtgatgaga | tgcggcaaga | agaaagtgtg | gttggaccct | aatgaaatca | acgaaatcgc | 60 |
| caacaccaac | tctaggcaaa | acatccgtaa | gctgatcaag | gatggtttga | tcatcaaaaa | 120 |
| gcctgtggct | gtccactcca | gagcccgcgt | ccgtaaaaac | acagaagcca | gacgaaggg | 180 |
| tcgtcactgt | ggcttcggta | gaggaaggg | taccgccaac | gccagaatgc | ctgtgaaggt | 240 |
| cctgtgggtc | aacagaatga | gagtcctgcg | acggctcctt | aaaaatacaa | gagaagccaa | 300 |
| gaagatcgat | aggcaaatgt | accacgacct | ttacatgaaa | gccaaggta | acgtcttcaa | 360 |
| aaacaagagg | gtactgatgg | acttcattca | caagaagaag | gctgaaaagg | cgagatcaaa | 420 |
| gatgttgaag | gaccaggcag | aggcgagacg | tctcaaggtc | aaggaggcga | agaagaggcg | 480 |
| cgaggagagg | atcgccacca | agaagcaaga | g | | | 511 |

<210> SEQ ID NO 102
<211> LENGTH: 1145
<212> TYPE: DNA
<213> ORGANISM: Lygus hesperus

<400> SEQUENCE: 102

| | | | | | |
|---|---|---|---|---|---|
| tgggttgttg | gagtgctcct | accccaacac | gggagcaaaa | gtcatgttgt | tccttggtgg | 60 |
| cccttgttcc | caagggcctg | gtcaagttgt | caatgatgac | ctgagggaac | ctatccgctc | 120 |
| tcatcatgac | atccagaaag | ataatgcccg | ctacatgaaa | aaagccatta | acattacga | 180 |
| ttctttggca | ttgagagcag | ccactaatgg | gcattcagta | gacatttatt | cctgtgcttt | 240 |
| agatcagaca | ggtttggcgg | aaatgaagca | atgttgcaat | tctactgggg | gtcatatggt | 300 |
| gatgggtgac | accttcaact | ccactttgtt | caaacagacg | ttccagaggg | tgctctcccg | 360 |
| tgatcaaaaa | ggcgaattca | aaatggcttt | caatggcgta | gttgaagtca | aaacctcccg | 420 |
| agagctaaaa | gttatgggag | ccattgggcc | ttgcgtttca | ttgaatacga | aggtccgtg | 480 |
| tgttagtgaa | actgacatag | gcttggagg | aacttgccag | tggaagttct | gcacatttaa | 540 |
| ccaaaatacc | actgctgcca | tgttctttga | ggtagtaaac | caacacgctg | ctcctatccc | 600 |
| tcaaggtgga | agaggatgta | tacagttcat | aactcaatac | cagcatgcgt | cgggccaaag | 660 |
| gcgcatccga | gtaaccactg | tagccaggaa | ttgggctgat | gcgactacca | acatgcacca | 720 |
| tgttagtgca | ggatttgatc | aggaagctgg | agcggtactc | atggccagga | tggtcgttca | 780 |
| cagagctgaa | actgatgatg | gacctgatgt | catgagatgg | gctgatcgca | tgttgattcg | 840 |
| tctttgccag | aaattcggcg | agtacaacaa | ggatgatcca | aatagtttcc | gcctcccaga | 900 |
| aaacttctcg | ctttacccac | agttcatgta | tcacttgaga | aggtcccaat | tcttgcaggt | 960 |
| attcaacaac | agcccagacg | aaacgtcgta | ctatcgtcac | atcttgatgc | gggaagattt | 1020 |
| gtcgcagagc | ttgatcatga | ttcagccgat | cctgtacagt | tacagtttca | acggtccaga | 1080 |
| accagtcctt | ttggacactt | ccagcattca | acctgatcgg | atcctgctga | tggacacctt | 1140 | cttcc                                                                    1145

<210> SEQ ID NO 103
<211> LENGTH: 258
<212> TYPE: DNA
<213> ORGANISM: Artificial
<220> FEATURE:
<223> OTHER INFORMATION: GFP

<400> SEQUENCE: 103
agatacccag atcatatgaa acggcatgac tttttcaaga gtgccatgcc cgaaggttat      60
gtacaggaaa gaactatatt tttcaaagat gacgggaact acaagacacg taagtttaaa     120
cagttcggta ctaactaacc atacatattt aaattttcag gtgctgaagt caagtttgaa     180
ggtgataccc ttgttaatag aatcgagtta aaaggtattg attttaaaga agatggaaac     240
attcttggac acaaattg                                                    258

<210> SEQ ID NO 104
<211> LENGTH: 745
<212> TYPE: DNA
<213> ORGANISM: Artificial
<220> FEATURE:
<223> OTHER INFORMATION: Pt coral fluorescent protein

<400> SEQUENCE: 104
agtgtaataa cttactttga gtctaccgtc atgagtgcaa ttaaaccagt catgaagatt      60
gaattggtca tggaaggaga ggtgaacggg cacaagttca cgatcacggg agagggacaa     120
ggcaagcctt acgagggaac acagactcta aaccttacag tcactaaagg cgtgcccctt     180
cctttcgctt tcgatatctt gtcaacagca ttccagtatg caacagggt atttaccaaa     240 tacccagatg ataccgga ctatttcaag cagacctttc cggaaggata ttcgtgggaa      300
agaactttca aatatgaaga gggcgttgc accacaaaga gtgacataag cctcaagaaa      360
ggccaaccag actgcttca atataaaatt aactttaaag gggagaagct tgaccccaac     420
ggcccaatta tgcagaagaa gaccctgaaa tgggagccat ccactgagag gatgtacatg     480
gacgtggata aagacggtgc aaaggtgctg aagggcgatg ttaatgcggc cctgttgctt     540
gaaggaggtg gccattatcg ttgtgacttt aacagtactt acaaggcgaa gaaaactgtg     600
tccttcccag catatcactt tgtggaccac cgcattgaga ttttgagcca caatacggat     660
tacagcaagg ttacactgta tgaagttgcc gtggctcgca attctcctct tcagattatg     720
gcgccccagt aaaggcttaa cgaaa                                           745

<210> SEQ ID NO 105
<211> LENGTH: 42
<212> TYPE: DNA
<213> ORGANISM: Artificial
<220> FEATURE:
<223> OTHER INFORMATION: Primer

<400> SEQUENCE: 105
gcgtaatacg actcactata ggtgatgaga tgcggcaaga ag                          42

<210> SEQ ID NO 106
<211> LENGTH: 22
<212> TYPE: DNA
<213> ORGANISM: Artificial
<220> FEATURE:
<223> OTHER INFORMATION: Primer

<400> SEQUENCE: 106
ctcttgcttc ttggtggcga tc                                              22

<210> SEQ ID NO 107
<211> LENGTH: 22
<212> TYPE: DNA
<213> ORGANISM: Artificial
<220> FEATURE:
<223> OTHER INFORMATION: Primer

<400> SEQUENCE: 107
ggtgatgaga tgcggcaaga ag                                              22

<210> SEQ ID NO 108
<211> LENGTH: 44
<212> TYPE: DNA
<213> ORGANISM: Artificial
<220> FEATURE:
<223> OTHER INFORMATION: Primer

<400> SEQUENCE: 108
gcgtaatacg actcactata ggctcttgct tcttggtggc gatc                      44

<210> SEQ ID NO 109
<211> LENGTH: 44
<212> TYPE: DNA
<213> ORGANISM: Artificial
<220> FEATURE:
<223> OTHER INFORMATION: Primer

<400> SEQUENCE: 109
gcgtaatacg actcactata ggtgggttgt tggagtgctc ctac                      44

<210> SEQ ID NO 110
<211> LENGTH: 22
<212> TYPE: DNA
<213> ORGANISM: Artificial
<220> FEATURE:
<223> OTHER INFORMATION: Primer

<400> SEQUENCE: 110
ggaagaaggt gtccatcagc ag                                              22

<210> SEQ ID NO 111
<211> LENGTH: 22
<212> TYPE: DNA
<213> ORGANISM: Artificial
<220> FEATURE:
<223> OTHER INFORMATION: Primer

<400> SEQUENCE: 111
tgggttgttg gagtgctcct ac                                              22

<210> SEQ ID NO 112
<211> LENGTH: 44
<212> TYPE: DNA
<213> ORGANISM: Artificial
<220> FEATURE:
<223> OTHER INFORMATION: Primer

<400> SEQUENCE: 112
gcgtaatacg actcactata ggggaagaag gtgtccatca gcag                      44

<210> SEQ ID NO 113
<211> LENGTH: 46
<212> TYPE: DNA

```
<213> ORGANISM: Artificial
<220> FEATURE:
<223> OTHER INFORMATION: Primer

<400> SEQUENCE: 113
gcgtaatacg actcactata ggagataccc agatcatatg aaacgg         46

<210> SEQ ID NO 114
<211> LENGTH: 24
<212> TYPE: DNA
<213> ORGANISM: Artificial
<220> FEATURE:
<223> OTHER INFORMATION: Primer

<400> SEQUENCE: 114
caatttgtgt ccaagaatgt ttcc                                  24

<210> SEQ ID NO 115
<211> LENGTH: 24
<212> TYPE: DNA
<213> ORGANISM: Artificial
<220> FEATURE:
<223> OTHER INFORMATION: Primer

<400> SEQUENCE: 115
agatacccag atcatatgaa acgg                                  24

<210> SEQ ID NO 116
<211> LENGTH: 46
<212> TYPE: DNA
<213> ORGANISM: Artificial
<220> FEATURE:
<223> OTHER INFORMATION: Primer

<400> SEQUENCE: 116
gcgtaatacg actcactata ggcaatttgt gtccaagaat gtttcc          46

<210> SEQ ID NO 117
<211> LENGTH: 43
<212> TYPE: DNA
<213> ORGANISM: Artificial
<220> FEATURE:
<223> OTHER INFORMATION: Primer

<400> SEQUENCE: 117
gcgtaatacg actcactata ggagtgtaat aacttacttt gag             43

<210> SEQ ID NO 118
<211> LENGTH: 20
<212> TYPE: DNA
<213> ORGANISM: Artificial
<220> FEATURE:
<223> OTHER INFORMATION: Primer

<400> SEQUENCE: 118
tttcgttaag cctttactgg                                       20

<210> SEQ ID NO 119
<211> LENGTH: 21
<212> TYPE: DNA
<213> ORGANISM: Artificial
<220> FEATURE:
<223> OTHER INFORMATION: Primer

<400> SEQUENCE: 119
agtgtaataa cttactttga g                                     21
```

<210> SEQ ID NO 120
<211> LENGTH: 42
<212> TYPE: DNA
<213> ORGANISM: Artificial
<220> FEATURE:
<223> OTHER INFORMATION: Primer

<400> SEQUENCE: 120
gcgtaatacg actcactata ggtttcgtta agcctttact gg        42

<210> SEQ ID NO 121
<211> LENGTH: 473
<212> TYPE: DNA
<213> ORGANISM: Lygus hesperus

<400> SEQUENCE: 121
tgccgggccg ctcgccgaac catctgggaa gcttggaatg ggctcgactg ccgaactgat    60
caactttttc ggtccacacc ttttctatca actccttata ccgctccagg atgccgcctt   120
caaacagttt tttcttgtcg tcataagatc tggtgtcaac tcttcgttca tatttggagg   180
cgacttggat tttgggtggg tacttgccgg tgagggcctc agggtccaag cctttttca   240 aggctttgtg ccgaagttgt tgcttctgtc tttccttcag ttctttaaga tcgtagtctt   300
gcctcttttg cctttcctca agatcgtatt tctcggtctc aagtttgaca atggcttccc   360
agagttcctg agctttgatg cgtagcctgt ctatgctcat attttctatc gccaggggct   420
tgagcctaat gctgagggag atacgtttct cttcctccag ctgctccttg gtc          473

<210> SEQ ID NO 122
<211> LENGTH: 773
<212> TYPE: DNA
<213> ORGANISM: Lygus hesperus

<400> SEQUENCE: 122
gctgctcgcc gtccagttcg ttttcgagtt ccctgacacg ttgttccagc ttggcgatgg    60
ccttcttgcc tcccttgagg gcgttgtttt cggcttcgtc caacctgact tggagttcct   120
tgatttgcgt ttccagagcc ttgcggagct tctcctgggt ctgagcgtgg tcctgttctg   180
ccctgagttc atcagctaac ctagcggcat caaccattgc cttcttggcc ttctcttcgg   240
agttcttggc ttcgttgaga agttcgtcga ggtcagcatg aagtgtctgc aactctccct   300
caagcttgcg tttggcggct gaggcgctgg tagcttgggc agccaactcg ttgatctgtt   360
cgtgggcatc tccaagttct tgttcggctt ggcgcctgcc cctgtcggcc tgttcgagga   420
gagtgcgcga ctcctcgagc tcgtttccga gagcgttggc cctcctttcg gcgattccga   480
gttgttcacg agcatcgtcg cgtgcccttt gttcttcctc aagagcggtc tgtacgtcct   540
tgagttgttg ttggtatttc ttgatggtct tctgggcttc ggcgttagcc ttgttggcgt   600
ggtcgagagc gatttcgagt tcgttgatgt cggcttcaag cttcttcttc atgcgaagag   660
cctcagcctt acccttggct tcagcctcca agctggcttg catggagtcg agtgcccgtt   720
ggtggttctt cctggtgttc tcgaactcct cctccttttc ctggatccgc cgg          773

<210> SEQ ID NO 123
<211> LENGTH: 771
<212> TYPE: DNA
<213> ORGANISM: Lygus hesperus

<400> SEQUENCE: 123

```
tggacgccat caagaagaaa atgcaggcga tgaagatgga aaggacacg gccatggaca        60 aggccgacac ctgcgagggg caggccaagg acgctaacac ccgcgccgac aaaatccttg      120
aagatgtgag ggacctccaa aagaaactca accaggtaga aagtgatctc gaaaggacca      180
agagggaact cgagacgaaa accaccgaac tcgaagagaa ggagaaggcc aacaccaacg      240
ctgagagcga ggtcgcctcc ctcaacagga aagtccagat ggttgaagag acttggaaa       300 gatctgaaga aaggtccggc accgcacaac aaaaactgtc cgaagcctcc cacgccgctg      360
atgaagcctc tcgtatgtgc aaagtattgg agaacaggtc acaacaggat gaggagagga      420
tggaccagct caccaaccag ctgaaagaag cccgactcct cgctgaagac gccgacggca      480
aatcggatga ggtatcaagg aagctggcct tcgttgaaga cgaactggaa gtagctgaag      540
atcgtgtcaa atctggagac tcgaagatca tggagcttga ggaggagttg aaagttgtcg      600
gtaacagctt gaaatctctc gaagtttcag aggagaaggc caaccagcga gtcgaagagt      660
acaaacgtca aatcaagcaa ctgactgtca agttgaagga ggctgaagct cgcgctgagt      720
tcgccgaaaa gacagtcaag aagttgcaga agaggtgga ccggctggag g                771

<210> SEQ ID NO 124
<211> LENGTH: 257
<212> TYPE: DNA
<213> ORGANISM: Lygus hesperus

<400> SEQUENCE: 124
tgcgggccct ggggcagaat cccacagaat ctgacgtgaa aagttcacc caccagcaca        60 aaccagatga aagaatcagc ttcgaggtgt ttctcccgat ataccaagcc atatcgaagg      120
gtaggacgtc agacacagct gaagacttca tcgagggtct cagacacttt gacaaagatg      180
gaaatggctt catttcaaca gctgagcttc gccacttgct cacaactttg ggcgaaaaac      240
tgaccgacga cgaggtg                                                     257

<210> SEQ ID NO 125
<211> LENGTH: 410
<212> TYPE: DNA
<213> ORGANISM: Lygus hesperus

<400> SEQUENCE: 125
gccacctcca acgtgtttgc catgttcgat caggctcaga ttcaagaatt caaggaggca        60
ttcaacatga tcgaccagaa cagggacggc ttcgtggata aggaagacct ccatgacatg      120
ctcgcttccc taggtaagaa cccctcagac gagtatctcg aggggatgat gaacgaggcg      180
cctggtccca tcaacttcac aatgttcctc accctcttcg gtgagcggct tcagggaact      240
gatccggagg aggttatcaa gaacgcattt gggtgttttg acgaagacaa caacggattc      300
atcaacgagg aaagactgcg cgagctgctc acctccatgg gggacaggtt cactgatgaa      360
gacgtggacg aaatgtaccg agaggccccc atcaagaacg gcatgttcga                 410

<210> SEQ ID NO 126
<211> LENGTH: 1021
<212> TYPE: DNA
<213> ORGANISM: Lygus hesperus

<400> SEQUENCE: 126
tgttcatcct ggagcaggag gagtatcaga gagaaggtat tgaatggaag ttcatcgact        60
tcggacttga tcttcagccg accattgatc tcattgataa gccaatggga gtcatggctc      120
tcctggatga agaatgttgg ttccccaaag ccactgacaa gaccttcgtt gagaagctgg      180
```

```
tcggtgctca cagcgttcac cccaaattca tcaaaactga tttccgtgga gtcgccgact    240
ttgctgtcgt ccattatgcc ggaaaagtcg attattcggc ggcgcagtgg ctgatgaaga    300
acatggaccc tctgaacgaa aacgtcgtgc agctcctcca gaactcgcaa gatccgttcg    360
tcatccacat ctggaaggac gcagagatcg tcggcatggc tcaccaagct ctcagcgaca    420
ctcagtttgg agctcgtacc aggaagggta tgttccgaac cgtgtctcaa ctctacaaag    480
accagctgtc caaactcatg atcacacttc gcaacacgaa ccccaacttc gtccgttgca    540
tcctccccaa ccacgagaag agagctggca agatcgatgc tcctttggtg ctggatcagc    600
tcagatgcaa cggtgtgttg gaaggcatca gaatttgcag acaaggtttc ccgaatagaa    660
tcccattcca ggaattccgg caaagatacg agctcttaac tcccaatgtc atccccaaag    720
ggttcatgga cggtaaaaag gcttgcgaga agatgatcaa cgctctcgaa ctggacccta    780
atctctacag agttggtcag tccaagatat tcttcagagc tggagtctta gctcatctag    840
aagaagagcg cgactataag attactgatc tgatagccaa tttccgggct ttctgtaggg    900
gatatcttgc ccgaaggaac taccaaaagc gtcttcagca gctcaacgcc attcgtatta    960
tccagcgaaa ttgctcagct tacttgaagt tgaggaactg gcaatggtgg cggctgtaca   1020
c                                                                   1021

<210> SEQ ID NO 127
<211> LENGTH: 325
<212> TYPE: DNA
<213> ORGANISM: Lygus hesperus

<400> SEQUENCE: 127
cggtcatcat ctccatgaac tcgtcgaagt caacagttcc ggaaccgtca gaatcaattt     60
cagcaatcat catgtcaagt tcttgggagg tgattttgtc gtcgagttcc ttcaggattt    120
ccctcaagac gtcagtggta atgtaaccgt tcccttcctt gtcgtagagc ctgaaggcct    180
ccctcagttc ttgctgcatg gcctcagcat cttgtgtctc atcttctgtc aggaaaccgg    240
cagccaaggc tacgaactcc tcaaattcaa gttgtccaga gccatcagcg tcgacctccg    300
caatgatctc ctccaggatc ttctt                                         325

<210> SEQ ID NO 128
<211> LENGTH: 463
<212> TYPE: DNA
<213> ORGANISM: Lygus hesperus

<400> SEQUENCE: 128
cggtcatcat ctccatgaac tcgtcgaagt cgacagttcc ggatccgtca gagtcgatct     60
cctcgatgat catgtccagc tcctcgttgg tcagctgctc gtccaattca tgaaggattt    120
ctttgaggca ggaggtcggg atgtagccat taccttcttt gtcgtagaga cggaaggctt    180
ctcgcagctc tttctgcatg gcttcatcgt cttcctcaac aatgaacttg ctgccaacg     240 tgatgaactc ttcaaactcc agccttcccg atttgtcagc gtcaacttct tcgatgagtt    300
catcgagaat cttcttgttg aagggttgac ccatgagtct gaggatgtcg gccaccatgt    360
ccgtcgggat ggaacccgag tgatcccggt cgaaagcgtt caacgcgatg gtcatgatgg    420
ggataattcg gttaattctg ttagaccagt ccgattagtg acg                     463

<210> SEQ ID NO 129
<211> LENGTH: 413
<212> TYPE: DNA
```

<213> ORGANISM: Lygus hesperus

<400> SEQUENCE: 129

| | | | | | |
|---|---|---|---|---|---|
| atgggtgaag | gagggtgcct | gctcagagca | gtcctccagg | atgacggcta | tggacaacgc | 60 |
| ctcgaagaac | gccgctgaga | tgatcgacaa | gctgaccttg | acgttcaaca | ggactcggca | 120 |
| agccgtcatc | accagggagc | tcatcgaaat | catctccggt | gcctctgctt | tggagtaacg | 180 |
| tctcagctca | cccagccacc | tcccgtagat | ccactagtgc | tgcgagagac | cgagtacctc | 240 |
| gttctattca | ccctgtacat | ttcttaatca | atattattgg | aattcgattc | gatagtcgta | 300 |
| tgctgggaaa | tatcttgttc | atattcatga | tacttgttca | acattgttct | ggtaaataat | 360 |
| ttatgtaata | caggttgagt | taccaaaaaa | aaaaaaaaaa | aaaaaaaaaa | aaa | 413 |

<210> SEQ ID NO 130
<211> LENGTH: 449
<212> TYPE: DNA
<213> ORGANISM: Lygus hesperus

<400> SEQUENCE: 130

| | | | | | |
|---|---|---|---|---|---|
| gcagctggag | gaagagaaac | gtatctccct | cagcattagg | ctcaagcccc | tggcgataga | 60 |
| aaatatgagc | atagacaggc | tacgcatcaa | agctcaggaa | ctctgggaag | ccattgtcaa | 120 |
| acttgagacc | gagaaatacg | atcttgagga | aaggcaaaag | aggcaagact | acgatcttaa | 180 |
| agaactgaag | gaaagacaga | agcaacaact | tcggcacaaa | gccttgaaaa | aaggcttgga | 240 |
| ccctgaggcc | ctcaccggca | gtacccacc | caaaatccaa | gtcgcctcca | aatatgaacg | 300 |
| aagagttgac | accagatctt | atgacgcaaa | gaaaaaactg | tttgaaggcg | gcatcctgga | 360 |
| gcggtataag | gagttgatag | aaaaggtgtg | gaccgaaaaa | gttgatcagt | tcggcagtcg | 420 |
| agcccattcc | aagcttccca | gatggttcg | | | | 449 |

<210> SEQ ID NO 131
<211> LENGTH: 719
<212> TYPE: DNA
<213> ORGANISM: Lygus hesperus

<400> SEQUENCE: 131

| | | | | | |
|---|---|---|---|---|---|
| aggagttcga | gaacaccagg | aagaaccacc | aacgggcact | cgactccatg | caagccagct | 60 |
| tggaggctga | agccaagggt | aaggctgagg | ctcttcgcat | gaagaagaag | cttgaagccg | 120 |
| acatcaacga | actcgaaatc | gctctcgacc | acgccaacaa | ggctaacgcc | gaagcccaga | 180 |
| agaccatcaa | gaaataccaa | caacaactca | aggacgtaca | gaccgctctt | gaggaagaac | 240 |
| aaagggcacg | cgacgatgct | cgtgaacaac | tcggaatcgc | cgaaaggagg | gccaacgctc | 300 |
| tcggaaacga | gctcgaggag | tcgcgcactc | tcctcgaaca | ggccgacagg | ggcaggcgcc | 360 |
| aagccgaaca | agaacttgga | gatgcccacg | aacagatcaa | cgagttggct | gcccaagcta | 420 |
| ccagcgcctc | agccgccaaa | cgcaagcttg | agggagagtt | gcagacactt | catgctgacc | 480 |
| tcgacgaact | tctcaacgaa | gccaagaact | ccgaagagaa | ggccaagaag | gcaatggttg | 540 |
| atgccgctag | gttagctgat | gaactcaggg | cagaacagga | ccacgctcag | acccaggaga | 600 |
| agctccgcaa | ggctctggaa | acgcaaatca | aggaactcca | agtcaggttg | gacgaagccg | 660 |
| aaaacaacgc | cctcaaggga | ggcaagaagg | ccatcgccaa | gctggaacaa | cgtgtcagg | 719 |

<210> SEQ ID NO 132
<211> LENGTH: 737
<212> TYPE: DNA
<213> ORGANISM: Lygus hesperus

<400> SEQUENCE: 132

```
gcaggcgatg aagatggaga aggacacggc catggacaag gccgacacct gcgagggca        60
ggccaaggac gctaacaccc gcgccgacaa aatccttgaa gatgtgaggg acctccaaaa       120
gaaactcaac caggtagaaa gtgatctcga aggaccaag  agggaactcg agacgaaaac       180
caccgaactc gaagagaagg agaaggccaa caccaacgct gagagcgagg tcgcctccct       240
caacaggaaa gtccagatgg ttgaagagga cttggaaaga tctgaagaaa ggtccggcac       300
cgcacaacaa aaactgtccg aagcctccca cgccgctgat gaagcctctc gtatgtgcaa       360
agtattggag aacaggtcac aacaggatga ggagaggatg gaccagctca ccaaccagct       420
gaaagaagcc cgactcctcg ctgaagacgc cgacggcaaa tcggatgagg tatcaaggaa       480
gctggccttc gttgaagacg aactggaagt agctgaagat cgtgtcaaat ctggagactc       540
gaagatcatg gagcttgagg aggagttgaa agttgtcggt aacagcttga aatctctcga       600
agtttcagag gagaaggcca accagcgagt cgaagagtac aaacgtcaaa tcaagcaact       660
gactgtcaag ttgaaggagg ctgaagctcg cgctgagttc gccgaaaaga cagtcaagaa       720
gttgcagaaa gaggtgg                                                     737
```

<210> SEQ ID NO 133
<211> LENGTH: 205
<212> TYPE: DNA
<213> ORGANISM: Lygus hesperus

<400> SEQUENCE: 133

```
cagaatccca cagaatctga cgtgaagaag ttcacccacc agcacaaacc agatgaaaga        60
atcagcttcg aggtgtttct cccgatatac caagccatat cgaagggtag gacgtcagac       120
acagctgaag acttcatcga gggtctcaga cactttgaca aagatggaaa tggcttcatt       180
tcaacagctg agcttcgcca cttgc                                             205
```

<210> SEQ ID NO 134
<211> LENGTH: 326
<212> TYPE: DNA
<213> ORGANISM: Lygus hesperus

<400> SEQUENCE: 134

```
ggaggcattc aacatgatcg accagaacag ggacggcttc gtggataagg aagacctcca        60
tgacatgctc gcttccctag gtaagaaccc ctcagacgag tatctcgagg ggatgatgaa       120
cgaggcgcct ggtcccatca acttcacaat gttcctcacc ctcttcggtg agcggcttca       180
gggaactgat ccggaggagg ttatcaagaa cgcatttggg tgttttgacg aagacaacaa       240
cggattcatc aacgaggaaa gactgcgcga gctgctcacc tccatggggg acaggttcac       300
tgatgaagac gtggacgaaa tgtacc                                            326
```

<210> SEQ ID NO 135
<211> LENGTH: 944
<212> TYPE: DNA
<213> ORGANISM: Lygus hesperus

<400> SEQUENCE: 135

```
gacttgatct tcagccgacc attgatctca ttgataagcc aatgggagtc atggctctcc        60
tggatgaaga atgttggttc cccaaagcca ctgacaagac cttcgttgag aagctggtcg       120
gtgctcacag cgttcacccc aaattcatca aaactgattt ccgtggagtc gccgactttg       180
```

| | |
|---|---|
| ctgtcgtcca ttatgccgga aaagtcgatt attcggcggc gcagtggctg atgaagaaca | 240 |
| tggaccctct gaacgaaaac gtcgtgcagc tcctccagaa ctcgcaagat ccgttcgtca | 300 |
| tccacatctg gaaggacgca gagatcgtcg gcatggctca ccaagctctc agcgacactc | 360 |
| agtttggagc tcgtaccagg aagggtatgt tccgaaccgt gtctcaactc tacaaagacc | 420 |
| agctgtccaa actcatgatc acacttcgca acacgaaccc caacttcgtc cgttgcatcc | 480 |
| tccccaacca cgagaagaga gctggcaaga tcgatgctcc tttggtgctg atcagctca | 540 |
| gatgcaacgg tgtgttggaa ggcatcagaa tttgcagaca aggtttcccg aatagaatcc | 600 |
| cattccagga attccggcaa agatacgagc tcttaactcc caatgtcatc cccaaagggt | 660 |
| tcatggacgg taaaaaggct tgcgagaaga tgatcaacgc tctcgaactg gaccctaatc | 720 |
| tctacagagt tggtcagtcc aagatattct tcagagctgg agtcttagct catctagaag | 780 |
| aagagcgcga ctataagatt actgatctga tagccaattt ccgggctttc tgtaggggat | 840 |
| atcttgcccg aaggaactac caaaagcgtc ttcagcagct caacgccatt cgtattatcc | 900 |
| agcgaaattg ctcagcttac ttgaagttga ggaactggca atgg | 944 |

<210> SEQ ID NO 136
<211> LENGTH: 318
<212> TYPE: DNA
<213> ORGANISM: Lygus hesperus

<400> SEQUENCE: 136

| | |
|---|---|
| atcctggagg agatcattgc ggaggtcgac gctgatggct ctggacaact tgaatttgag | 60 |
| gagttcgtag ccttggctgc cggtttcctg acagaagatg agacacaaga tgctgaggcc | 120 |
| atgcagcaag aactgaggga ggccttcagg ctctacgaca aggaagggaa cggttacatt | 180 |
| accactgacg tcttgaggga atcctgaagg gaactcgacg acaaaatcac ctcccaagaa | 240 |
| cttgacatga tgattgctga aattgattct gacggttccg gaactgttga cttcgacgag | 300 |
| ttcatggaga tgatgacc | 318 |

<210> SEQ ID NO 137
<211> LENGTH: 423
<212> TYPE: DNA
<213> ORGANISM: Lygus hesperus

<400> SEQUENCE: 137

| | |
|---|---|
| atccccatca tgaccatcgc gttgaacgct ttcgaccggg atcactcggg ttccatcccg | 60 |
| acggacatgg tggccgacat cctcagactc atgggtcaac ccttcaacaa gaagattctc | 120 |
| gatgaactca tcgaagaagt tgacgctgac aaatcgggaa ggctggagtt tgaagagttc | 180 |
| atcacgttgg cagccaagtt cattgttgag gaagacgatg aagccatgca gaaagagctg | 240 |
| cgagaagcct tccgtctcta cgacaaagaa ggtaatggct acatcccgac tcctgcctc | 300 |
| aaagaaatcc ttcatgaatt ggacgagcag ctgaccaacg aggagctgga catgatcatc | 360 |
| gaggagatcg actctgacgg atccggaact gtcgacttcg acgagttcat ggagatgatg | 420 |
| acc | 423 |

<210> SEQ ID NO 138
<211> LENGTH: 252
<212> TYPE: DNA
<213> ORGANISM: Lygus hesperus

<400> SEQUENCE: 138

| | |
|---|---|
| ggtgaaggag ggtgcctgct cagagcagtc ctccaggatg acggctatgg acaacgcctc | 60 |

```
gaagaacgcc gctgagatga tcgacaagct gaccttgacg ttcaacagga ctcggcaagc    120
cgtcatcacc agggagctca tcgaaatcat ctccggtgcc tctgctttgg agtaacgtct    180
cagctcaccc agccacctcc cgtagatcca ctagtgctgc gagagaccga gtacctcgtt    240
ctattcaccc tg                                                         252

<210> SEQ ID NO 139
<211> LENGTH: 1110
<212> TYPE: DNA
<213> ORGANISM: Lygus hesperus

<400> SEQUENCE: 139
gtctccgctc aagctggtca tcagacttca gctgagtcct ggggtaccgg tcgtgctgtg     60
gctcgtatcc cccgtgttcg cggaggtggt actcaccgct caggtcaggg tgcttttggc    120
aacatgtgtc gcggcggtag gatgttcgct cccactcgcc catggcgtcg ttggcaccgc    180
aagatcaacg ttaaccaaaa acgttatgcc gtcgtgtccg ccatcgctgc atccggcgtc    240
ccagccctcg tcatgtccaa aggacacatg gtgcaaagcg tccctgaatt cccccttgtt    300
gtgtctgaca agttcaggaa atacactaaa accaaacagg ctgtcatctt ccttcaccgc    360
atcaaagcct ggcaagacat ccagaaagtg tacaagtcga agaggttccg tgctggtaag    420
ggtaaaatga ggaaccgcag gaggatccag aggcgtggac ccctcatcat ctacgaccag    480
gatcagggtc tgaacagggc tttccgtaac attcccggcg tcgatttgat cgaagtgagc    540
cgcctcaact tgctgaagct cgctccagga ggtcacatcg gccggttcgt catctggact    600
cagtcggcct tcgagaagtt ggacgccctc tacggcacct ggaagaagaa gtccacccte    660 aaggctggat acaatctccc catgcccaag atggccaaca ccgactttc cgcctcttc     720 aaggccccgg agatcaaggc tgtcctcagg aatcccaaga gaccatcgt acgacgagtg    780 cgcaaactga accctctccg caacaccagg gctatgctgc gtctcaaccc atacgctgct    840
gtcctcaaga ggaaggccat ccttgatcaa ggaagttga aactccagaa gctcgtagaa    900
gctgccaaga agggagatac caagctgtcg ccccgcgtcg agcgtcacct gaagatgatc    960
gagagaagga aagccctgat caagaaagcc aaggctgcca gcccaagaa gcccaaaacg   1020 gccaagaaac caagaccgc cgagaaggca ccagcacccg ccaagaaggc ggcagcgccc   1080
aaaaaggcca ccaccccctgc caagaaatga                                    1110

<210> SEQ ID NO 140
<211> LENGTH: 729
<212> TYPE: DNA
<213> ORGANISM: Lygus hesperus

<400> SEQUENCE: 140
atggccaatg ctaagcctat ttctaagaag aagaagtttg tgtctgacgg tgtcttcaaa     60
gccgaattga cgaatttcct taccagagaa ctcgctgaag aggggtactc aggtgttgag    120
gtccgagtga ccccccaacaa gacagaaatt atcatcatgg cgacaaggac acaaagcgtt    180
cttggtgata agggccgccg aatcaggag ctcacgtctg tagttcagaa aagattcaat    240
ttcaagcctc agactttgga tctctatgct gaaaaggtcg ccaccagagg tttgtgtgct    300
attgcacaag ctgaatccct ccgttacaaa ctcattggcg tcttgctgt ccgaggggct    360 tgctatggtg tccttcgctt catcatggaa aatggtgcca agggttgcga agtcgtagta    420 tctggaaaaac tgcgtggtca gagagccaag tcaatgaagt tcgtggatgg tttgatgatc    480
```

```
cacagtgggg atccctgtaa cgaatatgtt gatactgcta cccgacatgt gctccttaga    540
caaggtgtcc tgggaataaa ggtgaagatt atgttgccgt gggacgttac cggcaaaaat    600
gggccgaaga accctcttcc cgaccacgtc agcgttctct tacctaagga ggagctacca    660
aatttggccg ttagtgtgcc tggatccgac atcaaaccaa agcctgaagt accagcaccc    720
gctttgtga                                                            729

<210> SEQ ID NO 141
<211> LENGTH: 789
<212> TYPE: DNA
<213> ORGANISM: Lygus hesperus

<400> SEQUENCE: 141
atggctgttg gtaaaaataa gggtctatcg aaaggaggaa agaagggagt taaaaaaaag     60
gtagtggacc ctttcaccag gaaggattgg tacgatgtta aggctccttc catgttcaaa    120
aagcgtcaag ttggcaaaac tttggtcaac cgaactcagg gaaccaagat tgcttctgaa    180
gggttgaaag acgagttttc gaagtttcg ctcgctgata tccaggagga cactgatgcc    240
gagcgctcct tcaggaaatt caggctcatc gctgaagatg tccaagccag aaacgtcctt    300
accaatttcc acggtatgga tttgaccact gacaaactcc ggagcatggt caagaagtgg    360
cagactctca tcgaagccaa cgttgacgtc aagaccaccg acggctacct cctgcgcgtc    420
ttctgcatag gattcaccaa taagatcaa cttttcccaga gaaagacttg ctatgcccag    480
cataatcagg tccgagaaat ccgcaaaaag atggttaaaa acatcagtga cagcatttcc    540
agctgtgatt tgaggagtgt tgtgaacaag ctgatcccag actccatcgc taaagatata    600
gaaaagaatt gccaaggaat ctacccactc cacgatgtgt acattcggaa ggtgaaggtg    660
ttgaagaagc cgaggttcga gctcagcaag ctccttgagc ttcacgtcga tggcaaaggg    720
atcgacgaac ccggcgcgaa agtgacgagg actgacgctt acgagcctcc agttcaagag    780
tctgtctaa                                                            789

<210> SEQ ID NO 142
<211> LENGTH: 473
<212> TYPE: DNA
<213> ORGANISM: Lygus hesperus

<400> SEQUENCE: 142
gaccaaggag cagctggagg aagagaaacg tatctccctc agcattaggc tcaagcccct     60
ggcgatagaa aatatgagca tagacaggct acgcatcaaa gctcaggaac tctgggaagc    120
cattgtcaaa cttgagaccg agaaatacga tcttgaggaa aggcaaaaga ggcaagacta    180
cgatcttaaa gaactgaagg aaagacagaa gcaacaactt cggcacaaag ccttgaaaaa    240
aggcttggac cctgaggccc tcaccggcaa gtacccaccc aaaatccaag tcgcctccaa    300
atatgaacga agagttgaca ccagatctta tgacgcaaag aaaaaactgt ttgaaggcgg    360
catcctggag cggtataagg agttgataga aaaggtgtgg accgaaaaag ttgatcagtt    420
cggcagtcga gcccattcca agcttcccag atggttcggc gagcggcccg gca           473

<210> SEQ ID NO 143
<211> LENGTH: 1463
<212> TYPE: DNA
<213> ORGANISM: Lygus hesperus

<400> SEQUENCE: 143
gggtctcagc tgaggcacat tccatctcgt cgcaaatctt tcctgcatct ctcctgggtg     60
```

```
accctttaggt gaccaatcac atccatcatg tcggacgagg agtattcgga gtcggaggaa      120
gagacccagc cggaaccaca gaaaaaacca gaggctgaag gaggcggcga cccagaattc      180
gtcaagcgta aggaagccca gacctcagcc ttagacgagc agcttaaaga ctatatcgca      240
gaatggagga aacaaagagc tcgcgaagaa gaagacctca agaagctgaa ggagaagcaa      300
gccaagcgca aggtcgctcg ggcagaagaa gaaagagat tggcggaaaa gaagaagcag       360
gaagaagaac gacgtgtgag ggaagcagaa gagaagaaac agagggaaat cgaagagaag      420
aggcgaaggc ttgaagaggc cgagaagaag agacaagcca tgatggctgc tctcaaggac      480
cagagcaaaa cgaagggacc caattttgtc gttaataaga aagccgaaac ccttggcatg      540
tcctccgctc aaattgagcg caacaagact aaggaacagc ttgaggaaga aaaacgtatc      600
tccctcagca ttaggctcaa gcccctggcg atagaaaata tgagcataga caggctacgc      660
ataaaagctc aggaactctg ggaagccatt gtcaaacttg agaccgagaa atacgatctt      720
gaggaaaggc aaaagaggca agactacgat cttaaagaac tgaaggaaag acagaagcaa      780
caacttcggc acaaagcctt gaaaaaaggc ttggaccctg aggccctcac cggcaagtac      840
ccacccaaaa tccaagtcgc ctccaaatat gaacgaagag ttgacaccag atcttatgac      900
gacaagaaaa aactgtttga aggcggcatc ctggagcggt ataaggagtt gatagaaaag      960
gtgtggaccg aaaagttga tcagttcggc agtcgagccc attccaagct tcccagatgg      1020
ttcggcgagc ggcccggcaa gaagaaggat gcccctgaaa gcccggaaga gaggaagtg      1080 aaggtagaag atgaacctga agctgaacca agcttcatgc tcgacgaaga agaagaagaa      1140
gcggaagaag aggaggcgga agaggaagag gaagccgagg aagaggagga agaagaagag      1200
gaagaggaag aggaggagga ggaagaagaa taggtctttt tcaacatttc actgcaccca      1260
cagttccacg gtctttccgc ccacaaactc aatctgtgct cacgagatct tagcaggaaa      1320
agtattgcga cccgataaga acaaattaaa ttatttttgg aatatctcgt tcagttattt      1380
cgtgagaaac aattttattc atgtaaacga ttaaagatc ccatacattt ccaaaaaaaa       1440
aaaaaaaaaa aaaaaaaaaa aaa                                             1463
```

<210> SEQ ID NO 144
<211> LENGTH: 773
<212> TYPE: DNA
<213> ORGANISM: Lygus hesperus

<400> SEQUENCE: 144

```
ccggcggatc caggaaaagg aggaggagtt cgagaacacc aggaagaacc accaacgggc       60
actcgactcc atgcaagcca gcttggaggc tgaagccaag ggtaaggctg aggctcttcg      120
catgaagaag aagcttgaag ccgacatcaa cgaactcgaa atcgctctcg accacgccaa      180
caaggctaac gccgaagccc agaagaccat caagaaatac caacaacaac tcaaggacgt      240
acagaccgct cttgaggaag aacaaagggc acgcgacgat gctcgtgaac aactcggaat      300
cgccgaaagg agggccaacg ctctcggaaa cgagctcgag gagtcgcgca ctctcctcga      360
acaggccgac aggggcaggc gccaagccga caagaacttt ggagatgccc acgaacagat      420
caacgagttg gctgcccaag ctaccagcgc ctcagccgcc aaacgcaagc ttgagggaga      480
gttgcagaca cttcatgctg acctcgacga acttctcaac gaagccaaga actccgaaga      540
gaaggccaag aaggcaatgg ttgatgccgc taggttagct gatgaactca gggcagaaca      600
ggaccacgct cagacccagg agaagctccg caaggctctg gaaacgcaaa tcaaggaact      660
```

```
ccaagtcagg ttggacgaag ccgaaaacaa cgccctcaag ggaggcaaga aggccatcgc    720
caagctggaa caacgtgtca gggaactcga aaacgaactg gacggcgagc agc           773

<210> SEQ ID NO 145
<211> LENGTH: 5446
<212> TYPE: DNA
<213> ORGANISM: Lygus hesperus

<400> SEQUENCE: 145
tcaggaaaac tggctggtgc tgatattgag acctatctgc tggagaaggc tcgtgtcatc     60
tcccaacaaa cactcgagag atcctaccac attttctacc agatgatgtc tggagctgtc    120
aagggcgtca aggaaatgtg cttgctggtc gacgatatct atacgtacaa cttcatatcc    180
cagggtaaag tcagcattgc aggcgttgat gacggagagg aaatggttct gaccgatcaa    240
gccttcgaca tcttgggttt caccaagcaa gagaaggaag acatctacaa gatcaccgcc    300
gctgtcattc acatgggtac catgaagttc aagcaaaggg gtcgtgaaga gcaggctgaa    360
gccgatggaa ctgaggaagg cggtaaggtc ggtgtgctcc tcggtatcga cggtgacgac    420
ttgtacaaga atatgtgcaa gcccagaatc aaggtcggaa ctgagttcgt gacccaggga    480
aagaacgtca accaggtctc atactctctc ggtgccatgt ccaagggtat gttcgatcgt    540
ctcttcaaat tcttggtcaa gaaatgtaac gaaactctgg acaccaaaca gaagagacag    600
cacttcattg gtgtactgga tattgccggg ttcgaaattt tcgacttcaa cggttttgag    660
caactgtgta tcaacttcac caacgagaaa ttgcaacaat tcttcaacca ccacatgttc    720
gtactcgagc aagaagagta caagagggaa ggcattaact gggctttcat tgatttcgga    780
atggacttgc tcgcttgtat tgaactgatt gagaagccca tgggtatctt gtccatcctt    840
gaagaagagt ctatgttccc caaggctact gacaagacct tgaggacaa actcatcacc     900 aaccacttgg gcaaatctcc caacttcagg aagcccgccg ttccaaagcc tggccaacaa    960
gctggtcact cgccatcgc tcactacgct ggttgcgtgt catacaacat caccggctgg   1020
cttgagaaga acaaggatcc gttgaacgac actgttgtcg atcagtacaa gaagggaacc   1080
aacaaactgt tgtgcgagat cttcgctgat catcctggcc aatctggtgc ccctggtggt   1140
gatgctggtg gcaagggtgg tcgtggcaag aaaggtggtg gcttcgccac tgtgtcatct   1200
tcctacaagg aacaattgaa caacttgatg accacttga agagcacaca gcctcacttc    1260
gtccgttgta tcatccccaa cgaattgaaa cagcccggtg ttattgattc tcacttggtc   1320
atgcaccagc tgacttgtaa cggtgtactt gaaggcatcc gtatttgccg taaaggcttc   1380
cccaacagga tgaactaccc tgacttcaag ctccgataca agatccttaa ccccgctgcc   1440
gtggacagag agagtgatat cctcaaggct gctggtctcg tccttgagtc aactgggctc   1500
gaccctgata tgtaccgtct cggccacacc aaggtgttct tcagggccgg agttttgggt   1560
caacttgaag aattgcgtga cgacaggctt agcaagatca tcggatggat gcaggccttc   1620
atgcgcggtt acctcgtcag gaaggagtac aagaagctcc aggaacagag gttagccctc   1680
caagttgtcc agcgcaactt gagaaggtac ctccaactga ggacctggcc ctggtggaag   1740
atgtggtcca gggtcaagcc cctcctcaac gtcgccaacg tcgaagagga gatgcggaaa   1800
ctcgaagagt tggtcgccga acccaggcc gctttggaga aggaggagaa gctgaggaag    1860
gaggccgaag cccttaacgc caagcttctc aagagaaga ccgaccttct caggaacttg     1920
gaaggagaga agggatccat cagcggtatc caggaacgat gtgccaagct gcaagcccaa   1980
aaggccgatc ttgagtctca actcatggac acccaagaaa ggctgcagaa cgaagaagat   2040
```

```
gccaggaacc agctcttcca acagaagaag aaattggaac aagaagccgc tgccctcaag    2100
aaggacatcg aagatctcga actctccaac caaaagaccg accaagataa ggccagcaag    2160
gaacaccaaa tcagaaacct caatgacgag atcgctcacc aagatgactt gatcaacaag    2220
ctcaacaagg agaagaaaat ccagagcgaa ctcaaccaaa agactgctga agaacttcag    2280
gccgctgaag acaaaatcaa ccacctcacc aaggttaagg tcaagcttga acagaccttg    2340
gatgaactcg aagacaccct cgaacgtgaa aagaaactcc gaggagatgt cgaaaaggcc    2400
aagaggaaga ctgaaggcga cctcaagctc actcaggaag ccgttgccga tcttgaaagg    2460
aacaagaaag aactcgaaca gaccatccag aggaaagaca aggaaattgc ttccctcacc    2520
gccaagctcg aagacgaaca atccatcgtc aacaagactg gcaaacagat caaggaactc    2580
cagagccgca ttgaagagct cgaggaggaa gtcgaggctg agaggcaagc ccgcggaaag    2640
gctgagaagc aacgtgctga cctcgcccgc gaacttgagg aactcggcga gaggttagag    2700
gaagctggtg gtgccacctc tgcccagatc gagctcaaca agaagcgtga agctgagatg    2760
agcaaactca ggagggacct ggaagaagcc aacatccagc acgaaggcac gctcgccaac    2820
ctccgcaaga agcacaacga tgctgtcagt gagatgggag accaaatcga ccagctcaac    2880
aaacttaaga ccaaggttga aaaggagaag tctcaatacc tcggtgaact caacgacgtc    2940
cgcgcctcca ttgaccactt gaccaacgag aaggctgcca ctgaaaaggt tgccaagcaa    3000
ctgcaacacc aaatcaatga agttcaaggc aaacttgatg aagctaacag gacgctcaac    3060
gacttcgatg ctgccaagaa gaagttgtct attgagaact ctgacctcct cagacagttg    3120
gaggaagctg agagccaagt ttctcaactt agcaagatca agatctccct caccactcaa    3180
ctcgaggaca ctaagcgtct cgccgatgag gaagctaggg aacgcgcaac ccttcttggc    3240
aagttccgca acttggaaca cgaccttgac aacctgaggg aacaggtgga ggaagaagcc    3300
gaagctaagg ctgatatcca acgtcaactc agcaaggcca acgctgaagc tcagttgtgg    3360
cgcagcaagt acgaaagcga gggtgttgcc cgcgctgagg agcttgagga ggccaagagg    3420
aaactccagg cccgtttggc tgaggctgag gagaccattg agtccctcaa ccagaaggtt    3480
atcgcccttg agaagacgaa gcagcgcctt gccactgaag tcgaggatct gcagctcgag    3540
gtcgaccgtg ccaacgccat tgccaatgcc gctgaaaaga aggctaaggc tattgacaag    3600
atcattggtg aatggaaact caaggttgat gaccttgctg ctgagcttga tgctagtcaa    3660
aaggaatgca gaaactactc cactgagctc ttcaggctca agggagctta tgaagaagga    3720
caggaacaac ttgaagctgt ccgcaggagg aacaagaacc ttgctgatga agtcaaggac    3780
ttgctcgacc agatcggtga gggtggccgc aacatccacg aaattgagaa gcagcgcaag    3840
aggctcgaag ttgagaagga cgaacttcag gccgctcttg aggaggctga agccgctctt    3900
gaacaggagg agaacaaagt actcagggct caacttgagc tcagccaggt cgtcaagaa    3960 attgaccgcc gcatccagga gaaggaagag gagttcgaga acaccaggaa gaaccaccaa    4020
cgggcactcg actccatgca agccagcttg gaggctgaag ccaagggtaa ggctgaggct    4080
cttcgcatga agaagaagct tgaagccgac atcaacgaac tcgaaatcgc tctcgaccac    4140
gccaacaagg ctaacgccga agcccagaag accatcaaga ataccaaca acaactcaag    4200 gacgtacaga ccgctcttga ggaagaacaa agggcacgcg acgatgctcg tgaacaactc    4260
ggaatcgccg aaaggagggc caacgctctc ggaaacgagc tcgaggagtc gcgcactctc    4320
ctcgaacagg ccgacagggg caggcgccaa gccgaacaag aacttggaga tgcccacgaa    4380
```

```
cagatcaacg agttggctgc ccaagctacc agcgcctcag ccgccaaacg caagcttgag    4440
ggagagttgc agacacttca tgctgacctc gacgaacttc tcaacgaagc caagaactcc    4500
gaagagaagg ccaagaaggc aatggttgat gccgctaggt tagctgatga actcagggca    4560
gaacaggacc acgctcagac ccaggagaag ctccgcaagg ctctggaaac gcaaatcaag    4620
gaactccaag tcaggttgga cgaagccgaa acaacgccc tcaagggagg caagaaggcc     4680
atcgccaagc tggaacaacg tgtcaggaa ctcgaaaacg aactggacgg cgagcagagg     4740
agacacgccg acgcacaaaa gaacctccgt aaatccgagc gtagaattaa ggagctcagt    4800
ttccagtccg acgaggaccg taagaaccac gaacgcatgc aagacctcgt agacaaactg    4860
caacagaaga tcaagactta caagaggcag attgaagaag ccgaagaaat cgcggcccTt    4920
aacctcgcca aattccgcaa agcacaacaa gaactcgaag aagctgaaga acgcgctgat    4980
ctcgctgaac aggctgtttc caaattcaga acaaagggtg gacgcgcagg atctgctgcc    5040
agagcgatga gccctgtcgg ccagaagtga aggaacgaat aagcggacgt ataagctatc    5100
aatacctcgc acacaaacct gccaggcctc aatttgacgg caatgccttc ccaccacgat    5160
tcgatctaca tcccgacgac ttttaagatc tttgatagca acgcaaaaca tcaaatgaaa    5220
atcttttaaa ttttatgtat ttattttgac ctatttatt aagttattgt taatacaaac     5280
ataattccat gagctagata tctagccaac gaaccatcac aatcacgatt attcgaactg    5340
tacgatagaa gcattatttg tacagctgga ccatttacaa aatattttg cttcgaataa     5400 taaagagttt atatcgcgaa aaaaaaaaaa aaaaaaaaaa aaaaaa                   5446

<210> SEQ ID NO 146
<211> LENGTH: 964
<212> TYPE: DNA
<213> ORGANISM: Lygus hesperus

<400> SEQUENCE: 146
tcctcctctg gtgcccgact cttcaaatac ccaaatccag tcatgtcttc ccgtaaaacc      60
gctggccgca gggcgaccac caagaagcgc gctcagcgtg cgacgtcaaa cgtattcgcc     120
atgttcgatc aggctcagat tcaagaattc aaggaggcat tcaacatgat cgaccagaac     180
agggacggct tcgtggataa ggaagacctc catgacatgc tcgcttccct aggtaagaac     240
ccctcagacg agtatctcga ggggatgatg aacgaggcgc tggtcccat caacttcaca      300 atgttcctca ccctcttcgg tgagcggctt cagggaactg atccggagga ggttatcaag     360
aacgcatttg ggtgttttga cgaagacaac aacggattca tcaacgagga aagactgcgc     420
gagctgctca cctccatggg ggacaggttc actgatgaag acgtggacga aatgtaccga     480
gaggccccca tcaagaacgg catgttcgac tacatcgaat tcactcggat cctcaagcac     540
ggagccaaag acaaagacga gcagtgacct atcaaatcct cgtcaacctc ccttcagtaa     600
tttgaaacca atccatcaaa ttttgtttaa aactcttact taaatccga tcatctacgt      660 cactttgcca ccaatcggta ttattttttg agccgttcct acataaatcg aattaatttt     720
atacctacga atcatattgt tggaaatttc tctcttgtac ttatactttc tgttatttcc     780
taatttttct aactaaccaa gttagtcgtt agttttatt cattcccttta taaattatta     840 gttatccatt tttaatcatc ttgaagttat tgttttcg agtggtagaa tatttataca      900
ttttccaata tataatggtt tattcattct taaaaacga aaaaaagaa aaaaaaaaa       960 aaaa                                                                 964
```

-continued

```
<210> SEQ ID NO 147
<211> LENGTH: 5872
<212> TYPE: DNA
<213> ORGANISM: Lygus hesperus

<400> SEQUENCE: 147
```

| | | | | | |
|---|---|---|---|---|---|
| gatcttacct | gcctgaacga | ggcgtccgtt | cttcacaaca | tcaaggacag | atattactcc | 60 |
| ggattgattt | atacgtattc | gggactcttc | tgcgtggtgg | tcaacccta | caagaaactg | 120 |
| ccaatctaca | cagagagaat | catggagaaa | tacaaaggcg | tcaaaagaca | cgacctccct | 180 |
| ccacacgtat | tcgccatcac | agacacagct | taccgttcta | tgctgcaaga | tagggaagat | 240 |
| caatcgatac | tctgcaccgg | cgaatcgggt | gcggggaaaa | ccgaaaacac | gaaaaaagta | 300 |
| atccagtact | tggcctacgt | tgcagcctcg | aaacccaaat | cttccgcatc | cccacatacg | 360 |
| gcccagagtc | aagctctgat | cattggagaa | ctcgaacaac | agctgcttca | agctaaccca | 420 |
| attttggaag | cattcggaaa | cgccaagact | gttaaaaacg | ataattcttc | tcgattcggt | 480 |
| aaattcattc | gtatcaattt | cgacgcatca | ggctacatcg | caggagccaa | catagaaacg | 540 |
| tatcttctag | agaaatctag | ggccatcaga | caagcgaaag | atgagcgaac | gttccacatc | 600 |
| ttttaccaac | ttctggccgg | agcatctgca | gaacaaagaa | aggagttcat | cctcgaagat | 660 |
| ccgaaaaact | acccttcct | cagcagcggg | atggtgtctg | tgcctggagt | tgacgatggt | 720 |
| gttgatttcc | aagcaactat | cgcctccatg | tccatcatgg | gcatgaccaa | cgacgatctt | 780 |
| tccgctctct | tccgcatcgt | cagtgccgtc | atgctgttcg | gcagcatgca | gttcaagcag | 840 |
| gagcgaaaca | gcgaccaggc | gacgctccca | gacaacactg | tagcgcaaaa | aatcgcccac | 900 |
| ctccttggtc | tctcaatcac | agagatgacc | aaagcgttcc | tcaggcctag | aatcaaagta | 960 |
| ggacgggatt | tcgtcaccaa | ggctcaaact | aaggaacaag | ttgagttcgc | agtggaagcc | 1020 |
| atttcgaaag | cctgctacga | acgtatgttc | cgatggctcg | tcaacagaat | caaccgctcc | 1080 |
| ctggatcgta | ccaaaaggca | gggagcatct | ttcattggta | ttcttgatat | ggctggtttc | 1140 |
| gaaatctttg | agatcaactc | cttcgagcag | cttgtatca | attacaccaa | tgagaaactt | 1200 |
| caacaactct | tcaaccacac | catgttcatt | ttggagcaag | aggagtacca | gagagaaggt | 1260 |
| attgaatgga | agttcatcga | cttcggactt | gatcttcagc | cgaccattga | tctcattgat | 1320 |
| aagccaatgg | gagtcatggc | tctcctggat | gaagaatgtt | ggttccccaa | agccactgac | 1380 |
| aagaccttcg | ttgagaagct | ggtcggtgct | cacagcgttc | accccaaatt | catcaaaaact | 1440 |
| gatttccgtg | gagtcgccga | ctttgctgtc | gtccattatg | ccggaaaagt | cgattattcg | 1500 |
| gcggcgcagt | ggctgatgaa | gaacatggac | cctctgaacg | aaaacgtcgt | gcagctcctc | 1560 |
| cagaactcgc | aagatccgtt | cgtcatccac | atctggaagg | acgcagagat | cgtcggcatg | 1620 |
| gctcaccaag | ctctcagcga | cactcagttt | ggagctcgta | ccaggaaggg | tatgttccga | 1680 |
| accgtgtctc | aactctacaa | agaccagctg | tccaaactca | tgatcacact | tcgcaacacg | 1740 |
| aaccccaact | tcgtccgttg | catcctcccc | aaccacgaga | agagagctgg | caagatcgat | 1800 |
| gctcctttgg | tgctggatca | gctcagatgc | aacggtgtgt | tggaaggcat | cagaatttgc | 1860 |
| agacaaggtt | tcccgaatag | aatcccattc | caggaattcc | ggcaaagata | cgagctctta | 1920 |
| actcccaatg | tcatccccaa | agggttcatg | acggtaaaa | aggcttgcga | agatgatc | 1980 |
| aacgctctcg | aactggaccc | taatctctac | agagttggtc | agtccaagat | attcttcaga | 2040 |
| gctggagtct | tagctcatct | agaagaagag | cgcgactata | agattactga | tctgatagcc | 2100 |
| aatttccggg | ctttctgtag | gggatatctt | gcccgaagga | actaccaaaa | gcgtcttcag | 2160 |

```
cagctcaacg ccattcgtat tatccagcga aattgctcag cttacttgaa gttgaggaac    2220
tggcaatggt ggcggctgta caccaaggtc aaacctctgc ttgaagtgac gaaacaagaa    2280
gagaagctga cgcaaaagga agacgaactg aagcaggtcc gcgagaaact ggacaaccag    2340
gtgaggtcca aggaagagta tgaaaagagg cttcaggacg cttttggagga gaaagctgct    2400 ctggcagagc aacttcaggc agaagtagag ctgtgtgcgg aagccgaaga aatgagagcc    2460
aggctcgctg tgaggaagca agaactagag gaaattctcc acgatctaga agccagaata    2520
gaggaagaag agcaacgaaa cacggtcctc atcaacgaaa agaagaagtt gaccctcaac    2580
atcgccgacc tcgaagaaca actggaagag gaagaaggag ctcgacgaaa actccaactc    2640
gaaaaagtcc agatcgaagc tcggctgaag aaaatggaag aggacctcgc tctggccgaa    2700
gacaccaaca ccaaagtcgt aaaggagaag aaagtgttgg aagagagggc tagtgacttg    2760
gcccagaccc tcgctgagga agaagaaaaa gctaaacacc tcgcgaagct caagaccaag    2820
cacgagacga cgatagcgga attggaagag aggttgctca agacaatca gcagaggcag    2880 gaaatggata ggaacaagag gaagatcgaa tcagaggtga atgatttgaa agaacaaatt    2940
aacgagaaga aggtccaagt agaggagctt cagttgcaac tcgggaagag ggaagaggaa    3000
atcgctcaag ctctgatgag aattgacgag gaaggagcag gcaaagctca gactcaaaag    3060
gctctcaggg aattggagtc tcagctggct gagctacaag aggatctaga ggctgaaaag    3120
gccgctcgcg ccaaggccga aaagcagaag cgcgacctca cgaagaact cgagtccctc    3180 aagaatgaac ttcttgactc actggacacg acagcagctc aacaggaatt gaggaccaag    3240
agagaacacg aactggcaac gctcaagaaa acattagaag aggaaacgca cattcacgaa    3300
gtatctctca ccgaaatgag gcacaaacac actcaagaag tcgctgcact caacgaacag    3360
ttggagcaac tcaaaaaggc caaatctgca ctcgaaaaat cgaaagcaca acttgaaggg    3420
gaagctgctg agctcgccaa cgaactggaa acagcaggaa cgagcaaggg cgagagtgaa    3480
aggaaacgga agcaggccga atcgtctctg caggagctct cgtcgcgact cttggaaatg    3540
gagagaacca agccgagct ccaagagagg gtccagaaac tgtctgcaga agccgactct    3600
gtcaatcagc agttggaagc agcggaactg aaagcatcag cagccctcaa ggcatctggt    3660
accttggaga ctcagctcca ggaggcgcaa gtgctcctgg aagaggaaac tcggcagaag    3720
ctgtcgttga ccaccaaact gaaaggcctc gaaagcgaaa gagatgctct caaagagcaa    3780
ctctacgaag aggacgaggg taggaagaac ctagaaaaac agatggcgat actcaatcaa    3840
caagtagctg aaagcaagaa gaagtctgaa gaagaaacgg aaaaaataac tgaactcgaa    3900
gaaagtcgca aaaaattgct caaagacata gaaattcttc aaaggcaagt cgaagaactt    3960
caagttacca cgacaaatt agagaaaggc aagaagaagc tgcagtcaga actggaagac    4020
ctcaccatcg acctggagtc tcagagaaca aaggtggtcg agctcgagaa gaaacaaaga    4080
aatttcgaca aagttttggc cgaagaaaaa gcgttgtcgc aacaaatcac gcacgagagg    4140
gatgcggctg aaagagaagc ccgtgaaaag gaaactagaa tactgtcgct gacgcgagaa    4200
ctcgatgaat tcatggagaa aatcgaggaa ctggagagaa gcaaacggca actccaggct    4260
gaactagacg agctggtcaa caaccaaggc accaccgaca aaagcgtgca cgaattggaa    4320
agggcgaaac gagttctgga gtcacaactt gcagagcaga agcacaaaa tgaagagctt    4380 gaagatgaac tccaaatgac ggaagacgcc aaattgaggc tcgaagtcaa catgcaagct    4440
ctgagagctc aattcgaaag agatctacag ggcaaagaag agtcgggaga agaaaagagg    4500
agaggattgc tgaaacagct gagggacatt gaggctgaac ttgaagacga gagaaaacaa    4560
```

```
aggaccgctg ctgttgcctc tagaaagaag attgaagcgg atttcaaaga tgtagaacag    4620
caactggaaa tgcacactaa ggtaaaggaa gatcttcaga agcaactgaa gaaatgccag    4680
gtccaactga aggacgcaat cagagacgcg gaagaggctc ggctcggtcg ggaagagctg    4740
caggctgccg ctaaagaggc cgaaggaag tggaagggtt tggaaacgga gctcattcaa     4800
gtgcaagagg atttgatggc gagcgaaagg cagcggcggg cagcggaagc cgaaagggat    4860
gaagtcgttg aagaagccaa caagaatgtc aagagcttat cgaatcttct cgacgaaaag    4920
aagaggctcg aagcccaatg ctcaggcctg gaagaggaac tcgaagaaga acttagcaac    4980
aatgaggccc tccaagacaa agcgagaaaa gcacaactca gcgttgagca acttaatgca    5040
gaacttgctg ccgaacggag taatgtgcag aaacttgagg gaacgagatt gtcgatggaa    5100
aggcaaaaca aggaactgaa ggccaaactg aacgaactgg aaacgttaca acgcaacaag    5160
ttcaaggcca atgcgtctct ggaggctaag attaccaatc ttgaagagca actggaaaat    5220
gaagccaagg aaaagctact tctccagaaa ggcaacagga agctcgacaa gaaaatcaaa    5280
gacctcctcg ttcaattgga ggatgaaagg aggcatgccg accagtataa agaacaagtc    5340
gagaagatca acgtcagggt gaagacgcta aagcgaactt tggacgacgc cgaagaagaa    5400
atgagtaggg agaagaccca gaagaggaaa gcacttcgcg aattggaaga cctcagggag    5460
aactacgatt ccctactccg agagaacgat aaccctcaaaa acaaactcag gcggggcggc    5520
ggtatttccg ggatctcgag caggctcgga ggctccaagc gaggttccat ccccggagag    5580
gattcccagg gtctcaacaa caccacagac gaatcagtcg atggtgacga tatctcgaat    5640
ccttaaacgc tacttggatt taccagccag catccaactt tccactgaag acgtctccca    5700
taaacgttga aagagacccg tcgaggaaga aaaaaaggct ctttaagaaa aactattctg    5760 ccttttttcaa aactttgtac ttaaaagtac tttcgcttaa caatgaaaga gaataaaaaa    5820
tgtaaagttt tcatttatac aaaaaaaaaa aaaaaaaaaa aaaaaaaaaa aa            5872

<210> SEQ ID NO 148
<211> LENGTH: 325
<212> TYPE: DNA
<213> ORGANISM: Lygus hesperus

<400> SEQUENCE: 148
aagaagatcc tggaggagat cattgcggag gtcgacgctg atggctctgg acaacttgaa     60
tttgaggagt tcgtagcctt ggctgccggt ttcctgacag aagatgagac acaagatgct    120
gaggccatgc agcaagaact gagggaggcc ttcaggctct acgacaagga agggaacggt    180
tacattacca ctgacgtctt gagggaaatc ctgaaggaac tcgacgacaa aatcacctcc    240
caagaacttg acatgatgat tgctgaaatt gattctgacg gttccggaac tgttgacttc    300
gacgagttca tggagatgat gaccg                                          325

<210> SEQ ID NO 149
<211> LENGTH: 428
<212> TYPE: DNA
<213> ORGANISM: Lygus hesperus

<400> SEQUENCE: 149
aattatcccc atcatgacca tcgcgttgaa cgctttcgac cgggatcact cgggttccat     60
cccgacggac atggtggccg acatcctcag actcatgggt caacccttca acaagaagat    120
tctcgatgaa ctcatcgaag aagttgacgc tgacaaatcg ggaaggctgg agtttgaaga    180
```

```
gttcatcacg ttggcagcca agttcattgt tgaggaagac gatgaagcca tgcagaaaga    240
gctgcgagaa gccttccgtc tctacgacaa agaaggtaat ggctacatcc cgacctcctg    300
cctcaaagaa atccttcatg aattggacga gcagctgacc aacgaggagc tggacatgat    360
catcgaggag atcgactctg acggatccgg aactgtcgac ttcgacgagt tcatggagat    420
gatgaccg                                                             428
```

<210> SEQ ID NO 150
<211> LENGTH: 538
<212> TYPE: DNA
<213> ORGANISM: Lygus hesperus

<400> SEQUENCE: 150

```
gcttctttta caaatcgcac acgccgact taattcattc ccggagggtt taaattttat     60
cgaagcagca tggtgcggat gaatgtgctg agcgatgctc tgaaaagcat caacaatgct   120
gagaagaggg gcaaaaggca ggtgctcctg aggccttgtt ccaaagtcat cattaaattc   180
cttacagtga tgatgaagaa aggttatatc ggcgaattcg aaatagtaga tgatcacaga   240
tctggtaaaa tcgtcgtcaa cctcaacggc agattgaaca aatgtggagt tatatcgccc   300
agattcgacg tacccatcac acaaatcgaa aaatggacga caacctcct gccttcccga    360 cagttcggtt atgtcgtact caccactagt ggagggatca tggatcacga agaagccagg   420
cgaaaacatc ttgggggtaa atattaggg ttttctttt aataaaaaaa gacgagatgt     480
aaattaataa aactctttta cgtttcgcta aaaaaaaaa aaaaaaaaa aaaaaaa        538
```

<210> SEQ ID NO 151
<211> LENGTH: 405
<212> TYPE: DNA
<213> ORGANISM: Lygus hesperus

<400> SEQUENCE: 151

```
ccacgccgac ttaattcatt cccggagggt ttaaatttta tcgaagcagc atggtgcgga    60
tgaatgtgct gagcgatgct ctgaaaagca tcaacaatgc tgagaagagg ggcaaaaggc   120
aggtgctcct gaggccttgt tccaaagtca tcattaaatt ccttacagtg atgatgaaga   180
aaggttatat cggcgaattc gaaatagtag atgatcacag atctggtaaa atcgtcgtca   240
acctcaacgg cagattgaac aaatgtggag ttatatcgcc cagattcgac gtacccatca   300
cacaaatcga aaaatggacg aacaacctcc tgccttcccg acagttcggt tatgtcgtac   360
tcaccactag tggagggatc atggatcacg aagaagccag gcgaa                    405
```

<210> SEQ ID NO 152
<211> LENGTH: 470
<212> TYPE: DNA
<213> ORGANISM: Lygus hesperus

<400> SEQUENCE: 152

```
tgtcgatggc ggtcttaaca tcccccattc caccaagagg ttccctgggt acgacagtga    60
gtctaaggaa ttcaacgctg aggtccacag gaagcacatt ttcggcattc acgtcgctga   120
ctacatgcgt cagctggctg aagaggatga cgatgcttac aagaagcagt tctcgcagta   180
tgtcaagaac ggagtcactg ctgacagcat tgaaagtatc tacaagaagg ctcacgaagc   240
aatccgagct gatccaactc gcaaaccact tgaagaagaa gaagtcaaga agaagaggtg   300
gaaccgcgcc aagctttcct tgtctgaaag gaagaacacc atcaaccaaa agaaggcaac   360
ttatctcaag aaagtggaag ctggagaaat cgaataagtt tttatattcc tgacattacc   420
```

```
cattaaaggt tcgttttaa cctaaaaaaa aaaaaaaaa aaaaaaaaaa              470
```

<210> SEQ ID NO 153
<211> LENGTH: 387
<212> TYPE: DNA
<213> ORGANISM: Lygus hesperus

<400> SEQUENCE: 153

```
tgtcgatggc ggtcttaaca tcccccattc caccaagagg ttccctgggt acgacagtga   60
gtctaaggaa ttcaacgctg aggtccacag gaagcacatt ttcggcattc acgtcgctga  120
ctacatgcgt cagctggctg aagaggatga cgatgcttac aagaagcagt tctcgcagta  180
tgtcaagaac ggagtcactg ctgacagcat tgaaagtatc tacaagaagg ctcacgaagc  240
aatccgagct gatccaactc gcaaaccact tgagaagaag gaagtcaaga agaagaggtg  300
gaaccgcgcc aagctttcct tgtctgaaag gaagaacacc atcaaccaaa agaaggcaac  360
ttatctcaag aaagtggaag ctggaga                                      387
```

<210> SEQ ID NO 154
<211> LENGTH: 745
<212> TYPE: DNA
<213> ORGANISM: Lygus hesperus

<400> SEQUENCE: 154

```
gtcctacgtg tttccggaaa aacgtgcatt tcgcgtaccc ctcgtggtga tccgttttca   60
tagaaataat ccaaaatggc tcccaagggg aataatatga ttcccaatgg ccatttccac  120
aaggattggc agaggttcat caaaacctgg ttcaaccagc ctgcccgcaa gttgaggagg  180
agaaacaaga ggttggagaa ggcccaacgg ctcgcgcccc gccccgcggg acctcttcgc  240
cccgctgtca gatgtcccac cgtcaggtac cacaccaagc tacgacctgg acgtggcttc  300
accttggaag aaatcaagag agccggtctg tgcaaaggat tcgcgatgtc catcggaatc  360
gctgtcgacc ccagaagaag gaataaatcc atcgagtccc tccaactcaa tgtacagaga  420
ctcaaggagt acagggctaa gcttatcctc ttcccacaca agaatgccaa gaaactgaag  480
aagggagaag ctactgagga agagaggaag gtggccaccc aacagcccct gccagttatg  540
cccatcaagc aaccagtcat caaattcaag gctcgcgtca ttacagacga tgagaagaaa  600
tactctgcct tcaccgccct ccgcaaggga cgagcagacc aaaggttggt cggtatccgt  660
gctaagcgcg caaaggaagc cgcagaaaac gccgaagacc cctctaaagc tcctaaaaaa  720
aaaaaaaaaa aaaaaaaaaa aaaaa                                        745
```

<210> SEQ ID NO 155
<211> LENGTH: 527
<212> TYPE: DNA
<213> ORGANISM: Lygus hesperus

<400> SEQUENCE: 155

```
aacgtgcatt tcgcgtaccc ctcgtggtga tccgttttca tagaaataat ccaaaatggc   60
tcccaagggg aataatatga ttcccaatgg ccatttccac aaggattggc agaggttcat  120
caaaacctgg ttcaaccagc ctgcccgcaa gttgaggagg agaaacaaga ggttggagaa  180
ggcccaacgg ctcgcgcccc gccccgcggg acctcttcgc cccgctgtca gatgtcccac  240
cgtcaggtac cacaccaagc tacgacctgg acgtggcttc accttggaag aaatcaagag  300
agccggtctg tgcaaaggat tcgcgatgtc catcggaatc gctgtcgacc ccagaagaag  360
```

```
gaataaatcc atcgagtccc tccaactcaa tgtacagaga ctcaaggagt acagggctaa    420
gcttatcctc ttcccacaca agaatgccaa gaaactgaag aagggagaag ctactgagga    480
agagaggaag gtggccaccc aacagcccct gccagttatg cccatca                  527

<210> SEQ ID NO 156
<211> LENGTH: 576
<212> TYPE: DNA
<213> ORGANISM: Lygus hesperus

<400> SEQUENCE: 156
gccttattga acgtggtcga cagaaaactc ggtttctgag ctcatctcaa catggatatc     60
gaagaaccgg ccgcggcccc tacggagccc tcggacgtca acaccgccct tcaagaggtc    120
ctcaaggccg cccttcaaca cggagtcgtc gtccacggta tccacgagtc cgccaaggcc    180
ctcgacaaga ggcaagcttt tgttgtgcgtc ctcgctgaga actgcgacga gccgatgtac   240
aagaagctgg tacaagccct ctgctcagag caccacatcc ccctcgtcaa agtagattcc    300
aataagaaac tcggcgaatg gacgggcctt tgcaagatca caagaccgg caaatctagg     360 aaaatcgtcg gctgctcttg tgtcgtcatc aaggactggg gtgaggacac gccccacttg    420
gacctcctca aggactacat cagggacgtc ttctaagaag tttctcctca atttcctttt    480
tataatgatt taacaactga gaattaataa taaaaatgtt aaattaaaca aaaaaatctc    540
aaaactgtaa aaaaaagaa gaaaaaaaaa aaaaaa                               576

<210> SEQ ID NO 157
<211> LENGTH: 442
<212> TYPE: DNA
<213> ORGANISM: Lygus hesperus

<400> SEQUENCE: 157
ccttattgaa cgtggtcgac agaaaactcg gtttctgagc tcatctcaac atggatatcg     60
aagaaccggc cgcggcccct acggagcccc cggacgtcaa caccgccctt caagaggtcc    120
tcaaggccgc ccttcaacac ggagtcgtcg tccacggtat ccacgagtcc gccaaggccc    180
tcgacaagag gcaagctttg ttgtgcgtcc tcgctgagaa ctgcgacgag ccgatgtaca    240
agaagctggt acaagccctc tgctcagagc accacatccc cctcgtcaaa gtagattcca    300
ataagaaact cggcgaatgg acgggccttt gcaagatcga caagaccggc aaatctagga    360
aaatcgtcgg ctgctcttgt gtcgtcatca aggactgggg tgaggacacg ccccacttgg    420
acctcctcaa ggactacatc ag                                             442

<210> SEQ ID NO 158
<211> LENGTH: 601
<212> TYPE: DNA
<213> ORGANISM: Lygus hesperus

<400> SEQUENCE: 158
ctttcatttg tatagtacgg acgggtagtt tagttgtgtc ggttcatcgt aattcatcgg     60
ctgaatcatg aagatgaata aattggtcac ttcctcgagg aggaagaaca ggaagaggca    120
cttcaccgcc ccatcccaca tccgtagaaa gttgatgtcg gcaccactgt ccaaagaact    180
taggcagaag tacaacgtcc gaactatgcc tgtgaggaag gacgatgaag tccaggttgt    240
acgaggacac tacaaaggcc aacaggttgg caaagtcctc caggtgtaca ggaagaagtt    300
cattatttac attgagcgga tccaaagaga aaaagccaat ggtgccagcg tttacgttgg    360
cattcacccc tcaaagtgtg tgatcgtcaa attgaaggtc gacaaggata ggaaagaaat    420
```

```
ccttgacaga agatccaaag gacgtgactt ggcacttggc aaggacaagg gcaaatacac    480
cgaagacagt acgactgcta tggacacgtc ttaaattaat ttggtttatt tggttcctta    540
actccgttct tctttaataa tgactttttt aaagcaaaaa aaaaaaaaaa aaaaaaaaa     600 a                                                                    601
```

<210> SEQ ID NO 159
<211> LENGTH: 448
<212> TYPE: DNA
<213> ORGANISM: Lygus hesperus

<400> SEQUENCE: 159

```
gtacggacgg gtagtttagt tgtgtcggtt catcgtaatt catcggctga atcatgaaga     60
tgaataaatt ggtcacttcc tcgaggagga agaacaggaa gaggcacttc accgccccat    120
cccacatccg tagaaagttg atgtcggcac cactgtccaa agaacttagg cagaagtaca    180
acgtccgaac tatgcctgtg aggaaggacg atgaagtcca ggttgtacga ggacactaca    240
aaggccaaca ggttggcaaa gtcctccagg tgtacaggaa gaagttcatt atttacattg    300
agcggatcca aagagaaaaa gccaatggtg ccagcgttta cgttggcatt cacccctcaa    360
agtgtgtgat cgtcaaattg aaggtcgaca aggataggaa agaaatcctt gacagaagat    420
ccaaaggacg tgacttggca cttggcaa                                       448
```

<210> SEQ ID NO 160
<211> LENGTH: 456
<212> TYPE: DNA
<213> ORGANISM: Lygus hesperus

<400> SEQUENCE: 160

```
ggctgttgtc ggctggtcat atcccgtttt ccacgtggtg tgtcgagtta ttttcttgt      60 aaattcgcat ttaaaatcgg atttataacc gaaattcatt atggaaaagc cagtagtttt    120
ggcccgtgtc atcaaaatcc tcggacgtac cggctcacag ggccaatgta cgcaagtgaa    180
ggtggagttc attggtgagc agaaccgaca gatcatcagg aacgtgaaag gaccagttag    240
agaaggcgac atcctcacac tcctagagtc tgaaagagaa gcgagaagac tgaggtagtg    300
ggaggtggcg atgcgttacg ttattttact tcattcaaca tttgaaaaaa accatcttcg    360
tgacaaaaaa catcttcacg caactatttg tattacctat gtttcgtaaa taagtaaacc    420
tcgttactta aaaaaaaaaa aaaaaaaaa aaaaaa                               456
```

<210> SEQ ID NO 161
<211> LENGTH: 321
<212> TYPE: DNA
<213> ORGANISM: Lygus hesperus

<400> SEQUENCE: 161

```
ctgttgtcgg ctggtcatat cccgttttcc acgtggtgtg tcgagttatt tttcttgtaa     60
attcgcattt aaaatcggat ttataaccga aattcattat ggaaaagcca gtagttttgg    120
cccgtgtcat caaaatcctc ggacgtaccg gctcacaggg ccaatgtacg caagtgaagg    180
tggagttcat tggtgagcag aaccgacaga tcatcaggaa cgtgaaagga ccagttagag    240
aaggcgacat cctcacactc ctagagtctg aaagagaagc gagaagactg aggtagtggg    300
aggtggcgat gcgttacgtt a                                              321
```

<210> SEQ ID NO 162

```
<211> LENGTH: 865
<212> TYPE: DNA
<213> ORGANISM: Lygus hesperus

<400> SEQUENCE: 162
aatcccggat tcatcgtttt attgaattgt ttttcgaagt ttctggtatt atcgttaaat      60
tagtctgtta agccctcatc cgtgatttgg caagttgttg attgttctat tttccttttt     120
ccagaaaatg gggagacgtc cagcgaggtg ttatcggtac tgtaaaaaca agccataccc     180
ccaaatcccg gttctgtcgt ggtgtccccg accccaagat caggatcttc gatctgggaa     240
agaagaaggc ccgcgtggaa gacttccccc tctgcgttca cctcgtctcc gatgagtacg     300
agcagctgtc ctccgaagcc ctcgaggcag gacgtatctg ctgcaacaag tacctcgtca     360
agaactgcgg caaggaccag ttccacatca ggatgaggct ccacccctcc acgtcatta      420 ggatcaacaa aatgttatcg tgcgctggag ctgataggcc cagacaggg atgagaggag      480 cgttcggaaa gccgcaagga accgtcgctc gcgtccgcat cggtcagccc atcatgagcg     540
tccgctcgtc cgacaggtac aaggccgccg tcatcaaggc tctgaggaga gccaaattca     600
agttccctgg tcgccagaag atctacgttt ccaagaaatg gggcttcacc aagttcgacc     660
gcgaagagta cgagggcctt aggaacgaca acaaactagc gaatgacggc tgcaacgtca     720
aattgaggcc ggatcacgga cctttgcagg cgtggaggaa ggctcagctt gacatcgctg     780
ctggcctcta aattactttc caatggtttt ataaatcaac aataaaact cgttttatgt      840 aaaaaaaaaa aaaaaaaaa aaaaa                                           865

<210> SEQ ID NO 163
<211> LENGTH: 792
<212> TYPE: DNA
<213> ORGANISM: Lygus hesperus

<400> SEQUENCE: 163
ggttcctttc tcagattttg actttgccgt gttgtctctc ccaatttttcc aaaatgggga     60 gacgtccagc gaggtgttat cggtactgta aaaacaagcc ataccccaaa tcccggttct    120
gtcgtggtgt ccccgacccc aagatcagga tcttcgatct gggaagaag aaggcccgcg     180 tggaagactt cccctctgc gttcacctcg tctccgatga gtacgagcag ctgtcctccg     240
aagccctcga ggcaggacgt atctgctgca acaagtacct cgtcaagaac tgcggcaagg    300
accagttcca catcaggatg aggctccacc ccttccacgt cattaggatc aacaaatgt     360 tatcgtgcgc tggagctgat aggctccaga cagggatgag aggagcattc ggaaagccgc    420
aaggaaccgt cgctcgcgtc cgcatcggtc agcccatcat gagcgtccgc tcgtccgaca    480
ggtacaaggc cgccgtcatc gaggctctga ggagagccaa attcaagttc ctggtcgcc    540 agaagatcta cgtttccaag aaatggggct tcaccaagtt cgaccgcgaa gagtacgagg    600
gccttaggaa cgacaacaaa ctagcgaatg cggctgcaa cgtcaaattg aggccggatc     660
acggaccttt gcaggcgtgg aggaaggctc agcttgacat cgctgctggc ctctaaatta    720
ctttccaatg gttttataaa tcaacaaata aaactcgttt tatctaaaaa aaaaaaaaa     780 aaaaaaaaaa aa                                                         792

<210> SEQ ID NO 164
<211> LENGTH: 645
<212> TYPE: DNA
<213> ORGANISM: Lygus hesperus

<400> SEQUENCE: 164
```

```
agccctcatc cgtgatttgg caagttgttg attgttctat tttccttttt ccagaaaatg    60
gggagacgtc cagcgaggtg ttatcggtac tgtaaaaaca agccataccc ccaaatcccg   120
gttctgtcgt ggtgtccccg accccaagat caggatcttc gatctgggaa agaagaaggc   180
ccgcgtggaa gacttccccc tctgcgttca cctcgtctcc gatgagtacg agcagctgtc   240
ctccgaagcc ctcgaggcag gacgtatctg ctgcaacaag tacctcgtca agaactgcgg   300
caaggaccag ttccacatca ggatgaggct ccaccccttc cacgtcatta ggatcaacaa   360
aatgttatcg tgcgctggag ctgataggct ccagacaggg atgagaggag cgttcggaaa   420
gccgcaagga accgtcgctc gcgtccgcat cggtcagccc atcatgagcg tccgctcgtc   480
cgacaggtac aaggccgccg tcatcaaggc tctgaggaga gccaaattca gttccctgg    540 tcgccagaag atctacgttt ccaagaaatg gggcttcacc aagttcgacc gcgaagagta   600
cgagggcctt aggaacgaca caaaactagc gaatgacggc tgcaa                   645

<210> SEQ ID NO 165
<211> LENGTH: 619
<212> TYPE: DNA
<213> ORGANISM: Lygus hesperus

<400> SEQUENCE: 165
gctttaccga ttccgttctt gtttagtcca cgtttctctg ctcattcgtg cagattttaa    60
aacatgacca actccaaagg ttatcgtcgc ggaacgaggg atctcttctc gaggcccttc   120
cgtcaccatg gtgtcatccc actctcaacg tacatgaaag tataccgagt aggagacatc   180
gtatctatca aggtaatgg agcagtgcaa aaaggtatgc cccacaaagt ttaccacggc   240
aagaccggac gagtctacaa tgttacacct cgcgcccttg gtgttattgt caacaagagg   300
gttcgtggaa aaatccttcc caagaggatc aacatcagga ttgaacacgt caaccacagt   360
aaatgcagag aagatttctt gaagcgagtg cgagaaaatg aaaggctccg caaattcgcc   420
aaagaaactg gcaccagggt tgaactcaaa agacagcctg ctcagccacg ccctgcacac   480
tttgtacaag ctaaagaagt cccagagctg ctggcccca taccttacga gttcatcgct   540 taaaaattt tcaattccat cttaactttta tatttgaa taaaattgtg ttctcaaaaa   600
aaaaaaaaaa aaaaaaaaa                                                619

<210> SEQ ID NO 166
<211> LENGTH: 461
<212> TYPE: DNA
<213> ORGANISM: Lygus hesperus

<400> SEQUENCE: 166
acgtttctct gctcattcgt gcagatttta aacatgacc aactccaaag gttatcgtcg    60
cggaacgagg gatctcttct cgaggcccttc cgtcaccat ggtgtcatcc cactctcaac   120
gtacatgaaa gtataccgag taggagacat cgtatctatc aaaggtaatg agcagtgca   180 aaaaggtatg cccacaaag tttaccacgg caagaccgga cgagtctaca atgttacacc   240 tcgcgcccttt ggtgttattg tcaacaagag ggttcgtgga aaaatccttc ccaagaggat   300
caacatcagg attgaacacg tcaaccacag taaatgcaga gaagatttct tgaagcgagt   360
gcgagaaaat gaaaggctcc gcaaattcgc caaagaaact ggcaccaggg ttgaactcaa   420
aagacagcct gctcagccac gccctgcaca ctttgtacaa g                       461

<210> SEQ ID NO 167
```

```
<211> LENGTH: 481
<212> TYPE: DNA
<213> ORGANISM: Lygus hesperus

<400> SEQUENCE: 167
caacgtacat gaaagtatac cgagtaggag acatcgtatc tatcaaaggt aatggagcag    60
tgcaaaaagg tatgccccac aaagtttacc acggcaagac cggacgagtc tataatgtta   120
cacctcgcgc ccttggtgtt attgtcaaca agagggttcg tggaaaaatc cttcccaaga   180
ggatcaacat caggattgaa cacgtcaacc acagtaaatg cagagaagat ttcttgaagc   240
gagtgcgaga aaatgagagg ctccgcaaat tcgccaaaga aactggcacc agggttgaac   300
tcaaaagaca gcctgctcag ccacgccctg cacactttgt acaagctaaa gaagtcccag   360
agctgctggc ccccatacct tacgagttca tcgcttaaac aattttcaat tccatcttaa   420
ctttatatat ttgaataaaa ttgtgttccc taaaaaaaaa aaaaaaaaaa aaaaaaaaaa   480
a                                                                   481

<210> SEQ ID NO 168
<211> LENGTH: 747
<212> TYPE: DNA
<213> ORGANISM: Lygus hesperus

<400> SEQUENCE: 168
gcataaatat ataggcgat tgatttagcg gccgcgaatt cgcccttaag cagtggtatc     60
aacgcagagg gggggtcttc tctcccggtt ttcttcttgc ccgaatcgtc catcctgatg   120
ttggggtcac tgtcaccacg accataccccc aatttggggt atggcttggt tgtcccctac  180
ccataaatcc tgattggaca tctccccatt atgaaagact gcgagaaaca ccctgcccc    240 cggctttaaa cccacggcta aggggggatt cgcggcggc aaatttcatt cggcccatag    300
tgagtcgtat tacaattcac tgggcgtcct ttttacacct tcggaccggg aaaaacctgg   360
cggttaccca aaatccgtta tttgccacat cccccttac tccactgggt tatataacaa    420
agaggcccct tccaatgtcc tttcccaaaa gtgcgcagcc ctatactaat ggcctttaaa   480 ggaacccccta ttaaaaaaaa aacccttaac cacaggttgg tgatgtaacc aaggaaaata  540
atgaacacac cgggccaaag aaggtgatac ccctggtctt ggcgaccgcc tgtcaaatct   600
tcctcccgga acgaaacccg tagtggcatc gaggaataac cttgcgcatc atagactcca   660
aatggccact gtggccgctc tcgattcatg gaagaaatga gatgacccct accccgcgca   720
aaaggattca gaaccaatac cagaatc                                       747

<210> SEQ ID NO 169
<211> LENGTH: 1052
<212> TYPE: DNA
<213> ORGANISM: Lygus hesperus
<220> FEATURE:
<221> NAME/KEY: misc_feature
<222> LOCATION: (662)..(665)
<223> OTHER INFORMATION: n is a, c, g, or t

<400> SEQUENCE: 169
ggttttcttc ttgcccgaat cgtccatcct gatgttgggg tcactgtcac cacgaccata    60
ccccaatttg gggtatggct tggttgtccc ctacccataa atcctgattg gacatctccc   120
cattatgaaa gactgcgaga aacacccctg ccccggcctt taaacccacg gctaaggggg   180
gattcgcggg cggcaaattt cattcggccc atagtgagtc gtattacaat tcactgggcg   240
tcctttttac accttcggac cgggaaaaac ctggcggtta cccaaaatcc gttatttgcc   300
```

```
acatccccct ttactccact gggttatata acaaagaggc cccttccaat gtcctttccc    360
aaaagtgcgc agccctatac taatggcctt taaaggaacc cctattaaaa aaaaaacccct   420
taaccacagg ttggtgatgt aaccaaggaa aataatgaac acaccgggcc aaagaaggtg    480
atacccctgg tcttggcgac cgcctgtcaa atcttcctcc cggaacgaaa cccgtagtgg    540
catcgaggaa taaccttgcg catcatagac tccaaatggc cactgtggcc gctctcgatt    600
catgaagaa atgagatgac ccctaccccg cgcaaaagga ttcagaacca ataccagaat     660
cnnnntagca aaacggctat ttccggttc tttgtcggat tcttttgcca gggccatgcc     720
ttttcccgga atggaaggcg ggctgtttga gaaacgcatt aaatgggatt agtccattca    780
taggccaccc aaggaaacca ctttaatttc gggttggtag gttgagagaa atggtgaggg    840
gtaacaattt tacaccggga accgtttatg cccagaatta ccccagcttc gaattaaccc    900
cccctaaagg ggatagttcc gccgggttaa agaaattcg ccttaaacca gtgttttaaa    960
gcaggagaca gaagtgtttc tcgcaagctt tcaaatggg gagatgtcca atcaggattt    1020
atgggtaggg tacaaccaag ccgaaccca aa                                  1052
```

<210> SEQ ID NO 170
<211> LENGTH: 555
<212> TYPE: DNA
<213> ORGANISM: Lygus hesperus

<400> SEQUENCE: 170

```
tagcaaaacg gctatttccc ggttctttgt cggattcttt tgccagggcc atgccttttc     60
ccggaatgga aggcgggctg tttgagaaac gcattaaatg ggattagtcc attcataggc    120
cacccaagga aaccacttta atttcgggtt ggtaggttga gagaaatggt gaggggtaac    180
aattttacac cgggaaccgt ttatgcccag aattacccca gcttcgaatt aaccccccct    240
aaaggggata gttccgccgg gttaaaagaa attcgcctta aaccagtgtt ttaaagcagg    300
agacagaagt gtttctcgca gctttcaaa atggggagat gtccaatcag gatttatggg    360
tagggtacaa ccagccgaa ccccaaatcc ctgttctgtc gtggtgacag tgaccccaag    420
atctggatgt tcgttttggg aaagaagaaa accgggaggg accacttcct cctctgcgtt    480
gataccactg cttaagggcg aattcgttta aacctgcagg actagtccct tagtgagggt    540
aatctagcag cccac                                                    555
```

<210> SEQ ID NO 171
<211> LENGTH: 1052
<212> TYPE: DNA
<213> ORGANISM: Lygus hesperus
<220> FEATURE:
<221> NAME/KEY: misc_feature
<222> LOCATION: (662)..(665)
<223> OTHER INFORMATION: n is a, c, g, or t

<400> SEQUENCE: 171

```
ggttttcttc ttgcccgaat cgtccatcct gatgttgggg tcactgtcac cacgaccata     60
ccccaatttg gggtatggct tggttgtccc ctacccataa atcctgattg gacatctccc    120
cattatgaaa gactgcgaga acacccctg ccccgggctt taaacccacg gctaaggggg    180
gattcgcggg cggcaaattt cattcggccc atagtgagtc gtattacaat tcactgggcg    240
tccttttac accttcggac cgggaaaaac ctgcggtta cccaaaatcc gttatttgcc    300
acatccccct ttactccact gggttatata acaaagaggc cccttccaat gtcctttccc    360
```

```
aaaagtgcgc agccctatac taatggcctt taaaggaacc cctattaaaa aaaaaaccct      420
taaccacagg ttggtgatgt aaccaaggaa aataatgaac acaccgggcc aaagaaggtg      480 ataccctgg tcttggcgac cgcctgtcaa atcttcctcc cggaacgaaa cccgtagtgg       540
catcgaggaa taaccttgcg catcatagac tccaaatggc cactgtggcc gctctcgatt      600
catggaagaa atgagatgac ccctaccccg cgcaaaagga ttcagaacca ataccagaat      660
cnnnntagca aaacggctat ttcccggttc tttgtcggat tcttttgcca gggccatgcc      720
ttttcccgga atggaaggcg ggctgtttga gaaacgcatt aaatgggatt agtccattca      780
taggccaccc aaggaaacca ctttaatttc gggttggtag gttgagagaa atggtgaggg      840
gtaacaattt tacaccggga accgtttatg cccagaatta ccccagcttc gaattaaccc      900
cccctaaagg ggatagttcc gccgggttaa aagaaattcg ccttaaacca gtgttttaaa      960
gcaggagaca gaagtgtttc tcgcaagctt tcaaaatggg gagatgtcca atcaggattt     1020
atgggtaggg tacaaccaag ccgaaccca aa                                    1052
```

<210> SEQ ID NO 172
<211> LENGTH: 1175
<212> TYPE: DNA
<213> ORGANISM: Lygus hesperus

<400> SEQUENCE: 172

```
ctcagcgaga tccctaagac aacgcctgcc acgtgggaga tatcggaca cgcctcccca       60 gagtgcggaa aggggaacgg cgttccgtat cggtcaaggt gcaagcttcg gaaccggagg     120
acgaccgttg caaggtgcaa ggggcaggta tcttgtattt tcattgtgcg tgtcgacatc     180
taccaaactg agacttggag ttcgatattt tgacgatggg gccgggggcc ggaggcaaaa     240
cgacaaacac aggcaccgtg accgtgttcc ggtccctggc ctgcgttgcc ttacgttcac     300
atcttgttct tgcgctttct ctggttttac gataacccta ctacgagttt agtagagccg     360
atcccgtagc cgaagccaaa gcccaagcgc tccgtatccg agaacgcgga agagcacgaa     420
ctccccaaac ccctccgccc ctccccgcg cgtatccgaa acacaaatgc agcgggcagt      480
acaggttttg gaaggggacg cgggcagtga gcgcaatgca agtaaatgtg attagctcat     540
ggctacgcag ccctgctttt tcagtttcgg ttcggatcgt taggggggtgt gggattggga    600 gcggattcaa tctggacagg aaacagctat gaccaaggtc acgccaagct ctgaattaac     660
cctcaggaaa gggactagtc cggcaggttg aaacgaactc gccctaagc agtggtatca     720 gagcacagtg gttttttttt tttgttttt tcgtagaaa aaaatatgta ttaagtcaat       780
taattaaatc attggttttc tggcttcaca acaggtggca cgtgctgtgc tcggagaaat    840
ttatgaacta tgttctgttc ttcaatgagg aaagatgaga tgatccattc tcagacacat    900
tcagacagag gacaccaccg taagccctat ccacagtctg tccacgtaag gggatcgtgt    960
ccccttccat gggcagagca gggagagggc cgtaagcttg ttcttgcgtc atcaacatgt    1020
gggggtaatg ttggtcatag cgatgttcgg tacacaagag aaccacctgg tgtaatcatt    1080
acagcacagc aatactctgt gttttgtaag ataacaaaaa aggtacttaa gacgctgaac    1140
cattttctac gatcggaaaa caaaaaaaaa gaaaa                               1175
```

<210> SEQ ID NO 173
<211> LENGTH: 1023
<212> TYPE: DNA
<213> ORGANISM: Lygus hesperus

<400> SEQUENCE: 173

```
tcagcgagat ccctaagaca acgcctgcca cgtgggagaa tatcggacac gcctccccag    60
agtgcggaaa ggggaacggc gttccgtatc ggtcaaggtg caagcttcgg aaccggagga   120
cgaccgttgc aaggtgcaag gggcaggtat cttgtatttt cattgtgcgt gtcgacatct   180
accaaactga gacttggagt tcgatatttt gacgatgggg ccggggccg gaggcaaaac    240 gacaaacaca ggcaccgtga ccgtgttccg gtccctggcc tgcgttgcct tacgttcaca   300
tcttgttctt gcgctttctc tggttttacg ataaccctac tacgagttta gtagagccga   360
tcccgtagcc gaagccaaag cccaagcgct ccgtatccga gaacgcggaa gagcacgaac   420
tccccaaacc cctccgcccc tcccccgcgc gtatccgaaa cacaaatgca gcgggcagta   480
caggttttgg aaggggacgc gggcagtgag cgcaatgcaa gtaaatgtga ttagctcatg   540
gctacgcagc cctgcttttt cagtttcggt tcggatcgtt aggggggtgtg ggattgggag  600 cggattcaat ctggacagga aacagctatg accaaggtca cgccaagctc tgaattaacc   660
ctcaggaaag ggactagtcc ggcaggttga aacgaactcg cccctaagca gtggtatcag   720
agcacagtgg tttttttttt ttgttttttt tcgtagaaaa aatatgtat taagtcaatt    780 aattaaatca ttggttttct ggcttcacaa caggtggcac gtgctgtgct cggagaaatt   840
tatgaactat gttctgttct tcaatgagga aagatgagat gatccattct cagacacatt   900
cagacagagg acaccaccgt aagccctatc cacagtctgt ccacgtaagg ggatcgtgtc    960
cccttccatg ggcagagcag ggagagggcc gtaagcttgt tcttgcgtca tcaacatgtg  1020
ggg                                                                1023

<210> SEQ ID NO 174
<211> LENGTH: 454
<212> TYPE: DNA
<213> ORGANISM: leptinotarsa decemlineata

<400> SEQUENCE: 174
ccaagaaggc caagaagggg tttatgaccc ctgagaggaa gaagaaactt aggttattgc    60
tgagaaagaa agcagcagaa gaactgaaaa aagaacaaga acgcaaagct gccgaaagga   120
gacgtattat tgaagagaga tgcggaaaac caaaactcat tgatgaggca aatgaagagc   180
aggtgaggaa ctattgcaag ttatatcacg gtagaatagc taaactggag gaccagaaat   240
ttgatttgga ataccttgtc aaaaagaaag acatggagat cgccgaattg aacagtcaag   300
tcaacgacct caggggtaaa ttcgtcaaac ccactctcaa gaaagtatcc aaatacgaga   360
acaaatttgc taaactccaa aagaaagcag cagaattcaa tttccgtaat caactgaaag   420
ttgtaaagaa gaaggagttc accctggagg agga                               454

<210> SEQ ID NO 175
<211> LENGTH: 431
<212> TYPE: DNA
<213> ORGANISM: leptinotarsa decemlineata

<400> SEQUENCE: 175
ggtttatgac ccctgagagg aagaagaaac ttaggttatt gctgagaaag aaagcagcag    60
aagaactgaa aaagaacaa gaacgcaaag ctgccgaaag gagacgtatt attgaagaga   120
gatgcggaaa accaaaactc attgatgagg caaatgaaga gcaggtgagg aactattgca   180
agttatatca cggtagaata gctaaactgg aggaccagaa atttgatttg gaataccttg   240
tcaaaaagaa agacatggag atcgccgaat tgaacagtca agtcaacgac ctcagggta    300
```

```
aattcgtcaa acccactctc aagaaagtat ccaaatacga gaacaaattt gctaaactcc      360
aaaagaaagc agcagaattc aatttccgta atcaactgaa agttgtaaag aagaaggagt      420
tcaccctgga g                                                          431

<210> SEQ ID NO 176
<211> LENGTH: 888
<212> TYPE: DNA
<213> ORGANISM: leptinotarsa decemlineata

<400> SEQUENCE: 176
agcagtggta tcaacgcaga gtacgcgggg acatcgagga gaagaggcaa cgcctcgaag       60
aggctgaaaa gaaacgccag gccatgatgc aggccctcaa ggaccagaac aagaacaagg      120
ggcccaactt caccatcacc aagagggatg cttcatctaa cctttctgcc gctcagttgg      180
aacgcaacaa gaccaaggag caactcgagg aagagaagaa aatttcccctt tccatccgca     240 tcaagcccct tggtcgttgat ggtctgggcg tagataaact ccgtctgaaa gcacaagaac     300
tttgggaatg catcgtcaag ttggagactg aaaagtacga cttggaagag aggcagaaac     360
gtcaagacta cgatctcaaa gagctgaaag aaagacagaa acaacagctg agacacaaag     420
ccttgaagaa gggtctagac ccagaagccc taaccggcaa atacccgcct aaaatccaag     480
tagcctccaa atatgaacgt cgtgttgaca cgaggtcgta tggagacaaa agaagctat      540 tcgaagggggg attagaagaa atcattaaag agaccaatga aaagagctgg aaagagaaat    600
ttggacagtt cgattccaga caaaaggcaa gacttcccaa gtggttcggt gaacgtcctg     660
gcaaaaaacc tggagatccc gaaactccag aaggcgagga ggaggggcaaa caagtcattg    720 atgaggatga cgacctcaag gagcctgtaa tcgaagctga aattgaagaa gaggaggaag    780
aagaggaagt cgaggtcgat gaagaagaag aggatgacga agaagaagaa gaagaagagt    840
gaatgccaaa ggcagaagat aatcatgaaa tcaacattag ataacgtc                  888

<210> SEQ ID NO 177
<211> LENGTH: 404
<212> TYPE: DNA
<213> ORGANISM: leptinotarsa decemlineata

<400> SEQUENCE: 177
caaggaccag aacaagaaca aggggcccaa cttcaccatc accaagaggg atgcttcatc       60
taacctttct gccgctcagt tggaacgcaa caagaccaag gagcaactcg aggaagagaa      120
gaaaatttcc ctttccatcc gcatcaagcc cttggtcgtt gatggtctgg gcgtagataa      180
actccgtctg aaagcacaag aactttggga atgcatcgtc aagttggaga ctgaaaagta     240
cgacttggaa gagaggcaga acgtcaaga ctacgatctc aaagagctga agaaagaca       300 gaaacaacag ctgagacaca aagccttgaa gaagggtcta gacccagaag ccctaaccgg     360
caaatacccg cctaaaatcc aagtagcctc caaatatgaa cgtc                      404

<210> SEQ ID NO 178
<211> LENGTH: 1155
<212> TYPE: DNA
<213> ORGANISM: leptinotarsa decemlineata

<400> SEQUENCE: 178
gctcttcaga atgaacttga agaatctcgt acactgttgg aacaagctga ccgtgcccgt       60
cgccaagcag aacaagaatt gggagatgct cacgaacaat tgaatgatct tggtgcacag      120
aatggttctc tgtctgccgc caagaggaaa ctggaaactg aactccaaac tctccattcc      180
```

```
gatcttgatg aacttctcaa tgaagccaag aactctgagg agaaggctaa gaaagccatg     240
gtcgatgcag ctcgtcttgc agatgaactg agagcagaac aagatcatgc acaaactcag     300
gagaaacttc gtaaagcctt agaatcacaa atcaaggacc ttcaagttcg tctcgacgag     360
gctgaagcta acgccctcaa aggaggtaag aaagcaatcg ctaaacttga caacgcgtc      420 agggaattgg agaatgagtt agatggtgaa caaagacgac acgccgatgc tcaaaagaat     480
ttgagaaagt ccgaacgtcg catcaaggag ctcagcctcc aagctgaaga agaccgtaag     540
aaccacgaaa aaatgcaaga cttagtcgac aaacttcaac agaaaatcaa gacccacaag     600
aggcaaatag aagaagctga gaaatagcg gctctcaatt tggccaaatt ccgtaaagca      660
caacaggaat tggaagaagc agaagagcgt gcagaccttg ctgaacaagc aattgtcaaa     720
ttccgtacca agggacgttc tggatcagca gctaggggag ccagccctgc gcctcagcga     780
cagcgtccca cattcggaat gggagattca cttggaggtg ccttccctcc aaggttcgat     840
cttgcacccg actttgaatg aatctgacat tgtgttataa gtgtaaggtg aacattctat     900
cgcagtgtaa atatcatccc aatgcgaatc aattctacat tcagtttaag tcattctatc     960
tctcaaaata ataatagtgt catccattct cactatcaaa tcaagacaag agatgatgat    1020
cagagaacac gtatcacatc tacagcaaac cctcagtcct cggcatctct gataatattt    1080
tcaattatcg agattgatga tatcgggtgt tgaatgctga tgaatagaag gcgccctatg    1140
gaaataagag agaag                                                    1155

<210> SEQ ID NO 179
<211> LENGTH: 523
<212> TYPE: DNA
<213> ORGANISM: leptinotarsa decemlineata

<400> SEQUENCE: 179
gaatctcgta cactgttgga acaagctgac cgtgcccgtc gccaagcaga acaagaattg      60
ggagatgctc acgaacaatt gaatgatctt ggtgcacaga atggttctct gtctgccgcc     120
aagaggaaac tggaaactga actccaaact ctccattccg atcttgatga acttctcaat     180
gaagccaaga actctgagga aaggctaag aaagccatgg tcgatgcagc tcgtcttgca      240
gatgaactga gagcagaaca agatcatgca caaactcagg agaaacttcg taaagcctta     300
gaatcacaaa tcaaggacct tcaagttcgt ctcgacgagg ctgaagctaa cgccctcaaa     360
ggaggtaaga aagcaatcgc taaacttgaa caacgcgtca gggaattgga gaatgagtta     420
gatggtgaac aaagacgaca cgccgatgct caaaagaatt tgagaaagtc cgaacgtcgc     480
atcaaggagc tcagcctcca agctgaagaa gaccgtaaga acc                      523

<210> SEQ ID NO 180
<211> LENGTH: 865
<212> TYPE: DNA
<213> ORGANISM: nilaparvata lugens

<400> SEQUENCE: 180
ctaggagtat ctcctacgta attcggtgct tgagccaact gcagctactc acttttttcc      60
aggttcagtg gtagggacgc aaacacagct aaaatggcgg acgatgaggc aaagaaggca     120
aagcaggcgg aaatcgaccg caagagagcc gaggtccgca agcggatgga ggaagcctcc     180
aaggccaaga aggccaagaa aggtttcatg acgcctgaca gaaagaagaa gctcaggttg     240
ttgctgagga aaaaggctgc tgaggaattg aagaaggaac aggagaggaa agccgcggaa     300
```

```
aggagaagga tcatcgagga gaggtgtggc aaggctgttg atctcgatga cggaagtgaa    360
gagaaagtca aggcaacttt aaaaacctat cacgacagaa ttggaaaatt ggaggatgaa    420
aaatttgacc tggaatatat tgtaaaaaag aaagacttcg agatcgctga cctcaacagc    480
caggtgaatg acctccgtgg taaatttgtc aagccaacct tgaaaaaagt ctccaaatat    540
gagaacaaat tcgccaagct ccagaagaaa gcagctgaat tcaatttcag aaatcagctc    600
aaagttgtca agaagaagga attcaccttg gaagaagaag acaaggagcc gaagaaatcg    660
gagaaagccg aatggcagaa gaaatgaact cacatcacct cttcataata ttgtcccaca    720
cttctacaac cttcatcaaa taacttttat tcgagtaaac ttactgttac taacaaaatt    780
acaaaaccaa actcttatca tcaacgtagg caatgtgctc aacttatttc ttaaacatat    840
tgtccagcta tttattgaaa ttaaa                                          865
```

<210> SEQ ID NO 181
<211> LENGTH: 269
<212> TYPE: DNA
<213> ORGANISM: nilaparvata lugens

<400> SEQUENCE: 181

```
aagaagaagc tcaggttgtt gctgaggaaa aaggctgctg aggaattgaa gaaggaacag     60
gagaggaaag ccgcggaaag gagaaggatc atcgaggaga ggtgtggcaa ggctgttgat    120
ctcgatgacg aagtgaaga gaaagtcaag gcaactttaa aaacctatca cgacagaatt    180
ggaaaattgg aggatgaaaa atttgacctg gaatatattg taaaaaagaa agacttcgag    240
atcgctgacc tcaacagcca ggtgaatga                                      269
```

<210> SEQ ID NO 182
<211> LENGTH: 553
<212> TYPE: DNA
<213> ORGANISM: nilaparvata lugens

<400> SEQUENCE: 182

```
aatgatggcg gctctcaagg accagagcaa atcgaaagga cccaacttca ccgtaaacaa     60
gaaaacagac ttgaacatga cgtcagctca atggaaagg aacaagacta aggagcagct    120
ggaggaggag aagaagatct ctctgtcgtt ccgcatcaag ccgttggcca tcgagaacat    180
gagcatcaac gcactgcgcg ccaaggccca ggaactgtgg gactgcatcg tcaagctcga    240
aactgagaag tacgatctgg aggaacgcca gaagaggcag gactacgatc tcaaagaatt    300
gaaagaaaga caaagcaac agctgaggca taaagccctc aaaaaaggtc tagaccctga    360
ggctctcaca ggaaagtacc caccaaaaat ccaagttgcc tccaaatatg aaagacgtgt    420
agatacaagg tcatacgacg acaagaagaa gctcttcgaa ggtggctggg acacattaac    480
atcagaaacc aatgagaaaa tatggaagag cagaaacgat cagttttcaa atcgtagcaa    540
ggctaaactg cca                                                       553
```

<210> SEQ ID NO 183
<211> LENGTH: 470
<212> TYPE: DNA
<213> ORGANISM: nilaparvata lugens

<400> SEQUENCE: 183

```
atgatggcgg ctctcaagga ccagagcaaa tcgaaaggac ccaacttcac cgtaaacaag     60
aaaacagact tgaacatgac gtcagctcaa atggaaagga caagactaa ggagcagctg    120 gaggaggaga agaagatctc tctgtcgttc cgcatcaagc cgttggccat cgagaacatg    180
```

```
agcatcaacg cactgcgcgc caaggcccag gaactgtggg actgcatcgt caagctcgaa    240
actgagaagt acgatctgga ggaacgccag aagaggcagg actacgatct caaagaattg    300
aaagaaagac aaaagcaaca gctgaggcat aaagccctca aaaaggtct agaccctgag     360 gctctcacag gaaagtaccc accaaaaatc caagttgcct ccaaatatga agacgtgta    420 gatacaaggt catacgacga caagaagaag ctcttcgaag gtggctggga             470
```

<210> SEQ ID NO 184
<211> LENGTH: 367
<212> TYPE: DNA
<213> ORGANISM: nilaparvata lugens

<400> SEQUENCE: 184

```
tgccttcgac cgtgaaaggt ctggaagtat cccaacagac atggtcgccg acatcctcag    60
gctcatggga cagcctttca acaagaagat cctcgacgaa ctcattgagg aagttgatgc   120
tgacaaatct ggccgtcttg agtttgacga attcgtgact ctggccgcca aattcattgt   180
tgaggaagac gatgaggcaa tgcagaagga attgaaggaa gctttcagat tatacgacaa   240
ggaaggtaac ggctacatcc ccacatcatg tctgaaggaa atcttaaggg aacttgacga   300
tcagctgaca aacgaggaac tcaacatgat gattgatgag atcgactctg acggatcagg   360
aactgtt                                                             367
```

<210> SEQ ID NO 185
<211> LENGTH: 204
<212> TYPE: DNA
<213> ORGANISM: nilaparvata lugens

<400> SEQUENCE: 185

```
acatcctcag gctcatggga cagcctttca acaagaagat cctcgacgaa cttattgagg    60
aggttgatgc tgacaagtct ggccgtctag agtttgacga attcgtgact ctggccgcca   120
aattcattgt tgaggaagac gatgaggcaa tgcagaagga attgaaggaa gctttcagat   180
tatacgacaa ggaaggtaac ggct                                          204
```

<210> SEQ ID NO 186
<211> LENGTH: 221
<212> TYPE: DNA
<213> ORGANISM: nilaparvata lugens

<400> SEQUENCE: 186

```
cgtaaaaact ctgaccggca agaccatcac cttggaagtg gagccttccg ataccattga    60
aaacgtgaag gccaagatcc aagacaagga gggaattcct cccgaccagc agagacttat   120
cttcgctgga aagcaactgg aggatggcag aaccctgtcc gactacaaca tccaaaaaga   180
atctacactc cacttggttc tcagacttcg tggtggaact a                       221
```

<210> SEQ ID NO 187
<211> LENGTH: 221
<212> TYPE: DNA
<213> ORGANISM: nilaparvata lugens

<400> SEQUENCE: 187

```
cgtaaaaaact ctgaccggca agaccatcac cttggaagtg gagccttccg ataccattga   60
aaacgtgaag gccaagatcc aagacaagga gggaattcct cccgaccagc agagacttat   120
cttcgctgga aagcaactgg aggatggcag aaccctgtcc gactacaaca tccaaaaaga   180
```

```
atctacactc cacttggttc tcagacttcg tggtggaact a                  221
```

<210> SEQ ID NO 188
<211> LENGTH: 759
<212> TYPE: DNA
<213> ORGANISM: Acyrthosiphon pisum

<400> SEQUENCE: 188

```
atggccgacg atgaagctaa gaaagcaaaa caggcggaaa tcgaccgcaa gagggccgaa    60
gtgcgcaagc gtatggaaga ggcgtccaag gccaagaagg ccaagaaggg tttcatgacc   120
ccagacagaa agaagaaact ccgtctgttg ttgaaaaaaa aggcggccga agagttgaag   180
aaagaacaag aacgcaaagc tgccgaacga aggcggatca tcgaagagcg gtgcggacaa   240
ccgaagaaca tcgacgacgc cggcgaagag gagcttgcgg aaatctgcga agaactatgg   300
aaacgggttt acaccgtaga gggcataaaa tttgacttgg aaagggatat caggatgaaa   360
gttttcgaga tcagcgaatt gaacagccaa gtcaatgact tacgaggaaa attcgtcaaa   420
ccaacattga agaaggtttc caaatacgaa aacaaattcg caaaactcca aaagaaagcg   480
gcggagttca acttcagaaa ccaactgaaa gtagtgaaga aaaaggagtt caccttggaa   540
gaagaagaca aagagaaaaa acccgattgg tccaaaaagg gagacgaaaa gaagggcgaa   600
ggagaagacg gcgacggtac cgaagacgaa aagaccgacg acggtttgac caccgaaggc   660
gaatcggtcg cggcgatct aacggacgcg acggaagacg cgcagagcga caacgagata   720
ctcgaaccag aacccgtggt tgaacccgaa ccagaacca                          759
```

<210> SEQ ID NO 189
<211> LENGTH: 759
<212> TYPE: DNA
<213> ORGANISM: Acyrthosiphon pisum

<400> SEQUENCE: 189

```
atggccgacg atgaagctaa gaaagcaaaa caggcggaaa tcgaccgcaa gagggccgaa    60
gtgcgcaagc gtatggaaga ggcgtccaag gccaagaagg ccaagaaggg tttcatgacc   120
ccagacagaa agaagaaact ccgtctgttg ttgaaaaaaa aggcggccga agagttgaag   180
aaagaacaag aacgcaaagc tgccgaacga aggcggatca tcgaagagcg gtgcggacaa   240
ccgaagaaca tcgacgacgc cggcgaagag gagcttgcgg aaatctgcga agaactatgg   300
aaacgggttt acaccgtaga gggcataaaa tttgacttgg aaagggatat caggatgaaa   360
gttttcgaga tcagcgaatt gaacagccaa gtcaatgact tacgaggaaa attcgtcaaa   420
ccaacattga agaaggtttc caaatacgaa aacaaattcg caaaactcca aaagaaagcg   480
gcggagttca acttcagaaa ccaactgaaa gtagtgaaga aaaaggagtt caccttggaa   540
gaagaagaca aagagaaaaa acccgattgg tccaaaaagg gagacgaaaa gaagggcgaa   600
ggagaagacg gcgacggtac cgaagacgaa aagaccgacg acggtttgac caccgaaggc   660
gaatcggtcg cggcgatct aacggacgcg acggaagacg cgcagagcga caacgagata   720
ctcgaaccag aacccgtggt tgaacccgaa ccagaacca                          759
```

<210> SEQ ID NO 190
<211> LENGTH: 759
<212> TYPE: DNA
<213> ORGANISM: Acyrthosiphon pisum

<400> SEQUENCE: 190

```
atggccgacg atgaagctaa gaaagcaaaa caggcggaaa tcgaccgcaa gagggccgaa    60
```

```
gtgcgcaagc gtatggaaga ggcgtccaag gccaagaagg ccaagaaggg tttcatgacc      120
ccagacagaa agaagaaact ccgtctgttg ttgaaaaaaa aggcggccga agagttgaag      180
aaagaacaag aacgcaaagc tgccgaacga aggcggatca tcgaagagcg gtgcggacaa      240
ccgaagaaca tcgacgacgc cggcgaagag gagcttgcgg aaatctgcga agaactatgg      300
aaacggtttt acaccgtaga gggcataaaa tttgacttgg aaagggatat caggatgaaa      360
gttttcgaga tcagcgaatt gaacagccaa gtcaatgact tacgaggaaa attcgtcaaa      420
ccaacattga agaaggtttc caaatacgaa aacaaattcg caaaactcca aaagaaagcg      480
gcggagttca acttcagaaa ccaactgaaa gtagtgaaga aaaaggagtt caccttggaa      540
gaagaagaca aagagaaaaa acccgattgg tccaaaaagg gagacgaaaa gaagggcgaa      600
ggagaagacg gcgacggtac cgaagacgaa aagaccgacg acggtttgac caccgaaggc      660
gaatcggtcg cgggcgatct aacggacgcg acggaagacg cgcagagcga caacgagata      720
ctcgaaccag aacccgtggt tgaacccgaa ccagaacca                             759

<210> SEQ ID NO 191
<211> LENGTH: 759
<212> TYPE: DNA
<213> ORGANISM: Acyrthosiphon pisum

<400> SEQUENCE: 191
atggccgacg atgaagctaa gaaagcaaaa caggcggaaa tcgaccgcaa gagggccgaa       60
gtgcgcaagc gtatggaaga ggcgtccaag gccaagaagg ccaagaaggg tttcatgacc      120
ccagacagaa agaagaaact ccgtctgttg ttgaaaaaaa aggcggccga agagttgaag      180
aaagaacaag aacgcaaagc tgccgaacga aggcggatca tcgaagagcg gtgcggacaa      240
ccgaagaaca tcgacgacgc cggcgaagag gagcttgcgg aaatctgcga agaactatgg      300
aaacggtttt acaccgtaga gggcataaaa tttgacttgg aaagggatat caggatgaaa      360
gttttcgaga tcagcgaatt gaacagccaa gtcaatgact tacgaggaaa attcgtcaaa      420
ccaacattga agaaggtttc caaatacgaa aacaaattcg caaaactcca aaagaaagcg      480
gcggagttca acttcagaaa ccaactgaaa gtagtgaaga aaaaggagtt caccttggaa      540
gaagaagaca aagagaaaaa acccgattgg tccaaaaagg gagacgaaaa gaagggcgaa      600
ggagaagacg gcgacggtac cgaagacgaa aagaccgacg acggtttgac caccgaaggc      660
gaatcggtcg cgggcgatct aacggacgcg acggaagacg cgcagagcga caacgagata      720
ctcgaaccag aacccgtggt tgaacccgaa ccagaacca                             759

<210> SEQ ID NO 192
<211> LENGTH: 759
<212> TYPE: DNA
<213> ORGANISM: Acyrthosiphon pisum

<400> SEQUENCE: 192
atggccgacg atgaagctaa gaaagcaaaa caggcggaaa tcgaccgcaa gagggccgaa       60
gtgcgcaagc gtatggaaga ggcgtccaag gccaagaagg ccaagaaggg tttcatgacc      120
ccagacagaa agaagaaact ccgtctgttg ttgaaaaaaa aggcggccga agagttgaag      180
aaagaacaag aacgcaaagc tgccgaacga aggcggatca tcgaagagcg gtgcggacaa      240
ccgaagaaca tcgacgacgc cggcgaagag gagcttgcgg aaatctgcga agaactatgg      300
aaacggtttt acaccgtaga gggcataaaa tttgacttgg aaagggatat caggatgaaa      360
```

```
gttttcgaga tcagcgaatt gaacagccaa gtcaatgact tacgaggaaa attcgtcaaa    420
ccaacattga agaaggtttc caaatacgaa aacaaattcg caaaactcca aaagaaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa aagaccgacg acggtttgac caccgaaggc    660
gaatcggtcg cgggcgatct aacggacgcg acggaagacg cgcagagcga caacgagata    720
ctcgaaccag aacccgtggt tgaacccgaa ccagaacca                           759

<210> SEQ ID NO 193
<211> LENGTH: 759
<212> TYPE: DNA
<213> ORGANISM: Acyrthosiphon pisum

<400> SEQUENCE: 193
atggccgacg atgaagctaa gaaagcaaaa caggcggaaa tcgaccgcaa gagggccgaa     60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga agaaggtttc caaatacgaa aacaaattcg caaaactcca aaagaaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa aagaccgacg acggtttgac caccgaaggc    660
gaatcggtcg cgggcgatct aacggacgcg acggaagacg cgcagagcga caacgagata    720
ctcgaaccag aacccgtggt tgaacccgaa ccagaacca                           759

<210> SEQ ID NO 194
<211> LENGTH: 759
<212> TYPE: DNA
<213> ORGANISM: Acyrthosiphon pisum

<400> SEQUENCE: 194
atggccgacg atgaagctaa gaaagcaaaa caggcggaaa tcgaccgcaa gagggccgaa     60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga agaaggtttc caaatacgaa aacaaattcg caaaactcca aaagaaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa aagaccgacg acggtttgac caccgaaggc    660
gaatcggtcg cgggcgatct aacggacgcg acggaagacg cgcagagcga caacgagata    720
```

```
ctcgaaccag aacccgtggt tgaacccgaa ccagaacca                                759
```

<210> SEQ ID NO 195
<211> LENGTH: 759
<212> TYPE: DNA
<213> ORGANISM: Acyrthosiphon pisum

<400> SEQUENCE: 195

```
atggccgacg atgaagctaa gaaagcaaaa caggcggaaa tcgaccgcaa gagggccgaa     60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga agaaggtttc caaatacgaa aacaaattcg caaaactcca aagagaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa aagaccgacg acggtttgac caccgaaggc    660
gaatcggtcg cgggcgatct aacggacgcg acggaagacg cgcagagcga caacgagata    720
ctcgaaccag aacccgtggt tgaacccgaa ccagaacca                           759
```

<210> SEQ ID NO 196
<211> LENGTH: 759
<212> TYPE: DNA
<213> ORGANISM: Acyrthosiphon pisum

<400> SEQUENCE: 196

```
atggccgacg atgaagctaa gaaagcaaaa caggcggaaa tcgaccgcaa gagggccgaa     60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga agaaggtttc caaatacgaa aacaaattcg caaaactcca aagagaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa aagaccgacg acggtttgac caccgaaggc    660
gaatcggtcg cgggcgatct aacggacgcg acggaagacg cgcagagcga caacgagata    720
ctcgaaccag aacccgtggt tgaacccgaa ccagaacca                           759
```

<210> SEQ ID NO 197
<211> LENGTH: 759
<212> TYPE: DNA
<213> ORGANISM: Acyrthosiphon pisum

<400> SEQUENCE: 197

| | |
|---|---|
| atggccgacg atgaagctaa gaaagcaaaa caggcggaaa tcgaccgcaa gagggccgaa | 60 |
| gtgcgcaagc gtatggaaga ggcgtccaag gccaagaagg ccaagaaggg tttcatgacc | 120 |
| ccagacagaa agaagaaact ccgtctgttg ttgaaaaaaa aggcggccga agagttgaag | 180 |
| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |
| gttttcgaga tcagcgaatt gaacagccaa gtcaatgact tacgaggaaa attcgtcaaa | 420 |
| ccaacattga agaaggtttc caaatacgaa aacaaattcg caaaactcca aaagaaagcg | 480 |
| gcggagttca acttcagaaa ccaactgaaa gtagtgaaga aaaaggagtt caccttggaa | 540 |
| gaagaagaca aagagaaaaa acccgattgg tccaaaaagg gagacgaaaa gaagggcgaa | 600 |
| ggagaagacg gcgacggtac cgaagacgaa aagaccgacg acggtttgac caccgaaggc | 660 |
| gaatcggtcg cgggcgatct aacggacgcg acggaagacg cgcagagcga caacgagata | 720 |
| ctcgaaccag aacccgtggt tgaacccgaa ccagaacca | 759 |

<210> SEQ ID NO 198
<211> LENGTH: 759
<212> TYPE: DNA
<213> ORGANISM: Acyrthosiphon pisum

<400> SEQUENCE: 198

| | |
|---|---|
| atggccgacg atgaagctaa gaaagcaaaa caggcggaaa tcgaccgcaa gagggccgaa | 60 |
| gtgcgcaagc gtatggaaga ggcgtccaag gccaagaagg ccaagaaggg tttcatgacc | 120 |
| ccagacagaa agaagaaact ccgtctgttg ttgaaaaaaa aggcggccga agagttgaag | 180 |
| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |
| gttttcgaga tcagcgaatt gaacagccaa gtcaatgact tacgaggaaa attcgtcaaa | 420 |
| ccaacattga agaaggtttc caaatacgaa aacaaattcg caaaactcca aaagaaagcg | 480 |
| gcggagttca acttcagaaa ccaactgaaa gtagtgaaga aaaaggagtt caccttggaa | 540 |
| gaagaagaca aagagaaaaa acccgattgg tccaaaaagg gagacgaaaa gaagggcgaa | 600 |
| ggagaagacg gcgacggtac cgaagacgaa aagaccgacg acggtttgac caccgaaggc | 660 |
| gaatcggtcg cgggcgatct aacggacgcg acggaagacg cgcagagcga caacgagata | 720 |
| ctcgaaccag aacccgtggt tgaacccgaa ccagaacca | 759 |

<210> SEQ ID NO 199
<211> LENGTH: 759
<212> TYPE: DNA
<213> ORGANISM: Acyrthosiphon pisum

<400> SEQUENCE: 199

| | |
|---|---|
| atggccgacg atgaagctaa gaaagcaaaa caggcggaaa tcgaccgcaa gagggccgaa | 60 |
| gtgcgcaagc gtatggaaga ggcgtccaag gccaagaagg ccaagaaggg tttcatgacc | 120 |
| ccagacagaa agaagaaact ccgtctgttg ttgaaaaaaa aggcggccga agagttgaag | 180 |
| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |

```
gttttcgaga tcagcgaatt gaacagccaa gtcaatgact tacgaggaaa attcgtcaaa      420
ccaacattga agaaggtttc caaatacgaa acaaattcg caaaactcca aaagaaagcg       480
gcggagttca acttcagaaa ccaactgaaa gtagtgaaga aaaggagtt caccttggaa       540 gaagaagaca aagagaaaaa acccgattgg tccaaaaagg gagacgaaaa gaagggcgaa      600
ggagaagacg gcgacggtac cgaagacgaa aagaccgacg acggtttgac caccgaaggc      660
gaatcggtcg cgggcgatct aacgacgcg acggaagacg cgcagagcga caacgagata      720
ctcgaaccag aacccgtggt tgaacccgaa ccagaacca                             759
```

```
<210> SEQ ID NO 200
<211> LENGTH: 541
<212> TYPE: DNA
<213> ORGANISM: Acyrthosiphon pisum

<400> SEQUENCE: 200
cggtaatgcg atgcggtaag aagaaggtat ggttggatcc aaacgaaata atgaaattg        60 ccaacaccaa ttccagacaa atattcgta agttgatcaa agatggtttg atcattaaaa      120
agccagtagc tgtacactct agggctcgtg cacgtaaaaa tgcagatgcc agaagaaaag      180
gtcgtcattg tggttttggt aaaaggaagg gtactgctaa tgctcgaaca cctcaaaaag      240
acctttgggt gaaaagaatg cgagtattaa ggcggttgct taaaaaatac cgtgaagcaa      300
agaaaattga caaccatctt taccatcagt tatacatgaa ggctaagggt aatgttttca      360
agaacaaacg tgtattgatg gagttcatcc acaaaaagaa ggcagagaag gcccgtgcca      420
agatgttgag tgatcaagct gaagctagac gtcaaaaggt taaggaagct aggaaacgta      480
aagaagcaag attttttacaa ataggaagg aacttttggc tgcatacgcc cgagaagatg      540
a                                                                      541
```

```
<210> SEQ ID NO 201
<211> LENGTH: 541
<212> TYPE: DNA
<213> ORGANISM: Acyrthosiphon pisum

<400> SEQUENCE: 201
cggtaatgcg atgcggtaag aagaaggtat ggttggatcc aaacgaaata atgaaattg        60 ccaacaccaa ttccagacaa atattcgta agttgatcaa agatggtttg atcattaaaa      120
agccagtagc tgtacactct agggctcgtg cacgtaaaaa tgcagatgcc agaagaaaag      180
gtcgtcattg tggttttggt aaaaggaagg gtactgctaa tgctcgaaca cctcaaaaag      240
acctttgggt gaaaagaatg cgagtattaa ggcggttgct taaaaaatac cgtgaagcaa      300
agaaaattga caaccatctt taccatcagt tatacatgaa ggctaagggt aatgttttca      360
agaacaaacg tgtattgatg gagttcatcc acaaaaagaa ggcagagaag gcccgtgcca      420
agatgttgag tgatcaagct gaagctagac gtcaaaaggt taaggaagct aggaaacgta      480
aagaagcaag attttttacaa ataggaagg aacttttggc tgcatacgcc cgagaagatg      540
a                                                                      541
```

```
<210> SEQ ID NO 202
<211> LENGTH: 823
<212> TYPE: DNA
<213> ORGANISM: Acyrthosiphon pisum

<400> SEQUENCE: 202
```

-continued

```
gttgtagtcg aaagggtac gtccgtcttc aagttgtttt ccggcaaaga tcaaacgttg      60
ttggtctggt gggatacctt ctttgtcttg gatcttggct tttacatttt caatggaatc    120
agatgattcc acctccaatg taatggtctt tccagtgagg gtctttacaa agatttgcat    180
accaccacgg agacgcaaca ctaagtgaag ggtagattct ttctggatgt tgtagtcaga    240
aagtgtgcgt ccgtcttcaa gttgctttcc ggcaaagatc aaacgttgtt ggtcaggtgg    300
aataccttct ttgtcttgga tcttagcttt tacattttca atggaatctg atgactcaac    360
ttccaatgta atggtctttc cagtgagggt ctttacaaag atttgcatac caccacggag    420
acgcaacact aagtgaaggg tagattcttt ctggatgttg tagtcggaaa gggtacgtcc    480
gtcttcaagt tgctttccgg caaagatcaa acgttgttgg tctggtggga taccttcttt    540
gtcttggatc ttggctttta cattttcaat ggaatcagat gattccacct ccaatgtaat    600
ggtctttcca gtgagggtct ttacaaagat ttgcatacca ccacggagac gcaacactaa    660
gtgaagggta gattctttct ggatgttgta gtcggaaagg gtacgtccgt cttcaagttg    720
cttttccagca aagatcaaac gttgctggtc tggtgggata ccttccttgt cttggatctt    780
ggccttaaca ttttcaatgg aatctgatga ctcaacttcc aaa                      823
```

<210> SEQ ID NO 203
<211> LENGTH: 823
<212> TYPE: DNA
<213> ORGANISM: Acyrthosiphon pisum

<400> SEQUENCE: 203

```
gttgtagtcg aaagggtac gtccgtcttc aagttgtttt ccggcaaaga tcaaacgttg      60
ttggtctggt gggatacctt ctttgtcttg gatcttggct tttacatttt caatggaatc    120
agatgattcc acctccaatg taatggtctt tccagtgagg gtctttacaa agatttgcat    180
accaccacgg agacgcaaca ctaagtgaag ggtagattct ttctggatgt tgtagtcaga    240
aagtgtgcgt ccgtcttcaa gttgctttcc ggcaaagatc aaacgttgtt ggtcaggtgg    300
aataccttct ttgtcttgga tcttagcttt tacattttca atggaatctg atgactcaac    360
ttccaatgta atggtctttc cagtgagggt ctttacaaag atttgcatac caccacggag    420
acgcaacact aagtgaaggg tagattcttt ctggatgttg tagtcggaaa gggtacgtcc    480
gtcttcaagt tgctttccgg caaagatcaa acgttgttgg tctggtggga taccttcttt    540
gtcttggatc ttggctttta cattttcaat ggaatcagat gattccacct ccaatgtaat    600
ggtctttcca gtgagggtct ttacaaagat ttgcatacca ccacggagac gcaacactaa    660
gtgaagggta gattctttct ggatgttgta gtcggaaagg gtacgtccgt cttcaagttg    720
cttttccagca aagatcaaac gttgctggtc tggtgggata ccttccttgt cttggatctt    780
ggccttaaca ttttcaatgg aatctgatga ctcaacttcc aaa                      823
```

<210> SEQ ID NO 204
<211> LENGTH: 172
<212> TYPE: DNA
<213> ORGANISM: Acyrthosiphon pisum

<400> SEQUENCE: 204

```
aagacttgct tcatcctact gcaattgaag aacgcaggaa acacaaatta agcgccttg      60
ttcaacaccc aaactctttt ttcatggatg tcaaatgccc tggatgttat aaaattacaa    120
ctgtattcag tcacgctcag agtgtagtta tatgtaccgg atgttccaca at            172
```

<210> SEQ ID NO 205
<211> LENGTH: 172
<212> TYPE: DNA
<213> ORGANISM: Acyrthosiphon pisum

<400> SEQUENCE: 205

```
aagacttgct tcatcctact gcaattgaag aacgcaggaa acacaaatta aagcgccttg      60
ttcaacaccc aaactctttt ttcatggatg tcaaatgccc tggatgttat aaaattacaa     120
ctgtattcag tcacgctcag agtgtagtta tatgtaccgg atgttccaca at             172
```

<210> SEQ ID NO 206
<211> LENGTH: 25
<212> TYPE: DNA
<213> ORGANISM: Artificial
<220> FEATURE:
<223> OTHER INFORMATION: Primer

<400> SEQUENCE: 206

```
cgaaccatct gggaagcttg gaatg                                            25
```

<210> SEQ ID NO 207
<211> LENGTH: 25
<212> TYPE: DNA
<213> ORGANISM: Artificial
<220> FEATURE:
<223> OTHER INFORMATION: Primer

<400> SEQUENCE: 207

```
gcagctggag gaagagaaac gtatc                                            25
```

<210> SEQ ID NO 208
<211> LENGTH: 47
<212> TYPE: DNA
<213> ORGANISM: Artificial
<220> FEATURE:
<223> OTHER INFORMATION: Primer

<400> SEQUENCE: 208

```
gcgtaatacg actcactata ggcgaaccat ctgggaagct tggaatg                    47
```

<210> SEQ ID NO 209
<211> LENGTH: 46
<212> TYPE: DNA
<213> ORGANISM: Artificial
<220> FEATURE:
<223> OTHER INFORMATION: Primer

<400> SEQUENCE: 209

```
gcgtaatacg actcactata ggcagctgga ggaagagaaa cgtatc                     46
```

<210> SEQ ID NO 210
<211> LENGTH: 20
<212> TYPE: DNA
<213> ORGANISM: Artificial
<220> FEATURE:
<223> OTHER INFORMATION: Primer

<400> SEQUENCE: 210

```
agttcgagaa caccaggaag                                                  20
```

<210> SEQ ID NO 211
<211> LENGTH: 22
<212> TYPE: DNA
<213> ORGANISM: Artificial
<220> FEATURE:

<223> OTHER INFORMATION: Primer

<400> SEQUENCE: 211
cctgacacgt tgttccagct tg                                          22

<210> SEQ ID NO 212
<211> LENGTH: 45
<212> TYPE: DNA
<213> ORGANISM: Artificial
<220> FEATURE:
<223> OTHER INFORMATION: Primer

<400> SEQUENCE: 212
gcgtaatacg actcactata ggaggagttc gagaacacca ggaag                 45

<210> SEQ ID NO 213
<211> LENGTH: 44
<212> TYPE: DNA
<213> ORGANISM: Artificial
<220> FEATURE:
<223> OTHER INFORMATION: Primer

<400> SEQUENCE: 213
gcgtaatacg actcactata ggcctgacac gttgttccag cttg                  44

<210> SEQ ID NO 214
<211> LENGTH: 20
<212> TYPE: DNA
<213> ORGANISM: Artificial
<220> FEATURE:
<223> OTHER INFORMATION: Primer

<400> SEQUENCE: 214
gcaggcgatg aagatggaga                                             20

<210> SEQ ID NO 215
<211> LENGTH: 24
<212> TYPE: DNA
<213> ORGANISM: Artificial
<220> FEATURE:
<223> OTHER INFORMATION: Primer

<400> SEQUENCE: 215
ccacctcttt ctgcaacttc ttga                                        24

<210> SEQ ID NO 216
<211> LENGTH: 42
<212> TYPE: DNA
<213> ORGANISM: Artificial
<220> FEATURE:
<223> OTHER INFORMATION: Primer

<400> SEQUENCE: 216
gcgtaatacg actcactata gggcaggcga tgaagatgga ga                    42

<210> SEQ ID NO 217
<211> LENGTH: 46
<212> TYPE: DNA
<213> ORGANISM: Artificial
<220> FEATURE:
<223> OTHER INFORMATION: Primer

<400> SEQUENCE: 217
gcgtaatacg actcactata ggccacctct ttctgcaact tcttga                46

```
<210> SEQ ID NO 218
<211> LENGTH: 25
<212> TYPE: DNA
<213> ORGANISM: Artificial
<220> FEATURE:
<223> OTHER INFORMATION: Primer

<400> SEQUENCE: 218
cagaatccca cagaatctga cgtga                                              25

<210> SEQ ID NO 219
<211> LENGTH: 20
<212> TYPE: DNA
<213> ORGANISM: Artificial
<220> FEATURE:
<223> OTHER INFORMATION: Primer

<400> SEQUENCE: 219
gcaagtggcg aagctcagct                                                    20

<210> SEQ ID NO 220
<211> LENGTH: 47
<212> TYPE: DNA
<213> ORGANISM: Artificial
<220> FEATURE:
<223> OTHER INFORMATION: Primer

<400> SEQUENCE: 220
gcgtaatacg actcactata ggcagaatcc cacagaatct gacgtga                      47

<210> SEQ ID NO 221
<211> LENGTH: 41
<212> TYPE: DNA
<213> ORGANISM: Artificial
<220> FEATURE:
<223> OTHER INFORMATION: Primer

<400> SEQUENCE: 221
gcgtaatacg actcactata ggcaagtggc gaagctcagc t                            41

<210> SEQ ID NO 222
<211> LENGTH: 21
<212> TYPE: DNA
<213> ORGANISM: Artificial
<220> FEATURE:
<223> OTHER INFORMATION: Primer

<400> SEQUENCE: 222
cgtgtttgcc atgttcgatc a                                                  21

<210> SEQ ID NO 223
<211> LENGTH: 23
<212> TYPE: DNA
<213> ORGANISM: Artificial
<220> FEATURE:
<223> OTHER INFORMATION: Primer

<400> SEQUENCE: 223
ggtacatttc gtccacgtct tca                                                23

<210> SEQ ID NO 224
<211> LENGTH: 43
<212> TYPE: DNA
<213> ORGANISM: Artificial
<220> FEATURE:
<223> OTHER INFORMATION: Primer
```

<400> SEQUENCE: 224
gcgtaatacg actcactata ggcgtgtttg ccatgttcga tca        43

<210> SEQ ID NO 225
<211> LENGTH: 43
<212> TYPE: DNA
<213> ORGANISM: Artificial
<220> FEATURE:
<223> OTHER INFORMATION: Primer

<400> SEQUENCE: 225
gcgtaatacg actcactata ggtacatttc gtccacgtct tca        43

<210> SEQ ID NO 226
<211> LENGTH: 23
<212> TYPE: DNA
<213> ORGANISM: Artificial
<220> FEATURE:
<223> OTHER INFORMATION: Primer

<400> SEQUENCE: 226
gacttgatct tcagccgacc att                              23

<210> SEQ ID NO 227
<211> LENGTH: 23
<212> TYPE: DNA
<213> ORGANISM: Artificial
<220> FEATURE:
<223> OTHER INFORMATION: Primer

<400> SEQUENCE: 227
ccattgccag ttcctcaact tca                              23

<210> SEQ ID NO 228
<211> LENGTH: 44
<212> TYPE: DNA
<213> ORGANISM: Artificial
<220> FEATURE:
<223> OTHER INFORMATION: Primer

<400> SEQUENCE: 228
gcgtaatacg actcactata ggacttgatc ttcagccgac catt       44

<210> SEQ ID NO 229
<211> LENGTH: 45
<212> TYPE: DNA
<213> ORGANISM: Artificial
<220> FEATURE:
<223> OTHER INFORMATION: Primer

<400> SEQUENCE: 229
gcgtaatacg actcactata ggccattgcc agttcctcaa cttca      45

<210> SEQ ID NO 230
<211> LENGTH: 21
<212> TYPE: DNA
<213> ORGANISM: Artificial
<220> FEATURE:
<223> OTHER INFORMATION: Primer

<400> SEQUENCE: 230
cgcaatgatc tcctccagga t                                21

<210> SEQ ID NO 231
<211> LENGTH: 24

<212> TYPE: DNA
<213> ORGANISM: Artificial
<220> FEATURE:
<223> OTHER INFORMATION: Primer

<400> SEQUENCE: 231
ggtcatcatc tccatgaact cgtc                                        24

<210> SEQ ID NO 232
<211> LENGTH: 43
<212> TYPE: DNA
<213> ORGANISM: Artificial
<220> FEATURE:
<223> OTHER INFORMATION: Primer

<400> SEQUENCE: 232
gcgtaatacg actcactata ggcgcaatga tctcctccag gat                   43

<210> SEQ ID NO 233
<211> LENGTH: 45
<212> TYPE: DNA
<213> ORGANISM: Artificial
<220> FEATURE:
<223> OTHER INFORMATION: Primer

<400> SEQUENCE: 233
gcgtaatacg actcactata gggtcatcat ctccatgaac tcgtc                 45

<210> SEQ ID NO 234
<211> LENGTH: 26
<212> TYPE: DNA
<213> ORGANISM: Artificial
<220> FEATURE:
<223> OTHER INFORMATION: Primer

<400> SEQUENCE: 234
cgtcactaat cggactggtc taacag                                      26

<210> SEQ ID NO 235
<211> LENGTH: 24
<212> TYPE: DNA
<213> ORGANISM: Artificial
<220> FEATURE:
<223> OTHER INFORMATION: Primer

<400> SEQUENCE: 235
ggtcatcatc tccatgaact cgtc                                        24

<210> SEQ ID NO 236
<211> LENGTH: 48
<212> TYPE: DNA
<213> ORGANISM: Artificial
<220> FEATURE:
<223> OTHER INFORMATION: Primer

<400> SEQUENCE: 236
gcgtaatacg actcactata ggcgtcacta atcggactgg tctaacag              48

<210> SEQ ID NO 237
<211> LENGTH: 45
<212> TYPE: DNA
<213> ORGANISM: Artificial
<220> FEATURE:
<223> OTHER INFORMATION: Primer

<400> SEQUENCE: 237

```
gcgtaatacg actcactata gggtcatcat ctccatgaac tcgtc          45
```

<210> SEQ ID NO 238
<211> LENGTH: 23
<212> TYPE: DNA
<213> ORGANISM: Artificial
<220> FEATURE:
<223> OTHER INFORMATION: Primer

<400> SEQUENCE: 238

```
ggtgaaggag ggtgcctgct cag                                   23
```

<210> SEQ ID NO 239
<211> LENGTH: 25
<212> TYPE: DNA
<213> ORGANISM: Artificial
<220> FEATURE:
<223> OTHER INFORMATION: Primer

<400> SEQUENCE: 239

```
cagggtgaat agaacgaggt actcg                                 25
```

<210> SEQ ID NO 240
<211> LENGTH: 40
<212> TYPE: DNA
<213> ORGANISM: Artificial
<220> FEATURE:
<223> OTHER INFORMATION: Primer

<400> SEQUENCE: 240

```
aatacgactc actatagggc gctatgaaat tccaagcaca                 40
```

<210> SEQ ID NO 241
<211> LENGTH: 47
<212> TYPE: DNA
<213> ORGANISM: Artificial
<220> FEATURE:
<223> OTHER INFORMATION: Primer

<400> SEQUENCE: 241

```
gcgtaatacg actcactata ggcagggtga atagaacgag gtactcg         47
```

<210> SEQ ID NO 242
<211> LENGTH: 29
<212> TYPE: DNA
<213> ORGANISM: Artificial
<220> FEATURE:
<223> OTHER INFORMATION: Primer

<400> SEQUENCE: 242

```
ctcaacgaag gtcttgtcag tggctttgg                             29
```

<210> SEQ ID NO 243
<211> LENGTH: 20
<212> TYPE: DNA
<213> ORGANISM: Artificial
<220> FEATURE:
<223> OTHER INFORMATION: Primer

<400> SEQUENCE: 243

```
ttcgcctggc ttcttcgtga                                       20
```

<210> SEQ ID NO 244
<211> LENGTH: 44
<212> TYPE: DNA
<213> ORGANISM: Artificial

```
<220> FEATURE:
<223> OTHER INFORMATION: Primer

<400> SEQUENCE: 244
gcgtaatacg actcactata ggccacgccg acttaattca ttcc          44

<210> SEQ ID NO 245
<211> LENGTH: 42
<212> TYPE: DNA
<213> ORGANISM: Artificial
<220> FEATURE:
<223> OTHER INFORMATION: Primer

<400> SEQUENCE: 245
gcgtaatacg actcactata ggttcgcctg gcttcttcgt ga            42

<210> SEQ ID NO 246
<211> LENGTH: 22
<212> TYPE: DNA
<213> ORGANISM: Artificial
<220> FEATURE:
<223> OTHER INFORMATION: Primer

<400> SEQUENCE: 246
tgtcgatggc ggtcttaaca tc                                  22

<210> SEQ ID NO 247
<211> LENGTH: 24
<212> TYPE: DNA
<213> ORGANISM: Artificial
<220> FEATURE:
<223> OTHER INFORMATION: Primer

<400> SEQUENCE: 247
tctccagctt ccactttctt gaga                                24

<210> SEQ ID NO 248
<211> LENGTH: 44
<212> TYPE: DNA
<213> ORGANISM: Artificial
<220> FEATURE:
<223> OTHER INFORMATION: Primer

<400> SEQUENCE: 248
gcgtaatacg actcactata ggtgtcgatg gcggtcttaa catc          44

<210> SEQ ID NO 249
<211> LENGTH: 46
<212> TYPE: DNA
<213> ORGANISM: Artificial
<220> FEATURE:
<223> OTHER INFORMATION: Primer

<400> SEQUENCE: 249
gcgtaatacg actcactata ggtctccagc ttccactttc ttgaga        46

<210> SEQ ID NO 250
<211> LENGTH: 20
<212> TYPE: DNA
<213> ORGANISM: Artificial
<220> FEATURE:
<223> OTHER INFORMATION: Primer

<400> SEQUENCE: 250
aacgtgcatt tcgcgtaccc                                     20
```

<210> SEQ ID NO 251
<211> LENGTH: 20
<212> TYPE: DNA
<213> ORGANISM: Artificial
<220> FEATURE:
<223> OTHER INFORMATION: Primer

<400> SEQUENCE: 251
tgatgggcat aactggcagg                                         20

<210> SEQ ID NO 252
<211> LENGTH: 42
<212> TYPE: DNA
<213> ORGANISM: Artificial
<220> FEATURE:
<223> OTHER INFORMATION: Primer

<400> SEQUENCE: 252
gcgtaatacg actcactata ggaacgtgca tttcgcgtac cc                 42

<210> SEQ ID NO 253
<211> LENGTH: 42
<212> TYPE: DNA
<213> ORGANISM: Artificial
<220> FEATURE:
<223> OTHER INFORMATION: Primer

<400> SEQUENCE: 253
gcgtaatacg actcactata ggtgatgggc ataactggca gg                 42

<210> SEQ ID NO 254
<211> LENGTH: 22
<212> TYPE: DNA
<213> ORGANISM: Artificial
<220> FEATURE:
<223> OTHER INFORMATION: Primer

<400> SEQUENCE: 254
ccttattgaa cgtggtcgac ag                                      22

<210> SEQ ID NO 255
<211> LENGTH: 20
<212> TYPE: DNA
<213> ORGANISM: Artificial
<220> FEATURE:
<223> OTHER INFORMATION: Primer

<400> SEQUENCE: 255
ctgatgtagt ccttgaggag                                         20

<210> SEQ ID NO 256
<211> LENGTH: 44
<212> TYPE: DNA
<213> ORGANISM: Artificial
<220> FEATURE:
<223> OTHER INFORMATION: Primer

<400> SEQUENCE: 256
gcgtaatacg actcactata ggccttattg aacgtggtcg acag               44

<210> SEQ ID NO 257
<211> LENGTH: 42
<212> TYPE: DNA
<213> ORGANISM: Artificial
<220> FEATURE:
<223> OTHER INFORMATION: Primer

```
<400> SEQUENCE: 257
gcgtaatacg actcactata ggctgatgta gtccttgagg ag                              42

<210> SEQ ID NO 258
<211> LENGTH: 26
<212> TYPE: DNA
<213> ORGANISM: Artificial
<220> FEATURE:
<223> OTHER INFORMATION: Primer

<400> SEQUENCE: 258
gtacggacgg gtagtttagt tgtgtc                                               26

<210> SEQ ID NO 259
<211> LENGTH: 20
<212> TYPE: DNA
<213> ORGANISM: Artificial
<220> FEATURE:
<223> OTHER INFORMATION: Primer

<400> SEQUENCE: 259
ttgccaagtg ccaagtcacg                                                     20

<210> SEQ ID NO 260
<211> LENGTH: 48
<212> TYPE: DNA
<213> ORGANISM: Artificial
<220> FEATURE:
<223> OTHER INFORMATION: Primer

<400> SEQUENCE: 260
gcgtaatacg actcactata gggtacggac gggtagttta gttgtgtc                       48

<210> SEQ ID NO 261
<211> LENGTH: 42
<212> TYPE: DNA
<213> ORGANISM: Artificial
<220> FEATURE:
<223> OTHER INFORMATION: Primer

<400> SEQUENCE: 261
gcgtaatacg actcactata ggttgccaag tgccaagtca cg                             42

<210> SEQ ID NO 262
<211> LENGTH: 22
<212> TYPE: DNA
<213> ORGANISM: Artificial
<220> FEATURE:
<223> OTHER INFORMATION: Primer

<400> SEQUENCE: 262
ctgttgtcgg ctggtcatat cc                                                   22

<210> SEQ ID NO 263
<211> LENGTH: 20
<212> TYPE: DNA
<213> ORGANISM: Artificial
<220> FEATURE:
<223> OTHER INFORMATION: Primer

<400> SEQUENCE: 263
taacgtaacg catcgccacc                                                      20

<210> SEQ ID NO 264
```

```
<211> LENGTH: 44
<212> TYPE: DNA
<213> ORGANISM: Artificial
<220> FEATURE:
<223> OTHER INFORMATION: Primer

<400> SEQUENCE: 264
gcgtaatacg actcactata ggctgttgtc ggctggtcat atcc          44

<210> SEQ ID NO 265
<211> LENGTH: 42
<212> TYPE: DNA
<213> ORGANISM: Artificial
<220> FEATURE:
<223> OTHER INFORMATION: Primer

<400> SEQUENCE: 265
gcgtaatacg actcactata ggtaacgtaa cgcatcgcca cc            42

<210> SEQ ID NO 266
<211> LENGTH: 20
<212> TYPE: DNA
<213> ORGANISM: Artificial
<220> FEATURE:
<223> OTHER INFORMATION: Primer

<400> SEQUENCE: 266
agccctcatc cgtgatttgg                                     20

<210> SEQ ID NO 267
<211> LENGTH: 20
<212> TYPE: DNA
<213> ORGANISM: Artificial
<220> FEATURE:
<223> OTHER INFORMATION: Primer

<400> SEQUENCE: 267
gatccggcct caatttgacg                                     20

<210> SEQ ID NO 268
<211> LENGTH: 42
<212> TYPE: DNA
<213> ORGANISM: Artificial
<220> FEATURE:
<223> OTHER INFORMATION: Primer

<400> SEQUENCE: 268
gcgtaatacg actcactata ggagccctca tccgtgattt gg            42

<210> SEQ ID NO 269
<211> LENGTH: 42
<212> TYPE: DNA
<213> ORGANISM: Artificial
<220> FEATURE:
<223> OTHER INFORMATION: Primer

<400> SEQUENCE: 269
gcgtaatacg actcactata gggatccggc ctcaatttga cg            42

<210> SEQ ID NO 270
<211> LENGTH: 22
<212> TYPE: DNA
<213> ORGANISM: Artificial
<220> FEATURE:
<223> OTHER INFORMATION: Primer

<400> SEQUENCE: 270
```
acgtttctct gctcattcgt gc                                                22

<210> SEQ ID NO 271
<211> LENGTH: 20
<212> TYPE: DNA
<213> ORGANISM: Artificial
<220> FEATURE:
<223> OTHER INFORMATION: Primer

<400> SEQUENCE: 271
cttgtacaaa gtgtgcaggg                                                   20

<210> SEQ ID NO 272
<211> LENGTH: 44
<212> TYPE: DNA
<213> ORGANISM: Artificial
<220> FEATURE:
<223> OTHER INFORMATION: Primer

<400> SEQUENCE: 272
gcgtaatacg actcactata ggacgtttct ctgctcattc gtgc                         44

<210> SEQ ID NO 273
<211> LENGTH: 42
<212> TYPE: DNA
<213> ORGANISM: Artificial
<220> FEATURE:
<223> OTHER INFORMATION: Primer

<400> SEQUENCE: 273
gcgtaatacg actcactata ggcttgtaca aagtgtgcag gg                           42

<210> SEQ ID NO 274
<211> LENGTH: 22
<212> TYPE: DNA
<213> ORGANISM: Artificial
<220> FEATURE:
<223> OTHER INFORMATION: Primer

<400> SEQUENCE: 274
ggttttcttc ttgcccgaat cg                                                22

<210> SEQ ID NO 275
<211> LENGTH: 20
<212> TYPE: DNA
<213> ORGANISM: Artificial
<220> FEATURE:
<223> OTHER INFORMATION: Primer

<400> SEQUENCE: 275
tttggggttc ggcttggttg                                                   20

<210> SEQ ID NO 276
<211> LENGTH: 44
<212> TYPE: DNA
<213> ORGANISM: Artificial
<220> FEATURE:
<223> OTHER INFORMATION: Primer

<400> SEQUENCE: 276
gcgtaatacg actcactata ggggttttct tcttgcccga atcg                         44

<210> SEQ ID NO 277
<211> LENGTH: 42
<212> TYPE: DNA

```
<213> ORGANISM: Artificial
<220> FEATURE:
<223> OTHER INFORMATION: Primer

<400> SEQUENCE: 277
gcgtaatacg actcactata ggtttggggt tcggcttggt tg                42

<210> SEQ ID NO 278
<211> LENGTH: 23
<212> TYPE: DNA
<213> ORGANISM: Artificial
<220> FEATURE:
<223> OTHER INFORMATION: Primer

<400> SEQUENCE: 278
tcagcgagat ccctaagaca acg                                    23

<210> SEQ ID NO 279
<211> LENGTH: 20
<212> TYPE: DNA
<213> ORGANISM: Artificial
<220> FEATURE:
<223> OTHER INFORMATION: Primer

<400> SEQUENCE: 279
ccccacatgt tgatgacgca                                        20

<210> SEQ ID NO 280
<211> LENGTH: 45
<212> TYPE: DNA
<213> ORGANISM: Artificial
<220> FEATURE:
<223> OTHER INFORMATION: Primer

<400> SEQUENCE: 280
gcgtaatacg actcactata ggtcagcgag atccctaaga caacg            45

<210> SEQ ID NO 281
<211> LENGTH: 42
<212> TYPE: DNA
<213> ORGANISM: Artificial
<220> FEATURE:
<223> OTHER INFORMATION: Primer

<400> SEQUENCE: 281
gcgtaatacg actcactata ggccccacat gttgatgacg ca               42

<210> SEQ ID NO 282
<211> LENGTH: 23
<212> TYPE: DNA
<213> ORGANISM: Artificial
<220> FEATURE:
<223> OTHER INFORMATION: Primer

<400> SEQUENCE: 282
ggtttatgac ccctgagagg aag                                    23

<210> SEQ ID NO 283
<211> LENGTH: 22
<212> TYPE: DNA
<213> ORGANISM: Artificial
<220> FEATURE:
<223> OTHER INFORMATION: Primer

<400> SEQUENCE: 283
ctccagggtg aactccttct tc                                     22
```

<210> SEQ ID NO 284
<211> LENGTH: 43
<212> TYPE: DNA
<213> ORGANISM: Artificial
<220> FEATURE:
<223> OTHER INFORMATION: Primer

<400> SEQUENCE: 284
gcgtaatacg actcactata ggtttatgac ccctgagagg aag    43

<210> SEQ ID NO 285
<211> LENGTH: 44
<212> TYPE: DNA
<213> ORGANISM: Artificial
<220> FEATURE:
<223> OTHER INFORMATION: Primer

<400> SEQUENCE: 285
gcgtaatacg actcactata ggctccaggg tgaactcctt cttc    44

<210> SEQ ID NO 286
<211> LENGTH: 24
<212> TYPE: DNA
<213> ORGANISM: Artificial
<220> FEATURE:
<223> OTHER INFORMATION: Primer

<400> SEQUENCE: 286
caaggaccag aacaagaaca aggg    24

<210> SEQ ID NO 287
<211> LENGTH: 26
<212> TYPE: DNA
<213> ORGANISM: Artificial
<220> FEATURE:
<223> OTHER INFORMATION: Primer

<400> SEQUENCE: 287
gacgttcata tttggaggct acttgg    26

<210> SEQ ID NO 288
<211> LENGTH: 46
<212> TYPE: DNA
<213> ORGANISM: Artificial
<220> FEATURE:
<223> OTHER INFORMATION: Primer

<400> SEQUENCE: 288
gcgtaatacg actcactata ggcaaggacc agaacaagaa caaggg    46

<210> SEQ ID NO 289
<211> LENGTH: 47
<212> TYPE: DNA
<213> ORGANISM: Artificial
<220> FEATURE:
<223> OTHER INFORMATION: Primer

<400> SEQUENCE: 289
gcgtaatacg actcactata ggacgttcat atttggaggc tacttgg    47

<210> SEQ ID NO 290
<211> LENGTH: 25
<212> TYPE: DNA
<213> ORGANISM: Artificial
<220> FEATURE:

<223> OTHER INFORMATION: Primer

<400> SEQUENCE: 290
aatctcgtac actgttggaa caagc					25

<210> SEQ ID NO 291
<211> LENGTH: 25
<212> TYPE: DNA
<213> ORGANISM: Artificial
<220> FEATURE:
<223> OTHER INFORMATION: Primer

<400> SEQUENCE: 291
ggttcttacg gtcttcttca gcttg					25

<210> SEQ ID NO 292
<211> LENGTH: 47
<212> TYPE: DNA
<213> ORGANISM: Artificial
<220> FEATURE:
<223> OTHER INFORMATION: Primer

<400> SEQUENCE: 292
gcgtaatacg actcactata ggaatctcgt acactgttgg aacaagc					47

<210> SEQ ID NO 293
<211> LENGTH: 45
<212> TYPE: DNA
<213> ORGANISM: Artificial
<220> FEATURE:
<223> OTHER INFORMATION: Primer

<400> SEQUENCE: 293
gcgtaatacg actcactata ggttcttacg gtcttcttca gcttg					45

<210> SEQ ID NO 294
<211> LENGTH: 22
<212> TYPE: DNA
<213> ORGANISM: Artificial
<220> FEATURE:
<223> OTHER INFORMATION: Primer

<400> SEQUENCE: 294
aagaagaagc tcaggttgtt gc					22

<210> SEQ ID NO 295
<211> LENGTH: 20
<212> TYPE: DNA
<213> ORGANISM: Artificial
<220> FEATURE:
<223> OTHER INFORMATION: Primer

<400> SEQUENCE: 295
tcattcacct ggctgttgag					20

<210> SEQ ID NO 296
<211> LENGTH: 44
<212> TYPE: DNA
<213> ORGANISM: Artificial
<220> FEATURE:
<223> OTHER INFORMATION: Primer

<400> SEQUENCE: 296
gcgtaatacg actcactata ggaagaagaa gctcaggttg ttgc					44

```
<210> SEQ ID NO 297
<211> LENGTH: 42
<212> TYPE: DNA
<213> ORGANISM: Artificial
<220> FEATURE:
<223> OTHER INFORMATION: Primer

<400> SEQUENCE: 297
gcgtaatacg actcactata ggtcattcac ctggctgttg ag        42

<210> SEQ ID NO 298
<211> LENGTH: 20
<212> TYPE: DNA
<213> ORGANISM: Artificial
<220> FEATURE:
<223> OTHER INFORMATION: Primer

<400> SEQUENCE: 298
acatcctcag gctcatggga                                 20

<210> SEQ ID NO 299
<211> LENGTH: 20
<212> TYPE: DNA
<213> ORGANISM: Artificial
<220> FEATURE:
<223> OTHER INFORMATION: Primer

<400> SEQUENCE: 299
agccgttacc ttccttgtcg                                 20

<210> SEQ ID NO 300
<211> LENGTH: 42
<212> TYPE: DNA
<213> ORGANISM: Artificial
<220> FEATURE:
<223> OTHER INFORMATION: Primer

<400> SEQUENCE: 300
gcgtaatacg actcactata ggacatcctc aggctcatgg ga        42

<210> SEQ ID NO 301
<211> LENGTH: 42
<212> TYPE: DNA
<213> ORGANISM: Artificial
<220> FEATURE:
<223> OTHER INFORMATION: Primer

<400> SEQUENCE: 301
gcgtaatacg actcactata ggagccgtta ccttccttgt cg        42

<210> SEQ ID NO 302
<211> LENGTH: 20
<212> TYPE: DNA
<213> ORGANISM: Artificial
<220> FEATURE:
<223> OTHER INFORMATION: Primer

<400> SEQUENCE: 302
acatcctcag gctcatggga                                 20

<210> SEQ ID NO 303
<211> LENGTH: 20
<212> TYPE: DNA
<213> ORGANISM: Artificial
<220> FEATURE:
<223> OTHER INFORMATION: Primer
```

<400> SEQUENCE: 303
agccgttacc ttccttgtcg                                              20

<210> SEQ ID NO 304
<211> LENGTH: 42
<212> TYPE: DNA
<213> ORGANISM: Artificial
<220> FEATURE:
<223> OTHER INFORMATION: Primer

<400> SEQUENCE: 304
gcgtaatacg actcactata ggacatcctc aggctcatgg ga                     42

<210> SEQ ID NO 305
<211> LENGTH: 42
<212> TYPE: DNA
<213> ORGANISM: Artificial
<220> FEATURE:
<223> OTHER INFORMATION: Primer

<400> SEQUENCE: 305
gcgtaatacg actcactata ggagccgtta ccttccttgt cg                     42

<210> SEQ ID NO 306
<211> LENGTH: 24
<212> TYPE: DNA
<213> ORGANISM: Artificial
<220> FEATURE:
<223> OTHER INFORMATION: Primer

<400> SEQUENCE: 306
cgtaaaaact ctgaccggca agac                                         24

<210> SEQ ID NO 307
<211> LENGTH: 26
<212> TYPE: DNA
<213> ORGANISM: Artificial
<220> FEATURE:
<223> OTHER INFORMATION: Primer

<400> SEQUENCE: 307
tagttccacc acgaagtctg agaacc                                       26

<210> SEQ ID NO 308
<211> LENGTH: 46
<212> TYPE: DNA
<213> ORGANISM: Artificial
<220> FEATURE:
<223> OTHER INFORMATION: Primer

<400> SEQUENCE: 308
gcgtaatacg actcactata ggcgtaaaaa ctctgaccgg caagac                 46

<210> SEQ ID NO 309
<211> LENGTH: 48
<212> TYPE: DNA
<213> ORGANISM: Artificial
<220> FEATURE:
<223> OTHER INFORMATION: Primer

<400> SEQUENCE: 309
gcgtaatacg actcactata ggtagttcca ccacgaagtc tgagaacc               48

<210> SEQ ID NO 310
<211> LENGTH: 21

```
<212> TYPE: DNA
<213> ORGANISM: Artificial
<220> FEATURE:
<223> OTHER INFORMATION: Primer

<400> SEQUENCE: 310
atggccgacg atgaagctaa g                                      21

<210> SEQ ID NO 311
<211> LENGTH: 20
<212> TYPE: DNA
<213> ORGANISM: Artificial
<220> FEATURE:
<223> OTHER INFORMATION: Primer

<400> SEQUENCE: 311
tggttgtggt tctggttcgg                                        20

<210> SEQ ID NO 312
<211> LENGTH: 43
<212> TYPE: DNA
<213> ORGANISM: Artificial
<220> FEATURE:
<223> OTHER INFORMATION: Primer

<400> SEQUENCE: 312
gcgtaatacg actcactata ggatggccga cgatgaagct aag              43

<210> SEQ ID NO 313
<211> LENGTH: 42
<212> TYPE: DNA
<213> ORGANISM: Artificial
<220> FEATURE:
<223> OTHER INFORMATION: Primer

<400> SEQUENCE: 313
gcgtaatacg actcactata ggtggttctg gttcgggttc aa               42

<210> SEQ ID NO 314
<211> LENGTH: 20
<212> TYPE: DNA
<213> ORGANISM: Artificial
<220> FEATURE:
<223> OTHER INFORMATION: Primer

<400> SEQUENCE: 314
cggtaatgcg atgcggtaag                                        20

<210> SEQ ID NO 315
<211> LENGTH: 20
<212> TYPE: DNA
<213> ORGANISM: Artificial
<220> FEATURE:
<223> OTHER INFORMATION: Primer

<400> SEQUENCE: 315
tcatcttctc gggcgtatgc                                        20

<210> SEQ ID NO 316
<211> LENGTH: 42
<212> TYPE: DNA
<213> ORGANISM: Artificial
<220> FEATURE:
<223> OTHER INFORMATION: Primer

<400> SEQUENCE: 316
```

```
gcgtaatacg actcactata ggcggtaatg cgatgcggta ag                          42
```

<210> SEQ ID NO 317
<211> LENGTH: 42
<212> TYPE: DNA
<213> ORGANISM: Artificial
<220> FEATURE:
<223> OTHER INFORMATION: Primer

<400> SEQUENCE: 317

```
gcgtaatacg actcactata ggtcatcttc tcgggcgtat gc                          42
```

<210> SEQ ID NO 318
<211> LENGTH: 25
<212> TYPE: DNA
<213> ORGANISM: Artificial
<220> FEATURE:
<223> OTHER INFORMATION: Primer

<400> SEQUENCE: 318

```
tttggaagtt gagtcatcag attcc                                             25
```

<210> SEQ ID NO 319
<211> LENGTH: 24
<212> TYPE: DNA
<213> ORGANISM: Artificial
<220> FEATURE:
<223> OTHER INFORMATION: Primer

<400> SEQUENCE: 319

```
gttgtagtcg gaaagggtac gtcc                                              24
```

<210> SEQ ID NO 320
<211> LENGTH: 47
<212> TYPE: DNA
<213> ORGANISM: Artificial
<220> FEATURE:
<223> OTHER INFORMATION: Primer

<400> SEQUENCE: 320

```
gcgtaatacg actcactata ggtttggaag ttgagtcatc agattcc                     47
```

<210> SEQ ID NO 321
<211> LENGTH: 46
<212> TYPE: DNA
<213> ORGANISM: Artificial
<220> FEATURE:
<223> OTHER INFORMATION: Primer

<400> SEQUENCE: 321

```
gcgtaatacg actcactata gggttgtagt cggaaagggt acgtcc                      46
```

<210> SEQ ID NO 322
<211> LENGTH: 23
<212> TYPE: DNA
<213> ORGANISM: Artificial
<220> FEATURE:
<223> OTHER INFORMATION: Primer

<400> SEQUENCE: 322

```
aagacttgct tcatcctact gca                                               23
```

<210> SEQ ID NO 323
<211> LENGTH: 20
<212> TYPE: DNA
<213> ORGANISM: Artificial

```
<220> FEATURE:
<223> OTHER INFORMATION: Primer

<400> SEQUENCE: 323
attgtggaac atccggtaca                                                    20

<210> SEQ ID NO 324
<211> LENGTH: 45
<212> TYPE: DNA
<213> ORGANISM: Artificial
<220> FEATURE:
<223> OTHER INFORMATION: Primer

<400> SEQUENCE: 324
gcgtaatacg actcactata ggaagacttg cttcatccta ctgca                        45

<210> SEQ ID NO 325
<211> LENGTH: 42
<212> TYPE: DNA
<213> ORGANISM: Artificial
<220> FEATURE:
<223> OTHER INFORMATION: Primer

<400> SEQUENCE: 325
gcgtaatacg actcactata ggattgtgga acatccggta ca                           42

<210> SEQ ID NO 326
<211> LENGTH: 424
<212> TYPE: PRT
<213> ORGANISM: Lygus hesperus

<400> SEQUENCE: 326
```

| | | | | | | | | | | | | | | |
|---|---|---|---|---|---|---|---|---|---|---|---|---|---|---|
| Met | Ile | Pro | Pro | Thr | Ser | Arg | Pro | Gln | Val | Thr | Val | Tyr | Ser | Asp | Lys |
| 1 | | | | 5 | | | | | 10 | | | | | 15 | |

Asn Glu Ala Thr Gly Thr Leu Leu Asn Leu Pro Ala Val Phe Asn Ala
              20                  25                  30

Pro Ile Arg Pro Asp Val Val Asn Phe Val His Gln Asn Val Ala Lys
          35                  40                  45

Asn His Arg Gln Pro Tyr Cys Val Ser Ala Gln Ala Gly His Gln Thr
     50                  55                  60

Ser Ala Glu Ser Trp Gly Thr Gly Arg Ala Val Ala Arg Ile Pro Arg
65                  70                  75                  80

Val Arg Gly Gly Gly Thr His Arg Ser Gly Gln Gly Ala Phe Gly Asn
                 85                  90                  95

Met Cys Arg Gly Gly Arg Met Phe Ala Pro Thr Arg Pro Trp Arg Arg
            100                 105                 110

Trp His Arg Lys Ile Asn Val Asn Gln Lys Arg Tyr Ala Val Val Ser
        115                 120                 125

Ala Ile Ala Ala Ser Gly Val Pro Ala Leu Val Met Ser Lys Gly His
    130                 135                 140

Met Val Gln Ser Val Pro Glu Phe Pro Leu Val Val Ser Asp Lys Val
145                 150                 155                 160

Gln Glu Tyr Thr Lys Thr Lys Gln Ala Val Ile Phe Leu His Arg Ile
                165                 170                 175

Lys Ala Trp Gln Asp Ile Gln Lys Val Tyr Lys Ser Lys Arg Phe Arg
            180                 185                 190

Ala Gly Lys Gly Lys Met Arg Asn Arg Arg Ile Gln Arg Arg Gly
        195                 200                 205

Pro Leu Ile Ile Tyr Asp Gln Asp Gln Gly Leu Asn Arg Ala Phe Arg

```
                210                 215                 220
Asn Ile Pro Gly Val Asp Leu Ile Glu Val Ser Arg Leu Asn Leu Leu
225                 230                 235                 240

Lys Leu Ala Pro Gly Gly His Ile Gly Arg Phe Val Ile Trp Thr Gln
                245                 250                 255

Ser Ala Phe Glu Lys Leu Asp Ala Leu Tyr Gly Thr Trp Lys Lys Lys
            260                 265                 270

Ser Thr Leu Lys Ala Gly Tyr Asn Leu Pro Met Pro Lys Met Ala Asn
        275                 280                 285

Thr Asp Leu Ser Arg Leu Phe Lys Ala Pro Glu Ile Lys Ala Val Leu
    290                 295                 300

Arg Asn Pro Lys Lys Thr Ile Val Arg Arg Val Arg Lys Leu Asn Pro
305                 310                 315                 320

Leu Arg Asn Thr Arg Ala Met Leu Arg Leu Asn Pro Tyr Ala Ala Val
                325                 330                 335

Leu Lys Arg Lys Ala Ile Leu Asp Gln Arg Lys Leu Lys Leu Gln Lys
            340                 345                 350

Leu Val Glu Ala Ala Lys Lys Gly Asp Thr Lys Leu Ser Pro Arg Val
        355                 360                 365

Glu Arg His Leu Lys Met Ile Glu Arg Arg Lys Ala Leu Ile Lys Lys
    370                 375                 380

Ala Lys Ala Ala Lys Pro Lys Pro Lys Thr Ala Lys Lys Pro Lys
385                 390                 395                 400

Thr Ala Glu Lys Ala Pro Ala Pro Ala Lys Lys Ala Ala Ala Pro Lys
                405                 410                 415

Lys Ala Thr Thr Pro Ala Lys Lys
            420

<210> SEQ ID NO 327
<211> LENGTH: 242
<212> TYPE: PRT
<213> ORGANISM: Lygus hesperus

<400> SEQUENCE: 327

Met Ala Asn Ala Lys Pro Ile Ser Lys Lys Lys Phe Val Ser Asp
1               5                   10                  15

Gly Val Phe Lys Ala Glu Leu Asn Glu Phe Leu Thr Arg Glu Leu Ala
                20                  25                  30

Glu Glu Gly Tyr Ser Gly Val Glu Val Arg Val Thr Pro Asn Lys Thr
            35                  40                  45

Glu Ile Ile Ile Met Ala Thr Arg Thr Gln Ser Val Leu Gly Asp Lys
        50                  55                  60

Gly Arg Arg Ile Arg Glu Leu Thr Ser Val Val Gln Lys Arg Phe Asn
65                  70                  75                  80

Phe Lys Pro Gln Thr Leu Asp Leu Tyr Ala Glu Lys Val Ala Thr Arg
                85                  90                  95

Gly Leu Cys Ala Ile Ala Gln Ala Glu Ser Leu Arg Tyr Lys Leu Ile
            100                 105                 110

Gly Gly Leu Ala Val Arg Gly Ala Cys Tyr Gly Val Leu Arg Phe Ile
        115                 120                 125

Met Glu Asn Gly Ala Lys Gly Cys Glu Val Val Val Ser Gly Lys Leu
    130                 135                 140

Arg Gly Gln Arg Ala Lys Ser Met Lys Phe Val Asp Gly Leu Met Ile
145                 150                 155                 160
```

-continued

His Ser Gly Asp Pro Cys Asn Glu Tyr Val Asp Thr Ala Thr Arg His
            165                 170                 175

Val Leu Leu Arg Gln Gly Val Leu Gly Ile Lys Val Lys Ile Met Leu
            180                 185                 190

Pro Trp Asp Val Thr Gly Lys Asn Gly Pro Lys Asn Pro Leu Pro Asp
        195                 200                 205

His Val Ser Val Leu Leu Pro Lys Glu Glu Leu Pro Asn Leu Ala Val
210                 215                 220

Ser Val Pro Gly Ser Asp Ile Lys Pro Lys Pro Glu Val Pro Ala Pro
225                 230                 235                 240

Ala Leu

<210> SEQ ID NO 328
<211> LENGTH: 262
<212> TYPE: PRT
<213> ORGANISM: Lygus hesperus

<400> SEQUENCE: 328

Met Ala Val Gly Lys Asn Lys Gly Leu Ser Lys Gly Gly Lys Lys Gly
1               5                   10                  15

Val Lys Lys Lys Val Val Asp Pro Phe Thr Arg Lys Asp Trp Tyr Asp
            20                  25                  30

Val Lys Ala Pro Ser Met Phe Lys Lys Arg Gln Val Gly Lys Thr Leu
        35                  40                  45

Val Asn Arg Thr Gln Gly Thr Lys Ile Ala Ser Glu Gly Leu Lys Gly
    50                  55                  60

Arg Val Phe Glu Val Ser Leu Ala Asp Ile Gln Glu Asp Thr Asp Ala
65                  70                  75                  80

Glu Arg Ser Phe Arg Lys Phe Arg Leu Ile Ala Glu Asp Val Gln Ala
                85                  90                  95

Arg Asn Val Leu Thr Asn Phe His Gly Met Asp Leu Thr Thr Asp Lys
            100                 105                 110

Leu Arg Ser Met Val Lys Lys Trp Gln Thr Leu Ile Glu Ala Asn Val
        115                 120                 125

Asp Val Lys Thr Thr Asp Gly Tyr Leu Leu Arg Val Phe Cys Ile Gly
    130                 135                 140

Phe Thr Asn Lys Asp Gln Leu Ser Gln Arg Lys Thr Cys Tyr Ala Gln
145                 150                 155                 160

His Asn Gln Val Arg Glu Ile Arg Lys Lys Met Val Lys Asn Ile Ser
                165                 170                 175

Asp Ser Ile Ser Ser Cys Asp Leu Arg Ser Val Val Asn Lys Leu Ile
            180                 185                 190

Pro Asp Ser Ile Ala Lys Asp Ile Glu Lys Asn Cys Gln Gly Ile Tyr
        195                 200                 205

Pro Leu His Asp Val Tyr Ile Arg Lys Val Lys Val Leu Lys Lys Pro
    210                 215                 220

Arg Phe Glu Leu Ser Lys Leu Leu Glu Leu His Val Asp Gly Lys Gly
225                 230                 235                 240

Ile Asp Glu Pro Gly Ala Lys Val Thr Arg Thr Asp Ala Tyr Glu Pro
                245                 250                 255

Pro Val Gln Glu Ser Val
            260

<210> SEQ ID NO 329
<211> LENGTH: 152

<212> TYPE: PRT
<213> ORGANISM: Lygus hesperus

<400> SEQUENCE: 329

Met Ser Leu Met Leu Pro Glu Lys Phe Gln His Ile Leu Arg Ile Met
1               5                   10                  15

Gly Thr Asn Ile Asp Gly Lys Arg Lys Val Met Phe Ala Met Thr Ala
            20                  25                  30

Ile Lys Gly Val Gly Arg Arg Tyr Ala Asn Ile Val Leu Lys Lys Ala
        35                  40                  45

Asp Val Asn Leu Asp Lys Arg Ala Gly Glu Cys Ser Glu Glu Glu Val
    50                  55                  60

Glu Lys Ile Val Thr Ile Met Gln Asn Pro Arg Gln Tyr Lys Ile Pro
65                  70                  75                  80

Asn Trp Phe Leu Asn Arg Gln Lys Asp Thr Val Glu Gly Lys Tyr Ser
                85                  90                  95

Gln Leu Thr Ser Ser Leu Leu Asp Ser Lys Leu Arg Asp Asp Leu Glu
            100                 105                 110

Arg Leu Lys Lys Ile Arg Ala His Arg Gly Met Arg His Tyr Trp Gly
        115                 120                 125

Leu Arg Val Arg Gly Gln His Thr Lys Thr Thr Gly Arg Arg Gly Arg
    130                 135                 140

Thr Val Gly Val Ser Lys Lys Lys
145                 150

<210> SEQ ID NO 330
<211> LENGTH: 381
<212> TYPE: PRT
<213> ORGANISM: Lygus hesperus

<400> SEQUENCE: 330

Met Ser Asp Glu Glu Tyr Ser Glu Ser Glu Glu Thr Gln Pro Glu
1               5                   10                  15

Pro Gln Lys Lys Pro Glu Ala Glu Gly Gly Asp Pro Glu Phe Val
            20                  25                  30

Lys Arg Lys Glu Ala Gln Thr Ser Ala Leu Asp Glu Gln Leu Lys Asp
        35                  40                  45

Tyr Ile Ala Glu Trp Arg Lys Gln Arg Ala Arg Glu Glu Asp Leu
    50                  55                  60

Lys Lys Leu Lys Glu Lys Gln Ala Lys Arg Lys Val Ala Arg Ala Glu
65                  70                  75                  80

Glu Glu Lys Arg Leu Ala Glu Lys Lys Gln Glu Glu Glu Arg Arg
                85                  90                  95

Val Arg Glu Ala Glu Glu Lys Lys Gln Arg Glu Ile Glu Glu Lys Arg
            100                 105                 110

Arg Arg Leu Glu Glu Ala Glu Lys Arg Gln Ala Met Met Ala Ala
        115                 120                 125

Leu Lys Asp Gln Ser Lys Thr Lys Gly Pro Asn Phe Val Val Asn Lys
    130                 135                 140

Lys Ala Glu Thr Leu Gly Met Ser Ser Ala Gln Ile Glu Arg Asn Lys
145                 150                 155                 160

Thr Lys Glu Gln Leu Glu Glu Lys Arg Ile Ser Leu Ser Ile Arg
                165                 170                 175

Leu Lys Pro Leu Ala Ile Glu Asn Met Ser Ile Asp Arg Leu Arg Ile
            180                 185                 190

```
Lys Ala Gln Glu Leu Trp Glu Ala Ile Val Lys Leu Glu Thr Glu Lys
            195                 200                 205
Tyr Asp Leu Glu Glu Arg Gln Lys Arg Gln Asp Tyr Asp Leu Lys Glu
        210                 215                 220
Leu Lys Glu Arg Gln Lys Gln Gln Leu Arg His Lys Ala Leu Lys Lys
225                 230                 235                 240
Gly Leu Asp Pro Glu Ala Leu Thr Gly Lys Tyr Pro Pro Lys Ile Gln
                245                 250                 255
Val Ala Ser Lys Tyr Glu Arg Arg Val Asp Thr Arg Ser Tyr Asp Asp
            260                 265                 270
Lys Lys Lys Leu Phe Glu Gly Gly Ile Leu Glu Arg Tyr Lys Glu Leu
        275                 280                 285
Ile Glu Lys Val Trp Thr Glu Lys Val Asp Gln Phe Gly Ser Arg Ala
    290                 295                 300
His Ser Lys Leu Pro Arg Trp Phe Gly Glu Arg Pro Gly Lys Lys Lys
305                 310                 315                 320
Asp Ala Pro Glu Ser Pro Glu Glu Glu Val Lys Val Glu Asp Glu
                325                 330                 335
Pro Glu Ala Glu Pro Ser Phe Met Leu Asp Glu Glu Glu Glu Ala
            340                 345                 350
Glu Glu Glu Glu Ala Glu Glu Glu Glu Ala Glu Glu Glu Glu
        355                 360                 365
Glu Glu Glu Glu Glu Glu Glu Glu Glu Glu
    370                 375                 380

<210> SEQ ID NO 331
<211> LENGTH: 1689
<212> TYPE: PRT
<213> ORGANISM: Lygus hesperus

<400> SEQUENCE: 331

Ser Gly Lys Leu Ala Gly Ala Asp Ile Glu Thr Tyr Leu Leu Glu Lys
1               5                   10                  15
Ala Arg Val Ile Ser Gln Gln Thr Leu Glu Arg Ser Tyr His Ile Phe
            20                  25                  30
Tyr Gln Met Met Ser Gly Ala Val Lys Gly Val Lys Glu Met Cys Leu
        35                  40                  45
Leu Val Asp Asp Ile Tyr Thr Tyr Asn Phe Ile Ser Gln Gly Lys Val
    50                  55                  60
Ser Ile Ala Gly Val Asp Asp Gly Glu Met Val Leu Thr Asp Gln
65                  70                  75                  80
Ala Phe Asp Ile Leu Gly Phe Thr Lys Gln Glu Lys Glu Asp Ile Tyr
                85                  90                  95
Lys Ile Thr Ala Ala Val Ile His Met Gly Thr Met Lys Phe Lys Gln
            100                 105                 110
Arg Gly Arg Glu Glu Gln Ala Glu Ala Asp Gly Thr Glu Glu Gly Gly
        115                 120                 125
Lys Val Gly Val Leu Leu Gly Ile Asp Gly Asp Leu Tyr Lys Asn
    130                 135                 140
Met Cys Lys Pro Arg Ile Lys Val Gly Thr Glu Phe Val Thr Gln Gly
145                 150                 155                 160
Lys Asn Val Asn Gln Val Ser Tyr Ser Leu Gly Ala Met Ser Lys Gly
                165                 170                 175
Met Phe Asp Arg Leu Phe Lys Phe Leu Val Lys Lys Cys Asn Glu Thr
            180                 185                 190
```

```
Leu Asp Thr Lys Gln Lys Arg Gln His Phe Ile Gly Val Leu Asp Ile
            195                 200                 205

Ala Gly Phe Glu Ile Phe Asp Phe Asn Gly Phe Glu Gln Leu Cys Ile
            210                 215                 220

Asn Phe Thr Asn Glu Lys Leu Gln Gln Phe Phe Asn His His Met Phe
225                 230                 235                 240

Val Leu Glu Gln Glu Glu Tyr Lys Arg Glu Gly Ile Asn Trp Ala Phe
                245                 250                 255

Ile Asp Phe Gly Met Asp Leu Leu Ala Cys Ile Glu Leu Ile Glu Lys
                260                 265                 270

Pro Met Gly Ile Leu Ser Ile Leu Glu Glu Ser Met Phe Pro Lys
            275                 280                 285

Ala Thr Asp Lys Thr Phe Glu Asp Lys Leu Ile Thr Asn His Leu Gly
            290                 295                 300

Lys Ser Pro Asn Phe Arg Lys Pro Ala Val Pro Lys Pro Gly Gln Gln
305                 310                 315                 320

Ala Gly His Phe Ala Ile Ala His Tyr Ala Gly Cys Val Ser Tyr Asn
                325                 330                 335

Ile Thr Gly Trp Leu Glu Lys Asn Lys Asp Pro Leu Asn Asp Thr Val
            340                 345                 350

Val Asp Gln Tyr Lys Lys Gly Thr Asn Lys Leu Leu Cys Glu Ile Phe
            355                 360                 365

Ala Asp His Pro Gly Gln Ser Gly Ala Pro Gly Gly Asp Ala Gly Gly
            370                 375                 380

Lys Gly Gly Arg Gly Lys Lys Gly Gly Gly Phe Ala Thr Val Ser Ser
385                 390                 395                 400

Ser Tyr Lys Glu Gln Leu Asn Asn Leu Met Thr Thr Leu Lys Ser Thr
                405                 410                 415

Gln Pro His Phe Val Arg Cys Ile Ile Pro Asn Glu Leu Lys Gln Pro
            420                 425                 430

Gly Val Ile Asp Ser His Leu Val Met His Gln Leu Thr Cys Asn Gly
            435                 440                 445

Val Leu Glu Gly Ile Arg Ile Cys Arg Lys Gly Phe Pro Asn Arg Met
            450                 455                 460

Asn Tyr Pro Asp Phe Lys Leu Arg Tyr Lys Ile Leu Asn Pro Ala Ala
465                 470                 475                 480

Val Asp Arg Glu Ser Asp Ile Leu Lys Ala Ala Gly Leu Val Leu Glu
                485                 490                 495

Ser Thr Gly Leu Asp Pro Asp Met Tyr Arg Leu Gly His Thr Lys Val
            500                 505                 510

Phe Phe Arg Ala Gly Val Leu Gly Gln Leu Glu Glu Leu Arg Asp Asp
            515                 520                 525

Arg Leu Ser Lys Ile Ile Gly Trp Met Gln Ala Phe Met Arg Gly Tyr
530                 535                 540

Leu Val Arg Lys Glu Tyr Lys Lys Leu Gln Glu Gln Arg Leu Ala Leu
545                 550                 555                 560

Gln Val Val Gln Arg Asn Leu Arg Arg Tyr Leu Gln Leu Arg Thr Trp
                565                 570                 575

Pro Trp Trp Lys Met Trp Ser Arg Val Lys Pro Leu Leu Asn Val Ala
            580                 585                 590

Asn Val Glu Glu Glu Met Arg Lys Leu Glu Glu Leu Val Ala Glu Thr
            595                 600                 605
```

```
Gln Ala Ala Leu Glu Lys Glu Lys Leu Arg Lys Glu Ala Glu Ala
610             615             620

Leu Asn Ala Lys Leu Leu Gln Glu Lys Thr Asp Leu Leu Arg Asn Leu
625                 630             635                 640

Glu Gly Glu Lys Gly Ser Ile Ser Gly Ile Gln Glu Arg Cys Ala Lys
                645             650                 655

Leu Gln Ala Gln Lys Ala Asp Leu Glu Ser Gln Leu Met Asp Thr Gln
            660             665             670

Glu Arg Leu Gln Asn Glu Asp Ala Arg Asn Gln Leu Phe Gln Gln
        675             680             685

Lys Lys Lys Leu Glu Gln Glu Ala Ala Ala Leu Lys Lys Asp Ile Glu
690             695             700

Asp Leu Glu Leu Ser Asn Gln Lys Thr Asp Gln Asp Lys Ala Ser Lys
705             710             715             720

Glu His Gln Ile Arg Asn Leu Asn Asp Glu Ile Ala His Gln Asp Asp
                725             730             735

Leu Ile Asn Lys Leu Asn Lys Glu Lys Lys Ile Gln Ser Glu Leu Asn
            740             745             750

Gln Lys Thr Ala Glu Glu Leu Gln Ala Ala Glu Asp Lys Ile Asn His
        755             760             765

Leu Thr Lys Val Lys Val Lys Leu Glu Gln Thr Leu Asp Glu Leu Glu
770             775             780

Asp Thr Leu Glu Arg Glu Lys Lys Leu Arg Gly Asp Val Glu Lys Ala
785             790             795             800

Lys Arg Lys Thr Glu Gly Asp Leu Lys Leu Thr Gln Glu Ala Val Ala
                805             810             815

Asp Leu Glu Arg Asn Lys Lys Glu Leu Glu Gln Thr Ile Gln Arg Lys
            820             825             830

Asp Lys Glu Ile Ala Ser Leu Thr Ala Lys Leu Glu Asp Glu Gln Ser
        835             840             845

Ile Val Asn Lys Thr Gly Lys Gln Ile Lys Glu Leu Gln Ser Arg Ile
850             855             860

Glu Glu Leu Glu Glu Glu Val Glu Ala Glu Arg Gln Ala Arg Gly Lys
865             870             875             880

Ala Glu Lys Gln Arg Ala Asp Leu Ala Arg Glu Leu Glu Glu Leu Gly
                885             890             895

Glu Arg Leu Glu Glu Ala Gly Gly Ala Thr Ser Ala Gln Ile Glu Leu
            900             905             910

Asn Lys Lys Arg Glu Ala Glu Met Ser Lys Leu Arg Arg Asp Leu Glu
        915             920             925

Glu Ala Asn Ile Gln His Glu Gly Thr Leu Ala Asn Leu Arg Lys Lys
930             935             940

His Asn Asp Ala Val Ser Glu Met Gly Asp Gln Ile Asp Gln Leu Asn
945             950             955             960

Lys Leu Lys Thr Lys Val Glu Lys Glu Lys Ser Gln Tyr Leu Gly Glu
                965             970             975

Leu Asn Asp Val Arg Ala Ser Ile Asp His Leu Thr Asn Glu Lys Ala
            980             985             990

Ala Thr Glu Lys Val Ala Lys Gln Leu Gln His Gln Ile Asn Glu Val
        995             1000            1005

Gln Gly Lys Leu Asp Glu Ala Asn Arg Thr Leu Asn Asp Phe Asp
        1010            1015            1020

Ala Ala Lys Lys Lys Leu Ser Ile Glu Asn Ser Asp Leu Leu Arg
```

-continued

```
            1025                1030                1035

Gln Leu Glu Glu Ala Glu Ser Gln Val Ser Gln Leu Ser Lys Ile
            1040                1045                1050

Lys Ile Ser Leu Thr Thr Gln Leu Glu Asp Thr Lys Arg Leu Ala
            1055                1060                1065

Asp Glu Glu Ala Arg Glu Arg Ala Thr Leu Leu Gly Lys Phe Arg
            1070                1075                1080

Asn Leu Glu His Asp Leu Asp Asn Leu Arg Glu Gln Val Glu Glu
            1085                1090                1095

Glu Ala Glu Ala Lys Ala Asp Ile Gln Arg Gln Leu Ser Lys Ala
            1100                1105                1110

Asn Ala Glu Ala Gln Leu Trp Arg Ser Lys Tyr Glu Ser Glu Gly
            1115                1120                1125

Val Ala Arg Ala Glu Glu Leu Glu Glu Ala Lys Arg Lys Leu Gln
            1130                1135                1140

Ala Arg Leu Ala Glu Ala Glu Glu Thr Ile Glu Ser Leu Asn Gln
            1145                1150                1155

Lys Val Ile Ala Leu Glu Lys Thr Lys Gln Arg Leu Ala Thr Glu
            1160                1165                1170

Val Glu Asp Leu Gln Leu Glu Val Asp Arg Ala Asn Ala Ile Ala
            1175                1180                1185

Asn Ala Ala Glu Lys Lys Ala Lys Ala Ile Asp Lys Ile Ile Gly
            1190                1195                1200

Glu Trp Lys Leu Lys Val Asp Asp Leu Ala Ala Glu Leu Asp Ala
            1205                1210                1215

Ser Gln Lys Glu Cys Arg Asn Tyr Ser Thr Glu Leu Phe Arg Leu
            1220                1225                1230

Lys Gly Ala Tyr Glu Glu Gly Gln Glu Gln Leu Glu Ala Val Arg
            1235                1240                1245

Arg Glu Asn Lys Asn Leu Ala Asp Glu Val Lys Asp Leu Leu Asp
            1250                1255                1260

Gln Ile Gly Glu Gly Gly Arg Asn Ile His Glu Ile Glu Lys Gln
            1265                1270                1275

Arg Lys Arg Leu Glu Val Glu Lys Asp Glu Leu Gln Ala Ala Leu
            1280                1285                1290

Glu Glu Ala Glu Ala Ala Leu Glu Gln Glu Glu Asn Lys Val Leu
            1295                1300                1305

Arg Ala Gln Leu Glu Leu Ser Gln Val Arg Gln Glu Ile Asp Arg
            1310                1315                1320

Arg Ile Gln Glu Lys Glu Glu Phe Glu Asn Thr Arg Lys Asn
            1325                1330                1335

His Gln Arg Ala Leu Asp Ser Met Gln Ala Ser Leu Glu Ala Glu
            1340                1345                1350

Ala Lys Gly Lys Ala Glu Ala Leu Arg Met Lys Lys Lys Leu Glu
            1355                1360                1365

Ala Asp Ile Asn Glu Leu Glu Ile Ala Leu Asp His Ala Asn Lys
            1370                1375                1380

Ala Asn Ala Glu Ala Gln Lys Thr Ile Lys Lys Tyr Gln Gln Gln
            1385                1390                1395

Leu Lys Asp Val Gln Thr Ala Leu Glu Glu Glu Gln Arg Ala Arg
            1400                1405                1410

Asp Asp Ala Arg Glu Gln Leu Gly Ile Ala Glu Arg Arg Ala Asn
            1415                1420                1425
```

Ala Leu Gly Asn Glu Leu Glu Glu Ser Arg Thr Leu Leu Glu Gln
    1430                1435                1440

Ala Asp Arg Gly Arg Arg Gln Ala Glu Gln Glu Leu Gly Asp Ala
    1445                1450                1455

His Glu Gln Ile Asn Glu Leu Ala Ala Gln Ala Thr Ser Ala Ser
    1460                1465                1470

Ala Ala Lys Arg Lys Leu Glu Gly Glu Leu Gln Thr Leu His Ala
    1475                1480                1485

Asp Leu Asp Glu Leu Leu Asn Glu Ala Lys Asn Ser Glu Glu Lys
    1490                1495                1500

Ala Lys Lys Ala Met Val Asp Ala Ala Arg Leu Ala Asp Glu Leu
    1505                1510                1515

Arg Ala Glu Gln Asp His Ala Gln Thr Gln Glu Lys Leu Arg Lys
    1520                1525                1530

Ala Leu Glu Thr Gln Ile Lys Glu Leu Gln Val Arg Leu Asp Glu
    1535                1540                1545

Ala Glu Asn Asn Ala Leu Lys Gly Gly Lys Lys Ala Ile Ala Lys
    1550                1555                1560

Leu Glu Gln Arg Val Arg Glu Leu Glu Asn Glu Leu Asp Gly Glu
    1565                1570                1575

Gln Arg Arg His Ala Asp Ala Gln Lys Asn Leu Arg Lys Ser Glu
    1580                1585                1590

Arg Arg Ile Lys Glu Leu Ser Phe Gln Ser Asp Glu Asp Arg Lys
    1595                1600                1605

Asn His Glu Arg Met Gln Asp Leu Val Asp Lys Leu Gln Gln Lys
    1610                1615                1620

Ile Lys Thr Tyr Lys Arg Gln Ile Glu Glu Ala Glu Glu Ile Ala
    1625                1630                1635

Ala Leu Asn Leu Ala Lys Phe Arg Lys Ala Gln Gln Glu Leu Glu
    1640                1645                1650

Glu Ala Glu Glu Arg Ala Asp Leu Ala Glu Gln Ala Val Ser Lys
    1655                1660                1665

Phe Arg Thr Lys Gly Gly Arg Ala Gly Ser Ala Ala Arg Ala Met
    1670                1675                1680

Ser Pro Val Gly Gln Lys
    1685

<210> SEQ ID NO 332
<211> LENGTH: 256
<212> TYPE: PRT
<213> ORGANISM: Lygus hesperus

<400> SEQUENCE: 332

Asp Ala Ile Lys Lys Lys Met Gln Ala Met Lys Met Glu Lys Asp Thr
1               5                   10                  15

Ala Met Asp Lys Ala Asp Thr Cys Glu Gly Gln Ala Lys Asp Ala Asn
            20                  25                  30

Thr Arg Ala Asp Lys Ile Leu Glu Asp Val Arg Asp Leu Gln Lys Lys
        35                  40                  45

Leu Asn Gln Val Glu Ser Asp Leu Glu Arg Thr Lys Arg Glu Leu Glu
    50                  55                  60

Thr Lys Thr Thr Glu Leu Glu Glu Lys Glu Lys Ala Asn Thr Asn Ala
65                  70                  75                  80

Glu Ser Glu Val Ala Ser Leu Asn Arg Lys Val Gln Met Val Glu Glu

```
                85                  90                  95
Asp Leu Glu Arg Ser Glu Arg Ser Gly Thr Ala Gln Gln Lys Leu
            100                 105                 110
Ser Glu Ala Ser His Ala Ala Asp Glu Ala Ser Arg Met Cys Lys Val
            115                 120                 125
Leu Glu Asn Arg Ser Gln Gln Asp Glu Glu Arg Met Asp Gln Leu Thr
        130                 135                 140
Asn Gln Leu Lys Glu Ala Arg Leu Leu Ala Glu Asp Ala Asp Gly Lys
145                 150                 155                 160
Ser Asp Glu Val Ser Arg Lys Leu Ala Phe Val Glu Asp Glu Leu Glu
                165                 170                 175
Val Ala Glu Asp Arg Val Lys Ser Gly Asp Ser Lys Ile Met Glu Leu
            180                 185                 190
Glu Glu Glu Leu Lys Val Val Gly Asn Ser Leu Lys Ser Leu Glu Val
            195                 200                 205
Ser Glu Glu Lys Ala Asn Gln Arg Val Glu Glu Tyr Lys Arg Gln Ile
        210                 215                 220
Lys Gln Leu Thr Val Lys Leu Lys Glu Ala Glu Ala Arg Ala Glu Phe
225                 230                 235                 240
Ala Glu Lys Thr Val Lys Lys Leu Gln Lys Glu Val Asp Arg Leu Glu
                245                 250                 255

<210> SEQ ID NO 333
<211> LENGTH: 85
<212> TYPE: PRT
<213> ORGANISM: Lygus hesperus

<400> SEQUENCE: 333

Arg Ala Leu Gly Gln Asn Pro Thr Glu Ser Asp Val Lys Lys Phe Thr
1               5                   10                  15
His Gln His Lys Pro Asp Glu Arg Ile Ser Phe Glu Val Phe Leu Pro
                20                  25                  30
Ile Tyr Gln Ala Ile Ser Lys Gly Arg Thr Ser Asp Thr Ala Glu Asp
            35                  40                  45
Phe Ile Glu Gly Leu Arg His Phe Asp Lys Asp Gly Asn Gly Phe Ile
        50                  55                  60
Ser Thr Ala Glu Leu Arg His Leu Leu Thr Thr Leu Gly Glu Lys Leu
65                  70                  75                  80
Thr Asp Asp Glu Val
                85

<210> SEQ ID NO 334
<211> LENGTH: 174
<212> TYPE: PRT
<213> ORGANISM: Lygus hesperus

<400> SEQUENCE: 334

Met Ser Ser Arg Lys Thr Ala Gly Arg Ala Thr Thr Lys Lys Arg
1               5                   10                  15
Ala Gln Arg Ala Thr Ser Asn Val Phe Ala Met Phe Asp Gln Ala Gln
                20                  25                  30
Ile Gln Glu Phe Lys Glu Ala Phe Asn Met Ile Asp Gln Asn Arg Asp
            35                  40                  45
Gly Phe Val Asp Lys Glu Asp Leu His Asp Met Leu Ala Ser Leu Gly
        50                  55                  60
Lys Asn Pro Ser Asp Glu Tyr Leu Glu Gly Met Met Asn Glu Ala Pro
```

```
            65                  70                  75                  80
Gly Pro Ile Asn Phe Thr Met Phe Leu Thr Leu Phe Gly Glu Arg Leu
                85                  90                  95

Gln Gly Thr Asp Pro Glu Val Ile Lys Asn Ala Phe Gly Cys Phe
            100                 105                 110

Asp Glu Asp Asn Asn Gly Phe Ile Asn Glu Glu Arg Leu Arg Glu Leu
            115                 120                 125

Leu Thr Ser Met Gly Asp Arg Phe Thr Asp Glu Asp Val Asp Glu Met
            130                 135                 140

Tyr Arg Glu Ala Pro Ile Lys Asn Gly Met Phe Asp Tyr Ile Glu Phe
145                 150                 155                 160

Thr Arg Ile Leu Lys His Gly Ala Lys Asp Lys Asp Glu Gln
                165                 170

<210> SEQ ID NO 335
<211> LENGTH: 1881
<212> TYPE: PRT
<213> ORGANISM: Lygus hesperus

<400> SEQUENCE: 335

Asp Leu Thr Cys Leu Asn Glu Ala Ser Val Leu His Asn Ile Lys Asp
1               5                   10                  15

Arg Tyr Tyr Ser Gly Leu Ile Tyr Thr Tyr Ser Gly Leu Phe Cys Val
                20                  25                  30

Val Val Asn Pro Tyr Lys Lys Leu Pro Ile Tyr Thr Glu Arg Ile Met
            35                  40                  45

Glu Lys Tyr Lys Gly Val Lys Arg His Asp Leu Pro Pro His Val Phe
50                  55                  60

Ala Ile Thr Asp Thr Ala Tyr Arg Ser Met Leu Gln Asp Arg Glu Asp
65                  70                  75                  80

Gln Ser Ile Leu Cys Thr Gly Glu Ser Gly Ala Gly Lys Thr Glu Asn
                85                  90                  95

Thr Lys Lys Val Ile Gln Tyr Leu Ala Tyr Val Ala Ala Ser Lys Pro
            100                 105                 110

Lys Ser Ser Ala Ser Pro His Thr Ala Gln Ser Gln Ala Leu Ile Ile
            115                 120                 125

Gly Glu Leu Glu Gln Gln Leu Leu Gln Ala Asn Pro Ile Leu Glu Ala
            130                 135                 140

Phe Gly Asn Ala Lys Thr Val Lys Asn Asp Asn Ser Ser Arg Phe Gly
145                 150                 155                 160

Lys Phe Ile Arg Ile Asn Phe Asp Ala Ser Gly Tyr Ile Ala Gly Ala
                165                 170                 175

Asn Ile Glu Thr Tyr Leu Leu Glu Lys Ser Arg Ala Ile Arg Gln Ala
            180                 185                 190

Lys Asp Glu Arg Thr Phe His Ile Phe Tyr Gln Leu Leu Ala Gly Ala
            195                 200                 205

Ser Ala Glu Gln Arg Lys Glu Phe Ile Leu Glu Asp Pro Lys Asn Tyr
            210                 215                 220

Pro Phe Leu Ser Ser Gly Met Val Ser Val Pro Gly Val Asp Asp Gly
225                 230                 235                 240

Val Asp Phe Gln Ala Thr Ile Ala Ser Met Ser Ile Met Gly Met Thr
                245                 250                 255

Asn Asp Asp Leu Ser Ala Leu Phe Arg Ile Val Ser Ala Val Met Leu
            260                 265                 270
```

```
Phe Gly Ser Met Gln Phe Lys Gln Glu Arg Asn Ser Asp Gln Ala Thr
            275                 280                 285
Leu Pro Asp Asn Thr Val Ala Gln Lys Ile Ala His Leu Leu Gly Leu
        290                 295                 300
Ser Ile Thr Glu Met Thr Lys Ala Phe Leu Arg Pro Arg Ile Lys Val
305                 310                 315                 320
Gly Arg Asp Phe Val Thr Lys Ala Gln Thr Lys Glu Gln Val Glu Phe
                325                 330                 335
Ala Val Glu Ala Ile Ser Lys Ala Cys Tyr Glu Arg Met Phe Arg Trp
            340                 345                 350
Leu Val Asn Arg Ile Asn Arg Ser Leu Asp Arg Thr Lys Arg Gln Gly
        355                 360                 365
Ala Ser Phe Ile Gly Ile Leu Asp Met Ala Gly Phe Glu Ile Phe Glu
    370                 375                 380
Ile Asn Ser Phe Glu Gln Leu Cys Ile Asn Tyr Thr Asn Glu Lys Leu
385                 390                 395                 400
Gln Gln Leu Phe Asn His Thr Met Phe Ile Leu Glu Gln Glu Glu Tyr
                405                 410                 415
Gln Arg Glu Gly Ile Glu Trp Lys Phe Ile Asp Phe Gly Leu Asp Leu
            420                 425                 430
Gln Pro Thr Ile Asp Leu Ile Asp Lys Pro Met Gly Val Met Ala Leu
        435                 440                 445
Leu Asp Glu Glu Cys Trp Phe Pro Lys Ala Thr Asp Lys Thr Phe Val
    450                 455                 460
Glu Lys Leu Val Gly Ala His Ser Val His Pro Lys Phe Ile Lys Thr
465                 470                 475                 480
Asp Phe Arg Gly Val Ala Asp Phe Ala Val Val His Tyr Ala Gly Lys
                485                 490                 495
Val Asp Tyr Ser Ala Ala Gln Trp Leu Met Lys Asn Met Asp Pro Leu
            500                 505                 510
Asn Glu Asn Val Val Gln Leu Leu Gln Asn Ser Gln Asp Pro Phe Val
        515                 520                 525
Ile His Ile Trp Lys Asp Ala Glu Ile Val Gly Met Ala His Gln Ala
    530                 535                 540
Leu Ser Asp Thr Gln Phe Gly Ala Arg Thr Arg Lys Gly Met Phe Arg
545                 550                 555                 560
Thr Val Ser Gln Leu Tyr Lys Asp Gln Leu Ser Lys Leu Met Ile Thr
                565                 570                 575
Leu Arg Asn Thr Asn Pro Asn Phe Val Arg Cys Ile Leu Pro Asn His
            580                 585                 590
Glu Lys Arg Ala Gly Lys Ile Asp Ala Pro Leu Val Leu Asp Gln Leu
        595                 600                 605
Arg Cys Asn Gly Val Leu Glu Gly Ile Arg Ile Cys Arg Gln Gly Phe
    610                 615                 620
Pro Asn Arg Ile Pro Phe Gln Glu Phe Arg Gln Arg Tyr Glu Leu Leu
625                 630                 635                 640
Thr Pro Asn Val Ile Pro Lys Gly Phe Met Asp Gly Lys Lys Ala Cys
                645                 650                 655
Glu Lys Met Ile Asn Ala Leu Glu Leu Asp Pro Asn Leu Tyr Arg Val
            660                 665                 670
Gly Gln Ser Lys Ile Phe Phe Arg Ala Gly Val Leu Ala His Leu Glu
        675                 680                 685
Glu Glu Arg Asp Tyr Lys Ile Thr Asp Leu Ile Ala Asn Phe Arg Ala
```

```
            690                 695                 700
Phe Cys Arg Gly Tyr Leu Ala Arg Arg Asn Tyr Gln Lys Arg Leu Gln
705                 710                 715                 720

Gln Leu Asn Ala Ile Arg Ile Ile Gln Arg Asn Cys Ser Ala Tyr Leu
            725                 730                 735

Lys Leu Arg Asn Trp Gln Trp Trp Arg Leu Tyr Thr Lys Val Lys Pro
                740                 745                 750

Leu Leu Glu Val Thr Lys Gln Glu Gly Lys Leu Thr Gln Lys Glu Asp
            755                 760                 765

Glu Leu Lys Gln Val Arg Glu Lys Leu Asp Asn Gln Val Arg Ser Lys
770                 775                 780

Glu Glu Tyr Glu Lys Arg Leu Gln Asp Ala Leu Glu Glu Lys Ala Ala
785                 790                 795                 800

Leu Ala Glu Gln Leu Gln Ala Glu Val Glu Leu Cys Ala Glu Ala Glu
                805                 810                 815

Glu Met Arg Ala Arg Leu Ala Val Arg Lys Gln Glu Leu Glu Glu Ile
                820                 825                 830

Leu His Asp Leu Glu Ala Arg Ile Glu Glu Glu Glu Gln Arg Asn Thr
            835                 840                 845

Val Leu Ile Asn Glu Lys Lys Lys Leu Thr Leu Asn Ile Ala Asp Leu
850                 855                 860

Glu Glu Gln Leu Glu Glu Glu Gly Ala Arg Gln Lys Leu Gln Leu
865                 870                 875                 880

Glu Lys Val Gln Ile Glu Ala Arg Leu Lys Lys Met Glu Glu Asp Leu
                885                 890                 895

Ala Leu Ala Glu Asp Thr Asn Thr Lys Val Val Lys Glu Lys Lys Val
                900                 905                 910

Leu Glu Glu Arg Ala Ser Asp Leu Ala Gln Thr Leu Ala Glu Glu Glu
            915                 920                 925

Glu Lys Ala Lys His Leu Ala Lys Leu Lys Thr Lys His Glu Thr Thr
            930                 935                 940

Ile Ala Glu Leu Glu Glu Arg Leu Leu Lys Asp Asn Gln Gln Arg Gln
945                 950                 955                 960

Glu Met Asp Arg Asn Lys Arg Lys Ile Glu Ser Glu Val Asn Asp Leu
                965                 970                 975

Lys Glu Gln Ile Asn Glu Lys Lys Val Gln Val Glu Gly Leu Gln Leu
            980                 985                 990

Gln Leu Gly Lys Arg Glu Glu Glu  Ile Ala Gln Ala Leu  Met Arg Ile
            995                 1000                1005

Asp Glu  Glu Gly Ala Gly Lys  Ala Gln Thr Gln Lys  Ala Leu Arg
    1010                1015                1020

Glu Leu  Glu Ser Gln Leu Ala  Glu Leu Gln Glu Asp  Leu Glu Ala
    1025                1030                1035

Glu Lys  Ala Ala Arg Ala Lys  Ala Glu Lys Gln Lys  Arg Asp Leu
    1040                1045                1050

Asn Glu  Glu Leu Glu Ser Leu  Lys Asn Glu Leu Leu  Asp Ser Leu
    1055                1060                1065

Asp Thr  Thr Ala Ala Gln Gln  Glu Leu Arg Thr Lys  Arg Glu His
    1070                1075                1080

Glu Leu  Ala Thr Leu Lys Lys  Thr Leu Glu Glu Glu  Thr His Ile
    1085                1090                1095

His Glu  Val Ser Leu Thr Glu  Met Arg His Lys His  Thr Gln Glu
    1100                1105                1110
```

```
Val Ala Ala Leu Asn Glu Gln Leu Glu Gln Leu Lys Lys Ala Lys
1115                1120                1125

Ser Ala Leu Glu Lys Ser Lys Ala Gln Leu Glu Gly Glu Ala Ala
1130                1135                1140

Glu Leu Ala Asn Glu Leu Glu Thr Ala Gly Thr Ser Lys Gly Glu
1145                1150                1155

Ser Glu Arg Lys Arg Lys Gln Ala Glu Ser Ser Leu Gln Glu Leu
1160                1165                1170

Ser Ser Arg Leu Leu Glu Met Glu Arg Thr Lys Ala Glu Leu Gln
1175                1180                1185

Glu Arg Val Gln Lys Leu Ser Ala Glu Ala Asp Ser Val Asn Gln
1190                1195                1200

Gln Leu Glu Ala Ala Glu Leu Lys Ala Ser Ala Ala Leu Lys Ala
1205                1210                1215

Ser Gly Thr Leu Glu Thr Gln Leu Gln Glu Ala Gln Val Leu Leu
1220                1225                1230

Glu Glu Glu Thr Arg Gln Lys Leu Ser Leu Thr Thr Lys Leu Lys
1235                1240                1245

Gly Leu Glu Ser Glu Arg Asp Ala Leu Lys Glu Gln Leu Tyr Glu
1250                1255                1260

Glu Asp Glu Gly Arg Lys Asn Leu Glu Lys Gln Met Ala Ile Leu
1265                1270                1275

Asn Gln Gln Val Ala Glu Ser Lys Lys Lys Ser Glu Glu Glu Thr
1280                1285                1290

Glu Lys Ile Thr Glu Leu Glu Glu Ser Arg Lys Lys Leu Leu Lys
1295                1300                1305

Asp Ile Glu Ile Leu Gln Arg Gln Val Glu Glu Leu Gln Val Thr
1310                1315                1320

Asn Asp Lys Leu Glu Lys Gly Lys Lys Lys Leu Gln Ser Glu Leu
1325                1330                1335

Glu Asp Leu Thr Ile Asp Leu Glu Ser Gln Arg Thr Lys Val Val
1340                1345                1350

Glu Leu Glu Lys Lys Gln Arg Asn Phe Asp Lys Val Leu Ala Glu
1355                1360                1365

Glu Lys Ala Leu Ser Gln Gln Ile Thr His Glu Arg Asp Ala Ala
1370                1375                1380

Glu Arg Glu Ala Arg Glu Lys Glu Thr Arg Val Leu Ser Leu Thr
1385                1390                1395

Arg Glu Leu Asp Glu Phe Met Glu Lys Ile Glu Glu Leu Glu Arg
1400                1405                1410

Ser Lys Arg Gln Leu Gln Ala Glu Leu Asp Glu Leu Val Asn Asn
1415                1420                1425

Gln Gly Thr Thr Asp Lys Ser Val His Glu Leu Glu Arg Ala Lys
1430                1435                1440

Arg Val Leu Glu Ser Gln Leu Ala Glu Gln Lys Ala Gln Asn Glu
1445                1450                1455

Glu Leu Glu Asp Glu Leu Gln Met Thr Glu Asp Ala Lys Leu Arg
1460                1465                1470

Leu Glu Val Asn Met Gln Ala Leu Arg Ala Gln Phe Glu Arg Asp
1475                1480                1485

Leu Gln Gly Lys Glu Glu Ser Gly Glu Glu Lys Arg Arg Gly Leu
1490                1495                1500
```

-continued

```
Leu Lys Gln Leu Arg Asp Ile Glu Ala Glu Leu Glu Asp Glu Arg
    1505                1510                1515
Lys Gln Arg Thr Ala Ala Val Ala Ser Arg Lys Lys Ile Glu Ala
    1520                1525                1530
Asp Phe Lys Asp Val Glu Gln Leu Glu Met His Thr Lys Val
    1535                1540                1545
Lys Glu Asp Leu Gln Lys Gln Leu Lys Lys Cys Gln Val Gln Leu
    1550                1555                1560
Lys Asp Ala Ile Arg Asp Ala Glu Glu Ala Arg Leu Gly Arg Glu
    1565                1570                1575
Glu Leu Gln Ala Ala Ala Lys Glu Ala Glu Arg Lys Trp Lys Gly
    1580                1585                1590
Leu Glu Thr Glu Leu Ile Gln Val Gln Glu Asp Leu Met Ala Ser
    1595                1600                1605
Glu Arg Gln Arg Arg Ala Ala Glu Ala Glu Arg Asp Glu Val Val
    1610                1615                1620
Glu Glu Ala Asn Lys Asn Val Lys Ser Leu Ser Asn Leu Leu Asp
    1625                1630                1635
Glu Lys Lys Arg Leu Glu Ala Gln Cys Ser Gly Leu Glu Glu Glu
    1640                1645                1650
Leu Glu Glu Glu Leu Ser Asn Asn Glu Ala Leu Gln Asp Lys Ala
    1655                1660                1665
Arg Lys Ala Gln Leu Ser Val Glu Gln Leu Asn Ala Glu Leu Ala
    1670                1675                1680
Ala Glu Arg Ser Asn Val Gln Lys Leu Glu Gly Thr Arg Leu Ser
    1685                1690                1695
Met Glu Arg Gln Asn Lys Glu Leu Lys Ala Lys Leu Asn Glu Leu
    1700                1705                1710
Glu Thr Leu Gln Arg Asn Lys Phe Lys Ala Asn Ala Ser Leu Glu
    1715                1720                1725
Ala Lys Ile Thr Asn Leu Glu Glu Gln Leu Glu Asn Glu Ala Lys
    1730                1735                1740
Glu Lys Leu Leu Leu Gln Lys Gly Asn Arg Lys Leu Asp Lys Lys
    1745                1750                1755
Ile Lys Asp Leu Leu Val Gln Leu Glu Asp Glu Arg Arg His Ala
    1760                1765                1770
Asp Gln Tyr Lys Glu Gln Val Glu Lys Ile Asn Val Arg Val Lys
    1775                1780                1785
Thr Leu Lys Arg Thr Leu Asp Asp Ala Glu Glu Glu Met Ser Arg
    1790                1795                1800
Glu Lys Thr Gln Lys Arg Lys Ala Leu Arg Glu Leu Glu Asp Leu
    1805                1810                1815
Arg Glu Asn Tyr Asp Ser Leu Leu Arg Glu Asn Asp Asn Leu Lys
    1820                1825                1830
Asn Lys Leu Arg Arg Gly Gly Gly Ile Ser Gly Ile Ser Ser Arg
    1835                1840                1845
Leu Gly Gly Ser Lys Arg Gly Ser Ile Pro Gly Glu Asp Ser Gln
    1850                1855                1860
Gly Leu Asn Asn Thr Thr Asp Glu Ser Val Asp Gly Asp Asp Ile
    1865                1870                1875
Ser Asn Pro
    1880
```

-continued

```
<210> SEQ ID NO 336
<211> LENGTH: 108
<212> TYPE: PRT
<213> ORGANISM: Lygus hesperus

<400> SEQUENCE: 336

Lys Lys Ile Leu Glu Glu Ile Ala Glu Val Asp Ala Asp Gly Ser
1               5                   10                  15

Gly Gln Leu Glu Phe Glu Glu Phe Val Ala Leu Ala Ala Gly Phe Leu
            20                  25                  30

Thr Glu Asp Glu Thr Gln Asp Ala Glu Ala Met Gln Gln Glu Leu Arg
        35                  40                  45

Glu Ala Phe Arg Leu Tyr Asp Lys Glu Gly Asn Gly Tyr Ile Thr Thr
    50                  55                  60

Asp Val Leu Arg Glu Ile Leu Lys Glu Leu Asp Asp Lys Ile Thr Ser
65                  70                  75                  80

Gln Glu Leu Asp Met Met Ile Ala Glu Ile Asp Ser Asp Gly Ser Gly
                85                  90                  95

Thr Val Asp Phe Asp Glu Phe Met Glu Met Met Thr
            100                 105

<210> SEQ ID NO 337
<211> LENGTH: 141
<212> TYPE: PRT
<213> ORGANISM: Lygus hesperus

<400> SEQUENCE: 337

Ile Pro Ile Met Thr Ile Ala Leu Asn Ala Phe Asp Arg Asp His Ser
1               5                   10                  15

Gly Ser Ile Pro Thr Asp Met Val Ala Asp Ile Leu Arg Leu Met Gly
            20                  25                  30

Gln Pro Phe Asn Lys Lys Ile Leu Asp Glu Leu Ile Glu Glu Val Asp
        35                  40                  45

Ala Asp Lys Ser Gly Arg Leu Glu Phe Glu Glu Phe Ile Thr Leu Ala
    50                  55                  60

Ala Lys Phe Ile Val Glu Glu Asp Asp Glu Ala Met Gln Lys Glu Leu
65                  70                  75                  80

Arg Glu Ala Phe Arg Leu Tyr Asp Lys Glu Gly Asn Gly Tyr Ile Pro
                85                  90                  95

Thr Ser Cys Leu Lys Glu Ile Leu His Glu Leu Asp Glu Gln Leu Thr
            100                 105                 110

Asn Glu Glu Leu Asp Met Ile Ile Glu Glu Ile Asp Ser Asp Gly Ser
        115                 120                 125

Gly Thr Val Asp Phe Asp Glu Phe Met Glu Met Met Thr
    130                 135                 140

<210> SEQ ID NO 338
<211> LENGTH: 58
<212> TYPE: PRT
<213> ORGANISM: Lygus hesperus

<400> SEQUENCE: 338

Trp Val Lys Glu Gly Ala Cys Ser Glu Gln Ser Ser Arg Met Thr Ala
1               5                   10                  15

Met Asp Asn Ala Ser Lys Asn Ala Ala Glu Met Ile Asp Lys Leu Thr
            20                  25                  30

Leu Thr Phe Asn Arg Thr Arg Gln Ala Val Ile Thr Arg Glu Leu Ile
        35                  40                  45
```

```
Glu Ile Ile Ser Gly Ala Ser Ala Leu Glu
    50                  55
```

```
<210> SEQ ID NO 339
<211> LENGTH: 130
<212> TYPE: PRT
<213> ORGANISM: Lygus hesperus

<400> SEQUENCE: 339

Met Val Arg Met Asn Val Leu Ser Asp Ala Leu Lys Ser Ile Asn Asn
1               5                   10                  15

Ala Glu Lys Arg Gly Lys Arg Gln Val Leu Leu Arg Pro Cys Ser Lys
            20                  25                  30

Val Ile Ile Lys Phe Leu Thr Val Met Met Lys Lys Gly Tyr Ile Gly
        35                  40                  45

Glu Phe Glu Ile Val Asp Asp His Arg Ser Gly Lys Ile Val Val Asn
    50                  55                  60

Leu Asn Gly Arg Leu Asn Lys Cys Gly Val Ile Ser Pro Arg Phe Asp
65                  70                  75                  80

Val Pro Ile Thr Gln Ile Glu Lys Trp Thr Asn Asn Leu Leu Pro Ser
                85                  90                  95

Arg Gln Phe Gly Tyr Val Val Leu Thr Thr Ser Gly Gly Ile Met Asp
            100                 105                 110

His Glu Ala Arg Arg Lys His Leu Gly Gly Lys Ile Leu Gly Phe
        115                 120                 125

Phe Phe
    130
```

```
<210> SEQ ID NO 340
<211> LENGTH: 131
<212> TYPE: PRT
<213> ORGANISM: Lygus hesperus

<400> SEQUENCE: 340

Val Asp Gly Gly Leu Asn Ile Pro His Ser Thr Lys Arg Phe Pro Gly
1               5                   10                  15

Tyr Asp Ser Glu Ser Lys Glu Phe Asn Ala Glu Val His Arg Lys His
            20                  25                  30

Ile Phe Gly Ile His Val Ala Asp Tyr Met Arg Gln Leu Ala Glu Glu
        35                  40                  45

Asp Asp Asp Ala Tyr Lys Lys Gln Phe Ser Gln Tyr Val Lys Asn Gly
    50                  55                  60

Val Thr Ala Asp Ser Ile Glu Ser Ile Tyr Lys Lys Ala His Glu Ala
65                  70                  75                  80

Ile Arg Ala Asp Pro Thr Arg Lys Pro Leu Glu Lys Lys Glu Val Lys
                85                  90                  95

Lys Lys Arg Trp Asn Arg Ala Lys Leu Ser Leu Ser Glu Arg Lys Asn
            100                 105                 110

Thr Ile Asn Gln Lys Lys Ala Thr Tyr Leu Lys Lys Val Glu Ala Gly
        115                 120                 125

Glu Ile Glu
    130
```

```
<210> SEQ ID NO 341
<211> LENGTH: 214
<212> TYPE: PRT
<213> ORGANISM: Lygus hesperus
```

<400> SEQUENCE: 341

```
Met Ala Pro Lys Gly Asn Asn Met Ile Pro Asn Gly His Phe His Lys
1               5                   10                  15

Asp Trp Gln Arg Phe Ile Lys Thr Trp Phe Asn Gln Pro Ala Arg Lys
            20                  25                  30

Leu Arg Arg Arg Asn Lys Arg Leu Glu Lys Ala Gln Arg Leu Ala Pro
        35                  40                  45

Arg Pro Ala Gly Pro Leu Arg Pro Ala Val Arg Cys Pro Thr Val Arg
    50                  55                  60

Tyr His Thr Lys Leu Arg Pro Gly Arg Gly Phe Thr Leu Glu Glu Ile
65                  70                  75                  80

Lys Arg Ala Gly Leu Cys Lys Gly Phe Ala Met Ser Ile Gly Ile Ala
                85                  90                  95

Val Asp Pro Arg Arg Asn Lys Ser Ile Glu Ser Leu Gln Leu Asn
                    100                 105                 110

Val Gln Arg Leu Lys Glu Tyr Arg Ala Lys Leu Ile Leu Phe Pro His
            115                 120                 125

Lys Asn Ala Lys Lys Leu Lys Lys Gly Glu Ala Thr Glu Glu Glu Arg
130                 135                 140

Lys Val Ala Thr Gln Gln Pro Leu Pro Val Met Pro Ile Lys Gln Pro
145                 150                 155                 160

Val Ile Lys Phe Lys Ala Arg Val Ile Thr Asp Glu Lys Lys Tyr
                165                 170                 175

Ser Ala Phe Thr Ala Leu Arg Lys Gly Arg Ala Asp Gln Arg Leu Val
                180                 185                 190

Gly Ile Arg Ala Lys Arg Ala Lys Glu Ala Ala Glu Asn Ala Glu Asp
            195                 200                 205

Pro Ser Lys Ala Pro Lys
        210
```

<210> SEQ ID NO 342
<211> LENGTH: 134
<212> TYPE: PRT
<213> ORGANISM: Lygus hesperus

<400> SEQUENCE: 342

```
Met Asp Ile Glu Glu Pro Ala Ala Pro Thr Glu Pro Ser Asp Val
1               5                   10                  15

Asn Thr Ala Leu Gln Glu Val Leu Lys Ala Ala Leu Gln His Gly Val
            20                  25                  30

Val Val His Gly Ile His Glu Ser Ala Lys Ala Leu Asp Lys Arg Gln
        35                  40                  45

Ala Leu Leu Cys Val Leu Ala Glu Asn Cys Asp Glu Pro Met Tyr Lys
    50                  55                  60

Lys Leu Val Gln Ala Leu Cys Ser Glu His His Ile Pro Leu Val Lys
65                  70                  75                  80

Val Asp Ser Asn Lys Lys Leu Gly Glu Trp Thr Gly Leu Cys Lys Ile
                85                  90                  95

Asp Lys Thr Gly Lys Ser Arg Lys Ile Val Gly Cys Ser Cys Val Val
                    100                 105                 110

Ile Lys Asp Trp Gly Glu Asp Thr Pro His Leu Asp Leu Leu Lys Asp
            115                 120                 125

Tyr Ile Arg Asp Val Phe
        130
```

<210> SEQ ID NO 343
<211> LENGTH: 148
<212> TYPE: PRT
<213> ORGANISM: Lygus hesperus

<400> SEQUENCE: 343

Met Lys Met Asn Lys Leu Val Thr Ser Ser Arg Arg Lys Asn Arg Lys
1               5                   10                  15

Arg His Phe Thr Ala Pro Ser His Ile Arg Arg Lys Leu Met Ser Ala
            20                  25                  30

Pro Leu Ser Lys Glu Leu Arg Gln Lys Tyr Asn Val Arg Thr Met Pro
        35                  40                  45

Val Arg Lys Asp Asp Glu Val Gln Val Val Arg Gly His Tyr Lys Gly
    50                  55                  60

Gln Gln Val Gly Lys Val Leu Gln Val Tyr Arg Lys Lys Phe Ile Ile
65                  70                  75                  80

Tyr Ile Glu Arg Ile Gln Arg Gly Lys Ala Asn Gly Ala Ser Val Tyr
                85                  90                  95

Val Gly Ile His Pro Ser Lys Cys Val Ile Val Lys Leu Lys Val Asp
            100                 105                 110

Lys Asp Arg Lys Glu Ile Leu Asp Arg Arg Ser Lys Gly Arg Asp Leu
        115                 120                 125

Ala Leu Gly Lys Asp Lys Gly Lys Tyr Thr Glu Asp Ser Thr Thr Ala
    130                 135                 140

Met Asp Thr Ser
145

<210> SEQ ID NO 344
<211> LENGTH: 65
<212> TYPE: PRT
<213> ORGANISM: Lygus hesperus

<400> SEQUENCE: 344

Met Glu Lys Pro Val Val Leu Ala Arg Val Ile Lys Ile Leu Gly Arg
1               5                   10                  15

Thr Gly Ser Gln Gly Gln Cys Thr Gln Val Lys Val Glu Phe Ile Gly
            20                  25                  30

Glu Gln Asn Arg Gln Ile Ile Arg Asn Val Lys Gly Pro Val Arg Glu
        35                  40                  45

Gly Asp Ile Leu Thr Leu Leu Glu Ser Glu Arg Glu Ala Arg Arg Leu
    50                  55                  60

Arg
65

<210> SEQ ID NO 345
<211> LENGTH: 229
<212> TYPE: PRT
<213> ORGANISM: Lygus hesperus

<400> SEQUENCE: 345

Leu Phe Tyr Phe Pro Phe Ser Arg Lys Trp Gly Asp Val Gln Arg Gly
1               5                   10                  15

Val Ile Gly Thr Val Lys Thr Ser His Thr Pro Lys Ser Arg Phe Cys
            20                  25                  30

Arg Gly Val Pro Asp Pro Lys Ile Arg Ile Phe Asp Leu Gly Lys Lys
        35                  40                  45

```
Lys Ala Arg Val Glu Asp Phe Pro Leu Cys Val His Leu Val Ser Asp
 50                  55                  60

Glu Tyr Glu Gln Leu Ser Ser Glu Ala Leu Glu Ala Gly Arg Ile Cys
 65                  70                  75                  80

Cys Asn Lys Tyr Leu Val Lys Asn Cys Gly Lys Asp Gln Phe His Ile
                 85                  90                  95

Arg Met Arg Leu His Pro Phe His Val Ile Arg Ile Asn Lys Met Leu
            100                 105                 110

Ser Cys Ala Gly Ala Asp Arg Leu Gln Thr Gly Met Arg Gly Ala Phe
            115                 120                 125

Gly Lys Pro Gln Gly Thr Val Ala Arg Val Arg Ile Gly Gln Pro Ile
130                 135                 140

Met Ser Val Arg Ser Ser Asp Arg Tyr Lys Ala Ala Val Ile Lys Ala
145                 150                 155                 160

Leu Arg Arg Ala Lys Phe Lys Phe Pro Gly Arg Gln Lys Ile Tyr Val
                165                 170                 175

Ser Lys Lys Trp Gly Phe Thr Lys Phe Asp Arg Glu Glu Tyr Glu Gly
            180                 185                 190

Leu Arg Asn Asp Asn Lys Leu Ala Asn Asp Gly Cys Asn Val Lys Leu
            195                 200                 205

Arg Pro Asp His Gly Pro Leu Gln Ala Trp Arg Lys Ala Gln Leu Asp
210                 215                 220

Ile Ala Ala Gly Leu
225

<210> SEQ ID NO 346
<211> LENGTH: 220
<212> TYPE: PRT
<213> ORGANISM: Lygus hesperus

<400> SEQUENCE: 346

Met Gly Arg Arg Pro Ala Arg Cys Tyr Arg Tyr Cys Lys Asn Lys Pro
1               5                   10                  15

Tyr Pro Lys Ser Arg Phe Cys Arg Gly Val Pro Asp Pro Lys Ile Arg
             20                  25                  30

Ile Phe Asp Leu Gly Lys Lys Lys Ala Arg Val Glu Asp Phe Pro Leu
         35                  40                  45

Cys Val His Leu Val Ser Asp Glu Tyr Glu Gln Leu Ser Ser Glu Ala
     50                  55                  60

Leu Glu Ala Gly Arg Ile Cys Cys Asn Lys Tyr Leu Val Lys Asn Cys
 65                  70                  75                  80

Gly Lys Asp Gln Phe His Ile Arg Met Arg Leu His Pro Phe His Val
                 85                  90                  95

Ile Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Val Ala Arg
            115                 120                 125

Val Arg Ile Gly Gln Pro Ile Met Ser Val Arg Ser Ser Asp Arg Tyr
130                 135                 140

Lys Ala Ala Val Ile Glu Ala Leu Arg Arg Ala Lys Phe Lys Phe Pro
145                 150                 155                 160

Gly Arg Gln Lys Ile Tyr Val Ser Lys Lys Trp Gly Phe Thr Lys Phe
                165                 170                 175

Asp Arg Glu Glu Tyr Glu Gly Leu Arg Asn Asp Asn Lys Leu Ala Asn
            180                 185                 190
```

```
Gly Gly Cys Asn Val Lys Leu Arg Pro Asp His Gly Pro Leu Gln Ala
        195                 200                 205

Trp Arg Lys Ala Gln Leu Asp Ile Ala Ala Gly Leu
    210                 215                 220

<210> SEQ ID NO 347
<211> LENGTH: 159
<212> TYPE: PRT
<213> ORGANISM: Lygus hesperus

<400> SEQUENCE: 347

Met Thr Asn Ser Lys Gly Tyr Arg Arg Gly Thr Arg Asp Leu Phe Ser
1               5                   10                  15

Arg Pro Phe Arg His His Gly Val Ile Pro Leu Ser Thr Tyr Met Lys
            20                  25                  30

Val Tyr Arg Val Gly Asp Ile Val Ser Ile Lys Gly Asn Gly Ala Val
        35                  40                  45

Gln Lys Gly Met Pro His Lys Val Tyr His Gly Lys Thr Gly Arg Val
    50                  55                  60

Tyr Asn Val Thr Pro Arg Ala Leu Gly Val Ile Val Asn Lys Arg Val
65                  70                  75                  80

Arg Gly Lys Ile Leu Pro Lys Arg Ile Asn Ile Arg Ile Glu His Val
                85                  90                  95

Asn His Ser Lys Cys Arg Glu Asp Phe Leu Lys Arg Val Arg Glu Asn
            100                 105                 110

Glu Arg Leu Arg Lys Phe Ala Lys Glu Thr Gly Thr Arg Val Glu Leu
        115                 120                 125

Lys Arg Gln Pro Ala Gln Pro Arg Pro Ala His Phe Val Gln Ala Lys
    130                 135                 140

Glu Val Pro Glu Leu Leu Ala Pro Ile Pro Tyr Glu Phe Ile Ala
145                 150                 155

<210> SEQ ID NO 348
<211> LENGTH: 131
<212> TYPE: PRT
<213> ORGANISM: Lygus hesperus

<400> SEQUENCE: 348

Thr Tyr Met Lys Val Tyr Arg Val Gly Asp Ile Val Ser Ile Lys Gly
1               5                   10                  15

Asn Gly Ala Val Gln Lys Gly Met Pro His Lys Val Tyr His Gly Lys
            20                  25                  30

Thr Gly Arg Val Tyr Asn Val Thr Pro Arg Ala Leu Gly Val Ile Val
        35                  40                  45

Asn Lys Arg Val Arg Gly Lys Ile Leu Pro Lys Arg Ile Asn Ile Arg
    50                  55                  60

Ile Glu His Val Asn His Ser Lys Cys Arg Glu Asp Phe Leu Lys Arg
65                  70                  75                  80

Val Arg Glu Asn Glu Arg Leu Arg Lys Phe Ala Lys Glu Thr Gly Thr
                85                  90                  95

Arg Val Glu Leu Lys Arg Gln Pro Ala Gln Pro Arg Pro Ala His Phe
            100                 105                 110

Val Gln Ala Lys Glu Val Pro Glu Leu Leu Ala Pro Ile Pro Tyr Glu
        115                 120                 125

Phe Ile Ala
    130
```

<210> SEQ ID NO 349
<211> LENGTH: 150
<212> TYPE: PRT
<213> ORGANISM: leptinotarsa decemlineata

<400> SEQUENCE: 349

Lys Lys Ala Lys Lys Gly Phe Met Thr Pro Glu Arg Lys Lys Lys Leu
1               5                   10                  15

Arg Leu Leu Arg Lys Lys Ala Ala Glu Glu Leu Lys Lys Glu Gln
            20                  25                  30

Glu Arg Lys Ala Ala Glu Arg Arg Ile Ile Glu Glu Arg Cys Gly
        35                  40                  45

Lys Pro Lys Leu Ile Asp Glu Ala Asn Glu Glu Gln Val Arg Asn Tyr
    50                  55                  60

Cys Lys Leu Tyr His Gly Arg Ile Ala Lys Leu Glu Asp Gln Lys Phe
65                  70                  75                  80

Asp Leu Glu Tyr Leu Val Lys Lys Lys Asp Met Glu Ile Ala Glu Leu
                85                  90                  95

Asn Ser Gln Val Asn Asp Leu Arg Gly Lys Phe Val Lys Pro Thr Leu
            100                 105                 110

Lys Lys Val Ser Lys Tyr Glu Asn Lys Phe Ala Lys Leu Gln Lys Lys
        115                 120                 125

Ala Ala Glu Phe Asn Phe Arg Asn Gln Leu Lys Val Lys Lys Lys
    130                 135                 140

Glu Phe Thr Leu Glu Glu
145                 150

<210> SEQ ID NO 350
<211> LENGTH: 279
<212> TYPE: PRT
<213> ORGANISM: leptinotarsa decemlineata

<400> SEQUENCE: 350

Gln Trp Tyr Gln Arg Arg Val Arg Gly Asp Ile Glu Glu Lys Arg Gln
1               5                   10                  15

Arg Leu Glu Glu Ala Glu Lys Lys Arg Gln Ala Met Met Gln Ala Leu
            20                  25                  30

Lys Asp Gln Asn Lys Asn Lys Gly Pro Asn Phe Thr Ile Thr Lys Arg
        35                  40                  45

Asp Ala Ser Ser Asn Leu Ser Ala Ala Gln Leu Glu Arg Asn Lys Thr
    50                  55                  60

Lys Glu Gln Leu Glu Glu Lys Lys Ile Ser Leu Ser Ile Arg Ile
65                  70                  75                  80

Lys Pro Leu Val Val Asp Gly Leu Gly Val Asp Lys Leu Arg Leu Lys
                85                  90                  95

Ala Gln Glu Leu Trp Glu Cys Ile Val Lys Leu Glu Thr Glu Lys Tyr
            100                 105                 110

Asp Leu Glu Glu Arg Gln Lys Arg Gln Asp Tyr Asp Leu Lys Glu Leu
        115                 120                 125

Lys Glu Arg Gln Lys Gln Leu Arg His Lys Ala Leu Lys Lys Gly
    130                 135                 140

Leu Asp Pro Glu Ala Leu Thr Gly Lys Tyr Pro Pro Lys Ile Gln Val
145                 150                 155                 160

Ala Ser Lys Tyr Glu Arg Arg Val Asp Thr Arg Ser Tyr Gly Asp Lys
                165                 170                 175

```
Lys Lys Leu Phe Glu Gly Gly Leu Glu Glu Ile Ile Lys Glu Thr Asn
            180                 185                 190

Glu Lys Ser Trp Lys Glu Lys Phe Gly Gln Phe Asp Ser Arg Gln Lys
        195                 200                 205

Ala Arg Leu Pro Lys Trp Phe Gly Glu Arg Pro Gly Lys Lys Pro Gly
    210                 215                 220

Asp Pro Glu Thr Pro Glu Gly Glu Glu Gly Lys Gln Val Ile Asp
225                 230                 235                 240

Glu Asp Asp Asp Leu Lys Glu Pro Val Ile Glu Ala Glu Ile Glu Glu
                245                 250                 255

Glu Glu Glu Glu Glu Val Glu Val Asp Glu Glu Glu Asp Asp
            260                 265                 270

Glu Glu Glu Glu Glu Glu Glu
            275

<210> SEQ ID NO 351
<211> LENGTH: 286
<212> TYPE: PRT
<213> ORGANISM: leptinotarsa decemlineata

<400> SEQUENCE: 351

Ala Leu Gln Asn Glu Leu Glu Glu Ser Arg Thr Leu Leu Glu Gln Ala
1               5                   10                  15

Asp Arg Ala Arg Arg Gln Ala Glu Gln Glu Leu Gly Asp Ala His Glu
            20                  25                  30

Gln Leu Asn Asp Leu Gly Ala Gln Asn Gly Ser Leu Ser Ala Ala Lys
        35                  40                  45

Arg Lys Leu Glu Thr Glu Leu Gln Thr Leu His Ser Asp Leu Asp Glu
    50                  55                  60

Leu Leu Asn Glu Ala Lys Asn Ser Glu Glu Lys Ala Lys Lys Ala Met
65                  70                  75                  80

Val Asp Ala Ala Arg Leu Ala Asp Glu Leu Arg Ala Glu Gln Asp His
                85                  90                  95

Ala Gln Thr Gln Glu Lys Leu Arg Lys Ala Leu Glu Ser Gln Ile Lys
            100                 105                 110

Asp Leu Gln Val Arg Leu Asp Glu Ala Glu Ala Asn Ala Leu Lys Gly
        115                 120                 125

Gly Lys Lys Ala Ile Ala Lys Leu Glu Gln Arg Val Arg Glu Leu Glu
    130                 135                 140

Asn Glu Leu Asp Gly Glu Gln Arg Arg His Ala Asp Ala Gln Lys Asn
145                 150                 155                 160

Leu Arg Lys Ser Glu Arg Arg Ile Lys Glu Leu Ser Leu Gln Ala Glu
                165                 170                 175

Glu Asp Arg Lys Asn His Glu Lys Met Gln Asp Leu Val Asp Lys Leu
            180                 185                 190

Gln Gln Lys Ile Lys Thr His Lys Arg Gln Ile Glu Glu Ala Glu Glu
        195                 200                 205

Ile Ala Ala Leu Asn Leu Ala Lys Phe Arg Lys Ala Gln Gln Glu Leu
    210                 215                 220

Glu Glu Ala Glu Glu Arg Ala Asp Leu Ala Glu Gln Ala Ile Val Lys
225                 230                 235                 240

Phe Arg Thr Lys Gly Arg Ser Gly Ser Ala Ala Arg Gly Ala Ser Pro
                245                 250                 255

Ala Pro Gln Arg Gln Arg Pro Thr Phe Gly Met Gly Asp Ser Leu Gly
```

```
                    260                 265                 270
Gly Ala Phe Pro Pro Arg Phe Asp Leu Ala Pro Asp Phe Glu
                275                 280                 285

<210> SEQ ID NO 352
<211> LENGTH: 197
<212> TYPE: PRT
<213> ORGANISM: nilaparvata lugens

<400> SEQUENCE: 352

Met Ala Asp Asp Glu Ala Lys Lys Ala Lys Gln Ala Glu Ile Asp Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Asp Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Ile Ile Glu Arg Cys Gly Lys
65                  70                  75                  80

Ala Val Asp Leu Asp Asp Gly Ser Glu Glu Lys Val Lys Ala Thr Leu
                85                  90                  95

Lys Thr Tyr His Asp Arg Ile Gly Lys Leu Glu Asp Glu Lys Phe Asp
            100                 105                 110

Leu Glu Tyr Ile Val Lys Lys Asp Phe Glu Ile Ala Asp Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Glu
                165                 170                 175

Phe Thr Leu Glu Glu Glu Asp Lys Glu Pro Lys Lys Ser Glu Lys Ala
            180                 185                 190

Glu Trp Gln Lys Lys
        195

<210> SEQ ID NO 353
<211> LENGTH: 184
<212> TYPE: PRT
<213> ORGANISM: nilaparvata lugens

<400> SEQUENCE: 353

Met Met Ala Ala Leu Lys Asp Gln Ser Lys Ser Lys Gly Pro Asn Phe
1               5                   10                  15

Thr Val Asn Lys Lys Thr Asp Leu Asn Met Thr Ser Ala Gln Met Glu
            20                  25                  30

Arg Asn Lys Thr Lys Glu Gln Leu Glu Glu Lys Lys Ile Ser Leu
        35                  40                  45

Ser Phe Arg Ile Lys Pro Leu Ala Ile Glu Asn Met Ser Ile Asn Ala
    50                  55                  60

Leu Arg Ala Lys Ala Gln Glu Leu Trp Asp Cys Ile Val Lys Leu Glu
65                  70                  75                  80

Thr Glu Lys Tyr Asp Leu Glu Glu Arg Gln Lys Arg Gln Asp Tyr Asp
                85                  90                  95

Leu Lys Glu Leu Lys Glu Arg Gln Lys Gln Gln Leu Arg His Lys Ala
```

Leu Lys Lys Gly Leu Asp Pro Glu Ala Leu Thr Gly Lys Tyr Pro Pro
              115                 120                 125

Lys Ile Gln Val Ala Ser Lys Tyr Glu Arg Arg Val Asp Thr Arg Ser
        130                 135                 140

Tyr Asp Asp Lys Lys Lys Leu Phe Glu Gly Gly Trp Asp Thr Leu Thr
145                 150                 155                 160

Ser Glu Thr Asn Glu Lys Ile Trp Lys Ser Arg Asn Asp Gln Phe Ser
                165                 170                 175

Asn Arg Ser Lys Ala Lys Leu Pro
            180

<210> SEQ ID NO 354
<211> LENGTH: 122
<212> TYPE: PRT
<213> ORGANISM: nilaparvata lugens

<400> SEQUENCE: 354

Ala Phe Asp Arg Glu Arg Ser Gly Ser Ile Pro Thr Asp Met Val Ala
1               5                   10                  15

Asp Ile Leu Arg Leu Met Gly Gln Pro Phe Asn Lys Lys Ile Leu Asp
            20                  25                  30

Glu Leu Ile Glu Glu Val Asp Ala Asp Lys Ser Gly Arg Leu Glu Phe
        35                  40                  45

Asp Glu Phe Val Thr Leu Ala Ala Lys Phe Ile Val Glu Glu Asp Asp
    50                  55                  60

Glu Ala Met Gln Lys Glu Leu Lys Glu Ala Phe Arg Leu Tyr Asp Lys
65                  70                  75                  80

Glu Gly Asn Gly Tyr Ile Pro Thr Ser Cys Leu Lys Glu Ile Leu Arg
                85                  90                  95

Glu Leu Asp Asp Gln Leu Thr Asn Glu Glu Leu Asn Met Met Ile Asp
            100                 105                 110

Glu Ile Asp Ser Asp Gly Ser Gly Thr Val
        115                 120

<210> SEQ ID NO 355
<211> LENGTH: 73
<212> TYPE: PRT
<213> ORGANISM: nilaparvata lugens

<400> SEQUENCE: 355

Val Lys Thr Leu Thr Gly Lys Thr Ile Thr Leu Glu Val Glu Pro Ser
1               5                   10                  15

Asp Thr Ile Glu Asn Val Lys Ala Lys Ile Gln Asp Lys Glu Gly Ile
            20                  25                  30

Pro Pro Asp Gln Gln Arg Leu Ile Phe Ala Gly Lys Gln Leu Glu Asp
        35                  40                  45

Gly Arg Thr Leu Ser Asp Tyr Asn Ile Gln Lys Glu Ser Thr Leu His
    50                  55                  60

Leu Val Leu Arg Leu Arg Gly Gly Thr
65                  70

<210> SEQ ID NO 356
<211> LENGTH: 253
<212> TYPE: PRT
<213> ORGANISM: Acyrthosiphon pisum

<400> SEQUENCE: 356

Met Ala Asp Asp Glu Ala Lys Ala Lys Gln Ala Glu Ile Asp Arg
1               5                  10                 15

Lys Arg Ala Glu Val Arg Lys Arg Met Glu Ala Ser Lys Ala Lys
                20                 25                 30

Lys Ala Lys Lys Gly Phe Met Thr Pro Asp Arg Lys Lys Leu Arg
            35                 40                 45

Leu Leu Leu Lys Lys Ala Ala Glu Glu Leu Lys Lys Glu Gln Glu
        50                 55                 60

Arg Lys Ala Ala Glu Arg Arg Ile Ile Glu Glu Arg Cys Gly Gln
65                  70                 75                 80

Pro Lys Asn Ile Asp Asp Ala Gly Glu Glu Leu Ala Glu Ile Cys
                85                 90                 95

Glu Glu Leu Trp Lys Arg Val Tyr Thr Val Glu Gly Ile Lys Phe Asp
                100                105                110

Leu Glu Arg Asp Ile Arg Met Lys Val Phe Glu Ile Ser Glu Leu Asn
                115                120                125

Ser Gln Val Asn Asp Leu Arg Gly Lys Phe Val Lys Pro Thr Leu Lys
                130                135                140

Lys Val Ser Lys Tyr Glu Asn Lys Phe Ala Lys Leu Gln Lys Lys Ala
145                 150                155                160

Ala Glu Phe Asn Phe Arg Asn Gln Leu Lys Val Val Lys Lys Glu
                165                170                175

Phe Thr Leu Glu Glu Glu Asp Lys Lys Lys Pro Asp Trp Ser Lys
                180                185                190

Lys Gly Asp Glu Lys Lys Gly Glu Gly Glu Asp Gly Asp Gly Thr Glu
                195                200                205

Asp Glu Lys Thr Asp Asp Gly Leu Thr Thr Glu Gly Glu Ser Val Ala
210                 215                220

Gly Asp Leu Thr Asp Ala Thr Glu Asp Ala Gln Ser Asp Asn Glu Ile
225                 230                235                240

Leu Glu Pro Glu Pro Val Val Glu Pro Glu Pro
                245                250

<210> SEQ ID NO 357
<211> LENGTH: 179
<212> TYPE: PRT
<213> ORGANISM: Acyrthosiphon pisum

<400> SEQUENCE: 357

Val Met Arg Cys Gly Lys Lys Val Trp Leu Asp Pro Asn Glu Ile
1               5                  10                 15

Asn Glu Ile Ala Asn Thr Asn Ser Arg Gln Asn Ile Arg Lys Leu Ile
                20                 25                 30

Lys Asp Gly Leu Ile Ile Lys Lys Pro Val Ala Val His Ser Arg Ala
            35                 40                 45

Arg Ala Arg Lys Asn Ala Asp Ala Arg Arg Lys Gly Arg His Cys Gly
        50                 55                 60

Phe Gly Lys Arg Lys Gly Thr Ala Asn Ala Arg Thr Pro Gln Lys Asp
65                  70                 75                 80

Leu Trp Val Lys Arg Met Arg Val Leu Arg Arg Leu Leu Lys Lys Tyr
                85                 90                 95

Arg Glu Ala Lys Lys Ile Asp Asn His Leu Tyr His Gln Leu Tyr Met
                100                105                110

Lys Ala Lys Gly Asn Val Phe Lys Asn Lys Arg Val Leu Met Glu Phe

```
            115                 120                 125

Ile His Lys Lys Lys Ala Glu Lys Ala Arg Ala Lys Met Leu Ser Asp
    130                 135                 140

Gln Ala Glu Ala Arg Arg Gln Lys Val Lys Glu Ala Arg Lys Arg Lys
145                 150                 155                 160

Glu Ala Arg Phe Leu Gln Asn Arg Lys Glu Leu Leu Ala Ala Tyr Ala
                165                 170                 175

Arg Glu Asp

<210> SEQ ID NO 358
<211> LENGTH: 275
<212> TYPE: PRT
<213> ORGANISM: Acyrthosiphon pisum

<400> SEQUENCE: 358

Gly Leu Glu Val Glu Ser Ser Asp Ser Ile Glu Asn Val Lys Ala Lys
1               5                   10                  15

Ile Gln Asp Lys Glu Gly Ile Pro Pro Asp Gln Gln Arg Leu Ile Phe
            20                  25                  30

Ala Gly Lys Gln Leu Glu Asp Gly Arg Thr Leu Ser Asp Tyr Asn Ile
        35                  40                  45

Gln Lys Glu Ser Thr Leu His Leu Val Leu Arg Leu Arg Gly Gly Met
    50                  55                  60

Gln Ile Phe Val Lys Thr Leu Thr Gly Lys Thr Ile Thr Leu Glu Val
65                  70                  75                  80

Glu Ser Ser Asp Ser Ile Glu Asn Val Lys Ala Lys Ile Gln Asp Lys
                85                  90                  95

Glu Gly Ile Pro Pro Asp Gln Gln Arg Leu Ile Phe Ala Gly Lys Gln
            100                 105                 110

Leu Glu Asp Gly Arg Thr Leu Ser Asp Tyr Asn Ile Gln Lys Glu Ser
        115                 120                 125

Thr Leu His Leu Val Leu Arg Leu Arg Gly Gly Met Gln Ile Phe Val
    130                 135                 140

Lys Thr Leu Thr Gly Lys Thr Ile Thr Leu Glu Val Glu Ser Ser Asp
145                 150                 155                 160

Ser Ile Glu Asn Val Lys Ala Lys Ile Gln Asp Lys Glu Gly Ile Pro
                165                 170                 175

Pro Asp Gln Gln Arg Leu Ile Phe Ala Gly Lys Gln Leu Glu Asp Gly
            180                 185                 190

Arg Thr Leu Ser Asp Tyr Asn Ile Gln Lys Glu Ser Thr Leu His Leu
        195                 200                 205

Val Leu Arg Leu Arg Gly Gly Met Gln Ile Phe Val Lys Thr Leu Thr
    210                 215                 220

Gly Lys Thr Ile Thr Leu Glu Val Glu Ser Ser Asp Ser Ile Glu Asn
225                 230                 235                 240

Val Lys Ala Lys Ile Gln Asp Lys Glu Gly Ile Pro Pro Asp Gln Gln
                245                 250                 255

Arg Leu Ile Phe Ala Gly Lys Gln Leu Glu Asp Gly Arg Thr Leu Ser
            260                 265                 270

Asp Tyr Asn
        275

<210> SEQ ID NO 359
<211> LENGTH: 56
<212> TYPE: PRT
```

<213> ORGANISM: Acyrthosiphon pisum

<400> SEQUENCE: 359

Asp Leu Leu His Pro Thr Ala Ile Glu Glu Arg Arg Lys His Lys Leu
1               5                   10                  15

Lys Arg Leu Val Gln His Pro Asn Ser Phe Phe Met Asp Val Lys Cys
            20                  25                  30

Pro Gly Cys Tyr Lys Ile Thr Thr Val Phe Ser His Ala Gln Ser Val
        35                  40                  45

Val Ile Cys Thr Gly Cys Ser Thr
    50                  55

<210> SEQ ID NO 360
<211> LENGTH: 20
<212> TYPE: DNA
<213> ORGANISM: Artificial
<220> FEATURE:
<223> OTHER INFORMATION: Primer

<400> SEQUENCE: 360
atcatgcagg cgtacgcccg                                              20

<210> SEQ ID NO 361
<211> LENGTH: 19
<212> TYPE: DNA
<213> ORGANISM: Artificial
<220> FEATURE:
<223> OTHER INFORMATION: Primer

<400> SEQUENCE: 361 cggaggggc gagatcact                                                19

<210> SEQ ID NO 362
<211> LENGTH: 62
<212> TYPE: DNA
<213> ORGANISM: Artificial
<220> FEATURE:
<223> OTHER INFORMATION: Amplicon

<400> SEQUENCE: 362
atcatgcagg cgtacgcccg agaagacgag gctgccgtca aaaagtgatc tcgccccctc   60
cg                                                                 62

<210> SEQ ID NO 363
<211> LENGTH: 22
<212> TYPE: DNA
<213> ORGANISM: Artificial
<220> FEATURE:
<223> OTHER INFORMATION: Primer

<400> SEQUENCE: 363
tgtgttggct actggtggct ac                                           22

<210> SEQ ID NO 364
<211> LENGTH: 25
<212> TYPE: DNA
<213> ORGANISM: Artificial
<220> FEATURE:
<223> OTHER INFORMATION: Primer

<400> SEQUENCE: 364
tcggatggaa ctggacaaat tcaag                                        25

-continued

```
<210> SEQ ID NO 365
<211> LENGTH: 137
<212> TYPE: DNA
<213> ORGANISM: Artificial
<220> FEATURE:
<223> OTHER INFORMATION: Amplicon

<400> SEQUENCE: 365
tgtgttggct actggtggct acggcagagc ttacttttca tgcacttcag ctcacacttg    60
cacgggagat ggccaagcaa tggtttcacg agctgggctt cccaacgaag atcttgaatt   120
tgtccagttc catccga                                                  137

<210> SEQ ID NO 366
<211> LENGTH: 21
<212> TYPE: DNA
<213> ORGANISM: Artificial
<220> FEATURE:
<223> OTHER INFORMATION: Primer

<400> SEQUENCE: 366
gcaacccgtg ttctccaaag c                                              21

<210> SEQ ID NO 367
<211> LENGTH: 28
<212> TYPE: DNA
<213> ORGANISM: Artificial
<220> FEATURE:
<223> OTHER INFORMATION: Primer

<400> SEQUENCE: 367
tcaactcgta ttctcgtact ttcaaacc                                       28

<210> SEQ ID NO 368
<211> LENGTH: 146
<212> TYPE: DNA
<213> ORGANISM: Artificial
<220> FEATURE:
<223> OTHER INFORMATION: Amplicon

<400> SEQUENCE: 368
gcaacccgtg ttctccaaag ccagatacac tgtgcgatcc ttcggtatca ggcgtaacga    60
aaaaatcgcc gttcactgca ctgtcagggg cgccaaagca gaggaaattc tggagcgtgg   120
tttgaaagta cgagaatacg agttga                                        146

<210> SEQ ID NO 369
<211> LENGTH: 21
<212> TYPE: DNA
<213> ORGANISM: Artificial
<220> FEATURE:
<223> OTHER INFORMATION: Primer

<400> SEQUENCE: 369
atggccgacg atgaagctaa g                                              21

<210> SEQ ID NO 370
<211> LENGTH: 20
<212> TYPE: DNA
<213> ORGANISM: Artificial
<220> FEATURE:
<223> OTHER INFORMATION: Primer

<400> SEQUENCE: 370
tggttctggt tcgggttcaa                                                20
```

```
<210> SEQ ID NO 371
<211> LENGTH: 20
<212> TYPE: DNA
<213> ORGANISM: Artificial
<220> FEATURE:
<223> OTHER INFORMATION: Primer

<400> SEQUENCE: 371
cggtaatgcg atgcggtaag                                                 20

<210> SEQ ID NO 372
<211> LENGTH: 20
<212> TYPE: DNA
<213> ORGANISM: Artificial
<220> FEATURE:
<223> OTHER INFORMATION: Primer

<400> SEQUENCE: 372
tcatcttctc gggcgtatgc                                                 20

<210> SEQ ID NO 373
<211> LENGTH: 25
<212> TYPE: DNA
<213> ORGANISM: Artificial
<220> FEATURE:
<223> OTHER INFORMATION: Primer

<400> SEQUENCE: 373
tttggaagtt gagtcatcag attcc                                           25

<210> SEQ ID NO 374
<211> LENGTH: 24
<212> TYPE: DNA
<213> ORGANISM: Artificial
<220> FEATURE:
<223> OTHER INFORMATION: Primer

<400> SEQUENCE: 374
gttgtagtcg gaaagggtac gtcc                                            24

<210> SEQ ID NO 375
<211> LENGTH: 20
<212> TYPE: DNA
<213> ORGANISM: Artificial
<220> FEATURE:
<223> OTHER INFORMATION: Primer

<400> SEQUENCE: 375
attgtggaac atccggtaca                                                 20

<210> SEQ ID NO 376
<211> LENGTH: 23
<212> TYPE: DNA
<213> ORGANISM: Artificial
<220> FEATURE:
<223> OTHER INFORMATION: Primer

<400> SEQUENCE: 376
aagacttgct tcatcctact gca                                             23

<210> SEQ ID NO 377
<211> LENGTH: 28
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (20)..(20)
<223> OTHER INFORMATION: n is a, c, g, or t

<400> SEQUENCE: 377
ccaagaaggc caagaagggn ttyatgac                                              28

<210> SEQ ID NO 378
<211> LENGTH: 29
<212> TYPE: DNA
<213> ORGANISM: Artificial
<220> FEATURE:
<223> OTHER INFORMATION: Primer

<400> SEQUENCE: 378
tcctcctcca gggtgaactc yttyttytt                                             29

<210> SEQ ID NO 379
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 379
gccaagaagg gcttcatgac nccnga                                                26

<210> SEQ ID NO 380
<211> LENGTH: 27
<212> TYPE: DNA
<213> ORGANISM: Artificial
<220> FEATURE:
<223> OTHER INFORMATION: Primer

<400> SEQUENCE: 380
gaagttgaac tcggcggcyt tyttytg                                               27

<210> SEQ ID NO 381
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (24)..(24)
<223> OTHER INFORMATION: n is a, c, g, or t

<400> SEQUENCE: 381
ctggaggagg ccgagaaraa rmgnca                                                26

<210> SEQ ID NO 382
<211> LENGTH: 22
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
```

<223> OTHER INFORMATION: n is a, c, g, or t

<400> SEQUENCE: 382
tgccgggccg ctcnccraac ca    22

<210> SEQ ID NO 383
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 383
agatcgccat cctgaggaan gcnttyra    28

<210> SEQ ID NO 384
<211> LENGTH: 31
<212> TYPE: DNA
<213> ORGANISM: Artificial
<220> FEATURE:
<223> OTHER INFORMATION: Primer

<400> SEQUENCE: 384
cggtcatcat ctccatgaac tcrtcraart c    31

<210> SEQ ID NO 385
<211> LENGTH: 170
<212> TYPE: DNA
<213> ORGANISM: Artificial
<220> FEATURE:
<223> OTHER INFORMATION: Intron

<400> SEQUENCE: 385
tctagaaggt aagtgtacac actacatttt catgaacatt attgcgaccg ttgagattct    60
cattgtttgg tgattgatta tctaaagtag aagcatgaat agatataaca taaactagta    120
actaatgggt tagttatggg tatacttcat gctttctct caggctcgag    170

<210> SEQ ID NO 386
<211> LENGTH: 521
<212> TYPE: DNA
<213> ORGANISM: leptinotarsa decemlineata

<400> SEQUENCE: 386 tcgattttc attttctttt tattatttgg agtgggcctg ttgtggtcgt tatcaaaatg    60
ggtaaaataa tgaaatctgg taaagtcgta ttggtccttg gaggccgata cgctggaaga    120
aaggcagtag tcataaaaaa ttacgatgat gggacgtcag ataaacaata tggacatgcc    180
gtggtggctg gaatcgatag gtaccctaga aaatccaca aacgtatggg caaaggaaaa    240
atgcacaaga ggtccaaaat caagcccttc cttaaggtgc tcaactataa ccatttgatg    300
cctacaagat attcagtgga tttgacttcg gacttgaaag tggcgcccaa agacctcaag    360
gatccagtga agaggaagaa gattaggttc caaaccagag ttaaattcga agagagatac    420
aagcaaggaa aacacaaatg gttttttccag aaattgaggt tctagattct ataaatttaa    480
ccattttgta atccacccac ctttttgttc aaataaattg t    521

<210> SEQ ID NO 387
<211> LENGTH: 475
<212> TYPE: DNA
<213> ORGANISM: leptinotarsa decemlineata

<400> SEQUENCE: 387

```
tatcgcgaaa aatatacaac ttacaaaatg aggaacacgt atgagttgag ccctaaagaa      60
gcagcaaatt tcactcgtcg aaatttagca gatactcttc gaagcaggag tccatatcat     120
gttaatcttc tcttggctgg atatgacaag aaagacgggg ctcagttgta ttacatggat     180
tatctagcgt ctgttgctag tgttgattac gctgcccatg gatacggagg atatttctcc     240
ctttccataa tggatcgcaa ttatttgaaa accctgtcga agatcaagg atacgaactt      300
ctgaaggaat gtgttaaaga agttcaaaag agacttgcta taaatttacc aaatttcaaa     360
gttcaggtta ttgataaaga tggtattaag gatatgccta atataacttc aaaaggtttg     420
aattgattaa gcaacttcag tttcagattt ttttctaaat aaacatttaa agtgt          475
```

<210> SEQ ID NO 388
<211> LENGTH: 467
<212> TYPE: DNA
<213> ORGANISM: leptinotarsa decemlineata

<400> SEQUENCE: 388

```
gcggggactg gatacatctc taaaacacag aaaaatgaaa ttcttcaagt caggaatata      60
ttctgttgta ttttttggcaa ttatattttc tttggtcact gaggaagtgg aaggtcgaag    120
gactatttta agagggcgta aaacactgac gagaacctat tttcgtgaca atgcagtccc     180
agcatacgtc atagtgatac tcgttggaat aggagaaatc attttgggag ctatcctgta     240
tgttataatg aggaaaacga taatagattt tcctttatca gggagttacg cagtggcccc     300
tactcaagaa gcataaatcc cattgaaatt gtgactgttt actttctttg gaaaatgtg      360
tataataaat acaattcatt tataatattt atatttggaa cttaaaatac ttacaaaatt     420
accatttaca tgatcaaata actaataaag ttctgtctca attataa                    467
```

<210> SEQ ID NO 389
<211> LENGTH: 906
<212> TYPE: DNA
<213> ORGANISM: leptinotarsa decemlineata

<400> SEQUENCE: 389

```
ggattggaag taaaaatata caattcatgc tgtagctgta gtgtaaaaac tgaactgaaa      60
gccataaaat aaagaccttg caagaaacat gtccaagatt aatgaggtgt ctaatttgta    120
caaacaactg aaatcagaat ggaacacatc caatccaaat ttaagcaaat gtgaaaagct    180
tttgtcagat ttgaagcttg agctaacaca cttaatgttc cttccaactt caaacgccac    240
tgcttcaaaa caagaacttc ttctggcaag agatgttctg gaaattgggg tacaatggag    300
tatagctgca aatgatatac ctgcctttga agatacatg gcacagttga atgttatta     360
tttcgattat aagaatcaac ttcccgaatc ttctttcaaa tatcagttac tgggtctgaa    420
tttactattt ttgttatcac aaaatagagt ggcagagttc cacacagaat tagaattgtt    480
gcctgctgac cacattcaga atgatgtata catcaggcac cctccatcta ttgaacagta    540
ccttatggaa ggaagttata ataagatatt tctggcaaag ggaaatgtcc cagcaacaaa    600
ttacaatttt tttatggata tacttctaga tactatcaga ggggagattg cagattgtct    660
```

```
agagaaagca tatgaaaaaa tatcaattaa agatgttgct aggatgctat acttgggcag    720
tgaagaatcg gccaaggcct ttgtaacaaa gagtaagaca tggaaattag aaaaggacaa    780
cttctttcac ttcacgcccg aggttaaaaa gacacatgag ccaattctat ccaaagaatt    840
ggcacaacaa gctattgaat atgcaaaaga actggaaatg attgtttaaa gtaataaagt    900
ttttca                                                               906

<210> SEQ ID NO 390
<211> LENGTH: 135
<212> TYPE: PRT
<213> ORGANISM: leptinotarsa decemlineata

<400> SEQUENCE: 390

Met Gly Lys Ile Met Lys Ser Gly Lys Val Val Leu Val Leu Gly Gly
1               5                   10                  15

Arg Tyr Ala Gly Arg Lys Ala Val Val Ile Lys Asn Tyr Asp Asp Gly
            20                  25                  30

Thr Ser Asp Lys Gln Tyr Gly His Ala Val Val Ala Gly Ile Asp Arg
        35                  40                  45

Tyr Pro Arg Lys Ile His Lys Arg Met Gly Lys Gly Lys Met His Lys
    50                  55                  60

Arg Ser Lys Ile Lys Pro Phe Leu Lys Val Leu Asn Tyr Asn His Leu
65                  70                  75                  80

Met Pro Thr Arg Tyr Ser Val Asp Leu Thr Ser Asp Leu Lys Val Ala
                85                  90                  95

Pro Lys Asp Leu Lys Asp Pro Val Lys Arg Lys Lys Ile Arg Phe Gln
            100                 105                 110

Thr Arg Val Lys Phe Glu Glu Arg Tyr Lys Gln Gly Lys His Lys Trp
        115                 120                 125

Phe Phe Gln Lys Leu Arg Phe
    130                 135

<210> SEQ ID NO 391
<211> LENGTH: 141
<212> TYPE: PRT
<213> ORGANISM: leptinotarsa decemlineata

<400> SEQUENCE: 391

Tyr Arg Glu Lys Tyr Thr Thr Tyr Lys Met Arg Asn Thr Tyr Glu Leu
1               5                   10                  15

Ser Pro Lys Glu Ala Ala Asn Phe Thr Arg Arg Asn Leu Ala Asp Thr
            20                  25                  30

Leu Arg Ser Arg Ser Pro Tyr His Val Asn Leu Leu Leu Ala Gly Tyr
        35                  40                  45

Asp Lys Lys Asp Gly Ala Gln Leu Tyr Tyr Met Asp Tyr Leu Ala Ser
    50                  55                  60

Val Ala Ser Val Asp Tyr Ala Ala His Gly Tyr Gly Gly Tyr Phe Ser
65                  70                  75                  80

Leu Ser Ile Met Asp Arg Asn Tyr Leu Lys Thr Leu Ser Lys Asp Gln
                85                  90                  95

Gly Tyr Glu Leu Leu Lys Glu Cys Val Lys Glu Val Gln Lys Arg Leu
            100                 105                 110

Ala Ile Asn Leu Pro Asn Phe Lys Val Gln Val Ile Asp Lys Asp Gly
        115                 120                 125

Ile Lys Asp Met Pro Asn Ile Thr Ser Lys Gly Leu Asn
    130                 135                 140
```

<210> SEQ ID NO 392
<211> LENGTH: 104
<212> TYPE: PRT
<213> ORGANISM: leptinotarsa decemlineata

<400> SEQUENCE: 392

```
Arg Gly Leu Asp Thr Ser Leu Lys His Arg Lys Met Lys Phe Phe Lys
1               5                   10                  15

Ser Gly Ile Tyr Ser Val Val Phe Leu Ala Ile Ile Phe Ser Leu Val
            20                  25                  30

Thr Glu Glu Val Glu Gly Arg Arg Thr Ile Leu Arg Gly Arg Lys Thr
        35                  40                  45

Leu Thr Arg Thr Tyr Phe Arg Asp Asn Ala Val Pro Ala Tyr Val Ile
    50                  55                  60

Val Ile Leu Val Gly Ile Gly Glu Ile Ile Leu Gly Ala Ile Leu Tyr
65                  70                  75                  80

Val Ile Met Arg Lys Thr Ile Ile Asp Phe Pro Leu Ser Gly Ser Tyr
                85                  90                  95

Ala Val Ala Pro Thr Gln Glu Ala
            100
```

<210> SEQ ID NO 393
<211> LENGTH: 266
<212> TYPE: PRT
<213> ORGANISM: leptinotarsa decemlineata

<400> SEQUENCE: 393

```
Met Ser Lys Ile Asn Glu Val Ser Asn Leu Tyr Lys Gln Leu Lys Ser
1               5                   10                  15

Glu Trp Asn Thr Ser Asn Pro Asn Leu Ser Lys Cys Glu Lys Leu Leu
            20                  25                  30

Ser Asp Leu Lys Leu Glu Leu Thr His Leu Met Phe Leu Pro Thr Ser
        35                  40                  45

Asn Ala Thr Ala Ser Lys Gln Glu Leu Leu Leu Ala Arg Asp Val Leu
    50                  55                  60

Glu Ile Gly Val Gln Trp Ser Ile Ala Ala Asn Asp Ile Pro Ala Phe
65                  70                  75                  80

Glu Arg Tyr Met Ala Gln Leu Lys Cys Tyr Tyr Phe Asp Tyr Lys Asn
                85                  90                  95

Gln Leu Pro Glu Ser Ser Phe Lys Tyr Gln Leu Leu Gly Leu Asn Leu
            100                 105                 110

Leu Phe Leu Leu Ser Gln Asn Arg Val Ala Glu Phe His Thr Glu Leu
        115                 120                 125

Glu Leu Leu Pro Ala Asp His Ile Gln Asn Asp Val Tyr Ile Arg His
    130                 135                 140

Pro Pro Ser Ile Glu Gln Tyr Leu Met Glu Gly Ser Tyr Asn Lys Ile
145                 150                 155                 160

Phe Leu Ala Lys Gly Asn Val Pro Ala Thr Asn Tyr Asn Phe Phe Met
                165                 170                 175

Asp Ile Leu Leu Asp Thr Ile Arg Gly Glu Ile Ala Asp Cys Leu Glu
            180                 185                 190

Lys Ala Tyr Glu Lys Ile Ser Ile Lys Asp Val Ala Arg Met Leu Tyr
        195                 200                 205

Leu Gly Ser Glu Glu Ser Ala Lys Ala Phe Val Thr Lys Ser Lys Thr
    210                 215                 220
```

-continued

```
Trp Lys Leu Glu Lys Asp Asn Phe Phe His Phe Thr Pro Glu Val Lys
225                 230                 235                 240

Lys Thr His Glu Pro Ile Leu Ser Lys Glu Leu Ala Gln Gln Ala Ile
                245                 250                 255

Glu Tyr Ala Lys Glu Leu Glu Met Ile Val
            260                 265

<210> SEQ ID NO 394
<211> LENGTH: 750
<212> TYPE: DNA
<213> ORGANISM: Leptinotarsa decemlineata

<400> SEQUENCE: 394
cgcccagcag tggtatcaac gcagagtacg cgggagacat tcaagtcttg tgatagtgca      60
ggcacggcag ttcaaataaa ctggtgcctt caatttattt atatatttat actttttttac    120 tagaaaccaa atactaacca atcaacatgt gtgacgaaga ggttgccgca ttagtcgtag    180
acaatggatc tggtatgtgc aaagctggat ttgctgggga tgatgccccc cgtgcagttt    240
tcccatccat tgttggtcgt ccaagacatc aaggagttat ggtaggaatg ggccaaaagg    300
actcgtatgt aggagatgaa gcccaaagca aaagaggtat ccttaccttg aaatacccca    360
ttgaacacgg tattgtcaca aactgggatg atatggagaa aatctggcac cataccttct    420
acaatgaact tcgagttgcc cccgaagagc accctgtttt gttgacagag gcaccattga    480
accccaaagc caacagggag aagatgaccc agatcatgtt tgaaaccttc aatacccccg    540
ccatgtacgt cgccatccaa gctgtattgt ctctgtatgc ttctggtcgt acaactggta    600
ttgtgctgga ttctggagat ggtgtttctc acacagtacc aatctatgaa ggttatgccc    660
ttcctcatgc catccttcgt ttggacttgg ctggtagaga cttgactgat taccttatga    720
aaattctgac tgaacgtggt tactctttca                                      750

<210> SEQ ID NO 395
<211> LENGTH: 204
<212> TYPE: PRT
<213> ORGANISM: Leptinotarsa decemlineata

<400> SEQUENCE: 395

Pro Ile Asn Met Cys Asp Glu Glu Val Ala Ala Leu Val Val Asp Asn
1               5                   10                  15

Gly Ser Gly Met Cys Lys Ala Gly Phe Ala Gly Asp Asp Ala Pro Arg
            20                  25                  30

Ala Val Phe Pro Ser Ile Val Gly Arg Pro Arg His Gln Gly Val Met
        35                  40                  45

Val Gly Met Gly Gln Lys Asp Ser Tyr Val Gly Asp Glu Ala Gln Ser
    50                  55                  60

Lys Arg Gly Ile Leu Thr Leu Lys Tyr Pro Ile Glu His Gly Ile Val
65                  70                  75                  80

Thr Asn Trp Asp Asp Met Glu Lys Ile Trp His His Thr Phe Tyr Asn
                85                  90                  95

Glu Leu Arg Val Ala Pro Glu Glu His Pro Val Leu Leu Thr Glu Ala
            100                 105                 110

Pro Leu Asn Pro Lys Ala Asn Arg Glu Lys Met Thr Gln Ile Met Phe
        115                 120                 125

Glu Thr Phe Asn Thr Pro Ala Met Tyr Val Ala Ile Gln Ala Val Leu
    130                 135                 140
```

Ser Leu Tyr Ala Ser Gly Arg Thr Thr Gly Ile Val Leu Asp Ser Gly
145                 150                 155                 160

Asp Gly Val Ser His Thr Val Pro Ile Tyr Glu Gly Tyr Ala Leu Pro
                165                 170                 175

His Ala Ile Leu Arg Leu Asp Leu Ala Gly Arg Asp Leu Thr Asp Tyr
            180                 185                 190

Leu Met Lys Ile Leu Thr Glu Arg Gly Tyr Ser Phe
        195                 200

```
<210> SEQ ID NO 396
<211> LENGTH: 44
<212> TYPE: DNA
<213> ORGANISM: Artificial
<220> FEATURE:
<223> OTHER INFORMATION: Primer

<400> SEQUENCE: 396
gcgtaatacg actcactata ggatgtgtga cgaagaggtt gccg                    44

<210> SEQ ID NO 397
<211> LENGTH: 24
<212> TYPE: DNA
<213> ORGANISM: Artificial
<220> FEATURE:
<223> OTHER INFORMATION: Primer

<400> SEQUENCE: 397
gtcaacaaaa cagggtgctc ttcg                                          24

<210> SEQ ID NO 398
<211> LENGTH: 22
<212> TYPE: DNA
<213> ORGANISM: Artificial
<220> FEATURE:
<223> OTHER INFORMATION: Primer

<400> SEQUENCE: 398
atgtgtgacg aagaggttgc cg                                            22

<210> SEQ ID NO 399
<211> LENGTH: 46
<212> TYPE: DNA
<213> ORGANISM: Artificial
<220> FEATURE:
<223> OTHER INFORMATION: Primer

<400> SEQUENCE: 399
gcgtaatacg actcactata gggtcaacaa aacagggtgc tcttcg                  46

<210> SEQ ID NO 400
<211> LENGTH: 320
<212> TYPE: DNA
<213> ORGANISM: Leptinotarsa decemlineata

<400> SEQUENCE: 400
atgtgtgacg aagaggttgc cgcattagtc gtagacaatg gatctggtat gtgcaaagct   60
ggatttgctg gggatgatgc ccccgtgca gttttcccat ccattgttgg tcgtccaaga  120
catcaaggag ttatggtagg aatgggccaa aaggactcgt atgtaggaga tgaagcccaa  180
agcaaaagag gtatccttac cttgaaatac cccattgaac acggtattgt cacaaactgg  240
gatgatatgg agaaaatctg gcaccatacc ttctacaatg aacttcgagt tgcccccgaa  300
gagcaccctg ttttgttgac                                              320
```

<210> SEQ ID NO 401
<211> LENGTH: 1152
<212> TYPE: DNA
<213> ORGANISM: Artificial
<220> FEATURE:
<223> OTHER INFORMATION: Hairpin

<400> SEQUENCE: 401

| | |
|---|---|
| tgacgacctt gagttggttt ctgaagttga actcggcagc cttcttctgg agcttggcga | 60 |
| atttgttttc gtacttggaa acctttttca aggtaggttt gacgaattta ccacggaggt | 120 |
| cgttgacctg gctgttgagg tcggcgatct caaggtcacg tctctccact tcgaattcga | 180 |
| tgtcaatttt actcctctcc agagcgtcaa ttcgcttatg gtagtctgtg cagagtttct | 240 |
| tcaaggttgc ttcattggcg ttgtcgacgt cggcaatttg cccgcagcgc tcctcaatcg | 300 |
| ttcgcctcct ctcagctgct ttgcgttcct gctccttctt cagttcctca gcggcttttt | 360 |
| tcctcagcag gagtcggagt ttcttcttcc tttccgggt catgaaaccc ttcttggctt | 420 |
| tcttcgcctt agaggcttcc tccatcctct gcgcacttc agcgcgcttc ctctcgattt | 480 |
| cggcctgttt gtctagaagg taagtgtaca cactacattt tcatgaacat tattgcgacc | 540 |
| gttgagattc tcattgtttg gtgattgatt atctaaagta gaagcatgaa tagatataac | 600 |
| ataaactagt aactaatggg ttagttatgg gtatacttca tgcttttctc tcaggctcga | 660 |
| gcaaacaggc cgaaatcgag aggaagcgcg ctgaagtgcg caagaggatg gaggaagcct | 720 |
| ctaaggcgaa gaaagccaag aagggtttca tgaccccgga aaggaagaag aaactccgac | 780 |
| tcctgctgag gaaaaaagcc gctgaggaac tgaagaagga gcaggaacgc aaagcagctg | 840 |
| agaggaggcg aacgattgag gagcgctgcg ggcaaattgc cgacgtcgac aacgccaatg | 900 |
| aagcaacctt gaagaaactc tgcacagact accataagcg aattgacgct ctggagagga | 960 |
| gtaaaattga catcgaattc gaagtggaga gacgtgacct tgagatcgcc gacctcaaca | 1020 |
| gccaggtcaa cgacctccgt ggtaaattcg tcaaacctac cttgaaaaag gtttccaagt | 1080 |
| acgaaaacaa attcgccaag ctccagaaga aggctgccga gttcaacttc agaaaccaac | 1140 |
| tcaaggtcgt ca | 1152 |

<210> SEQ ID NO 402
<211> LENGTH: 1192
<212> TYPE: DNA
<213> ORGANISM: Artificial
<220> FEATURE:
<223> OTHER INFORMATION: Hairpin

<400> SEQUENCE: 402

| | |
|---|---|
| ctcttgcttc ttggtggcga tcctctcctc gcgcctcttc ttcgcctcct tgaccttgag | 60 |
| acgtctcgcc tctgcctggt ccttcaacat ctttgatctc gccttttcag ccttcttctt | 120 |
| gtgaatgaag tccatcagta ccctcttgtt tttgaagacg ttacctttgg ctttcatgta | 180 |
| aaggtcgtgg tacatttgcc tatcgatctt cttggcttct ctgtattttt taaggagccg | 240 |
| tcgcaggact ctcattctgt tgacccacag gaccttcaca ggcattctgg cgttggcggt | 300 |
| acccttcctc ttaccgaagc cacagtgacg acccttccgt ctggcttctg tgttttacg | 360 |
| gacgcgggct ctggagtgga cagccacagg cttttgatg atcaaaccat ccttgatcag | 420 |
| cttacggatg ttttgcctag agttggtgtt ggcgatttcg ttgatttcat tagggtccaa | 480 |
| ccacacttc ttcttgccgc atctcatcac ctctagaagg taagtgtaca cactacattt | 540 |

```
tcatgaacat tattgcgacc gttgagattc tcattgtttg gtgattgatt atctaaagta    600
gaagcatgaa tagatataac ataaactagt aactaatggg ttagttatgg gtatacttca    660 tgctttttctc tcaggctcga gggtgatgag atgcggcaag aagaaagtgt ggttggaccc    720
taatgaaatc aacgaaatcg ccaacaccaa ctctaggcaa acatccgta agctgatcaa    780 ggatggtttg atcatcaaaa agcctgtggc tgtccactcc agagcccgcg tccgtaaaaa    840
cacagaagcc agacggaagg gtcgtcactg tggcttcggt aagaggaagg gtaccgccaa    900
cgccagaatg cctgtgaagg tcctgtgggt caacagaatg agagtcctgc gacggctcct    960
taaaaaatac agagaagcca agaagatcga taggcaaatg taccacgacc tttacatgaa   1020
agccaaaggt aacgtcttca aaaacaagag ggtactgatg gacttcattc acaagaagaa   1080
ggctgaaaag gcgagatcaa agatgttgaa ggaccaggca gaggcgagac gtctcaaggt   1140
caaggaggcg aagaagaggc gcgaggagag gatcgccacc aagaagcaag ag           1192

<210> SEQ ID NO 403
<211> LENGTH: 792
<212> TYPE: DNA
<213> ORGANISM: Artificial
<220> FEATURE:
<223> OTHER INFORMATION: Hairpin

<400> SEQUENCE: 403
actctgtctg gcttttggct gtgacgcaca gttcatagag ataaccttca cccgaatatg     60
ccttgcgagg tcgcaaaatc ggcgaaattc catacctgtt caccgacgac ggcgctggat    120
caattccaca gttttcgcga tccagactga atgcccacag gccgtcgagt tttttgattt    180
cagatacgta cacttttccc ggcaataaca tacggcgtga catcggcttc aaatggcgta    240
tagccgccct gatgctccat cacactttgc cgtaatgagt gaccgcatcg aaacgcagca    300
cgatacgctg gtctagaagg taagtgtaca cactacattt tcatgaacat tattgcgacc    360
gttgagattc tcattgtttg gtgattgatt atctaaagta gaagcatgaa tagatataac    420
ataaactagt aactaatggg ttagttatgg gtatacttca tgctttttctc tcaggctcga    480 gccagcgtat cgtgctgcgt ttcgatgcgt tcactcatta cggcaaagtg tgatggagca    540
tcagggcggc tatacgccat ttgaagccga tgtcacgccg tatgttattg ccgggaaaag    600
tgtacgtatc tgaaatcaaa aaactcgacg gcctgtgggc attcagtctg gatcgcgaaa    660
actgtggaat tgatccagcg ccgtcgtcgg tgaacaggta tggaatttcg ccgattttgc    720
gacctcgcaa ggcatattcg ggtgaaggtt atctctatga actgtgcgtc acagccaaaa    780
gccagacaga gt                                                        792

<210> SEQ ID NO 404
<211> LENGTH: 839
<212> TYPE: DNA
<213> ORGANISM: leptinotarsa decemlineata

<400> SEQUENCE: 404
cagtcagcac cgagtccttg ttgactgctc acatttttcca tcgtttctac cagaacaaca     60
gcaacaactt tcatcatggc ggacgacgag gaaaagagga ggaaacaagc ggaaattgaa    120
cgcaagaggg ctgaggtcag ggctcgcatg gaagaggcct ccaaggccaa aaaagccaag    180
aaaggtttca tgacccctga gaggaagaag aaacttaggt tattgctgag aaagaaagca    240
gcagaagaac tgaaaaaaga acaagaacgc aaagctgccg aaaggcgtat tattgaagag    300
agatgcggaa aaccaaaact cattgatgag gcaaatgaag agcaggtgag gaactattgc    360
```

-continued

```
aagttatatc acggtagaat agctaaactg gaggaccaga aatttgattt ggaataccct    420
gtcaaaaaga aagacatgga gatcgccgaa ttgaacagtc aagtcaacga cctcaggggt    480
aaattcgtca aacccactct caagaaagta tccaaatacg agaacaaatt tgctaaactc    540
caaaagaaag cagcagaatt caatttccgt aatcaactga aagttgtaaa gaagaaggag    600
ttcaccctgg aggaggaaga caaagaaaag aagcccgatt ggtcgaagaa gggagacgaa    660
aagaaggtac aagaagtgga agcatgatct gtccctacaa tttaatattt cccttcgtcc    720
gtggaaattt tacaacttaa gatatattta ttttattcgc ttcttatgag actatgaaag    780
tgatgtctgc atgtatatta ttcgttttat gtatgtatta aaaaaagaac ttgattgaa    839
```

<210> SEQ ID NO 405
<211> LENGTH: 203
<212> TYPE: PRT
<213> ORGANISM: leptinotarsa decemlineata

<400> SEQUENCE: 405

```
Met Ala Asp Asp Glu Glu Lys Arg Arg Lys Gln Ala Glu Ile Glu Arg
1               5                   10                  15

Lys Arg Ala Glu Val Arg Ala Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Ile Ile Glu Glu Arg Cys Gly Lys Pro
65                  70                  75                  80

Lys Leu Ile Asp Glu Ala Asn Glu Glu Gln Val Arg Asn Tyr Cys Lys
                85                  90                  95

Leu Tyr His Gly Arg Ile Ala Lys Leu Glu Asp Gln Lys Phe Asp Leu
            100                 105                 110

Glu Tyr Leu Val Lys Lys Lys Asp Met Glu Ile Ala Glu Leu Asn Ser
        115                 120                 125

Gln Val Asn Asp Leu Arg Gly Lys Phe Val Lys Pro Thr Leu Lys Lys
    130                 135                 140

Val Ser Lys Tyr Glu Asn Lys Phe Ala Lys Leu Gln Lys Lys Ala Ala
145                 150                 155                 160

Glu Phe Asn Phe Arg Asn Gln Leu Lys Val Val Lys Lys Glu Phe
                165                 170                 175

Thr Leu Glu Glu Glu Asp Lys Glu Lys Lys Pro Asp Trp Ser Lys Lys
            180                 185                 190

Gly Asp Glu Lys Lys Val Gln Glu Val Glu Ala
        195                 200
```

UNITED STATES PATENT AND TRADEMARK OFFICE
CERTIFICATE OF CORRECTION

PATENT NO. : 9,845,479 B2
APPLICATION NO. : 13/462610
DATED : December 19, 2017
INVENTOR(S) : Beghyn et al.

It is certified that error appears in the above-identified patent and that said Letters Patent is hereby corrected as shown below:

At Column 351, in Claim 1, Line 65, remove "91" and insert therefor --91%--

Signed and Sealed this
Thirteenth Day of March, 2018

Andrei Iancu
*Director of the United States Patent and Trademark Office*